(12) United States Patent
Ramadugu et al.

(10) Patent No.: US 7,919,601 B2
(45) Date of Patent: Apr. 5, 2011

(54) IDENTIFICATION AND USE OF GENES ENCODING HOLINS AND HOLIN-LIKE PROTEINS IN PLANTS FOR THE CONTROL OF MICROBES AND PESTS

(75) Inventors: Chandrika Ramadugu, Riverside, CA (US); Dean William Gabriel, Gainsville, FL (US)

(73) Assignees: Integrated Plant Genetics, Inc., Alachua, FL (US); University of Florida Research Foundation, Gainesville, FL (US)

( * ) Notice: Subject to any disclaimer, the term of this patent is extended or adjusted under 35 U.S.C. 154(b) by 784 days.

(21) Appl. No.: 10/556,563

(22) PCT Filed: May 14, 2004

(86) PCT No.: PCT/US2004/015099
§ 371 (c)(1),
(2), (4) Date: Aug. 14, 2007

(87) PCT Pub. No.: WO2004/104169
PCT Pub. Date: Dec. 2, 2004

(65) Prior Publication Data
US 2009/0136914 A1 May 28, 2009

Related U.S. Application Data

(60) Provisional application No. 60/470,799, filed on May 14, 2003.

(51) Int. Cl.
*C07H 21/04* (2006.01)
*C12N 7/00* (2006.01)

(52) U.S. Cl. .................................. 536/23.1; 435/235.1
(58) Field of Classification Search ....................... None
See application file for complete search history.

(56) References Cited

U.S. PATENT DOCUMENTS

| 6,783,930 B1 | 8/2004 | Pelletier et al. |
| 6,858,707 B1 | 2/2005 | Wei et al. |
| 2009/0036307 A1 | 2/2009 | Gabriel et al. |

OTHER PUBLICATIONS

Grundling et al., Dimerization between the Holin and Holin Inhibitor of Phage Lambda, Journal of Virology, 2000, 182(21):6075-6081.*
Masaya Oki, et al., "Functional and structural features of the holing HOL protein of the *Lactobacillus plantarum* phage Φgle: analysis in *Escherichia coli* system", GENE 197 (1997) pp. 137-145.

* cited by examiner

*Primary Examiner* — Zachariah Lucas
*Assistant Examiner* — Nicole Kinsey White
(74) *Attorney, Agent, or Firm* — Cooley LLP

(57) ABSTRACT

This invention provides: 1) methods for the identification of broad-spectrum holins with a high level of nonenzymatic activity in membranes; 2) conditions required for maintaining and increasing the anti-microbial and anti-pest efficacy of holins in gene fusions; 3) a method for effective targeting of holins expressed in plants through use of a leader peptide to direct the holin protein to the plant apoplast and xylem; 4) methods for the control of bacterial and fungal diseases of plants and control of insect and nematode pests that attack plants by expression of gene fusions involving holins, C-terminal additions and leader peptides, and optionally, endolysins; 5) methods for increasing the shelf-life of cut flowers, and 6) transgenic plants useful for the production of novel antimicrobial proteins based upon holins.

14 Claims, 14 Drawing Sheets

904B (pIPG409)

Control

SEQUENCE LISTING

<160> NUMBER OF SEQ ID NOS: 110

<210> SEQ ID NO 1
<211> LENGTH: 55770

```
<212> TYPE: DNA
<213> ORGANISM: Phage P15
<220> FEATURE:
<221> NAME/KEY: misc_feature
<222> LOCATION: (13629)..(13629)
<223> OTHER INFORMATION: n is a, c, g, or t
<220> FEATURE:
<221> NAME/KEY: misc_feature
<222> LOCATION: (13662)..(13662)
<223> OTHER INFORMATION: n is a, c, g, or t
<220> FEATURE:
<221> NAME/KEY: misc_feature
<222> LOCATION: (13701)..(13701)
<223> OTHER INFORMATION: n is a, c, g, or t
<220> FEATURE:
<221> NAME/KEY: misc_feature
<222> LOCATION: (13721)..(13721)
<223> OTHER INFORMATION: n is a, c, g, or t
<220> FEATURE:
<221> NAME/KEY: misc_feature
<222> LOCATION: (13730)..(13730)
<223> OTHER INFORMATION: n is a, c, g, or t
<220> FEATURE:
<221> NAME/KEY: misc_feature
<222> LOCATION: (13747)..(13747)
<223> OTHER INFORMATION: n is a, c, g, or t
<220> FEATURE:
<221> NAME/KEY: misc_feature
<222> LOCATION: (13973)..(13973)
<223> OTHER INFORMATION: n is a, c, g, or t
<220> FEATURE:
<221> NAME/KEY: misc_feature
<222> LOCATION: (28140)..(28140)
<223> OTHER INFORMATION: n is a, c, g, or t
<220> FEATURE:
<221> NAME/KEY: misc_feature
<222> LOCATION: (28220)..(28220)
<223> OTHER INFORMATION: n is a, c, g, or t

<400> SEQUENCE: 1
ccccagggca tggctcattt ggcctccccg ccgctaact  atggcatcga ggcgacgtcc      60
attgaccctc tgtgacatcg aggcgacgtt ctttggccat cttactgagt ccaatgaccc     120
ctgaggctca ttccctgtgc caccgatcag cattgcggca ttctacgatg cccagaagaa     180
ccttgaggcg acgtacgaag tccattatgc tgctcccttg aggaactcat accaaaacgc     240
agtgatgatg gttccaatca tgatgaccgt tgccaccttg atcgcctggg agcgccatgt     300
gcgcgtcacg tgggtgccct tgggcatgta ggcggtgtgc ttcgtacgtc gccattcgga     360
ttcagaggtg cggagttctt tgcgggacat tggaaggact catcagggcg gtactgttcc     420
gccgacctga cccctgtatg gggccaggtt tcgtccgagg ttaacttact cggtcacttc     480
agcgtcacga acttccttgt gaatcgactt gaaggtgaat cccttacggg cggagtagat     540
ttgtccgtag gacaagccca gttgttctgc cgcgtccttg tgagggacat ccttcatttc     600
gccgatgatg accttacgcg catcttcctc tgtcatggtg cgctctgcct tcggaccgcg     660
atcccgaggt gcgctctgag cattcagcgc ttcgatgact tcgttcagct ttgctgccag     720
agcagcgttg gagagcttct gggacagatc gatcagttcg atggcgttca tttggtgtaa     780
cctctaagtt atttaggatg gtgtgcttgg tagcacaagg atatagtact acgattggag     840
gttgatgtgt taagaatatg ttaaagtatg aaaatatttt ggcatattta ttaacgcggt     900
tatgtatggc atggcgcgga tgggtatgca tactgtctac catagtgcat gttaagatga     960
tgtgaatgac taagtatcta tcatgtgatg tgttaagata atgtgaatgg catcgggcat    1020
agtacatcta acacatacga tggacaaagt acatggtttg attatgaatg attaatatag    1080
attaatgatt catgattggt ataatggacg atgcactatg cacgtggtgc agtactgggg    1140
tagagcagta tatgagtata tggctacatg ggtactgtgg tagtatggta tatggtttca    1200
```

```
tatgatatag tatgatgtga tataatatca tgtgatatga ttacgattga tatgattaca    1260
tatgatatga tatcatatga tatgatatgg tttcatatga tatagttaca atcgtaatca    1320
ttaatataca ttaatcgttt atgtttgtga tagtttcagg tgaaagcgtt taacttcatt    1380
aacagggccc cctagtctcc caggagacc gccccacttg acggggcatt tttctaaaaa     1440
gtgagaagca acacgcgttt agtacctatg ccggtgcgcg ttccgagcca tctgtaggag    1500
gcgacggggc atcgcgctta gggcgaagtg cttttgttccg tgtgcttagc gtatcagacc   1560
aggtccctca ttcatgggtc caaaattaaa atgattccat gtgggataga atccttgtac    1620
aatgaacctt gccctacgg gtctatatgc taggcccta cgcccttgg aggattcatg       1680 tctgatctaa tggccgcaga tgaccaaaag actcggcgtg agctcttgct tggaatgatc    1740
cagcaggagt atccttccta ccatccgctc gtgagcattg ccagaatcgc ccatcaccac    1800
gatgccgatc tgaagttgca attcgagtgc caccgtacaa tcgcaaagta cgtggagccc    1860
gaactcaagt ccattgaggt caagggtgaa atcactggtc gacacaaagt ttcggtttcg    1920
ttgttcgagc cgaagcagga atctttccct cctgtgtccg ggggtggggc ctctcatatc    1980
gaaggcgaga gcactcgtgt gctaccgtcg ggacagcagc aatctggcgg tgagatgagc    2040
agactcgaca tggacccgtc cgtggtggac cgggtcacgc tagcaggctg ggagtaatac    2100
atgccgactc aaaccaacaa gctcgcctcc gggactgctg ggggaacgag tagcgacatc    2160
gcggtggatc agggccaact ggttgtggtg ggagtttatg ccgccgacgg aggctctctc    2220
ccggccaata cgcaggccca actcttgcgg aaggtgggga ctgcgtatat ccccgagccc    2280
gatgtgttcg ggggcaacac catcatcacc tccgagcggc agaccgtggt actcggggct    2340
ccagggacct acgccatccg cgttcagccg agctccaagg ctgtgtccgt ggaggagtgg    2400
cgctaatatg accgtcatcc ggaggcgcat atccaagcct ggcgcagtca aaggagcctt    2460
gagccgttcg gtgggggcg caattgccgg cgccctgagt gctcgaggct cgggtaattt     2520
cgtgccgcct ccggtgatta gcgatcttat gatcgcctcg atgaacggca ttacgccgca    2580
taatcttcaa gacagtcaaa atttcgataa ccatgtggcc agatggattt acaccactgg    2640
gtccggaaaa ttaaaatccc tggctttgcg tttttgatgcc tggttcatca acgcgaccag   2700
cgcaatcact aatacctcca atccaattcc tatcttcgat gcgtctctgg aatcaacgg     2760 cgtagtggtc cctgtaacat tcgggaatat tcgatccaag acactccagc ctggcgactt    2820
cgacgttctc agcgatgaaa ttcaggtaag cgcgtttggc gtaacgaata tccctcgtgg    2880
atccaatgta tccttgaaga ttcgatatac gtttccaggc gccagtgcca atcgtatgct    2940
cattggatta caacgcccg aatctcaagg cggccaatgt cgatggttca atgcggcaaa     3000
cacgactgta tcttccacag acgcgcccgg accgtatact ttcactggaa cggcgccgac    3060
tgcccggcaa ggcagttatc gtccaggcct tttaggtcga tatgagggcg cttttgagcc    3120
gatttggctc ttttacggcg attcaatcac gatgggacc ggtgacagcg actatactcg     3180
caactatgga attggctggc cagccgaggc atgtcgaatt gccagcccca atggcggcct    3240
atcatatgga aacatggcca ttcacggttc ttccaccgca atgtcgacct tcggtgaaaa    3300
aattgaggct ccgctaaagt acgcgactca tgtgcatatc ggatgggta cgaatgactt     3360 cggcaccagc gccgcggatc ctcgtcctac gtctcagcca cgcttgactg ctggcgtgaa    3420
tagcatgaaa gctcgacctg gttcgaaagt aacgaactgg tatttcggct atttgggacc    3480
tcgtactacc acgacagaca actacgttac agaagaaaat cagagctatc tcactgccaa    3540
ttggggtcct agcccttgta atgtggagag ttggaatagt tggctcgtta ccaacttctc    3600
```

```
accgaatggc gtaaatacat ggccctcaat tcgaggtgta gacccgttga agtggagggt   3660
aaatgggacg gctcgatatt caaataccga tgatgcacat ccgagcactg taggacatct   3720
actgatgggc caagatgccg ccgctatgat gcgtgctaat caaggagtaa gtttagcatg   3780
aagacttttg atccggctgg caatttgatc gatatttctg gtgagattgt ggtcaatgat   3840
ctcaatgtgg cccctgtgct gaataccatc ccaatggccg gaaataacta tgtcgtgatg   3900
tcgattatga cggattccgg ccatcgtcga ttggtacttg tgaatccggc cctaatcgcc   3960
caagcatctc aacttcaaag cctcgaacac tcgttggcgc tgaccgataa tatggtggtg   4020
actcgcacca agatggtcga attgccggtc cagactctca cctactctgc ggccattgcc   4080
atgggcgctg gagctatgaa attcaccaaa accggaattg ctggagttaa gacgactgac   4140
atcatcgtgg ctcgaccaca gactcctttg gcggaaggct acatggtagg cgacgcggtt   4200
tgcaccacgg acggcacgat cgactacaga ctgtttcggc ccgccttggc tatcggagcg   4260
aatctcagca tcaacatgcg aacgttcgca ttgcgattgg aaaattcatg actcgatcta   4320
aattccgttc gatgcacggc cggtcgaacg ggattggctt tgaatcaggg ttcgagaaga   4380
aatttctgct tcagtgctac cagttgggaa tcaaggtcga gaggtcacta gagcaggtcg   4440
cgtaccaaga ttcgaaaggc atttggcacc ggtataatcc ggatttttat tggcccgatg   4500
ttaacttcac agtagagatc aagggatcct gggccttccg gataaccat gggaatgtaa   4560 aggagaaatt ctacgcagca atggtctact tcaaaaaccg ctatacactc atcactgaga   4620
aagaattgcg gtccgactac gtagccaagc tgtatagatc actccatggc aactgacttt   4680
aaactttatc cgccccaaca acgagccctg atcactccgg ctcgtgaaat tttgtatggc   4740
ggtgcagcag gtggcggtaa gtcgtatcta ctccgtgttg caagcatcgt gtacagcctg   4800
gaaattcctg gtctgatcac ctacctgttt cgtcgaacgt tcaaagaggt cctgagcaac   4860
cacgtttata ccccaggcgg ctacctggaa atgatgaagg gcctgattga tgcaggcgac   4920
gttgtttact ccaagtcgga caactccttc accttttaca atggttcacg tattcagctg   4980
gctcactccc agttcgaaaa cgacatctat acccaccagg gagcccagat cggcttcctg   5040
atcatcgacg aggcaacgca cttcactcct ccgatgattc gcttcattcg gtctcgtgtg   5100
cgcttgggct ccatgattat cccaccgaag tggaaggctc tgttcccacg gatcctgtac   5160
acggctaacc ccggtggcgt tgggcatcac tacttcaaat cgaatttcgt tgacattggt   5220
tctggccatg tattccaggc gcctgaagat gagggctcca tgttgcggga atacatccct   5280
gcaaagctgg aagataacaa ggtcatgatg gaaacggacc cggactaccg ggcacgtctt   5340
aaaggtatgg gcgactccgc gaccgtccaa gcaatgcttg agggtgactg ggaggtggtt   5400
agcgcaggtg gaattgcgga tctctggcga tccaagatcc atgtggtgca ccctttcaaa   5460
atcccacata cctggaagat cgatcgtgga tatgactacg gctcatcaaa gccggcagcg   5520
tatctactgt ttgctgagtc agacggctcg gaatttcgtg accagcaagg tcgagtttgt   5580
tgggtaccgg ctggtacggt gttcgtgatt ggggaagatt atattgccaa taagcgtcaa   5640
gaaggccttc gtctcactgc aatcgaacaa gggcgtcgta tggcgcgata tgaagctgaa   5700
tccggctatc aaaaccgaat ccagccaggc ccagcggata atgcgatttt cagcgcagag   5760 cccgacatc gtactgtggc agatgatatc ggtattcatg gcgtaacatt tactcgtagt   5820
aacaaaaatc ctggttcacg aatcgaaggt ctccaactgt ttcgtacacg tttgaaggcc   5880
gccacagagc gcccaatgga gaacccaggg ttcttcgtgt tcaatacgtg ctttaacacc   5940
attcgtacca ttccaaatct ccaaaattcc ccaaagaatt cagaagattt agatacagcg   6000
```

```
ggtgaggatc acatctggga cgtcattcgg taccgcctcc ttaaagcggc caagcaaatc    6060
aaactgatcg agactgaggg ccactaagta tgccaatcga aaccaaacat cctgaatatc    6120
tggcatacga gaacgactgg atcgactgtc gtgtggcgag cctcggtcag cgcgaagtca    6180
agaaaaaggg cgtccgcttc ctaccgaaac tgtccggcca aaccgatgat atgtataatg    6240
cctacaagca acgggcattg ttctactcga tcacgtccaa aaccctctcg gcccttcctg    6300
gcatggtgct tgatcagcca cctgtgatca cgcaccccga tgctatgagc aagtacttcg    6360
aagatcagtc tggcattcag ttctacgaag tattcacccg cgccgtcgaa gaaaccctct    6420
tgatgggccg cgttggcgtg ttcatcgatc gcccactaac tggcggcgac ccgtatatct    6480
cggtctacac caccgagaac attctgaatt gggaagaaga cgaagacggc cgtttgctga    6540
tggtcgtatt gcgcgagttc tataccgttc gggatactgc tgaccggtat gtccagaaca    6600
tccgcgttcg ttatcgctgt ctggagttgg ttgatggtct gctgcaaatt acggtccacg    6660
agactcaaga tggtaaggtc tgggaattgg cgaagacctc gacgattcag aatgtcggcg    6720
tgacgatgga ttatatccca ttcttctgca tcacgccgag tggcttatcc atgactccgg    6780
cgaagccgcc gatgatcgac atcgttgaca tcaactattc gcattaccgc acctctgcag    6840
acctagagca tggccgccac ttcaccggcc tgcccacgcc atggatcacc ggtgctgagt    6900
ctcagtcgac catgcatatt ggttcgacca aagcctgggt gattcctgaa gtggccgcga    6960
aggtcggctt cctggagttt actggccagg gtctgcagag cttggagaaa gctctctcgg    7020
aaaagcaagc acagttggca tccttgagtg cgcgactgat cgacaattca acccgtggtt    7080
cggaagcaac ggagaccgtc aaactccgtt acatgtccga acggcatct ttgaagtctg    7140 tgacgcgagc agtggaagcc ttgctcaaca aggcctactc ctgcatcatg gatatggaga    7200
gtatgggcgg aaccctcaac atcaagttga actccgcgtt tcttgattca aaacttaccg    7260
ccgccgagct caaagcgtgg gtcgaggctt acctgtctgg gggcatctca aaggagattt    7320
acattcacgc cctcaaagtt ggcaaagtct taccccgcc gggcgagagt atgggagtta    7380
ttccagaccc gccggcgccg gagcctagtc catccaacac acctccaaac ccatcctcaa    7440
aggcataatt tatgaagctc aagttcaaaa tcggcaagct ggaagacgtc gcagaggcct    7500
accgcaacct gtactcgcaa ggtccggacg gttcgtacta tctggacgtc gacggtgccg    7560
tggacaagtc caagctggat gagttccgcg acaacaatgt ggctctgcgc gcccagatcg    7620
aaaagttcaa ggacgtcgat ccggccaagt atcaggaact aatggcggag cacgccaaga    7680
tccatgaggg tgagctgatc aagaagggcg acgtggaagg cctggtcaat caccgcaccc    7740
agaccatgag gaccgagtat gaaggtaagc tgaactcgtt gagcaagaac tacgagatcg    7800
ctcagcgcca gctcgaaacg ctgaccatcg acaatgtggt ccgtgatcgc tcgatcaagc    7860
tcggcgtcgc gcccaccgct gtggaggatg tgctgttgcg ggccaagagc gtcttccgtg    7920
tcgaagaagg ccgccctgtg gcgaaggatc cggaaggcaa gatcgtctat ggcaagaacg    7980
gcaccgatcc gatggacatc ggcgagtggc ttggtggctt gaaggatcag gcaccccatc    8040
tgttccagcc gtccactggc tctggcggca acggtggcaa tcgccaggcc ggcaacggtg    8100
gtgagaagtt gtcggcggct cagaagatcg cttctggtct gtcctctggc tcgaccatca    8160
tgcaataacg ggattccatc ctaattatgg atccataaac aagggcgaaa gcccttgttt    8220
acttttgagt cccatgaagg tataatatcc ttgcgggtta gaggtgcgga tcatcgggga    8280
tggttcgaat ctgtactccg cctctccggg ggagatggcg aacactcacc catcaatttc    8340
cggagctcaa aatgcccacc gttaccctgg cggaatccgc caagctctcg caggaccacc    8400
```

```
tcgtttctgg cctgatcgag accatcgtgg aggtcaatcc cctctacgag atgatgccct   8460
tcaccgaaat cgagggcaac gcactggcct acaatcgcga gaacgtgctg ggcgacgtcc   8520
agtttctcgc cgtcggtggt accatcaccg ccaagaatcc ggccaccttc accaaggtta   8580
cctcggaact gaccaccttg atcggcgacg ccgaagtcaa cggtctgatc caggccaccc   8640
gctccgactt catggatcag acctctgtgc aggtcgcgtc caaggcgaag tccatcggtc   8700
gtcagtatca ggcgtcgatg atcaccggcg acggcacggg caactcgttc cagggcatga   8760
tgggcctggt ggctgcgtcg cagaccatct cggccggcgc caacggcggc acgctcacct   8820
tcgaactgct ggatcagctg ctcgatctgg tgaaggacaa ggacggtcag gtggactact   8880
tgatgtcgtc cttcgcgatg cgccgcaagt acttctccct gttgcgtgca ctcggtggcg   8940
cagcgatcgg tgaagtcatg accctcccga gcggtcgtca aatcccgacc taccgcggcg   9000
tgccgtggtt cgtgaacgac ttcatcccga gcaacatgac gcagggtacc gccaccaacg   9060
ccactgcgat cttcgctggt acgttcgacg acggttccaa caagtacggc atcgccggcc   9120
tgacggcccg cggttcggcc ggtctgcgtg tccagaacgt cggcgcgaag gaaaacgccg   9180
atgaaaccat caccgtgtg aagatgtact gcggtttcgc caacttctcg cagctgggtc   9240
tggcggcgat caagggcctc atcccgggct aatcgcttca ccagcagaac ccaggctagt   9300
cctgggtttt gttgtttccc aaccctctgt aggagatcca tcatggcaaa ggtattcgtt   9360
accgatcgca agaacaaggg cctggaagtc gtggccggca agtacaactt catcgacggc   9420
atcatgccgg tgagcgactc cgatgcgtg ttgctggagc cgatcctgac ccgttactac   9480
ggcgccaccc tggaagacgt ggcttcgcgt accgtcgaag atctggatga aaccgtggat   9540
tcgtccatcc tggctgcgca gaccaaggcg cggagctgg ccggttcggg cttctccacc   9600
gatgcagcag ttgccgctgg caaagctgcc ggcgacccct ctgtgaccgg caccgtttcc   9660
ggttcggacg caggcgagac cgccgacgac atcaacaagc agaacgagaa gtctggcggc   9720
gccacggcca ccgcgacccc gaccaaggtc gaagttgcgg atccgaaggc taccacccag   9780
gctgctccgg ccaagccggc cgccgctgcg gataagaagt aatctgatgc cgaccgtaga   9840
cgccactccc ggttcgatca cggccaacag ctacgttact gtagccgagg caaactcgta   9900
cttcgatggt tcctacggtc ggcctctttg gacttcggct agcgaggatg aaaaagcctc   9960
gctagtgatc tctgcctcca gatatctgga ccagatgatg gcgtggatcg gcgctccgac  10020
caatcccgaa cagtcaatgt ggtggccttg caaaaatgca gttattgggg ggatgacgct  10080
gagccaagtg tctatccctg taaaagttaa aatagcggtc ttcgagctcg catacttcat  10140
gctggagagc ggggctgcac tgtcattcgc ggatcaaacc atcgacagcg tgaaggtcgg  10200
cacaattcga gtcgaattca cgaagaactc cacggatgcg ggcctgccca ctttcgtcga  10260
ggcgatgttg agcggatttg gttctccggt cctgtatgga tcgaatgccg caagaagtat  10320
tgacttggtg agagcatgag cctatcgcgg cagatcttca atgcgattcg gactgccaag  10380
cgatcactgg gcgacatgat tctcacaggg cagttaatca cgtataccac cgagtatcaa  10440
gatggcgagt atgtgaatgt aggtgtggaa cggaatattg atattgttcc cgatcagttt  10500
tcctacgaag aactcacatc ccttaacatc aacgagattg aagtcaaact cctggtgttt  10560
aacgtcaatg atgatttggt gatcaagaca gaagacaaga ttcgatataa gggcgacgaa  10620
tatagcatct atctcgtcaa gccagagtca gtaggcttac ttaccccggt ttatacggtg  10680
atgttgaaga aatgatctcc atgaaattca atgtcaatct ttctcgccta cgcagcaatt  10740
tgcgcgaaga ggcgaagaag aaggccattc ggattgctca ggaaatcgta aacggagtca  10800
```

```
ttgcaaggtc ccctgtatta gctggcgatt atcgatcctc ctggaatgtc agtgagggat    10860
cgatggagtt caagttcaat aacggcggca atccggccaa tccaactccg gcaccagcca    10920
ttgtcgttag ctccaacgta gctctgccac atttttacat caccaatggc gcgccatatg    10980
cgcagcagtt ggagaagggc tcgtccactc aagcaccact cggaattgtc cgggttacac    11040
tggcatccct gagatgagtt acttccaaga aaagcttgac atcgagaatt atttcaaggc    11100
caattggccg gatacgccaa ttttctacga gaacagaacc gccaatagca ctggcacttg    11160
ggttcgactg acgattcaaa atggcgacgc atttcaggcg tccaatggcg aagtctcata    11220
tcgtcatcca ggtgtagtct tcgtacagat tttcacgaag aaagaagttg gctccggtga    11280
agcattgaag ttggccgata aggtcgatgc actgtttcgg tcgaaaactc tcggcaacat    11340
ccaattcaaa gttccacagg ttcagaaagt tccctcaacg accgagtggt atcaggtcaa    11400
cgtctccaca gaattttaca gaggatccta actcatggca tttcaagccg gcacctccaa    11460
tcgtaccgcg atctgcctgg ttaaggaggt cacgttcaac accacgcccg ccactccggc    11520
attccagagc cagcgttaca cgagtgagaa cgttgcgttc acgaagacca ctgtgacctc    11580
cagcgaaatc cgttccgatc gcatgaccgc ggacttggtg caggttggcg catctgtggc    11640
tggcgacgtg aatttcgaat tgtcctacgc ctccttcgat gaagtcattc gtgctgcact    11700
ggcttcgagc tggagcgccc cggcttcggg cgtcagcacg atcgtcaacg gcaccgaact    11760
gcattcgtac acgttccaga agcgtttcca ggatctggct gccccgatct atcagaactt    11820
ctctggttgc cgtatcggtg gcttgaacct gaacttccag accggcgcga ttctgaccgg    11880
ttcgtacagc gtgatgggtt gcaaggctct gtccggtacg actcagatcg ttggtgcaac    11940
caccacctct ccaggtgctg gcaacgagcc gatgaactcg gtgggcaacc tcacggccat    12000
caccaagaac ggcacgccga tggccgccaa gattcgctcc acgactctgg cgctcaacaa    12060
caacctgcgt ggtcaggaag caattggcac gctgggttat atcggcatcg cgctgggtcg    12120
tttggaaatc accggcaaca tcgagatcta cttcgagaat gccgatgaat acaatacgtt    12180
cctgaaccac gacgatttcg ccttctcctt cactgtgacc gacgcggatc tcaactcgta    12240
caagttcgag ttgccgcgaa tcaagtacga aacgggtacg atcgtttccg gtggtctcga    12300
tcaagacctg atgatcagcg gttcctggcg cgcactgttc gattccgcct cgaactcgat    12360
gatcaaaatc accaaaacca ccgcataata aaaacgagaa acgacatgtt tgagatttcg    12420
gagcaaccga acgagaagtt ggaagaaggc gtatgggccg agtaccaggg cggtcagttc    12480
ctgatcgcct acgccggcgg tgtcaagttc caacgtcgta tgaccgcgct gcgtaagccc    12540
ttccgtcgtc aggaagagcg cggtgatcag atcgacccgg ctgtcctgcg caagatcacg    12600
tgccaggcca tctccgaggt catcctcctg gattggaaag aagtcgccag caagggcgaa    12660
cctgttccgt actcccgcga aatggcgttc aaggctctcg tcaatgacga acgcttccgc    12720
aatttcgtga tggagcactc gatggagttg cagaacttcg aagagtcgga gcgtgagatc    12780
gagggaaact cctaagccag tatgtttcgt ggtatgtgga gtgggtaat agcatcgcct    12840 tctttgagga tcttgaggat ggtggtgcta aacccaaggc gttagaatct aagccagtaa    12900
tgtactcatg gatgaccgag tacttactgg cattccaggt tctaaaccag actcgacagg    12960
ttggattttc tgccaatcca attccaatct cggaaatact ggcttacatc caagtgtacg    13020
gagcttctga cccgaaaaact ctagttgatt atattttgga aatggatggc gcgtatctag    13080
agatgagggc taagaaggcc gagaagaaca aacctccaga taaggccccg actccaaatg    13140
gcaaacatcc aagctgacgg cactgtagtc gttgaagtcg atagccgaac tgccgatgct    13200
```

```
ggcatttctg caatcgagcg ccgcttcatg cagcttggta ctgtggccgg cgccgctatc   13260
aaccgaatca atgccgcatt tcagaccatg actcgtatgg ctggcggtat gggtggagct   13320
gctggcggcg gtggcggtgg cggtggctgg ggcaacttct tcaacacact tatcaacggc   13380
gccaacggcg cctcgaatgc gtttggtggc cgtaatggcc tgaataacag catcagcggg   13440
ttcagttcgg cggcttccaa ggccatcggc tatatcggcg gattctacgc catccgcgga   13500
ctgatcggac tcatgactga gttcggcaac cgcatgatcg aggtaaatcg aacctatacc   13560
gggttcattg cttcgatgtc tgtgatcaag ggcactactg aggccgcggc caaagagtac   13620
gactggctna tgtctgtgtc caacaagttg ggcatctctg tngaagactc gatcacccaa   13680
ttccatcgac tcgccgcatc natgaagaac gtcgattcgt ncggtgagtn gactcgtcat   13740
ctgtttntcg gcctctctga agcggccgtg gttctgcatg ctcgaggcat ggatgttagc   13800
ctcatgtttg cggcagtcca acagatcgca tctaagggca agttgtctct cgaagaattg   13860
cagcgccagt tgggtaatac cctcccgggc gctatggccc tctctgctcg agccatgatg   13920
ggctctgctt cgttcatggc gaagggcatc acgaatgtgt gcgaggctga acntgaattg   13980
cgtacccaga tctctaaggg cactatcaat gcctatgagt tcctggctcg ctttgcgaat   14040
cagttgaaga aagaatatgg cgatgccacg gattatgctt cggataagtt caccgcgaac   14100
ttcaaccgta tgcgtaactc tgtgttcgag ctgtatcgaa ccgttggtag cagcggtgca   14160
atggatggcc tgaccaaagt cgtcaaggaa ttgactggct tgtttggaga ttctcagagt   14220
ggcgcagccc aagggctggg caaagggctt ggtgaattgt tcgacggcct ggccgggtat   14280
ttgtcgaatc tagacgccaa agatgtggtt tcgttcttcg cggctttcca aggggccatt   14340
caggccacga cgattgtcat gactcagctg atcggtacgg tcggcgacct cactggcgag   14400
actgagacca acccattgct cctgtttgta gagggtgtga gccgcgcgtt tgcaggtctt   14460
gcagacgtga tcaagggcgt tgctcttggt ttggccaacc tgtataacgg cgccaatctg   14520
gccttggctg gtctggcaaa agccagcact gctccgggcg agatggttgg caatgcagtg   14580
gatcgtgtag gggccatgtt cggtgtgacc atgccgggca aggacgtacg tgacaagaac   14640
cgcggtatgg ccgcagatgc caatgcctgg ttttacgagg cacagaagca gaatctcaat   14700
ggcatggccg cttctgagga cttcgttaac ggtaacaacg cttctaccaa gacgcgtgac   14760
ctgtttgatg cggccaaaaa gcgggccaac gccacttcca ctgctaaggc cggtaccacg   14820
gctgatgcag cggctagcta cgtgaatccg ctcggtgata tggatttgca gaagcaaatt   14880
gaaggcattc tggccaactc cagttctcca aacgcaacca agaccaagac taagaaggat   14940
cctgtacaga gcaactatct gcgcgaaacc acccgcctgt tgaagggtat ttccgaggca   15000
gagaacgaat actccaatgt catggataac cgctatcggt cccagggcaa gaacgaaaca   15060
cagatgaaaa gcttgatggc gacggacgaa cgttacgtca agctgtcggc tgagaagaaa   15120
gccacgctga tggcgctgat ggattatgct cgtcagttgg atgcggcatc gttgaaggta   15180
gagaatgcga aaaagtgca ggatgcatac ttcgattcct tgcagcgtgg gtttgacgct   15240
caagatcgta tgaacgaact gcagtccact ggattccagt cccagttccg tgaagagtcc   15300
aaagcccgta attcgttcaa gcgcggcggt gacaatgagt tcatgagtga agctgataag   15360
gctcagatcc tgcagtcggc aattactgat gacatcaatg atcgtatggt cgcgtatcaa   15420
actcaaaccg aagaaatccg gaatgccaat aaggaatccg aattccaggc tagcctgatc   15480
ggtaagagtg ctctggaggt cgagaaactc acaaagttcc gtgaaatcga tctgcaacc   15540
tcacgtctac ttgtaggggc aagtgatgag cagattcaga agtaccagaa gatggcagaa   15600
```

```
gtcctcaagg atgaggtcgg cgccagtctg gatgaggttt accagaaaca aaccgatgca  15660
ttcggtggta tggagcaagc gctcacggac tatcgtgata gcgcactaaa cttcggccag  15720
gagtttggcg gtgcaatgac cagcactctc ggaaatctcg agagtgccat ggtcgacttc  15780
acgactaagg gtaaactgag cttcagttcg ctgatcaact ccatcatggc tgatttggtt  15840
aagctggccg ctcgtcagat gatctctagc atcgctggat cttgatggg cgcgttcatg  15900 ggtccaagcg ttggggcttc aggcgccgct gctgtaacca gcggaactca gggaatcaat  15960
cagcaattgg ccggtcgatt tgctaagggc ggtgacttca ccaatcagat cgtctccact  16020
ccgactctgt tccgctttgc gaatggttcg aagatgggcg aaatgggtga agctggtcca  16080
gaggcaatca tgccgctcaa gcagccaag aatggtgaat tgggtgtagt tctagccgag  16140
tcgcacgcac ctcgtactgg ctcaggtatg ggcgacgtga ttatcaacaa ctacaccgat  16200
tctgaagtca gtgcacagaa gaccactcag aaggggccac agggcgagat gatggaggcg  16260
tgggtcgtat ctgtggtggc aaaggacatg gctaatggcg gcaagacggc caaggcttcc  16320
aagaatcgct tcggcttgaa ggaaaccgca taatggcttc gctaccatcg tacgtgatca  16380
tctcaccggc aggataccag gaggatttcg atccctctgt gtccatgacc gaaatggagc  16440
gaggctcgcc caagtatcgt gtcaagaact cgcgtgtatt gatgaaaatt aacatgcgat  16500
tcgtctttga caagaaggct gatgcggcta gtttcttcaa ctggtacatg atggaggtca  16560
agcgtatcct gccatttaca atgacccatc ctcgaactgg acagcaaatc gaagtccagt  16620
tcgaggctgg caagatcgga ccactcacac caatcgatac gctgctggaa atacgtatc  16680 gagatgtaat cgttgaatac cttgtagctc caggatccca ataatgtcaa cattcaaaga  16740
gcgtaaacaa cgagtacgag atccgtccgg tttgctgatt ctaatggagc tttcagcaaa  16800
ctcgtttcaa gaaacacttc gaattgccaa tgacacggat aactggacca gcaatggtct  16860
tttgtactat gggtttccgt ttaagttcac tggcccggat gattctgatg cagcaacgc   16920 atcttccaag attgtgatcg acaacaccgg tcgtggtatg tcggacgatc tggaaagtct  16980
acagcccaat gagattatct tggtcaagct catgattacc gacttctaca atccttcggc  17040
aatcatccgc acactgtatc tgccgatgat gggtgcaacc atccgagtga ctcagatgga  17100
aggccgttgc ggtgtggatt atatcatgcg gcaacgttct gtgcagctcg catcaagtcc  17160
ctacaccgca ccgggtagct attgatggac gcgtacaagt tggatccatt cgttggcgtt  17220
aagttcaata aggacacaat ggattgtgct gatctagtga tgaagattcg tcgtgaactg  17280
tttgatcacg acatcattct cccgcaaggc caccctcgtg gtcctctcaa ttttcgtcaa  17340
atcggcgatc tatcgaaagc attcgccgaa ctcactactc gaccggaaga tggcgatctg  17400
gtgctgatga aggatggcgg tacagaattt ccaggacatg ttggcgtgtg gttctttgtg  17460
gcatatgtgc catatgtatt acacgtcaca gagaagctca agttcagcat gctggataag  17520
ctctctgact tgccggatcg cggtctacga ctcgaaggta tttatcgatg gaagtaatcg  17580
acaaaacgca tcaagtaatc gttagccctc accctgtagt tgtcgatgat cagaagaacc  17640
tgatcttggc attcaagcag ggtgaaagtc tattcgagat cctcagccgg tctgtggata  17700
acttcgaaga gcgtgagtgg gttgtaacca tcaacgggcg acgtgttccg gtcgagatgt  17760
ggactaaggc gttccccaag cctggccaca ttatcgaagt gcgtggtaat gtgggcaagc  17820
aggcattgta catcattgcc atgatcgccc tcacctactt caccttcggt atcggtacgg  17880
ccgcaggttg gggtgcaggc gcagccgctg gcgcatttgg cggaggtgtc gcgggtgcgc  17940
tatttgcctc tgctgtattc gttgcaggct ccatgatcat caacaaagtc ttgggtccga  18000
```

```
aagcccagga cattcgtgga tcaaaccctg actcggttta ttctatcggt gcatcgagaa   18060
accaaaaacg cccgtatgaa ccgtttccct atgtcatcgg ccgggtcaag gttctgccgg   18120
acgtcatcag tgatgcctac tcctggtatg agggcaacga tcagtatgtc gggttcgttc   18180
taactccggg cctcaatgtt catgacgttg agaccctata tatcggtgat acgccgatca   18240
cgaactacga aggcgtaact ctgtattaca acggcttctc tggtcgccct gatcaggaca   18300
ttccgttgta cagcaacgct gacttcgtgg acggtgctac tcttccgaat acgggcgcct   18360
gggtaacccg gacgacgtcc atcgatactg tgcgtgtcat gatcaacctc gagtatatct   18420
tgggcggcca gggcacgtct ggcaaaagct acactgtatc agagaccatc ttcgtagagt   18480
ataagccggt cggctctcag acctggtccc agctgatcac tcgtcgatac agccatcaag   18540
acttcgagac tctccgcgct actctgtcag ctgaactccc tcgtggccag tatgacatcc   18600
gtgttcgtat gcagggcgaa ggtaactacg aaggcaagaa cactcaacgc aacgacttca   18660
acttcactca gttggtcagt gttcagtttg atggcgcaga ctacgatggc attcctcgga   18720
tcggcgtcaa gatccgggcc actgatcaat tgaacggcgc accggacacg atcaactgtg   18780
tggcaatctc caagcccgta cctgtatggg acggatttca gtgggtcacc cagacgacag   18840
gtaatatcgg cgccaacatg ctggcccact gtcgtggcat cacttccagg agtggtcgta   18900
agatcatcgg catcggtctg caagacgagc tgattaacat cgagaacttc aaggcgttca   18960
tgctccactg tacggcgaac aactacgagt acaactactg tgttcgtggt tctcgtagtc   19020
acgccgagca gttggaagtc atggcgctgg ccggcttcgc ggacatctcg tgggccggcg   19080
gtaagttggc tccgatctgg actgcggacg gccagccgtt gaatggtgtg gtcaatatgg   19140
ccacgatcac agatacccag ttccagatcg attacacttt ggccaatgcg gctgatggcg   19200
tcgagtatac gtactacgac gacgttactt gggagcccett gaccettcgt gttccgatgc   19260
ctggcaaatac gggcggaatc ctgaacccaa tctctatctc gggtgaaggg gttatcaagg   19320
aggcccatgc tgctgaactg gctcgattcc acctcgctca gtccctgtat cagagcaaag   19380
acatcacgta taccactgac gttgagttcc tcagctataa gcggtatgat gttcttgcgg   19440
ttcagcatga cttgactcag tacggatttg gcggtcgatt ggtgggtggt gactacgact   19500
ttgtttttgga cgctcgtcgt aacatcaagc ttcaaatcga tgatatggtc cgtccaccac   19560
cgagtggcgt tgattcgtat gtaggtgtgc gtattcctgg cgaagatgca tatcgagttt   19620
tcacagtcaa accgttcgct caagagatgg acgtgctgta tctagtcgaa gcctggcctt   19680
cagatgcacc gtttccaggc gaatctttgg agaatccgcc ggatgacttc ctctggatct   19740
tcgacttcaa ggctactcca ggtctgcgta gtcgagtagc ggccatttct ccaggtgatg   19800
acttcgaaac ggctcagatc agtgttgttc ctgagccgcc cgaatattgg acgttcatca   19860
agactggcgt ttacaatccg ccagttcgtc aatctctcct tcagactcgc cctgtggcct   19920
cgaacttggc tgtatcggaa gttcaggttg ttcagggcaa cacggtgtat acagagcttc   19980
gtgcagtctt cgacatcagc ggtgacatcg gctatacccg agtctactcg gatttggatg   20040
gcaacgggac tttggaagag gtggcaaata ctcgtactcg gactgcctct tggaggatcc   20100
ctggtgcggg cacttacgcg atcgtcgttc gcccattcaa tccacaaggt gttccaggta   20160
tcgcggttag cactacgtat gtgaccatca atgcggatgc tgcgcctgca ctggtggaca   20220
atctgctgat cgaagaattg acaggtggtg tgcgacgtta ctcttggtcg ttcgatgata   20280
cgacgatgca gagtccagac ttcatcggtg tgcagatcag gtatttgggt ggcagtgttg   20340
gagatcctaa ctgggtggat atgattccac ttggcgaagg tactcacacg gcaaccttcg   20400
```

```
aatcgattct acctccagct ggtgcatgga cctttgcagt tcgttcggtg aactcgtcag   20460
gctcactgtc ttccagcatg cggatcgtga ataagactct tactgacagt ctgggcgagc   20520
gtgttgtcaa gatcattcag gatttctcgc tcaatgagca gaggttgctg gagaccatcg   20580
aggaggttga tcagtactct gaatctgtaa tccagcaagc tatcaacatt tctgaaatca   20640
acggccgagt agtacaaaat cgctcgttca tcagtctctt gcaagacacc gctgtaaccg   20700
aggattctgc caagacgttg atcacccagc aggttggtgc tcagacaggc gatctacggg   20760
ccacagtcga gcagaccttt ggagctgtaa ccaatatcaa cggagaactc tccgcgtatg   20820
ccaacaccaa ggttcaaacg acgattgatg gtaagaagta tttggctggc attgggcttg   20880
gtattgatgc tagtggtggc gtggctcaat ctgaaattgc catcttggct gatcggttcg   20940
tgttcctgaa ctccactgct ggcggtaact actactatcc attcgagatc gtgaatggcg   21000
tagtgtatgc taacgctgca atgatccgtg acggaacgat caccaacgcc aagatcggcg   21060
aagaaatcaa gtcggtcaat tatcagtggg acggtgcaaa tggcatttac attggctggc   21120
gtattggtaa ggatggtacg gctcagtttg gtggcgatgt tgaaattcgt ggcaatgtat   21180
ctgccaacag catcacgggt acattcgagt ctgctgtggc tgttgactat tctggcaact   21240
tggcaacggg cgttacctct gtgttcaccc tcccgccgcc actcaaggtt actgaatcac   21300
atcgtccaga attgactttg gcgattcaac tgcagactgg cgacgggcaa gatgcaacga   21360
gctgcttcat cacgctacag cgtgaaaatc cgaacaaccc tggcgagtgg tggaatatca   21420
cctcacgtga gtatgccatt ttcaagttca tgaacatctc caccgcattc atgttcctcg   21480
atgcctggac caatgtggca aacaacttcc ggttctcgat cactcaaggc tctggccaag   21540
acgtcagaat cactcgtatc aacggccgca tccgcggcgc ccgataaggc actactatgg   21600
cagatcctgg ctacctaagc aacgctgaac tggctaacca agtagtggcg ttggtccaga   21660
agtataacgt gtttaccgat gatcagatgg acttcttcac ctcggcggat gacaccgtgg   21720
tgatccataa tccaaacggt gatccgatca ctgtgcccag cctcaagtcg attcttgagg   21780
ctgctggccc tgtggcatcc ggtgatctgt cggtttatga ctctgtggaa gagggcgtag   21840
catcagttat cgatggcgcc tacttcttcg tgtccattgt caacggcact taccttggat   21900
tgttcaagcg tagcgccaat ctgggcatcg agattggtcg ctatccgtct tcacgtgtgg   21960
acaatagtgt gaacgacctg gcttcggcca tggagcacgc tgatgccatc atgatgacgc   22020
cattcaatga gttcgatctg gatactgtga agcagatgtc caactcgggc aatggcttca   22080
acacggtcat ggatgagtat gtgaacaacc tacagttcga tgtggctcgc gccaatatcg   22140
agcacacagt ggctgatgac ttgggcgcca tgccgagcat caagactgtg atggtgtgga   22200
cacagtggtt ctcactctgt gactcgaccg aaggtctgaa tcctggtgtc gttcagccag   22260
ccatcaacgg cggcatttac ggaaagctgc tgaatacgaa tcagtggatg tctggcaacg   22320
tgactgcgcc caacgccctt aaactccagg gcgacgcggg tggtagccag aacgatatga   22380
gcatgatccg tggcatgaag tatatgcagg ctcgtggtta cgatatcggc atggttccaa   22440
tcgtgttggg ctgggttaac caggctggcc tgccaaattc gcagtcactc gtatggcgtg   22500 gcttttccg ttgggatacg acggccaagt tccaaacgtg gatcaatagc tataaggcat   22560
ttttggtcca ctacatcaac ctcttttcaag ccaacgcat ctcacctact cgatggctgg   22620
tcggttccga gttcgatcga atcatcactg tatccactcc ggagcagtgg ggcattttcg   22680
ttgaggcgtg taaggaattg gctgccagat tcaaagcggc attcccggct tgtaaggtca   22740
cgtatgccgc caactactcc gactatggcg taggtggcaa gttcaggttg gatgccctct   22800
```

```
ggagtcatcc caatatcgat gaagtaggta tcgagtggta cttcagacta tctgacaatc   22860
cgaacgttgg caatgagggc ttgatccagg gccagatggc cggtgaggac gtggattaca   22920
cgtacaatct gagcgatgac aatcagcgta agttgattgg ctcgaatggc cgtggtaaac   22980
tggatgagac ccgcgttccg atgggtgcca atgccggcat caagaatgtc caagggttct   23040
ggaatggttg tcattacatc gagaagtttg ccggttctct ggccatggca actccaacgc   23100
ctggcttcag tgccgactat gcgcccttca atctgaagac catgcagggt actggtcaag   23160
tcattgctcc agcagattct cccttgacgt ctggccaaca tcctgaaccg ttcctgcggt   23220
ccacgtactt ccagacaaat ggctccacga cctggggtga gttcaagacc cctgtattca   23280
ccggcggtaa ccagagttct tggcgtatgg aggttgactt ccaaggtacg caggctccca   23340
gtggtaatta tgcccgtccg ttccggttgg gtggggccat cgagtttctg gtggacacgg   23400
gtacattgaa gttcggcatc ggtccggacg gcaatcaata cttcgcagat attgggcctt   23460
tcaacactgc cgcccattcg ttggtggcaa cgctcgataa aaatagtggc atgctgacta   23520
tcgtctatga cggaatcacg agtcagtact caattcctgt agcccagcgt tctgccatcc   23580
caagtgatac gactgcttat ttgggtgggt ataacacgaa tagtaacatg gctgcgatgc   23640
ggttttataa gctgggtttg acgttcgttc gtgatggcat tacttggggt ggcaccttt   23700 ggtttgatga gtcatatgca ggaacccgta cggcctgggt gcctcgtatg aagaaactct   23760
ccgccactga actcggatac gcatccatct ctggcacgtc cgttgaacca agtcagtttg   23820
tgtatgctga catcggtaca actccaccta ctctgcccag ctttatcgat gacacgacga   23880
gggcgctatt caactcgttc ttcgcacgta gctggtatcc ggcgcagatc tatgcgagtt   23940
atggcagtag cttcaattat gacccatttg agcaagccgc tgcgatccgt gagacctgcc   24000
gatttatggc cgcgctacgt cgacgaggtg cctttgaatc catctgtatc tacaacattg   24060
atgcacgccc ctcgaaagcc tttacagcaa ttttgcaaaa caagttctat tacagcgatg   24120
cgccgaccat gatctttagc catgctgtga atggcaagtt ggccggcggt agcactttct   24180
tccacgaact aatcacaaaa caaggcaaga ttgcctagga gtaacgtatg ttcgcattgt   24240
cccagaagag tcagcacatc ctcgacaccg ttcagcaccc ccttcgcgat gtcgtccgtc   24300
tcgccatcac tcgtacaact gtggacttcg gtgttatcca aggcggtcgt acacttgacg   24360
aacaaatgcg tttgtacggg aaggggcgca acgccgctga atgtgccaag atgggcgtcc   24420
ctgccgccta tgctaagcct aaggaatcta aggttacttg ggtcaatcca cgaaacggca   24480
accatgtagt ggacgggtct ggatttggcc gagcagtgga tctcgccccg tacatccagg   24540
gtaaattgga atgggataac gacggcaaac tcggactgta tcccaagatt gccgaagcaa   24600
tgttcagcgc agcaaatgag ctgggcatcc agatcgtatg gggtggaaat tggaagtcta   24660
cgcccgatcg cccgcacttc gaactggcga atgataaaa tgtatgcaaa gctcttattc   24720
gcagcaggcg cggctgccac aaccgcgatc caagtagccg ctgaggcacc gacgagtaaa   24780
gagtgggctt ttattgatgt aactgtggct tatgttggag taccattcaa tgtcttgatc   24840
atggcggcta tcgtagtat cattgctgta atgagaaatc gagtgtctga cccacgcact   24900
ctgattgtat cattcctgta cagtactctc tttgcccttg gtgcgagtgt tggtattgcg   24960
gagtttacag gttaccagtg gtcgagcaca ggggctcagg ccatattcac ggccatccta   25020
ggttttacgg ctcagaactg gggcccagtc ctattggaca atatagcccc agctgtggat   25080
ctgtggctta aacgtcagat taaacggatt ttcaatatca gcattgagga taagaaacat   25140
gatgactccc aatgagattc cggtttggtc tcttctgaca accccatctc tgatagtctt   25200
```

```
cttcctgacg ggcctatatg gtgtgaatga gtggagattg cgccccgtcc ggcagatcgt   25260
tggaaaacgt ggcttggttg agttgggttt gggcttgtcc ctcggaacga tgtgtgtact   25320
gagttttgtg acgttgatcg ctgtgatcat gatggcgaat ctatattcgt ggcgtggctg   25380
tctgctactc accagcatcg ctggcgtgtt gttgacggtc ggccgtcacg ccccttggcg   25440
tttttggatt catcgttttc cggagaacta aatgcctatc ctagcgcaaa tcaaagccta   25500
ttccgaagtg attaagctcg ttgtgctagg tgcattggtg ataatccttg gcatcctctg   25560
ttacgtcgca tggtcttcgt atcaagacgg acaagatgcc aaggtattat ctggagtact   25620
ggctcagaaa gcggaagata ctgctggagt ccagaacgcc ttgaccggtg cgcaagcgca   25680
gccagctgta atcgaacacc gaatcttgga gaccagaacc cagtatatca ctcaatatga   25740
gaagctgaag aatgaagacg ctattgtggc tgagtttgct aacaccgctg ttcctgacag   25800
cctgcgtaaa ctcgcctgtg agagacgagt cgcccgcgac ggacttactg atactcaagg   25860
cgggtgtcaa cgctttggca agggagcgac ggacttcggg gcaaatccaa cgccttgaag   25920
atgcaacgaa ttctggcgat gtatataact acgccatgga tttggaagac gttaacaaac   25980
tccactctac tgacaaagca tcaatcgtcc aattcgtcaa tgatacggtt gggatcatgg   26040
agagatcaag gattggcaaa tgtaagtggt atgactttgg gtgtcgggct ttgaggcgac   26100
gtaccacgcc cctcactgaa gtcccataat ttctgctcgt ttgagcgctc caacccatc    26160
tgtattagat gggtttcttt ttgaatgcta tcttctaaag taacttttca aacatactca   26220
gaacgctctg agtgcgctca gattaagcca cgtaggggcc agcccgtagc taactgcgca   26280
ctatgttaag taactattca gagcgcattc agagcgctcc aagattatac gcaaaataag   26340
ggcctcgtac gaggccctta gattacagcc aaaccaggct attcgccgat atacttgcca   26400
aacagagcca agatcttcgc ctggtaaatg gcgtcgtcca aggcattgtg atacgtaccc   26460
tcccgagcag gttcagccac catgtgaccg aggcttttcc ggatcgtccg gaagcagcgg   26520
ttgttgtaaa agcgccacgg aatgggcgag ccggcgaggt tgtaggcggt ggtgagaatg   26580
gtgttgtcga agtctgagcc gttgccccac agcttgacgc tgttcacgcc gaagatgcga   26640
agatacgtcg caaactcgcc caatgcctga atcacaggaa tattcgggtc ggtgaagacc   26700
ttccgggctt cggggctttg tttatcccac cacgacttcg tagcgctgga cgttgtcaag   26760
ccgagagcgg aagaactatc gcagttcacg actcgataga acttgtccga gatctcgcct   26820
gtatccagat cgactttgca cgcgccgatc gagagaattg ctgcggtgtg ggcggtgtcc   26880
atggtctcca ggtcgaccat gatgtggttg gatttgcgtg gcatacttag cgtcccttgt   26940
agttgcgttg gttgaattcg aacttggtct ggcagtgaat acaccggaag cgcagtgg     27000
ccaaccgatc cttggggatt tcctgatcac aatcgtaaca atccggagat acccagtccg   27060
aaggtacttt gccatcacga agtaccttct gtattgcgtc ctccttggcc aactcttcca   27120
atttgctggc caaatcagat tcatctgtga tacgttccat cagacgtcct cacgccacct   27180
tatggctgtt ggttggaagg ggattccgtc gtcggtccag tgggcgaact cgatggtgag   27240
ggatcgcccg agatatttac cctggttatc ccagacatct tgcttttcag agacgcttcc   27300
aggtgctgaa caatcgaatt cccttccagt ctcagtaacg caacggcaga ccgcccagcc   27360
cgtcttggac tggctgaatc caacgaccct gaattcggca tcttcaaact ccttgatttt   27420
taagaggtga ctggatctaa cacctggctg atagccagct ccgttaagtc ggagcataag   27480
gccctcatag ccttgtccac gcacttctcg aaagtaacgg ttggtttctt ccgcagattc   27540
gtaaggtcga tagggtaagg ccaggacttt tccaggagtt ccagtatcga ctcctgcaat   27600
```

```
gatttccgaa agctccttat gtcggtcgac gtaagagtcc tcactgatga ggtcgtagac   27660
aacatagtgg agccgggctg tatctgcttg ctcacgcttg atccaggaac cgatggtttg   27720
gagcttgatg ccgtgacagt aaagttcacc gtcaagcgtt gttcccggcg ggagtcgatt   27780
cttgagtgcg cgcaagatat gtcgaattgc gggtattggc tttcccagtc tggaatacgc   27840
caatggctcg gcaccgtcaa gtgtaacgag acatctgtgg ccgtcaagtt tcttctggag   27900
gagcccctga ctgaagttga cattcttcac cttgccgatt tgcttggcca gcattggccg   27960
gtccaggccg agctggttgc caggattatc gatggcctct tgcactgtgt ccttgtagcc   28020
tttatcgcgc atccgtgaga tatgagattt gatgcgtaga tcgatttgct cgtggagcga   28080
actaccagat tggttacggg tgacctcctc cgtatgccac acttcagatc caccttggan   28140
cgtagcgtga gcaatgttga tcgtaccctc ttcgtagatg gggaagatcc gccaagtccc   28200
aatggagttg acgttcttcn tgtataactt cacttcatcc atgatcttcg atctacatat   28260
ggatcgagcc agggccgtct gatgtatcac cttcgatgga cgagacgctg actgtgagtg   28320
gctgaacatc aatcacactt ccgtccccaa cactcaccca tacctcgtaa tgacctgggt   28380
ggggtcgcag aagggctatc agttcgtcaa ctcgtatggc ttttttcgac atatccaatc   28440
tccaaatgaa ctcaccctgc tattatacag ggtgagctct cgttagtaca tcgctctaat   28500
tacggattac ttggtcatgt tcttcttacg accatgcact tcttcgaacg gaacttcacc   28560
gaaatggacg ttcagcttga ccatctcgtc gccgaaagct ctcagggcat cgtccaaggt   28620
cacgccctta ctcgcatcct tggccacttc gtccacgacc ttctcactca gattcgagcc   28680
acaatggatc ttagactcag attccggcgt attgatgcga tgctgcaacg cggcatagcc   28740
cgcctgatcg gtgagtgaat ccgcatgggt cggattggat atgaggcgag ctgtcttgag   28800
cagaatcatc aactgtgaca cgtcctcggc ctcaatttc aaaccatcga taccccaact   28860
gtggaagcga cgatgcatgt aaaccgacca cagttgggcg atcgtgtcca gattgaaccg   28920
aggggatccg taggctttct cacgatcacc gtaaatgatg tcgttggcct tgtgcaggat   28980
gttcaccact gtttcaggct tcgacttttc atcgagatgc ttgatcaggt cgtgggccga   29040
gttcaagcct tcacgcagtc gagccacttc gttttgcagc tccgcgatct tctccatttt   29100
ctggttggcg agggcattga cgttgtggta cttgtcctgc caggtcaaag actcttgttc   29160
aggcacatac gtgatacctg tggcgtgttc cacgagttgc ttcaggttgt gtactgcacg   29220
agcggcagcc acagcctgcg gtgcgacgcc agttgccacg atcttgtgaa cacgcttggc   29280
atcattgatt gcgttggtct gagtgtacgt catgactcta cctcttcggt taatggtttg   29340
taaaacgtct gtatcacttc attatgctgg ttgatacaca tcccacacgg cacccaacct   29400
tcctcgatta actgagtagc atagtctgta ccgtgtgtac taaacaacga tttgccggcc   29460
tctccgagag cgccgagatt ttgcaagaga aaccgcttca ttttgatgct ctccggtgcg   29520
ctctgaatag ttactaagtt agtacgcagt cagctattgg tactacttag cggacgtaat   29580
cagagcgctg tcagagcgtt ctgccaacat gtggaagagc tgctgtagct gaactttttc   29640
ttgaagactg accgtacaca tattccggcc ggagctgagc cacagatccc gaccactatt   29700
ggggtaggca tcgaggtaaa caatccactt ggcaccagtg ttcatcagga gcttggtgca   29760
tgtaaggcat ggttgcgttg tgcaatatac cgtgtgaatc ttctccacat ccatacattg   29820
cagaagggca ttctgctctg cgtgagtggc catgcacccg tccaactgtg tgccagaact   29880
ggcattcatt cccgggcaaa tatgcgagcc gcaatgggca acgttcctgg gggtcccatt   29940
gtagcccgtc gccaacacat gattcagatc atcgacgaga atgcacccga cctgcctcct   30000
```

```
cttacacgtc cccctcgaag cggccagcat cgccatcgcc atcatgtatg agatgatatt   30060
cggtcggtcc aagggtcaat ctccgtagat aaagcggtat aggtgccagg atgctggaag   30120
acgttgagcg atgccccgat gcgctatgat cgccatggcc tcgtcagggc cagaacactg   30180
tggcaggatg acaatttcag aatccggaat atcctccaga ttatctagaa tcttatcgac   30240
catcctgtag tggcgctcgt agatgtgaga gctggccgcc gtaatggtca tggatccaac   30300
ctgaagggac ggataattgg cttggagcag cccatgcacc aaatgtgtca gcacagagaa   30360
ggtcgggata tcagtgccta gaccaaagat ctgatctgac gatcgcatat ggacactggt   30420
atacagcgta ttatggcgaa tatgaaacga caccgcctca gtacacactg tgtccacagt   30480
ttccggagac agatgatcgt ctgtcagcat tggaatgatg gcacgacggg agtcctgatc   30540
acggatcagt tccatcacaa ccttcataac acccatctgc tggccgaacc agaactggcc   30600
gtagttggag ttgaatgtgc catctggatt ctggaccgac tcccacatct tggcatgctg   30660
cttgataaga tcatcgaact tggatgcgcc caatttccaa cgcatctctt tcttgaaata   30720
cccgatatcg tacttccgat caggccagca ctgaaaaggt acgaaagttt gaactgtgac   30780
ctgagcattc aggagttcac ggatttccat tccacgaggc ttcgatacaa acccctgagt   30840
gaatgtccgc agcatcaaat ctctcaatgc actcagtgta gcattatgat acgacattac   30900
ttgcctccta aggcgagcga tacaatgttg ggattcggat tggtgtaatc ataggtcagg   30960
tgcggcaact gactcatgat ggcatcatac cgaataatga tctcagaccc gaacttcttt   31020
aaccaggcca aatgagcctc ggtatcatgg tccttgacgt tgtgcctgga gaaatccaac   31080
atcacttctg tggggggcg acagtaaatc agcactaccc cttcagtctg caccagatcc   31140
atcgatcggc ggaacaagta cttcggatca ggataatcaa agcaatatgc attatgcgaa   31200
attgccgtga cccgatccat taccacatgc tgtgtcgctt gctcttgctg gagatggata   31260
caatccaaga cggcctccaa tgtcctaggc ctcgggcctg ggtgcaaaat cggaagccca   31320
aaagggaag acaatgatgt cttcccactg ttgtcaaaac cttcaagaat aatggccata   31380
tcaaatccca agaaaccccc taccgaagta agggggttgtt acaggtggcg ttacttagcc   31440
cagaatagcg gcgatccgct cctccggacc cacccagcct tccggcttcg tggcatcagc   31500
gacaccgtcg atgttgcgcg ctgccaccct accgagcttc ttttccatgt tggcgtcgtt   31560
gatcgccatc atgacttgat tgacttggtc cggcgtgagg cccatccgga agaagaaccc   31620
gatggcaaaa taccagat cgcccactgc atccacggcg ccaacgaaat cttgttgacg   31680
atgtgcctgg ataaactcct ccagctcctc gagaacggcc ttcttcgacc actcgagctc   31740
ttgagcattg agcagacgaa gttcgggttc gttcaggttc aggacctgct tgttgaactg   31800
gaagatggcg tgagtgaagt ctttcggctt ttcagcgtgg ctatacgtgt tcatattaat   31860
ccttgacaac gatgatggtg agaacctttg gattgcgttc gtactgtttc cggtgcgtat   31920
cgatgatctg ctccgggcta cgtacgatgg gcactccgtg atagttgaaa cttgtgttga   31980
tcagcggccc gaattcctcc aggagcgaca ccatcagagg gtccctagtg atttgtggac   32040
ggccagtaaa cactttctcc ttgggatacc agtgggctgc gccactgagt tgcgatccaa   32100
cgccggcctg gtattggcgg gcgacgatca tatactctgc cgacttgtgg atcttgtcga   32160
tgtcgtaaaa gcaatcacgt gcctgatcca aggtcatcac cggcgccatc ggcatttcag   32220
ccgtacggtc attggcgaag ttgatctcct cagcgaattg agcgtgtggc agcgagagcg   32280
ttgcggtatg gcacaagctg cgagggccga actccatcgc ccctcgcacc acgtttaccc   32340
agccgtgagt gctgatgtag ctggcaatct cggcaaacgc ttgactctct gtgaccacga   32400
```

```
ccatacccgg aacgttgatg aattccaacg gatccagatt cctgtcaccc cagaacaaat    32460
gctcgggcca cgtcagatcg ccgtgataag cttggtacac acccagagct gcaccctggt    32520
caccggccaa cggcatgaca cagagttgac ctttgatcga gttggcgagg agatggttca    32580
acttgacatt gtagaacagg ccgccaacca caagcaagtt cgagcggtcg ttgtacatct    32640
gcaccatcgt caccatcacg gcttcgacca cgtgctgcac gaagtaggag atgataatcc    32700
gcttcgtacg atcgtcggag ttagctgcct cagccattcc gagatccacc aagaccttcg    32760
acaacagatc gttgatcttt tcctgcacat tcggcagagc tgagatttct gtgacaggat    32820
cgaactcgtt ggtgatcttg ttggactgga acatcttgag gtagtgcgat gcttgggttt    32880
tcaccatgtg atccagacga tcgatctggt ccacatcaag cacttcgccg atatgcactt    32940
cgtatgccag catcttgtat tcatggttgt gcatcttcat gcccatgaat gccgttgcgt    33000
actgatacaa catgcccagg gacttctcga acccgaacac acggtgcttg acgctgtacg    33060 actgccggt gacagcgtag atggtcaggc attcgccgta cgatccgaag ccatcagcta    33120
caaccgctgt gtacgacttg tccgaccact cttcgccagc gaacaccatt gccgaagcca    33180
gatggctatc gtggtgagta aagtctgcgt taaggctatc gatcgaaccg ttggggaagt    33240
ggctacgcag gaagtccgga tcccaatact tattcgggc cggcaattga gcatcgagga    33300
accaatgccc cacaaagctg tcggtatcac taggtaggtc gaagcggcgt ttcaactcga    33360
ggatggattg gtacggaaac ttggaatcag acttaactcc agagaaccgt tcttcttcgt    33420
acccggccaa acaacgcca tcctgtatca ggatggcgct gctgttatgg cccaggctaa    33480
tcgcgagggc gtatgtcatt accagttacc cgtcgcttcg tccacagata cggtggaggt    33540
ggtaacgccc ggttctgcgg ccgctgcctt gtgttccagc agtgcgtcgg cgccaggggc    33600
cttcatcggc tgcttcgggc cggtgtcgtg ttcgagcatc ggcgccgagg acttgaggtc    33660
ccaattcttc tgctcgttac gcagcattgc ttgttccatg ggttcctcgg agaggacgcc    33720
ggcgaaagcg aattccagtt ccggaaattc actgtccttc atgctcaggc gggtgatgac    33780
cgaggcagcc ggaacgccgt tgctcttcag catagctccg tactctgaca tcgccttcaa    33840
cgaggtaacc gggatgccca aggcaaacac tgttccgttg atgttgtccg gctccacgac    33900
ccacaagcgc ttgctgtcct tgcacgcctt ggtcttcttg ccgttggtgg atgtggccga    33960
accgaagaca ttcttcgggc agccattgca cttggcactg acaggatcgg agatccatgc    34020
atcaggagtt acaccgttcg agctggcaca gtccggtgga gcggattctc cagagacata    34080
gcccttcgca tagaaagtct tctgcatcag gcccgcaccc ggctcgactg ccaggataac    34140
gcaaagcagt tcatcggcgg gcttacggat ttcttcgccg ccttccacca acctgaactt    34200
gcgtccacgg agggagatgc ggggaatcga tacgctagct gcggccattg catcggcatc    34260
ggagctggtg cccgaattgg tcaagaattt cttgagatgt tcgggattg aaatctgttg    34320 gcttgccatt gtgttacttc tccagagaat aactaagggc caccatggcc cttagtgtct    34380
agacccgtcg gtctaaatag gcggatgccg ccgctttcgc ttcactcgta gccaccataa    34440
ctcgtcttat ctacccgcta gagacggtga gcttatctc cacaggatct ctaagttata    34500
gcggcgacgg catcctaaaa cttacttgct cggcctacga acatcgaact caacttccga    34560
gtagaattcc aggcccggag gcacttcgcc cgtttcttcg tgaatttcct tgacagcgtt    34620
cttcgctgca cgcttttcca agcagtggaa attctctgtg gccttcatcc actccacgaa    34680
ctggtcgaag ctgccgaccc gatactgcgt cttcacagaa cgataggccg taccggcctg    34740
agtcttgaag ctgtccacac ccatctcatc ggctttgtca cgcagataca tggaaatacg    34800
```

```
ttccatataa gccttcgccc gaagctcgta ggagttgtag gctttgcgtt cagccgcaag    34860
ttgatcgcgc gtcgccacat agacttccac tgcctgagag atagtgttaa aattgatgtc    34920
ctcaggaaca tcggggtaag ttacttttgc gactttatct tcagacattt tatgctccag    34980
gaatatggtg gttgagcgca gccctactga aagggtcacc ggcctatgtt cgggctgcac    35040
tcaaccatag tgctattgta ttccaaaatt aacctcttgt acaccgcttt aatttaagaa    35100
tccttcagga gttcgaacat ctccagcaaa ttctggctcg tggataccct gccctccaga    35160
atgtccagca catgacgttc aggacggcag ccgatgaggt gatagatcgt ctgcttccga    35220
gactgaccag ctcgagtgat tcggccgttg gcctgcacat agatttcgcc agagggtacg    35280
agactatacc acactatggt acaggatgct gtgagcgtaa tgccgtgtgc agaactctgt    35340
ggctgaatga tcagcacttg caggtcgcta tcttgaaagt cctgaacatg tttggcacga    35400
agggcatggg gcacatcccc gttgatcgtc gccactttga cgttacgatc ttggaaatag    35460
cccactagat ggtcaatcgt ggctctgaac gccgcgaaga taaccagctt ggtctcacct    35520
gtaccctcga agatttccca gagggcatcc tcacgagtac tagcatcgac cttaacgatg    35580
cgaccttcat cgtccttcac agcaccagac gcgatctgta aagtttcat tgctttgacc    35640 gcagcattga ccgctgtaat ctcgcccgct tcatactcca cgagaagatc agacttcatc    35700
ttctcataca ttttcttctg ctcaggcgtg aactcaacaa cctgcgtgat atactggcaa    35760
tccggaatat caatacagtc gtcacgcttg aatcggatcg cgggctgcaa gattttattg    35820
gcgatctcgt tggcgccctc atggggcagc cagaggtatg ggcccacctg atattcgacc    35880
atcatctgga attgcttata gtaacgcggc agatgacgat tcttcggatt cacgaccttc    35940
gcttgaccga aagcctctgt ggcccgattc ggtgtcggtg cgccagtgat accatgcacg    36000
ccgaccttat cgccgcaggc attggcaatt cgttgcatcg ccttgctacg cttcgtcgtg    36060
tgcttcttat aggcggtcag ctcatcgata atcacaagcc cgatttcgcc agacttgatt    36120
tgcttgatga tctcacccct cacgaccgga atagttactg cgtcgtgatt ggtgataaca    36180
aactcgacct tcgctcgcag agcagccagg cgttcaggct gcgttccatg gctatacta    36240 tagcgccgat gagggaagtt caagaagatc tctcgacccc acacagattt gagtgtggat    36300
aacggcccaa tgatcaagac tttcttgatc ttctcgttta ccatcaagaa gtcagcacac    36360
catagatggc ttaacgtctt acctgtgccc aggtcggaga agttgtaggc ccgcttgttt    36420
tggagtaaga acacagccgt tcgttttga tgatcgaacg gcttatgatt cttgttggcc    36480
atgggccacg catattcgct aaatggtact cgaagtgtca tgtctgacct ttgccataac    36540
tgcggcgtag atttgaagaa gccgtatgtt gtctttcccc acaatgatgg ctgcaactcc    36600
gcctgcatcc ctaattgcac ggagacttt aagctggaga gcagttggct tgccgccttc    36660
agccttgact tccaatccaa cgaagaccga tcgccacaca aataggcaat ccggcgttcc    36720
agagcttccg aacattccac ctggtggttt atagagccag atgggtcctt cgaaagtttt    36780
gtagagttgg cctggctttt gtctggttcc gtagagccag tctttaaccc tgccttcagg    36840
tgtttgagcc atttcatatt cctatattac tacagtggta ggcctggagt aaaccgcttt    36900
aattaaggaa agccgaggag catagtgcta cgacccgtct gcactggtcc atatcaaaca    36960
tgccaatatg acacttggcc ggaggtacat tcatctcctt gctaagccag gcgtaggcct    37020
tcgtccgact catcacgctc tgtcgccaga tggtgtcaaa ggccttatgt gcctcggacc    37080
ttgccgctcg cagatacgca tctgctaaag tgcccagtgg tgtatcagag tctgggtgac    37140
atcccaccca cgccttacac ggcgcacaga gatagtactt tttgctatgg atactaggaa    37200
```

```
tgtgtggata gatacgtcgc cccaaaacca attcagaaac tgcgttgcaa tatgggcata    37260
tcgggttcat ataacgtgct ctctggtgcg ctctgaatgt tgttactatt tagtagtatg    37320
tagctacggg ctggccaggt acggacatac tcagagcgca atcagagcgc tctgagtatg    37380
tttgattaac tactttgtat atagttccaa tacaccaagc ccatcaaccc gctcgatcca    37440
gaacccatac agcttgctgg gaatagcgga ttgcgatcga tcgaaatccg cccctgatct    37500
tcagacttgg cctgaatata ggcgtccgta ctgatcttga tgtgggtcgg atcgagactg    37560
gttttttcgt agtgcttctg caacaggtca tcatacacga tgtcccggat ctttctgtct    37620
tcagagaact ttctcattac agtttcctgg agtaggggca atccttgcga gttacggggc    37680
agtacttgca gaactcattg accgtgggct tgaactcacg atcactattg accttcgcat    37740
gttcagcatc gaaatgctct gtgagagcct tccgatcatc ctgtgagaag gttttcggca    37800
gcgtatgctt gtgatccaca tacgcatacg tggtggatac agtggggacg tccggccaca    37860
ggttgagcgc gatcgcgccc gagaggtgca actgacccct tacccgatggg ccgccatcat    37920 aatctcgaat cttgccggtc ttgtaatcta tgatcgctac atcggagggc cgaagtgcaa    37980
tcaagtcgaa gatcgcccgg tagtaggcat cccgactgaa ccattcgaca cgttcccagt    38040
tcttgttgac ggcgatctgg gtttcaggaa tcacagtggc gtagttgttg aggaagcgat    38100
ccacaaacgg cttggtggat tctacttccg gcaacgatgt gatcttgact tccagctggc    38160
cattggacag cttttggacc acatagtctt cgagtttctt gtgcacatta gagccacgaa    38220
ccaagtgcgg gctctgcgag tcgtcttcct tgaaaatcga cgatttgtcg atgtacttca    38280
tcttgaactt gagcggacac tggttgtaat ccgacaagcg tgaccaactt agggcaattg    38340
ccattctacc tctccttact tcacttctgc gaaagttttg ccacgctttg attcgtatgg    38400
cagttcgatt tccaacttaa atccccaata cttttcgtaa tcgatggtat taagagtgtg    38460
atccagcttc tcgtggagat caaccgcatt gaccgagggt acgtagaaga agttagcgtc    38520
gtgcaagtcc agcaagaaca atgcctctgg caccttctcg aacgtctcct tgatagcgat    38580
ctctttcatg tctgcaccag caccttgaat cggcacattg atggcagatg attcagtgat    38640
ccatttgtgt gagtgccagt cagtcaactt ataccgacga ccaccgaaag tctccgtata    38700
accttgcttt ctggattccc agaccacatc ttcccagtac tgtggcacgc ctttatatgt    38760
gcgattgaac gtctgcacta agaacaagcc agtctgaact gtcaagaaag tgtcataatc    38820
caagaatgct ttctgtgaca acgccttgcc gccaattcgg tagttacaag acaggttagt    38880
gagtttgcct aactggcgtt gttcggtgta ataaccacct tcatcaccett cggccttgta    38940 cttcacctga aagtctgagt aatcctcgcc gataatgctg gcacccgtca tgctgtggaa    39000
attcatgtct ttcgagaaaa tctcgatcat aacaggatcc ttggagcgaa gtgccatgag    39060
cctggattcc tggccgctag catccgcttc gtagatctcg tagccttctg gcgcaatcat    39120
actcttacgc accatcttat ctcgacgtgg aatctggtgc acagcaattg cagacttgaa    39180
cttcttggtc ttggcattat catcctcgta gtccttacca ttcgtggtac tagaatacgt    39240
gaaccgccct gtgtacgtgc cgaaaatacg tggagatgcg tagatatacc cgtcgccggt    39300
atgctccaat gcctcgatca tggatttaac atacttcgag tgaagcgtgg agtattgctt    39360
agcctccaag atcaatccca acttatcggc catttctgtg ttaccggcct cattgagctg    39420
atattgcagg agcttcagcg tatcggcatt gcaagatgga ttgccagagg gtgtcttgga    39480
aataaccggg agcaaccatt ccttaaacag cagatcgggc aagcgcttcg tcgatgtgaa    39540
gatgccttcg tccagaccga gcttttttggc aatcgccgtc ttggattcag agaagaactt    39600
```

```
gtcgtttcta cgaacctgct cacgatcgat cctaatgccc ataatccacg aattggccac   39660
aggtagtaga caatcctgtt cagttaagaa tccagtacgc tgttctttcg acatatgcgc   39720
ttgcaattta agcgccagct ttagggtcat aatggcatcg agctcaccac gcttttcgca   39780
gtactcaggg ttgtcaccgg gtgacacgcc ttggcttttc atcttcacga agaatggcgt   39840
catctcgtca tccttcagga acgtcgccac tagattggcc aacgagtaac tgaaacgcat   39900
agtctcaggt tgctggccat tgatcagcca tttggtcagt aaccctgtat ctcgccactt   39960
cacccgcttc agcacgtcag gaatggcccc catacgtctt ggctggagct gggcaatcat   40020
gaacgcgata tcgaagagcg cattgtgagc gtacacaaca tcgttgccca ctgagtccaa   40080
tagatcgatc atttcacgaa gccacaacgt attatcgcct cggttcacaa tctgatcgac   40140
tgtaaatccg gggcgacata ccgcgatgga tgtaattctc gatcgccctt ggcggagccg   40200
ccagggctgc agagcagcgt atagtttctc tgctggatcg actgcttctg tttcgatgtc   40260
cagtgaatta attttcatgc ataaactccg gagtttctcg ttttgtccat actgcgattc   40320
tacttttctc acctcgataa tacgcttgat aggctttcac agggtcgatt tgcttgtaga   40380
cgtcgtccat tgccagagca aacttcagag gccagatact tgtggaaac tttggaagtt   40440 gctcgataac tcgtgatgtt tgagttactg taccgtagcg ataggtatgc tcatgacaaa   40500
tggcttcggc gtgctcacga agccattgat aattcctaac tcgcatagcc catttagtac   40560
atgggtggtt tctatgggtg ggccggtagg ctcggataga ctcggcacgt tccggactat   40620
cccagtcatc acgccaatct gacgcgtcat actgtatacc ttggactcca cagaggctca   40680
gcgcagagct tagcatctgc gctgattcca aggccatctt aaccacatgc ttatcgcaaa   40740
gcatctgggc cgctaccact ggattgtaat cgagtatgaa gatattcata cacccattat   40800
acaccacgaa atgaccagga tgatactgct atttacaatg aacttgcgat ggaggaactt   40860
cgattcaaga tgctttcacg cttccactta ttaattccat tcacattcgc caaatacatc   40920
tgaagaatgg cctcgttggt ctcatcattg aggtccccat gttgacgtgt tgtatacagc   40980
acgtcccgac cttcaccttc ctgagaaatt ccaccgtcgc ccttcacaat aggcacgttc   41040
cgcatattgc gagtttgata gttgttgcct ttggttctga tcggctgtaa cagacctcga   41100
cgcttcaatt cccgaaatgt accctctgga tcttcacgcc aacgagagtt cattagacgt   41160
tcagcgatcg atatgaggta gatcacagca gacttggtga gcactggtgt gcgggccagc   41220
aaattgtcac gatcttcgaa gtaagtaatc caccattctt cgatgtcact caaggtggac   41280
aagtacatct cacgcttaat ctcgttcatc ggcgccttca tcctatcgag tttaagcttg   41340
atcggatggt tgtccaggga aaccagcaat ccctggataa tctcacgctt ctgttcccga   41400
ctcatccggt ttttggtaat gtcgtagaac tcatcgatca agccctcctc cattgccggc   41460
gggtcattgt cgatcaacca gatacgacga tcgaactctt ccagcgggaa gttagagcca   41520
gtgttgccgg ccagaacgac gccagcatac agcggcattt gcactgtgtc accaccctta   41580
aattccacgg gcacagtctc gagtgtgatc agcgacttca agtgacgcca gaacgtggcg   41640
gactcttgcc gcatgttacg gtgtactggg aactggattt catcgaagat aagaagcgat   41700
gcgccgttgg gattgaagaa tcgcccaccg atctggtcta cttcaaacat ctgaccttgc   41760
atgtccccgt ccttactgaa tccgaacagt gtgtcagca tgctcagata cacggacttg   41820
ccagcaccac ggacacgtga catcacgtaa ggcgcaatga ctgggcgaat gcctggattc   41880
tgaatcagcc acgctgggaa gtcaatgccc agctgatatt cctcagaacc ctctggccca   41940
aagatgcgtg acaccaggaa tttgaattta tcccaaatct cttgattctg atgtgcgcct   42000
```

```
tgaatctgaa tccttggatc acgccaggta ttgagatatt tcttaccgcc ctcagcctca   42060
gtaatcgtaa acacttccga agcacctggc ttaaatccga tcgtagccac ctctcgatca   42120
ggcgtaatca tgccatccaa gacatcaatt ggatttacga gtttcaactt gccgtcttgg   42180
ttcgccatct tccgtgcaaa cctcgacatc aactgtttca tcgaggtgag gtcatgtggc   42240
gttttggtat cgagatactg gttgttctcg aggcagacat acatcagttt gctgcgaaag   42300
ttcgtcagcc ggtacagacc gccctcgatg agatcccgac atacgtcata gggattgttc   42360
tgatcgatct tccagatgcg ggccagcata tcctcaacat cgatagagtc ctcgatagtc   42420
tccggatttt ctgtgacctt aatgagttcc ttgatgtagc ggcgtgcagt ctcctgcgag   42480
aagcctttat tacgcaaggc attcagatac aggtagaacc cgttgttgcg gttgccatta   42540
ctgactttat ccggaatttc accgcgcttc agaatctcca gctcatccat cgagccagct   42600
tgcggagtga gtacttctgg ggcgtccatg gtgatgctgg acttggacat actcatgagg   42660
gcctgggtgg gcacctccga gagagccgtg tctgtattac ccttgacgat ggtataagtt   42720
ccttcaaccc attgaccttc ggccatcggc ccaacaacca tgccaccttc accgcgaacg   42780
tccaaacctg gatatttcgt gcccccaatg gtcagacctg caactgtctt aaccgctaga   42840
ctgcgtagct tctcgggctt tgcgtagtaa agatggaatc cgccggattt ggacttgacc   42900
acaaactccg acttaggaat accgtatttc tcgctgaact tattaaactc ggcaataccg   42960
tttacgccac ctttaacatc gaggtcaaag ataacgcagt taacgcccag tacgccgtaa   43020
cctaccagct tggcgccctt gtagcctgcc gcaatgagtt ccggccacgt ctcgacgatc   43080
tcaggatcat ctgtggccgg aataatctta cgcgggtcaa tgccctcttt agttacagtg   43140
ttgcgtgccc agccgtaggg cttttgcggg ccttcacttg aaccataaaa cggaaataca   43200
tagtagccat ctcttgcaaa tcgctttgca aaatgtagga cttgctgctc cataaaagaa   43260
gcgctcccaa ttctaattgt ttggactcgg aattgaaccc cagaaacgac gcccagagga   43320
ttaactcctt ctgggcgtcg atatcgcctg gccgggcgac ggagtccaac tctttattat   43380
accacgtatt gttacctacg tgtgaacttt aattagagcc catgcttaga gattgacacg   43440
ctcacggaac tgagtccaac cataaaagtt gcgagaccgc atatccgtcg ccaccgagtt   43500
gctaagagcg aaggcttgat gctcgaatac agaggcatgc ttgtcagcca gaagacgacg   43560
tgccaagaga atatcctgat gcacatcagc cttcgtaccg tcgtgattca ggtacgacac   43620
ccgagcacag cggccggccg aagccatgca gatgtcttcc acggatacgc cctggctcaa   43680
catctcttcc acattcacat acggcgcatg caacccacca gtcccaacat gctgaggttc   43740
gaatcgatac atcgctcgta tcatcttccg tgcgagctcg cggatattgg gctcggcctg   43800
atcagagagg cgaagcatga agaaattatc ccactcggtc gcggtgacaa tgaccttgat   43860
gtgagcgaat ggctccagaa tacgattgac gatttgcttg tggcaaccca ggtctttgag   43920
cacacgggca tgcttcacag cgtcgttgca ggccttgatc caagcatcct tgcttcgga    43980 tatttccctg gcaccaagca cgtcgccacc ttgcatgcca ggcttgtttt gcatccacga   44040
gttcggcatg gccggattct cctggatgtc ccggatcata cggtcgatcg ggaccgcacg   44100
cgaacttgat gcgttccggg aaaatacacg gtgggtcatc agctctgcgt ggatgaaccg   44160
tgggtagcag agttccatcg aggtaatggt tttaaccggt ccaacagaca tctgtaatac   44220
gttagcgctg atcacggaat ttctccagaa tttgattgac agagtcctcg gaagtttgga   44280
ctccactgtc attatgaact cgcaggaact ctacatattc gatccacatc ttgcacggca   44340
attctccgtg attctccaag gcctccatga tttgactcat aacgtccttg ttcaggcaga   44400
```

```
ccagggcgaa cgcgattaga agcgatcgct cttgagtagt aaggtggtcc atgccaagca   44460
tgtagtactt agccagcaaa atactcacca tctcagacac gaatcgcacg taggcaggac   44520
ttaacttcat atcagattcc ctataacgtc gcagcactct agcactgtct gccggattg    44580 cttgttcatg atgtcttgct gaatcaactc atcgagttta ctgccccaa gcccgaagcc    44640 ctttgccaca acctgtaagt ttactcgata caggtcagac caggttttga cagtataagg   44700
cttacgagtc caagagcatc gcatgatact cagtgtgatc catccgaaat ttcctgaaga   44760
tttgtgcgtt gcatctcgca ctatcctcaa cgatccatta acgagaatca agtcaccagg   44820
ctccaaagac ttaagcaggc tcttcctggc ctcatgggcc tttgcatcca cgggcctcat   44880
cggattactc gagccttgag ttcgcacatg atctcgtaca gacttcgaat tctgtgatcc   44940
agtgatgcat gctcgaagat cacatcgaaa cgcattccac ggacggattc cagatcactg   45000
taacccttga tacagagtac atctaccgtg ctgccgtccg cgtgcaacag cctcggcggg   45060
ttggacttga atacgatgtc cttcttcacc atctggtgaa gcgtctcttg catgtaacgc   45120
atatcggatc ccacaagcaa aatcttcatc ccttaatctc cgttctggtc actttaatcg   45180
tcgcacctcg aatcttgttc ttattcgaga tatcccactc tactacgccg tccataagtc   45240
cagcgtgctt acgaatcatg tcctcgagct cttctttcgt gaactcgtat ttgacttcag   45300
ctgaaaatac gttagcggta actctcttca cttgtgctct ccggtgcgct ctgaatgtag   45360
ttacttttga tgcgcagctg catatagcat agctgctccg aacgtattca gagcgcatct   45420
gatagtctga aactatgctc gaaagagcac cttactagta cttttgaact taccagtatg   45480
ggcccagagg gcccatactt agatcttaaa cgacctgata cttctttaaa tcagccacag   45540
gaatggcgtt cttgatcatc ccggacttaa tttgacggag ccgtcgggcg acttccgaag   45600
caccgcctcc ggacttcttt gcaaatccaa gaccgcgtct gtgggctgca aggtatcgac   45660
ggtcgcgatt ggataggaac atggtacatt ctccagtttg atgaaacgca gttctgcgta   45720
gcgaaggcaa ttgtccgaaa gatccatgac aatcgccaca gggcgtaccg cacttccaac   45780
atccgaattc ggacagtgca gactgaaacc aagcaccatc acatcctgct ccgcaggatg   45840
attgttggaa ctcgatgatt gcttgatcca cttggctttg atcgggaaca tttgaaacct   45900
tctggtgtgt aattattagc cgacccaggc gagattgtcc ctggactccc attctttctg   45960
caccacggcc caaactgctc ggtctccgta ccacatacag atgtgagcca tcatggcgtc   46020
ggtgatgatg gctttggtga ataccaggtc cacgtaagtg ttttcccgg aaggccgatg     46080 tccgattttc ttgacacctc gcacgtggcc ctcaagcgcg ataggcccct tttcggattt   46140
gggaatacat ggaatggggc gaccatgctc gtcgcccgca atacctcgca cttgaaactc   46200
agccttcacg aaatcataaa acagatcgcc gttgaaaact cgatcatctg tatctacggt   46260
gaagtagaag ccagtcttga tgcactcaca gaagggcct ttttcgatga tcgtgctcat    46320
ttgcctgcac catcgagcgg caaatcgttc tgcgggctca ggcgagcctg gatgatcgtg   46380
cgatcagtgt aaaacgattg gccgttgatg tatccgttgg ccgacgcccg aaccttctcg   46440
tacttatcat tgttccagtg gatgctcgga atgttgatac gaatgaagtc atggattacg   46500
tctaaggctt tacgtgcagt ccctacgggg gtgactgaga tgtgttcagt cgtgtgctca   46560
tgcggtccgg tgacctggac ttgtacctgc acatcgtcat tcatctggct ctccatcttg   46620
gcctgcaaca gatggtaggc ctggaggtct tcagcaatct gcctagacac cggataatcc   46680
gcagagccac tcagaaactc caagtgttcg gccagacggc gcactttgcg ggcgctgtac   46740
ttgggatagt ttgcgagaag attttggaaa atggacatgg ctatccttaa ataagatcga   46800
```

```
cagattcagg tggaagaggg ttgctctgag actcaagctc agcaagagcg tcaccgcgca   46860
tttcatacat cacatgggtc tcgatcagat cgagtgcttc gcccagcgct tctttgcacc   46920
ggtcatagtc atcgacggtg atggcctcag ccagcagggc cgcgaaatca tcgcgtgctt   46980
gagactgctc atcaagcacc gcagagatcc attctgccac agtggaagga ttcttcatcc   47040
actcctgtat caattcatca gcgcgctcgt ttttggcgtc gctggcatct tcagttgcta   47100
agtgaaggtt taactcgtta tcaggactcg acataagact ctccaggaaa gttacaactc   47160
agtgttgctg tttcttcaac cactcattat actcgcgctt ccaattggcc cgagccgttc   47220
ggtaggcctc gatcgttttg cgatccatca tcggtcgagg ttcaaacgag atgatggcct   47280
tgaagtactt gctctggtca caaagctctt ggtatgtcat ggacatcacc tcgtttgcat   47340
gtgtatatag tacaggtaga tgcatgtcgt gtacacaccc taattcatgg gtctatgtca   47400
gtaatacagt ttcatcaggc catctgcacc gtccaacctg gcgagactcc agctgataag   47460
agtatggaca ttcggaatca gcacatagtc catcagctga ttcagatcca caaccagaac   47520
ttcttcatca gtcatggtcg tggcattgtc gatgttgatg ttgccggcat acaaatgcac   47580
ggtccagtca tcaccaacca ttttccctgt gtagagccat tcgctagcga gggtctttac   47640
tccagtctcc tcgaagaact cacgagccat tgccgcacga gatgattcgt ccgagacctc   47700
gacatggccg ccgacaccgt tgaagtgatt ctcttgccat ttcggccgat tcttacggat   47760
caggcagacc tggttattcc aaaaggcgaa tccgagtacg tacacggtca tcacagagct   47820
ccgatattag aagtcgcttc ggatgtggaa ttgctttcca catcgtttgc acttgaggga   47880
atcgtggtcg atgcgatgcc agaagcagcc attcacttcg ccagaccacc acaggcgaag   47940
tttctggatg agactcatat cgtcaccgcc cagttacgca gaaattcatc tggcgaatat   48000
acgccttcct tgcccatgta atatgcggtg cagccaacca tgccatcgaa gtagatggca   48060
ctcgtatagt gagcccgcgg actggctgtc ccatcactct tgagaacccg gaaccagcca   48120
tcgaagtcca tttcgatctc gtacttcgga ggtggcgtat gcttgagtcc ttccggatcc   48180
accggagagc acgaactgcc gctcttcgag tcatgataca gatacacagt gtgtccgagt   48240
tgcgtggcga acatcttggc cagggcttga ggactcacgc cgcgatcgat caagcgcatc   48300
ggcttgtggt ccatgtacag aatcccgttg tagccctcca gacgtcccaa agggtagtcc   48360
gggtgaggct ctgaagcgcg gctcttggcg atcacgatga atgaattcat ctgaccacgc   48420
acgtccacac cagtatcctc aaacaaatcc tgtgatccga ccttccacgg ccccttctgg   48480
gtctccgtgg tgccatcgat cagctcgaag ctgatatcgc gcttgccaaa tcctcttttg   48540
tcacggttag acaggtaaat gaagtccgaa gcttcgtcac aatcgcccac gtaccagatg   48600
cccttcttgc cgacatactt gcgatacttg accttctcca cttcggcgga ggcacagatc   48660
tgcgagtacg gcttcttgat gtagtccata agaatctcca agtcatttaa cgtacatcta   48720
ctatactgcc ctattacatc cttgtacacc gctttaattt aaacagccct gcgcttgcta   48780
ttccatgccg gattgcagac gactcgtctg gtctcatggt gctccttgcg tgcagcgttc   48840
tccgcgtcag aggccttgca ccgctcgcac aaaacctcac ccgtcttcac gggcctcttg   48900
catcggcact tcttagccac agtatttcac ccggccccag ccaaagctgt gcgtgttcat   48960
gtactgtgtt ccgtacttgt cttcccacag atacaccgtc ttgccgctca ctcgatctac   49020
gaagagcgcc ttcacctggg tcattggggt gaagtaggac gtgagtcttt tgatcatgat   49080
acttctccaa taattacgag gcctctagac cagggcccat cttggatggc ctcttgcaga   49140
taggccagtt cttcggacag cagaggattt aacttccagc cgctcactgc gatccgcatc   49200
```

```
aatacctcgt ggacacccgt cctgttgacc ctcaaatcat tcactgggat cttccggatg   49260
tccttcgaaa tctcaatggt ctgaggatcc acgaggacta ggatttgctt gcccttgtta   49320
actcgcttga agtgatccca gcctaggaga tcctcatcgg cgcatacccct accggctagt   49380 tctgggagaa cccctggcac aagcaacata caaccatggc catcctggac acagagtagt   49440
cgcaccataa tggccgtgga tacagagatc acaggacgag ccacctcagg aataggcgta   49500
aggcttggaa tgctgcgagg ctattgacgg ccaaataaat cacgccaatc agggctttaa   49560
ccacatcgcc tttcacgata ggtccaggtg tcgtagccat ccaggaattc gggatacaca   49620
tgaagatcat gttcaccacc catgcaatca tgaagatctt catcgtttga tccttggctt   49680
gcgagtgaag gcctgggtgt tcaggaactc ggcaaacttg ggccatgcct tatccttggc   49740
ccagtcgatg attacccaca ggccgaggat aatgttgatc actgggacaa tgtagataag   49800
tacccaggcc aagatctcac cgtaagtcac cgctccgcac gaatcgtact cgtcatacag   49860
gaaggcgaag ttcagtacga atgcgatgac cgtagtgccg atataccagt agaggattat   49920
gtccatcttt gtcctttgtt cttcttacgt tgcccttttgc caagacgagt cttggtatac   49980
aaaggaatga agtctcgacg ctcttccaag agtagctcag gcgctctgat acgcatctct   50040
tcgaaatgct tgatagctgt atgcacgtca agcgcatcgt cgtcagagcg caccagcgct   50100
actctgttag attccaaaaa acatctgctg gatccatgac ttaccatgcg atctgaagtt   50160
gcctgtatac agcattacta ctttcggggc ttcctcaccc gaggccactt cgctttctgt   50220
cgggtcccgt aatagaacaa cccgctccag agtgtcgcgg ctgaggctga atcaggatc   50280 ctctcccaca acaagtactc ttggccgtgt ccgagtccga tcatcaccag cgtcgccacc   50340
gccgcccaga acattgtcaa tactatccac atcactgcct ccgtaaaatt tcgagttctt   50400
ccactgtgag accaagcgat tgagccttgg ccatgacttc ctttcgacgt ttctctattg   50460
cggcttcctt atccagcaac atctgggacc gactatcctc ctgtgtcggc tttattacct   50520
gtacagggcc atacacgcgc ccgttataat cgaataactc caccttggat acaatggggg   50580
agatggtggc gcttcgagcc gtggcggctg agatacgtcg cgccgttgcc tcaagcaagg   50640
ccactgcctc aggttggcca ctatcaaata ccgcatacccc atccatggga cccgtcacta   50700
ctatcaccaa cttgtcatcg atgagtttgg ctagctcctt cagctcttca ccaacttttg   50760
catcaagcgc cggatggaca tgccgcacta gcctgtccat gaatctccga agctcttcgc   50820
aatttcgcat atttcacctg aatgtgtatg atgtgaggtg cccatatttc cggacatagc   50880
accgttgtcc gcccacgaca gtccatacga gcttgtggcc cgcaatataa gacgccatga   50940
taattcgaat ttgcaagccc aaggtcatta ggaatccaga ttaatcagca tcttgacgat   51000
cagcttcaga tcgccccaga ccacagcacg atcggccgct tcgagtaatg ccttacggcg   51060
caagatggcc ttggcctcca tctgaccgca accggtttct tcacggtaag caatgatctc   51120
ctcggatgac ggactatgca cgtagaaccc aatgcttgga tcccatgggg ctggctctgg   51180
tacaggggcg ggcttcggcc tgatcgggcg gtgattgatg caccacttgt ggcccttcgt   51240
agcgaagtgc gggcagccgg ggtgggcgca ctttgcagcc ttgcccctca tcacgagcca   51300
cctaagatca tcacgtccac atatggactg atctgggcca gcaccttgtc aatctcttcc   51360
tgcacgtgat gctcatacgt aggaacacca tcccacatagt cagacggagt cacagtggta   51420
atcaccgtgc tatcaggctt gcgcgtgatc gtgaccacat tattcggatt gaagtacata   51480
acccgcccac tgaagtacgt cactttaatc agttgcattt cctgtcctca ataagagtca   51540
tagaccgatg ccagtcactg gcatcacgag tccatatatt tccattatcc cctacataga   51600
```

```
tcaccgtcac aggataccga ggattctcgc tcgcgatatt tgctatggcc aatacttcgt   51660
attgcttgcc gttatagtgg cgccacatgg tgccaggttg aggtacgtcg ctcatcgagt   51720
tctcccttta catccaatta acatgcacac cgtagcagct acatagagcc ccacgaacca   51780
gcccggcgac gtcgtgtaaa tactcgcccc caggaaaacc aacccgatat aaatccacat   51840
cactctttct cgaattctgc cgcagtgatt ttggcccgca gcgcgatcat ttccgtgtgg   51900
aaattagcgc attgcgtgcg gaactctttc tcctgcttct tgtcaccgcg gaacgttgcc   51960
gccatgtggt cgtgcctggc cgactccaga agatcagaca gccggaagta ctggaggatg   52020
tcagacatgg tcgtccacca tctgagtgtc gtagagcctc gccacgatgt tccgcaccgc   52080
acggatctct tcagcactgg ggctctgcac gaccacaatc agtgcctggc cctcagggcg   52140
gatattgtcg atcccatagt gggtcagtcc ataccggagc ttagacactt ctacctcatc   52200
gacgcccgta agcaccacat cgccatgcat gttcttaatc aaactcaatc gcttcatgtt   52260
cccctacctt cgttcgaccg atggcttatt atatagcgcg atttctgtct tgtacacgcc   52320
cttatttatg gagccatgtc aggcgtcaca ccactgtgcg atgcccaagg atacaccttg   52380
taatgcccct tcatgtaatg ccacgcggct gacagactca agcggaggtc agacaggtaa   52440
gtatacgcca catggtcagg cctgatgtag ctctggcact caaggagttt agcaatgtg   52500 tccacctcgg agctcttcag cacgatcttc ggccaatgct tctttctctc ggccggcctc   52560
aagtcaagca tccactcctc atggttccgc aatatcacca ctgcacgctc actaatctga   52620
tccgctgctc tctggcagac accgtcgtag tggactcgag ccaatgccct caacccttgc   52680
actaggccct ccgataccct gacctcaaac ctcaactctg taaccccatc aactcttggt   52740
gccgtcatac gaatctccaa tatcaggtag tgtacgacca tattactgcc ctatatcatc   52800
cctgtacaca tctctaatat caatgcccat atactgcagc gcatcccgga cttcagccac   52860
agtaagatcc actctatgcc taggttcgcg actgttactt gcgttcggct attccatggc   52920
tacgccatga gggatattgt aataagtatt acctgaatac gaaacatatt ttacaaactt   52980
tgatccctgg gtctataatt tatgtccgaa caaattataa tgtttgtcca agtttgtct   53040 cataaatgga tccatgggcg tcgcactttg ccccgatgcc aacattttga ctaccaatta   53100
ggtcgcgtag ccaaggacaa ggaacttaga acgatgcccc gttgccacaa gttgttgttt   53160
tgattagcct tcagcgacgt tccttctctt taatctacta ctataactat aagtagtatt   53220
gtagtagtat aagtagaaaa agatataagt aacatatata agtaagagat ataatatata   53280
tgttaataat atctaggatt actatagtaa aaaaggaggg atgtcacttt ggagataact   53340
acaaatataa tttaattatg gaccttatga tttgtgcgcg caccgagcgc ctacctgtgg   53400
tagaatatac gtacacattc cttaggattt tatatgggcc ggctatcctt cgcagttctg   53460
gataaatacg aatacttgcc atcgaaacaa gagggcacgt gctatttctg tggtgcgggc   53520
ggtcgtctat ccaacgatct aaccccggcc aataccgcca cggtcagcgc gcaagcgatg   53580
ttcatggata agtgggtcta tgtaaaggcc tgccagaaat gctggcacaa gatttacaca   53640
gccaacacgt ttaaccaggg taagaattat aaggttctgt ccgggtgcat gacgctcgat   53700
atgaagttcc atctgttggg catcggcaat ttgcccgata ataagcgatc caatgggatt   53760
gggtgggtca aagagggcac gaggctaatt ccactgtgtc tggcacctac ggatcaggat   53820
gattatttct gggaccagta tcgaatcact ggtgaagaga ttcaggccct ccagggcaca   53880
ctcgctacac tgtatatggg tcttccacga ctaaccgtca atcggacttt cgatgcggca   53940
ttggccagtg gtgatctcga attggatcgc atcgatctat accgtggaat gatgggtatg   54000
```

```
aacgatttgg aagatagact cgaagccaaa tcgcctaatt acgaggaaaa caaggataaa    54060
ttgccatggt aagtctgaat ctacccagca gcggggcatt gatcggtgat acatcatcca    54120
tggtggatcc gcacaaactc ggtaaggtta tgtggagtcg tagtatggag ggcgacatgg    54180
ctccgctcga tctgcacaat caattggagc gtgaagacct catggcattg aatcatgtct    54240
atgagatgct ccgtgcctac aggaaaatac ggccagcgtt gcagattgtg gtccgacgta    54300
agtggtcccg catggatctc attaagccgt atttgattgc caccatggaa ggcaggtccg    54360
aagcaaggga atgattgca agcgatgact ggcatcaatt ctgggctaac ctgtaattaa    54420
agcgttgtac atacgtacgt atacgcgcta ctatttaatc atcgaataaa cgagtaagcg    54480
aatggcctcc tcaaagaaaa gcactatcgt gacattgttc agcatcacga ttcttgcacc    54540
tgtaatcttc gtcatcgctc tcgttgttgg atgtcttaaa gcactgctcc atcataaata    54600
agcatgggcc gttgaattag gatgtgtaca agtagttagt agcgttatat agtatcccta    54660
cagtcaatca acctttagcc cagactgtgg ctaatcccaa tcaaggagtc acaccaatgt    54720
ccgaccagac cgataccacc cagaccacgc cggccgagaa ggcgccgccc aaggaaatca    54780
tccgcggtcg tatgccgatc gcagtggtcg ccctggcccg cttcggcagc cagtccacca    54840
ccaccaccaa ggccgcagcg gatgccctgg caccaccgt cggcaagatc gacgacatcc     54900
gcaagaaccg caacttcgcc tacgtcaccg ccgacttcaa gccgaccgaa gcccagaagg    54960
ccgacggcat cgagtggctg aagcgtcatc cggtcggtgc ggatgccctg atcgaagagc    55020
tgcagaacct gccggtcgcc accgccgaag agtcggccgc attcgagcag gtccgcgcat    55080
cggctcgcgg ccagaacgcc aagaccgccg agggtgaagt cgctcaggcc ggcggtggca    55140
atcgtcgcaa gaagaaggaa aagccggccg aagccggtga agtgcagaac ccgccggccg    55200
ccgatggcga ctcgctcctg agctaatccc ttcggggaa gcggttagcg taagggataa     55260
gggctccttg atggagccct tatttatgcg cgaacggaaa gtcgacacga ttgcacctca    55320
ctgtgaagtc gacacgattg cacctcactg tgaagtcgac acgttgcaca tgtatgccaa    55380
tcaatggcgt taactctgag ctgaccggtg cgtttctgag ctgcgcgcaa cacatacctg    55440
catttagcta cgcacttccg agcaaacgcg atcagagcgc accggccatt taacatactc    55500
gggttgcatt gttgtaaagt actagttagg tagcttgtca gaatcagccg gagcataccct    55560 ctttgcgctc tgagcgctca cgtacgtagt agtacgtagg cataccaaac taactttgaa    55620
cgttcgttca gagcgcaccg gagagcatcg gtccatggcc atgggtatgc acgcaaaaca    55680
aaggacccta tacgggtcct ttatgggttc agcgacaaaa attcggccgt gactcggggt    55740
atgtcgctgt taaagtagc tccggagtgg                                      55770
```

<210> SEQ ID NO 2
<211> LENGTH: 61
<212> TYPE: PRT
<213> ORGANISM: Phage P15

<400> SEQUENCE: 2

Met Ser Arg Lys Glu Leu Arg Thr Ser Glu Ser Glu Trp Arg Arg Thr
1               5                   10                  15

Lys His Thr Ala Tyr Met Pro Lys Gly Thr His Val Thr Arg Thr Trp
            20                  25                  30

Arg Ser Gln Ala Ile Lys Val Ala Thr Val Ile Met Ile Gly Thr Ile
        35                  40                  45

Ile Thr Ala Phe Trp Tyr Glu Phe Leu Lys Gly Ala Ala
    50                  55                  60

<210> SEQ ID NO 3
<211> LENGTH: 101
<212> TYPE: PRT
<213> ORGANISM: Phage P15

<400> SEQUENCE: 3

```
Met Asn Ala Ile Glu Leu Ile Asp Leu Ser Gln Lys Leu Ser Asn Ala
1               5                   10                  15

Ala Leu Ala Ala Lys Leu Asn Glu Val Ile Glu Ala Leu Asn Ala Gln
                20                  25                  30

Ser Ala Pro Arg Asp Arg Gly Pro Lys Ala Glu Arg Thr Met Thr Glu
            35                  40                  45

Glu Asp Ala Arg Lys Val Ile Ile Gly Glu Met Lys Asp Val Pro His
50                  55                  60

Lys Asp Ala Ala Glu Gln Leu Gly Leu Ser Tyr Gly Gln Ile Tyr Ser
65                  70                  75                  80

Ala Arg Lys Gly Phe Thr Phe Lys Ser Ile His Lys Glu Val Arg Asp
                85                  90                  95

Ala Glu Val Thr Glu
            100
```

<210> SEQ ID NO 4
<211> LENGTH: 139
<212> TYPE: PRT
<213> ORGANISM: Phage P15

<400> SEQUENCE: 4

```
Met Ser Asp Leu Met Ala Ala Asp Asp Gln Lys Thr Arg Arg Glu Leu
1               5                   10                  15

Leu Leu Gly Met Ile Gln Gln Glu Tyr Pro Ser Tyr His Pro Leu Val
                20                  25                  30

Ser Ile Ala Arg Ile Ala His His His Asp Ala Asp Leu Lys Leu Gln
            35                  40                  45

Phe Glu Cys His Arg Thr Ile Ala Lys Tyr Val Glu Pro Glu Leu Lys
50                  55                  60

Ser Ile Glu Val Lys Gly Glu Ile Thr Gly Arg His Lys Val Ser Val
65                  70                  75                  80

Ser Leu Phe Glu Pro Lys Gln Glu Ser Phe Pro Val Ser Gly Gly
                85                  90                  95

Gly Ala Ser His Ile Glu Gly Ser Thr Arg Val Leu Pro Ser Gly
                100                 105                 110

Gln Gln Gln Ser Gly Gly Glu Met Ser Arg Leu Asp Met Asp Pro Ser
            115                 120                 125

Val Val Asp Arg Val Thr Leu Ala Gly Trp Glu
    130                 135
```

<210> SEQ ID NO 5
<211> LENGTH: 527
<212> TYPE: PRT
<213> ORGANISM: Phage P15

<400> SEQUENCE: 5

```
Met Pro Pro Thr Glu Ala Leu Ser Arg Pro Ile Arg Arg Pro Asn Ser
1               5                   10                  15

Cys Gly Arg Trp Gly Leu Arg Ile Ser Pro Ser Pro Met Cys Ser Gly
                20                  25                  30

Ala Thr Pro Ser Ser Pro Pro Ser Gly Arg Pro Trp Tyr Ser Gly Leu
```

-continued

```
                35                  40                  45
Gln Gly Pro Thr Pro Ser Ala Phe Ser Arg Ala Pro Arg Leu Cys Pro
 50                  55                  60
Trp Arg Ser Gly Ala Asn Met Thr Val Ile Arg Arg Ile Ser Lys
 65                  70                  75                  80
Pro Gly Ala Val Arg Arg Ser Leu Ser Arg Ser Val Gly Gly Ala Ile
                 85                  90                  95
Ala Gly Ala Leu Ser Ala Arg Gly Ser Gly Asn Phe Val Pro Pro
                100                 105                 110
Val Ile Ser Asp Leu Met Ile Ala Ser Met Asn Gly Ile Thr Pro His
                115                 120                 125
Asn Leu Gln Asp Ser Gln Asn Phe Asp Asn His Val Ala Arg Trp Ile
                130                 135                 140
Tyr Thr Thr Gly Ser Gly Lys Leu Lys Ser Leu Ala Leu Arg Phe Asp
 145                 150                 155                 160
Ala Trp Phe Ile Asn Ala Thr Ser Ala Ile Thr Asn Thr Ser Asn Pro
                165                 170                 175
Ile Pro Ile Phe Asp Ala Ser Leu Glu Tyr Asn Gly Val Val Pro
                180                 185                 190
Val Thr Phe Gly Asn Ile Arg Ser Lys Thr Leu Gln Pro Gly Asp Phe
                195                 200                 205
Asp Val Leu Ser Asp Glu Ile Gln Val Ser Ala Phe Gly Val Thr Asn
                210                 215                 220
Ile Pro Arg Gly Ser Asn Val Ser Leu Lys Ile Arg Tyr Thr Phe Pro
 225                 230                 235                 240
Gly Ala Ser Ala Asn Arg Met Leu Ile Gly Leu Gln Arg Pro Glu Ser
                245                 250                 255
Gln Gly Gly Gln Cys Arg Trp Phe Asn Ala Ala Asn Thr Thr Val Ser
                260                 265                 270
Ser Thr Asp Ala Pro Gly Pro Tyr Thr Phe Thr Gly Thr Ala Pro Thr
                275                 280                 285
Ala Arg Gln Gly Ser Tyr Arg Pro Gly Leu Leu Gly Arg Tyr Glu Gly
                290                 295                 300
Ala Phe Glu Pro Ile Trp Leu Phe Tyr Gly Asp Ser Ile Thr Met Gly
 305                 310                 315                 320
Thr Gly Asp Ser Asp Tyr Thr Arg Asn Tyr Gly Ile Gly Trp Pro Ala
                325                 330                 335
Glu Ala Cys Arg Ile Ala Ser Pro Asn Gly Gly Leu Ser Tyr Gly Asn
                340                 345                 350
Met Ala Ile His Gly Ser Ser Thr Ala Met Ser Thr Phe Gly Glu Lys
                355                 360                 365
Ile Glu Ala Pro Leu Lys Tyr Ala Thr His Val His Ile Gly Trp Gly
 370                 375                 380
Thr Asn Asp Phe Gly Thr Ser Ala Ala Asp Pro Arg Pro Thr Ser Gln
 385                 390                 395                 400
Pro Arg Leu Thr Ala Gly Val Asn Ser Met Lys Ala Arg Pro Gly Ser
                405                 410                 415
Lys Val Thr Asn Trp Tyr Phe Gly Tyr Leu Gly Pro Arg Thr Thr
                420                 425                 430
Thr Asp Asn Tyr Val Thr Glu Glu Asn Gln Ser Tyr Leu Thr Ala Asn
                435                 440                 445
Trp Gly Pro Ser Pro Cys Asn Val Glu Ser Trp Asn Ser Trp Leu Val
 450                 455                 460
```

```
Thr Asn Phe Ser Pro Asn Gly Val Asn Thr Trp Pro Ser Ile Arg Gly
465                 470                 475                 480

Val Asp Pro Leu Lys Trp Arg Val Asn Gly Thr Ala Arg Tyr Ser Asn
                485                 490                 495

Thr Asp Ala His Pro Ser Thr Val Gly His Leu Leu Met Gly Gln
            500                 505                 510

Asp Ala Ala Met Met Arg Ala Asn Gln Gly Val Ser Leu Ala
            515                 520                 525

<210> SEQ ID NO 6
<211> LENGTH: 177
<212> TYPE: PRT
<213> ORGANISM: Phage P15

<400> SEQUENCE: 6

Met Lys Thr Phe Asp Pro Ala Gly Asn Leu Ile Asp Ile Ser Gly Glu
1               5                   10                  15

Ile Val Val Asn Asp Leu Asn Val Ala Pro Val Leu Asn Thr Ile Pro
                20                  25                  30

Met Ala Gly Asn Asn Tyr Val Val Met Ser Ile Met Thr Asp Ser Gly
            35                  40                  45

His Arg Arg Leu Val Leu Val Asn Pro Ala Leu Ile Ala Gln Ala Ser
        50                  55                  60

Gln Leu Gln Ser Leu Glu His Ser Leu Ala Leu Thr Asp Asn Met Val
65                  70                  75                  80

Val Thr Arg Thr Lys Met Val Glu Leu Pro Val Gln Thr Leu Thr Tyr
                85                  90                  95

Ser Ala Ala Ile Ala Met Gly Ala Gly Ala Met Lys Phe Thr Lys Thr
            100                 105                 110

Gly Ile Ala Gly Val Lys Thr Thr Asp Ile Ile Val Ala Arg Pro Gln
        115                 120                 125

Thr Pro Leu Ala Glu Gly Tyr Met Val Gly Asp Ala Val Cys Thr Thr
    130                 135                 140

Asp Gly Thr Ile Asp Tyr Arg Leu Phe Arg Pro Ala Leu Ala Ile Gly
145                 150                 155                 160

Ala Asn Leu Ser Ile Asn Met Arg Thr Phe Ala Leu Arg Leu Glu Asn
                165                 170                 175

Ser

<210> SEQ ID NO 7
<211> LENGTH: 122
<212> TYPE: PRT
<213> ORGANISM: Phage P15

<400> SEQUENCE: 7

Met Thr Arg Ser Lys Phe Arg Ser Met His Gly Arg Ser Asn Gly Ile
1               5                   10                  15

Gly Phe Glu Ser Gly Phe Glu Lys Lys Phe Leu Leu Gln Cys Tyr Gln
                20                  25                  30

Leu Gly Ile Lys Val Glu Arg Ser Leu Glu Gln Val Ala Tyr Gln Asp
            35                  40                  45

Ser Lys Gly Ile Trp His Arg Tyr Asn Pro Asp Phe Tyr Trp Pro Asp
        50                  55                  60

Val Asn Phe Thr Val Glu Ile Lys Gly Ser Trp Ala Phe Arg Asp Asn
65                  70                  75                  80

His Gly Asn Val Lys Glu Lys Phe Tyr Ala Ala Met Val Tyr Phe Lys
                85                  90                  95
```

```
Asn Arg Tyr Thr Leu Ile Thr Glu Lys Glu Leu Arg Ser Asp Tyr Val
                100                 105                 110

Ala Lys Leu Tyr Arg Ser Leu His Gly Asn
            115                 120

<210> SEQ ID NO 8
<211> LENGTH: 473
<212> TYPE: PRT
<213> ORGANISM: Phage P15

<400> SEQUENCE: 8

Met Ala Thr Asp Phe Lys Leu Tyr Pro Pro Gln Gln Arg Ala Leu Ile
1               5                   10                  15

Thr Pro Ala Arg Glu Ile Leu Tyr Gly Gly Ala Ala Gly Gly Gly Lys
            20                  25                  30

Ser Tyr Leu Leu Arg Val Ala Ser Ile Val Tyr Ser Leu Glu Ile Pro
        35                  40                  45

Gly Leu Ile Thr Tyr Leu Phe Arg Arg Thr Phe Lys Glu Val Leu Ser
    50                  55                  60

Asn His Val Tyr Thr Pro Gly Gly Tyr Leu Glu Met Met Lys Gly Leu
65                  70                  75                  80

Ile Asp Ala Gly Asp Val Val Tyr Ser Lys Ser Asp Asn Ser Phe Thr
                85                  90                  95

Phe Tyr Asn Gly Ser Arg Ile Gln Leu Ala His Ser Gln Phe Glu Asn
            100                 105                 110

Asp Ile Tyr Thr His Gln Gly Ala Gln Ile Gly Phe Leu Ile Ile Asp
        115                 120                 125

Glu Ala Thr His Phe Thr Pro Pro Met Ile Arg Phe Ile Arg Ser Arg
    130                 135                 140

Val Arg Leu Gly Ser Met Ile Ile Pro Pro Lys Trp Lys Ala Leu Phe
145                 150                 155                 160

Pro Arg Ile Leu Tyr Thr Ala Asn Pro Gly Gly Val Gly His His Tyr
                165                 170                 175

Phe Lys Ser Asn Phe Val Asp Ile Gly Ser Gly His Val Phe Gln Ala
            180                 185                 190

Pro Glu Asp Glu Gly Ser Met Leu Arg Glu Tyr Ile Pro Ala Lys Leu
        195                 200                 205

Glu Asp Asn Lys Val Met Met Glu Thr Asp Pro Asp Tyr Arg Ala Arg
    210                 215                 220

Leu Lys Gly Met Gly Asp Ser Ala Thr Val Gln Ala Met Leu Glu Gly
225                 230                 235                 240

Asp Trp Glu Val Val Ser Ala Gly Gly Ile Ala Asp Leu Trp Arg Ser
                245                 250                 255

Lys Ile His Val Val His Pro Phe Lys Ile Pro His Thr Trp Lys Ile
            260                 265                 270

Asp Arg Gly Tyr Asp Tyr Gly Ser Ser Lys Pro Ala Ala Tyr Leu Leu
        275                 280                 285

Phe Ala Glu Ser Asp Gly Ser Glu Phe Arg Asp Gln Gln Gly Arg Val
    290                 295                 300

Cys Trp Val Pro Ala Gly Thr Val Phe Ile Gly Glu Asp Tyr Ile
305                 310                 315                 320

Ala Asn Lys Arg Gln Glu Gly Leu Arg Leu Thr Ala Ile Glu Gln Gly
                325                 330                 335

Arg Arg Met Ala Arg Tyr Glu Ala Glu Ser Gly Tyr Gln Asn Arg Ile
            340                 345                 350
```

```
Gln Pro Gly Pro Ala Asp Asn Ala Ile Phe Ser Ala Glu Pro Gly His
            355                 360                 365

Arg Thr Val Ala Asp Asp Ile Gly Ile His Gly Val Thr Phe Thr Arg
    370                 375                 380

Ser Asn Lys Asn Pro Gly Ser Arg Ile Glu Gly Leu Gln Leu Phe Arg
385                 390                 395                 400

Thr Arg Leu Lys Ala Ala Thr Glu Arg Pro Met Glu Asn Pro Gly Phe
                405                 410                 415

Phe Val Phe Asn Thr Cys Phe Asn Thr Ile Arg Thr Ile Pro Asn Leu
            420                 425                 430

Gln Asn Ser Pro Lys Asn Ser Glu Asp Leu Asp Thr Ala Gly Glu Asp
        435                 440                 445

His Ile Trp Asp Val Ile Arg Tyr Arg Leu Leu Lys Ala Ala Lys Gln
    450                 455                 460

Ile Lys Leu Ile Glu Thr Glu Gly His
465                 470

<210> SEQ ID NO 9
<211> LENGTH: 452
<212> TYPE: PRT
<213> ORGANISM: Phage P15

<400> SEQUENCE: 9

Met Pro Ile Glu Thr Lys His Pro Glu Tyr Leu Ala Tyr Glu Asn Asp
1               5                   10                  15

Trp Ile Asp Cys Arg Val Ala Ser Leu Gly Gln Arg Glu Val Lys Lys
            20                  25                  30

Lys Gly Val Arg Phe Leu Pro Lys Leu Ser Gly Gln Thr Asp Asp Met
        35                  40                  45

Tyr Asn Ala Tyr Lys Gln Arg Ala Leu Phe Tyr Ser Ile Thr Ser Lys
    50                  55                  60

Thr Leu Ser Ala Leu Ser Gly Met Val Leu Asp Gln Pro Pro Val Ile
65                  70                  75                  80

Thr His Pro Asp Ala Met Ser Lys Tyr Phe Glu Asp Gln Ser Gly Ile
                85                  90                  95

Gln Phe Tyr Glu Val Phe Thr Arg Ala Val Glu Glu Thr Leu Leu Met
            100                 105                 110

Gly Arg Val Gly Val Phe Ile Asp Arg Pro Leu Thr Gly Gly Asp Pro
        115                 120                 125

Tyr Ile Ser Val Tyr Thr Thr Glu Asn Ile Leu Asn Trp Glu Glu Asp
    130                 135                 140

Glu Asp Gly Arg Leu Leu Met Val Val Leu Arg Glu Phe Tyr Thr Val
145                 150                 155                 160

Arg Asp Thr Ala Asp Arg Tyr Val Gln Asn Ile Arg Val Arg Tyr Arg
                165                 170                 175

Cys Leu Glu Leu Val Asp Gly Leu Leu Gln Ile Thr Val His Glu Thr
            180                 185                 190

Gln Asp Gly Lys Val Trp Glu Leu Ala Lys Thr Ser Thr Ile Gln Asn
        195                 200                 205

Val Gly Val Thr Met Asp Tyr Ile Pro Phe Phe Cys Ile Thr Pro Ser
    210                 215                 220

Gly Leu Ser Met Thr Pro Ala Lys Pro Pro Met Ile Asp Ile Val Asp
225                 230                 235                 240

Ile Asn Tyr Ser His Tyr Arg Thr Ser Ala Asp Leu Glu His Gly Arg
                245                 250                 255
```

-continued

His Phe Thr Gly Leu Pro Thr Pro Trp Ile Thr Gly Ala Glu Ser Gln
                260                 265                 270

Ser Thr Met His Ile Gly Ser Thr Lys Ala Trp Val Ile Pro Glu Val
            275                 280                 285

Ala Ala Lys Val Gly Phe Glu Phe Thr Gly Gln Gly Leu Gln Ser
        290                 295                 300

Leu Glu Lys Ala Leu Ser Glu Lys Gln Ala Gln Leu Ala Ser Leu Ser
305                 310                 315                 320

Ala Arg Leu Ile Asp Asn Ser Thr Arg Gly Ser Glu Ala Thr Glu Thr
                325                 330                 335

Val Lys Leu Arg Tyr Met Ser Glu Thr Ala Ser Leu Lys Ser Val Thr
            340                 345                 350

Arg Ala Val Glu Ala Leu Leu Asn Lys Ala Tyr Ser Cys Ile Met Asp
        355                 360                 365

Met Glu Ser Met Gly Gly Thr Leu Asn Ile Lys Leu Asn Ser Ala Phe
    370                 375                 380

Leu Asp Ser Lys Leu Thr Ala Ala Glu Leu Lys Ala Trp Val Glu Ala
385                 390                 395                 400

Tyr Leu Ser Gly Gly Ile Ser Lys Glu Ile Tyr Ile His Ala Leu Lys
                405                 410                 415

Val Gly Lys Val Leu Pro Pro Gly Glu Ser Met Gly Val Ile Pro
            420                 425                 430

Asp Pro Pro Ala Pro Glu Pro Ser Pro Ser Asn Thr Pro Pro Asn Pro
        435                 440                 445

Ser Ser Lys Ala
    450

<210> SEQ ID NO 10
<211> LENGTH: 238
<212> TYPE: PRT
<213> ORGANISM: Phage P15

<400> SEQUENCE: 10

Met Lys Leu Lys Phe Lys Ile Gly Lys Leu Glu Asp Val Ala Glu Ala
1               5                   10                  15

Tyr Arg Asn Leu Tyr Ser Gln Gly Pro Asp Gly Ser Tyr Tyr Leu Asp
            20                  25                  30

Val Asp Gly Ala Val Asp Lys Ser Lys Leu Asp Glu Phe Arg Asp Asn
        35                  40                  45

Asn Val Ala Leu Arg Ala Gln Ile Glu Lys Phe Lys Asp Val Asp Pro
    50                  55                  60

Ala Lys Tyr Gln Glu Leu Met Ala Glu His Ala Lys Ile His Glu Gly
65                  70                  75                  80

Glu Leu Ile Lys Lys Gly Asp Val Glu Gly Leu Val Asn His Arg Thr
                85                  90                  95

Gln Thr Met Arg Thr Glu Tyr Glu Gly Lys Leu Asn Ser Leu Ser Lys
            100                 105                 110

Asn Tyr Glu Ile Ala Gln Arg Gln Leu Glu Thr Leu Thr Ile Asp Asn
        115                 120                 125

Val Val Arg Asp Arg Ser Ile Lys Leu Gly Val Ala Pro Thr Ala Val
    130                 135                 140

Glu Asp Val Leu Leu Arg Ala Lys Ser Val Phe Arg Val Glu Glu Gly
145                 150                 155                 160

Arg Pro Val Ala Lys Asp Pro Glu Gly Lys Ile Val Tyr Gly Lys Asn
                165                 170                 175

```
Gly Thr Asp Pro Met Asp Ile Gly Glu Trp Leu Gly Gly Leu Lys Asp
                180                 185                 190

Gln Ala Pro His Leu Phe Gln Pro Ser Thr Gly Ser Gly Gly Asn Gly
            195                 200                 205

Gly Asn Arg Gln Ala Gly Asn Gly Gly Glu Lys Leu Ser Ala Ala Gln
210                 215                 220

Lys Ile Ala Ser Gly Leu Ser Ser Gly Ser Thr Ile Met Gln
225                 230                 235

<210> SEQ ID NO 11
<211> LENGTH: 330
<212> TYPE: PRT
<213> ORGANISM: Phage P15

<400> SEQUENCE: 11

Met Val Arg Ile Cys Thr Pro Pro Leu Arg Gly Arg Trp Arg Thr Leu
1               5                   10                  15

Thr His Gln Phe Pro Glu Leu Lys Met Pro Thr Val Thr Leu Ala Glu
            20                  25                  30

Ser Ala Lys Leu Ser Gln Asp His Leu Val Ser Gly Leu Ile Glu Thr
        35                  40                  45

Ile Val Glu Val Asn Pro Leu Tyr Glu Met Met Pro Phe Thr Glu Ile
50                  55                  60

Glu Gly Asn Ala Leu Ala Tyr Asn Arg Glu Asn Val Leu Gly Asp Val
65                  70                  75                  80

Gln Phe Leu Ala Val Gly Gly Thr Ile Thr Ala Lys Asn Pro Ala Thr
                85                  90                  95

Phe Thr Lys Val Thr Ser Glu Leu Thr Thr Leu Ile Gly Asp Ala Glu
            100                 105                 110

Val Asn Gly Leu Ile Gln Ala Thr Arg Ser Asp Phe Met Asp Gln Thr
        115                 120                 125

Ser Val Gln Val Ala Ser Lys Ala Lys Ser Ile Gly Arg Gln Tyr Gln
130                 135                 140

Ala Ser Met Ile Thr Gly Asp Gly Thr Gly Asn Ser Phe Gln Gly Met
145                 150                 155                 160

Met Gly Leu Val Ala Ala Ser Gln Thr Ile Ser Ala Gly Ala Asn Gly
                165                 170                 175

Gly Thr Leu Thr Phe Glu Leu Leu Asp Gln Leu Leu Asp Leu Val Lys
            180                 185                 190

Asp Lys Asp Gly Gln Val Asp Tyr Leu Met Ser Ser Phe Ala Met Arg
        195                 200                 205

Arg Lys Tyr Phe Ser Leu Leu Arg Ala Leu Gly Ala Ala Ile Gly
210                 215                 220

Glu Val Met Thr Leu Pro Ser Gly Arg Gln Ile Pro Thr Tyr Arg Gly
225                 230                 235                 240

Val Pro Trp Phe Val Asn Asp Phe Ile Pro Ser Asn Met Thr Gln Gly
                245                 250                 255

Thr Ala Thr Asn Ala Thr Ala Ile Phe Ala Gly Thr Phe Asp Asp Gly
            260                 265                 270

Ser Asn Lys Tyr Gly Ile Ala Gly Leu Thr Ala Arg Gly Ser Ala Gly
        275                 280                 285

Leu Arg Val Gln Asn Val Gly Ala Lys Glu Asn Ala Asp Glu Thr Ile
290                 295                 300

Thr Arg Val Lys Met Tyr Cys Gly Phe Ala Asn Phe Ser Gln Leu Gly
305                 310                 315                 320
```

```
Leu Ala Ala Ile Lys Gly Leu Ile Pro Gly
            325                 330
```

<210> SEQ ID NO 12
<211> LENGTH: 159
<212> TYPE: PRT
<213> ORGANISM: Phage P15

<400> SEQUENCE: 12

```
Met Ala Lys Val Phe Val Thr Asp Arg Lys Asn Lys Gly Leu Glu Val
1               5                   10                  15

Val Ala Gly Lys Tyr Asn Phe Ile Asp Gly Ile Met Pro Val Ser Asp
            20                  25                  30

Ser Asp Ala Val Leu Leu Glu Pro Ile Leu Thr Arg Tyr Tyr Gly Ala
        35                  40                  45

Thr Leu Glu Asp Val Ala Ser Arg Thr Val Glu Asp Leu Asp Glu Thr
    50                  55                  60

Val Asp Ser Ser Ile Leu Ala Ala Gln Thr Lys Ala Ala Glu Leu Ala
65                  70                  75                  80

Gly Ser Gly Phe Ser Thr Asp Ala Ala Val Ala Ala Gly Lys Ala Ala
                85                  90                  95

Gly Asp Pro Ser Val Thr Gly Thr Val Ser Gly Ser Asp Ala Gly Glu
            100                 105                 110

Thr Ala Asp Asp Ile Asn Lys Gln Asn Glu Lys Ser Gly Gly Ala Thr
        115                 120                 125

Ala Thr Ala Thr Pro Thr Lys Val Glu Val Ala Asp Pro Lys Ala Thr
    130                 135                 140

Thr Gln Ala Ala Pro Ala Lys Pro Ala Ala Ala Asp Lys Lys
145                 150                 155
```

<210> SEQ ID NO 13
<211> LENGTH: 170
<212> TYPE: PRT
<213> ORGANISM: Phage P15

<400> SEQUENCE: 13

```
Met Pro Thr Val Asp Ala Thr Pro Gly Ser Ile Thr Ala Asn Ser Tyr
1               5                   10                  15

Val Thr Val Ala Glu Ala Asn Ser Tyr Phe Asp Gly Ser Tyr Gly Arg
            20                  25                  30

Pro Leu Trp Thr Ser Ala Ser Glu Asp Glu Lys Ala Ser Leu Val Ile
        35                  40                  45

Ser Ala Ser Arg Tyr Leu Asp Gln Met Met Ala Trp Ile Gly Ala Pro
    50                  55                  60

Thr Asn Pro Glu Gln Ser Met Trp Trp Pro Cys Lys Asn Ala Val Ile
65                  70                  75                  80

Gly Gly Met Thr Leu Ser Gln Val Ser Ile Pro Val Lys Val Lys Ile
                85                  90                  95

Ala Val Phe Glu Leu Ala Tyr Phe Met Leu Glu Ser Gly Ala Ala Leu
            100                 105                 110

Ser Phe Ala Asp Gln Thr Ile Asp Ser Val Lys Val Gly Thr Ile Arg
        115                 120                 125

Val Glu Phe Thr Lys Asn Ser Thr Asp Ala Gly Leu Pro Thr Phe Val
    130                 135                 140

Glu Ala Met Leu Ser Gly Phe Gly Ser Pro Val Leu Tyr Gly Ser Asn
145                 150                 155                 160
```

Ala Ala Arg Ser Ile Asp Leu Val Arg Ala
            165                 170

<210> SEQ ID NO 14
<211> LENGTH: 119
<212> TYPE: PRT
<213> ORGANISM: Phage P15

<400> SEQUENCE: 14

Met Ser Leu Ser Arg Gln Ile Phe Asn Ala Ile Arg Thr Ala Lys Arg
1               5                   10                  15

Ser Leu Gly Asp Met Ile Leu Thr Gly Gln Leu Ile Thr Tyr Thr Thr
            20                  25                  30

Glu Tyr Gln Asp Gly Glu Tyr Val Asn Val Gly Val Glu Arg Asn Ile
        35                  40                  45

Asp Ile Val Pro Asp Gln Phe Ser Tyr Glu Glu Leu Thr Ser Leu Asn
    50                  55                  60

Ile Asn Glu Ile Glu Val Lys Leu Leu Val Phe Asn Val Asn Asp Asp
65                  70                  75                  80

Leu Val Ile Lys Thr Glu Asp Lys Ile Arg Tyr Lys Gly Asp Glu Tyr
                85                  90                  95

Ser Ile Tyr Leu Val Lys Pro Glu Ser Val Gly Leu Leu Thr Pro Val
            100                 105                 110

Tyr Thr Val Met Leu Lys Lys
        115

<210> SEQ ID NO 15
<211> LENGTH: 121
<212> TYPE: PRT
<213> ORGANISM: Phage P15

<400> SEQUENCE: 15

Met Ile Ser Met Lys Phe Asn Val Asn Leu Ser Arg Leu Arg Ser Asn
1               5                   10                  15

Leu Arg Glu Glu Ala Lys Lys Ala Ile Arg Ile Ala Gln Glu Ile
            20                  25                  30

Val Asn Gly Val Ile Ala Arg Ser Pro Val Leu Ala Gly Asp Tyr Arg
        35                  40                  45

Ser Ser Trp Asn Val Ser Glu Gly Ser Met Glu Phe Lys Phe Asn Asn
    50                  55                  60

Gly Gly Asn Pro Ala Asn Pro Thr Pro Ala Pro Ala Ile Val Val Ser
65                  70                  75                  80

Ser Asn Val Ala Leu Pro His Phe Tyr Ile Thr Asn Gly Ala Pro Tyr
                85                  90                  95

Ala Gln Gln Leu Glu Lys Gly Ser Ser Thr Gln Ala Pro Leu Gly Ile
            100                 105                 110

Val Arg Val Thr Leu Ala Ser Leu Arg
        115                 120

<210> SEQ ID NO 16
<211> LENGTH: 125
<212> TYPE: PRT
<213> ORGANISM: Phage P15

<400> SEQUENCE: 16

Met Ser Tyr Phe Gln Glu Lys Leu Asp Ile Glu Asn Tyr Phe Lys Ala
1               5                   10                  15

Asn Trp Pro Asp Thr Pro Ile Phe Tyr Glu Asn Arg Thr Ala Asn Ser
            20                  25                  30

```
Thr Gly Thr Trp Val Arg Leu Thr Ile Gln Asn Gly Asp Ala Phe Gln
            35                  40                  45

Ala Ser Asn Gly Glu Val Ser Tyr Arg His Pro Gly Val Val Phe Val
 50                  55                  60

Gln Ile Phe Thr Lys Lys Glu Val Gly Ser Gly Glu Ala Leu Lys Leu
 65                  70                  75                  80

Ala Asp Lys Val Asp Ala Leu Phe Arg Ser Lys Thr Leu Gly Asn Ile
                 85                  90                  95

Gln Phe Lys Val Pro Gln Val Gln Lys Val Pro Ser Thr Thr Glu Trp
                100                 105                 110

Tyr Gln Val Asn Val Ser Thr Glu Phe Tyr Arg Gly Ser
                115                 120                 125

<210> SEQ ID NO 17
<211> LENGTH: 317
<212> TYPE: PRT
<213> ORGANISM: Phage P15

<400> SEQUENCE: 17

Met Ala Phe Gln Ala Gly Thr Ser Asn Arg Thr Ala Ile Cys Leu Val
 1               5                  10                  15

Lys Glu Val Thr Phe Asn Thr Thr Pro Ala Thr Pro Ala Phe Gln Ser
                20                  25                  30

Gln Arg Tyr Thr Ser Glu Asn Val Ala Phe Thr Lys Thr Val Thr
             35                  40                  45

Ser Ser Glu Ile Arg Ser Asp Arg Met Thr Ala Asp Leu Val Gln Val
 50                  55                  60

Gly Ala Ser Val Ala Gly Asp Val Asn Phe Glu Leu Ser Tyr Ala Ser
 65                  70                  75                  80

Phe Asp Glu Val Ile Arg Ala Ala Leu Ala Ser Ser Trp Ser Ala Pro
                 85                  90                  95

Ala Ser Gly Val Ser Thr Ile Val Asn Gly Thr Glu Leu His Ser Tyr
                100                 105                 110

Thr Phe Gln Lys Arg Phe Gln Asp Leu Ala Ala Pro Ile Tyr Gln Asn
                115                 120                 125

Phe Ser Gly Cys Arg Ile Gly Gly Leu Asn Leu Asn Phe Gln Thr Gly
130                 135                 140

Ala Ile Leu Thr Gly Ser Tyr Ser Val Met Gly Cys Lys Ala Leu Ser
145                 150                 155                 160

Gly Thr Thr Gln Ile Val Gly Ala Thr Thr Thr Ser Pro Gly Ala Gly
                165                 170                 175

Asn Glu Pro Met Asn Ser Val Gly Asn Leu Thr Ala Ile Thr Lys Asn
                180                 185                 190

Gly Thr Pro Met Ala Ala Lys Ile Arg Ser Thr Leu Ala Leu Asn
                195                 200                 205

Asn Asn Leu Arg Gly Gln Glu Ala Ile Gly Thr Leu Gly Tyr Ile Gly
                210                 215                 220

Ile Ala Leu Gly Arg Leu Glu Thr Gly Asn Ile Glu Ile Tyr Phe
225                 230                 235                 240

Glu Asn Ala Asp Glu Tyr Asn Thr Phe Leu Asn His Asp Phe Ala
                245                 250                 255

Phe Ser Phe Thr Val Thr Asp Ala Asp Leu Asn Ser Tyr Lys Phe Glu
                260                 265                 270

Leu Pro Arg Ile Lys Tyr Glu Thr Gly Thr Ile Val Ser Gly Gly Leu
                275                 280                 285
```

Asp Gln Asp Leu Met Ile Ser Gly Ser Trp Arg Ala Leu Phe Asp Ser
        290                 295                 300

Ala Ser Asn Ser Met Ile Lys Ile Thr Lys Thr Thr Ala
305                 310                 315

<210> SEQ ID NO 18
<211> LENGTH: 129
<212> TYPE: PRT
<213> ORGANISM: Phage P15

<400> SEQUENCE: 18

Met Phe Glu Ile Ser Glu Gln Pro Asn Glu Lys Leu Glu Glu Gly Val
1               5                   10                  15

Trp Ala Glu Tyr Gln Gly Gly Gln Phe Leu Ile Ala Tyr Ala Gly Gly
            20                  25                  30

Val Lys Phe Gln Arg Arg Met Thr Ala Leu Arg Lys Pro Phe Arg Arg
        35                  40                  45

Gln Glu Glu Arg Gly Asp Gln Ile Asp Pro Ala Val Leu Arg Lys Ile
    50                  55                  60

Thr Cys Gln Ala Ile Ser Glu Val Ile Leu Leu Asp Trp Lys Glu Val
65                  70                  75                  80

Ala Ser Lys Gly Glu Pro Val Pro Tyr Ser Arg Glu Met Ala Phe Lys
                85                  90                  95

Ala Leu Val Asn Asp Glu Arg Phe Arg Asn Phe Val Met Glu His Ser
            100                 105                 110

Met Glu Leu Gln Asn Phe Glu Gly Ser Glu Arg Glu Ile Glu Gly Asn
        115                 120                 125

Ser

<210> SEQ ID NO 19
<211> LENGTH: 85
<212> TYPE: PRT
<213> ORGANISM: Phage P15

<400> SEQUENCE: 19

Met Tyr Ser Trp Met Thr Glu Tyr Leu Leu Ala Phe Gln Val Leu Asn
1               5                   10                  15

Gln Thr Arg Gln Val Gly Phe Ser Ala Asn Pro Ile Pro Ile Ser Glu
            20                  25                  30

Ile Leu Ala Tyr Ile Gln Val Tyr Gly Ala Ser Asp Pro Lys Thr Leu
        35                  40                  45

Val Asp Tyr Ile Leu Glu Met Asp Gly Ala Tyr Leu Glu Met Arg Ala
    50                  55                  60

Lys Lys Ala Glu Lys Asn Lys Pro Pro Asp Lys Ala Pro Thr Pro Asn
65                  70                  75                  80

Gly Lys His Pro Ser
                85

<210> SEQ ID NO 20
<211> LENGTH: 1071
<212> TYPE: PRT
<213> ORGANISM: Phage P15
<220> FEATURE:
<221> NAME/KEY: misc_feature
<222> LOCATION: (195)..(195)
<223> OTHER INFORMATION: Xaa can be any naturally occurring amino acid
<220> FEATURE:
<221> NAME/KEY: misc_feature
<222> LOCATION: (198)..(198)
<223> OTHER INFORMATION: Xaa can be any naturally occurring amino acid -continued

```
<220> FEATURE:
<221> NAME/KEY: misc_feature
<222> LOCATION: (204)..(204)
<223> OTHER INFORMATION: Xaa can be any naturally occurring amino acid
<220> FEATURE:
<221> NAME/KEY: misc_feature
<222> LOCATION: (279)..(279)
<223> OTHER INFORMATION: Xaa can be any naturally occurring amino acid

<400> SEQUENCE: 20

Met Ala Asn Ile Gln Ala Asp Gly Thr Val Val Glu Val Asp Ser
1               5                   10                  15

Arg Thr Ala Asp Ala Gly Ile Ser Ala Ile Glu Arg Arg Phe Met Gln
            20                  25                  30

Leu Gly Thr Val Ala Gly Ala Ala Ile Asn Arg Ile Asn Ala Ala Phe
            35                  40                  45

Gln Thr Met Thr Arg Met Ala Gly Met Gly Gly Ala Ala Gly Gly
50                  55                  60

Gly Gly Gly Gly Gly Trp Gly Asn Phe Phe Asn Thr Leu Ile Asn
65                  70                  75                  80

Gly Ala Asn Gly Ala Ser Asn Ala Phe Gly Gly Arg Asn Gly Leu Asn
            85                  90                  95

Asn Ser Ile Ser Gly Phe Ser Ser Ala Ala Ser Lys Ala Ile Gly Tyr
            100                 105                 110

Ile Gly Gly Phe Tyr Ala Ile Arg Gly Leu Ile Gly Leu Met Thr Glu
            115                 120                 125

Phe Gly Asn Arg Met Ile Glu Val Asn Arg Thr Tyr Thr Gly Phe Ile
130                 135                 140

Ala Ser Met Ser Val Ile Lys Gly Thr Thr Glu Ala Ala Lys Glu
145                 150                 155                 160

Tyr Asp Trp Leu Met Ser Val Ser Asn Lys Leu Gly Ile Ser Val Glu
            165                 170                 175

Asp Ser Ile Thr Gln Phe His Arg Leu Ala Ala Ser Met Lys Asn Val
            180                 185                 190

Asp Ser Xaa Gly Glu Xaa Thr Arg His Leu Phe Xaa Gly Leu Ser Glu
            195                 200                 205

Ala Ala Val Val Leu His Ala Arg Gly Met Asp Val Ser Leu Met Phe
210                 215                 220

Ala Ala Val Gln Gln Ile Ala Ser Lys Gly Lys Leu Ser Leu Glu Glu
225                 230                 235                 240

Leu Gln Arg Gln Leu Gly Asn Thr Leu Pro Gly Ala Met Ala Leu Ser
            245                 250                 255

Ala Arg Ala Met Met Gly Ser Ala Ser Phe Met Ala Lys Gly Ile Thr
            260                 265                 270

Asn Val Cys Glu Ala Glu Xaa Glu Leu Arg Thr Gln Ile Ser Lys Gly
275                 280                 285

Thr Ile Asn Ala Tyr Glu Phe Leu Ala Arg Phe Ala Asn Gln Leu Lys
            290                 295                 300

Lys Glu Tyr Gly Asp Ala Thr Asp Tyr Ala Ser Asp Lys Phe Thr Ala
305                 310                 315                 320

Asn Phe Asn Arg Met Arg Asn Ser Val Phe Glu Leu Tyr Arg Thr Val
            325                 330                 335

Gly Ser Ser Gly Ala Met Asp Gly Leu Thr Lys Val Val Lys Glu Leu
            340                 345                 350

Thr Gly Leu Phe Gly Asp Ser Gln Ser Gly Ala Ala Gln Gly Leu Gly
            355                 360                 365
```

```
Lys Gly Leu Gly Glu Leu Phe Asp Gly Leu Ala Gly Tyr Leu Ser Asn
    370                 375                 380

Leu Asp Ala Lys Asp Val Val Ser Phe Phe Ala Ala Phe Gln Gly Ala
385                 390                 395                 400

Ile Gln Ala Thr Thr Ile Val Met Thr Gln Leu Ile Gly Thr Val Gly
                405                 410                 415

Asp Leu Thr Gly Glu Thr Glu Thr Asn Pro Leu Leu Leu Phe Val Glu
            420                 425                 430

Gly Val Ser Arg Ala Phe Ala Gly Leu Ala Asp Val Ile Lys Gly Val
            435                 440                 445

Ala Leu Gly Leu Ala Asn Leu Tyr Asn Gly Ala Asn Leu Ala Leu Ala
    450                 455                 460

Gly Leu Ala Lys Ala Ser Thr Ala Pro Gly Glu Met Val Gly Asn Ala
465                 470                 475                 480

Val Asp Arg Val Gly Ala Met Phe Gly Val Thr Met Pro Gly Lys Asp
                485                 490                 495

Val Arg Asp Lys Asn Arg Gly Met Ala Ala Asp Ala Asn Ala Trp Phe
            500                 505                 510

Tyr Glu Ala Gln Lys Gln Asn Leu Asn Gly Met Ala Ala Ser Glu Asp
    515                 520                 525

Phe Val Asn Gly Asn Asn Ala Ser Thr Lys Thr Arg Asp Leu Phe Asp
530                 535                 540

Ala Ala Lys Lys Arg Ala Asn Ala Thr Ser Thr Ala Lys Ala Gly Thr
545                 550                 555                 560

Thr Ala Asp Ala Ala Ser Tyr Val Asn Pro Leu Gly Asp Met Asp
                565                 570                 575

Leu Gln Lys Gln Ile Glu Gly Ile Leu Ala Asn Ser Ser Ser Pro Asn
    580                 585                 590

Ala Thr Lys Thr Lys Thr Lys Lys Asp Pro Val Gln Ser Asn Tyr Leu
                595                 600                 605

Arg Glu Thr Thr Arg Leu Leu Lys Gly Ile Ser Glu Ala Glu Asn Glu
    610                 615                 620

Tyr Ser Asn Val Met Asp Asn Arg Tyr Arg Ser Gln Gly Lys Asn Glu
625                 630                 635                 640

Thr Gln Met Lys Ser Leu Met Ala Thr Asp Glu Arg Tyr Val Lys Leu
                645                 650                 655

Ser Ala Glu Lys Lys Ala Thr Leu Met Ala Leu Met Asp Tyr Ala Arg
            660                 665                 670

Gln Leu Asp Ala Ala Ser Leu Lys Val Glu Asn Ala Lys Lys Val Gln
    675                 680                 685

Asp Ala Tyr Phe Asp Ser Leu Gln Arg Gly Phe Asp Ala Gln Asp Arg
            690                 695                 700

Met Asn Glu Leu Gln Ser Thr Gly Phe Gln Ser Gln Phe Arg Glu Glu
705                 710                 715                 720

Ser Lys Ala Arg Asn Ser Phe Lys Arg Gly Asp Asn Glu Phe Met
                725                 730                 735

Ser Glu Ala Asp Lys Ala Gln Ile Leu Gln Ser Ala Ile Thr Asp Asp
            740                 745                 750

Ile Asn Asp Arg Met Val Ala Tyr Gln Thr Gln Thr Glu Glu Ile Arg
        755                 760                 765

Asn Ala Asn Lys Glu Ser Glu Phe Gln Ala Ser Leu Ile Gly Lys Ser
    770                 775                 780

Ala Leu Glu Val Glu Lys Leu Thr Lys Phe Arg Glu Ile Asp Leu Ala
785                 790                 795                 800
```

Thr Ser Arg Leu Leu Val Gly Ala Ser Asp Glu Gln Ile Gln Lys Tyr
            805                 810                 815

Gln Lys Met Ala Glu Val Leu Lys Asp Glu Val Gly Ala Ser Leu Asp
            820                 825                 830

Glu Val Tyr Gln Lys Gln Thr Asp Ala Phe Gly Met Glu Gln Ala
            835                 840                 845

Leu Thr Asp Tyr Arg Asp Ser Ala Leu Asn Phe Gly Gln Glu Phe Gly
            850                 855                 860

Gly Ala Met Thr Ser Thr Leu Gly Asn Leu Glu Ser Ala Met Val Asp
865                 870                 875                 880

Phe Thr Thr Lys Gly Lys Leu Ser Phe Ser Ser Leu Ile Asn Ser Ile
            885                 890                 895

Met Ala Asp Leu Val Lys Leu Ala Ala Arg Gln Met Ile Ser Ser Ile
            900                 905                 910

Ala Gly Ser Leu Met Gly Ala Phe Met Gly Pro Ser Val Gly Ala Ser
            915                 920                 925

Gly Ala Ala Ala Val Thr Ser Gly Thr Gln Gly Ile Asn Gln Gln Leu
            930                 935                 940

Ala Gly Arg Phe Ala Lys Gly Gly Asp Phe Thr Asn Gln Ile Val Ser
945                 950                 955                 960

Thr Pro Thr Leu Phe Arg Phe Ala Asn Gly Ser Lys Met Gly Glu Met
            965                 970                 975

Gly Glu Ala Gly Pro Glu Ala Ile Met Pro Leu Lys Arg Ala Lys Asn
            980                 985                 990

Gly Glu Leu Gly Val Val Leu Ala Glu Ser His Ala Pro Arg Thr Gly
            995                 1000                1005

Ser Gly Met Gly Asp Val Ile Ile Asn Asn Tyr Thr Asp Ser Glu
            1010                1015                1020

Val Ser Ala Gln Lys Thr Thr Gln Lys Gly Pro Gln Gly Glu Met
            1025                1030                1035

Met Glu Ala Trp Val Val Ser Val Val Ala Lys Asp Met Ala Asn
            1040                1045                1050

Gly Gly Lys Thr Ala Lys Ala Ser Lys Asn Arg Phe Gly Leu Lys
            1055                1060                1065

Glu Thr Ala
    1070

<210> SEQ ID NO 21
<211> LENGTH: 123
<212> TYPE: PRT
<213> ORGANISM: Phage P15

<400> SEQUENCE: 21

Met Ala Ser Leu Pro Ser Tyr Val Ile Ile Ser Pro Ala Gly Tyr Gln
1               5                   10                  15

Glu Asp Phe Asp Pro Ser Val Ser Met Thr Glu Met Glu Arg Gly Ser
            20                  25                  30

Pro Lys Tyr Arg Val Lys Asn Ser Arg Val Leu Met Lys Ile Asn Met
            35                  40                  45

Arg Phe Val Phe Asp Lys Lys Ala Asp Ala Ala Ser Phe Phe Asn Trp
        50                  55                  60

Tyr Met Met Glu Val Lys Arg Ile Leu Pro Phe Thr Met Thr His Pro
65                  70                  75                  80

Arg Thr Gly Gln Gln Ile Glu Val Gln Phe Glu Ala Gly Lys Ile Gly
            85                  90                  95

```
Pro Leu Thr Pro Ile Asp Thr Leu Leu Glu Asn Thr Tyr Arg Asp Val
            100                 105                 110

Ile Val Glu Tyr Leu Val Ala Pro Gly Ser Gln
            115                 120

<210> SEQ ID NO 22
<211> LENGTH: 153
<212> TYPE: PRT
<213> ORGANISM: Phage P15

<400> SEQUENCE: 22

Met Ser Thr Phe Lys Glu Arg Lys Gln Arg Val Arg Asp Pro Ser Gly
1               5                   10                  15

Leu Leu Ile Leu Met Glu Leu Ser Ala Asn Ser Phe Gln Glu Thr Leu
            20                  25                  30

Arg Ile Ala Asn Asp Thr Asp Asn Trp Thr Ser Asn Gly Leu Leu Tyr
        35                  40                  45

Tyr Gly Phe Pro Phe Lys Phe Thr Gly Pro Asp Asp Ser Asp Gly Ser
    50                  55                  60

Asn Ala Ser Ser Lys Ile Val Ile Asp Asn Thr Gly Arg Gly Met Ser
65                  70                  75                  80

Asp Asp Leu Glu Ser Leu Gln Pro Asn Glu Ile Ile Leu Val Lys Leu
                85                  90                  95

Met Ile Thr Asp Phe Tyr Asn Pro Ser Ala Ile Ile Arg Thr Leu Tyr
            100                 105                 110

Leu Pro Met Met Gly Ala Thr Ile Arg Val Thr Gln Met Glu Gly Arg
        115                 120                 125

Cys Gly Val Asp Tyr Ile Met Arg Gln Arg Ser Val Gln Leu Ala Ser
    130                 135                 140

Ser Pro Tyr Thr Ala Pro Gly Ser Tyr
145                 150

<210> SEQ ID NO 23
<211> LENGTH: 121
<212> TYPE: PRT
<213> ORGANISM: Phage P15

<400> SEQUENCE: 23

Met Asp Ala Tyr Lys Leu Asp Pro Phe Val Gly Val Lys Phe Asn Lys
1               5                   10                  15

Asp Thr Met Asp Cys Ala Asp Leu Val Met Lys Ile Arg Arg Glu Leu
            20                  25                  30

Phe Asp His Asp Ile Ile Leu Pro Gln Gly His Pro Arg Gly Pro Leu
        35                  40                  45

Asn Phe Arg Gln Ile Gly Asp Leu Ser Lys Ala Phe Ala Glu Leu Thr
    50                  55                  60

Thr Arg Pro Glu Asp Gly Asp Leu Val Leu Met Lys Gly Gly Thr
65                  70                  75                  80

Glu Phe Pro Gly His Val Gly Val Trp Phe Phe Val Ala Tyr Val Pro
                85                  90                  95

Tyr Val Leu His Val Thr Glu Lys Leu Lys Phe Ser Met Leu Asp Lys
            100                 105                 110

Leu Ser Asp Leu Pro Asp Arg Gly Leu
        115                 120

<210> SEQ ID NO 24
<211> LENGTH: 1339
```

```
<212> TYPE: PRT
<213> ORGANISM: Phage P15

<400> SEQUENCE: 24
```

Met Glu Val Ile Asp Lys Thr His Gln Val Ile Val Ser Pro His Pro
1               5                   10                  15

Val Val Val Asp Asp Gln Lys Asn Leu Ile Leu Ala Phe Lys Gln Gly
                20                  25                  30

Glu Ser Leu Phe Glu Ile Leu Ser Arg Ser Val Asp Asn Phe Glu Glu
            35                  40                  45

Arg Glu Trp Val Val Thr Ile Asn Gly Arg Arg Val Pro Val Glu Met
        50                  55                  60

Trp Thr Lys Ala Phe Pro Lys Pro Gly His Ile Ile Glu Val Arg Gly
65                  70                  75                  80

Asn Val Gly Lys Gln Ala Leu Tyr Ile Ile Ala Met Ile Ala Leu Thr
                85                  90                  95

Tyr Phe Thr Phe Gly Ile Gly Thr Ala Ala Gly Trp Gly Ala Gly Ala
            100                 105                 110

Ala Ala Gly Ala Phe Gly Gly Val Ala Gly Ala Leu Phe Ala Ser
        115                 120                 125

Ala Val Phe Val Ala Gly Ser Met Ile Ile Asn Lys Val Leu Gly Pro
130                 135                 140

Lys Ala Gln Asp Ile Arg Gly Ser Asn Pro Asp Ser Val Tyr Ser Ile
145                 150                 155                 160

Gly Ala Ser Arg Asn Gln Lys Arg Pro Tyr Glu Pro Phe Pro Tyr Val
                165                 170                 175

Ile Gly Arg Val Lys Val Leu Pro Asp Val Ile Ser Asp Ala Tyr Ser
            180                 185                 190

Trp Tyr Glu Gly Asn Asp Gln Tyr Val Gly Phe Val Leu Thr Pro Gly
        195                 200                 205

Leu Asn Val His Asp Val Glu Thr Leu Tyr Ile Gly Asp Thr Pro Ile
210                 215                 220

Thr Asn Tyr Glu Gly Val Thr Leu Tyr Tyr Asn Gly Phe Ser Gly Arg
225                 230                 235                 240

Pro Asp Gln Asp Ile Pro Leu Tyr Ser Asn Ala Asp Phe Val Asp Gly
                245                 250                 255

Ala Thr Leu Pro Asn Thr Gly Ala Trp Val Thr Arg Thr Thr Ser Ile
            260                 265                 270

Asp Thr Val Arg Val Met Ile Asn Leu Glu Tyr Ile Leu Gly Gly Gln
        275                 280                 285

Gly Thr Ser Gly Lys Ser Tyr Thr Val Ser Glu Thr Ile Phe Val Glu
290                 295                 300

Tyr Lys Pro Val Gly Ser Gln Thr Trp Ser Gln Leu Ile Thr Arg Arg
305                 310                 315                 320

Tyr Ser His Gln Asp Phe Glu Thr Leu Arg Ala Thr Leu Ser Ala Glu
                325                 330                 335

Leu Pro Arg Gly Gln Tyr Asp Ile Arg Val Arg Met Gln Gly Glu Gly
            340                 345                 350

Asn Tyr Glu Gly Lys Asn Thr Gln Arg Asn Asp Phe Asn Phe Thr Gln
        355                 360                 365

Leu Val Ser Val Gln Phe Asp Gly Ala Asp Tyr Asp Gly Ile Pro Arg
370                 375                 380

Ile Gly Val Lys Ile Arg Ala Thr Asp Gln Leu Asn Gly Ala Pro Asp
385                 390                 395                 400

```
Thr Ile Asn Cys Val Ala Ile Ser Lys Pro Val Pro Val Trp Asp Gly
                405                 410                 415

Phe Gln Trp Val Thr Gln Thr Thr Gly Asn Ile Gly Ala Asn Met Leu
            420                 425                 430

Ala His Cys Arg Gly Ile Thr Ser Arg Ser Gly Arg Lys Ile Ile Gly
        435                 440                 445

Ile Gly Leu Gln Asp Glu Leu Ile Asn Ile Glu Asn Phe Lys Ala Phe
    450                 455                 460

Met Leu His Cys Thr Ala Asn Asn Tyr Glu Tyr Asn Tyr Cys Val Arg
465                 470                 475                 480

Gly Ser Arg Ser His Ala Glu Gln Leu Glu Val Met Ala Leu Ala Gly
                485                 490                 495

Phe Ala Asp Ile Ser Trp Ala Gly Gly Lys Leu Ala Pro Ile Trp Thr
            500                 505                 510

Ala Asp Gly Gln Pro Leu Asn Gly Val Val Asn Met Ala Thr Ile Thr
        515                 520                 525

Asp Thr Gln Phe Gln Ile Asp Tyr Thr Leu Ala Asn Ala Ala Asp Gly
    530                 535                 540

Val Glu Tyr Thr Tyr Tyr Asp Asp Val Thr Trp Glu Pro Leu Thr Leu
545                 550                 555                 560

Arg Val Pro Met Pro Gly Asn Thr Gly Gly Ile Leu Asn Pro Ile Ser
                565                 570                 575

Ile Ser Gly Glu Gly Val Ile Lys Glu Ala His Ala Ala Glu Leu Ala
            580                 585                 590

Arg Phe His Leu Ala Gln Ser Leu Tyr Gln Ser Lys Asp Ile Thr Tyr
        595                 600                 605

Thr Thr Asp Val Glu Phe Leu Ser Tyr Lys Arg Tyr Asp Val Leu Ala
    610                 615                 620

Val Gln His Asp Leu Thr Gln Tyr Gly Phe Gly Gly Arg Leu Val Gly
625                 630                 635                 640

Gly Asp Tyr Asp Phe Val Leu Asp Ala Arg Arg Asn Ile Lys Leu Gln
                645                 650                 655

Ile Asp Asp Met Val Arg Pro Pro Ser Gly Val Asp Ser Tyr Val
            660                 665                 670

Gly Val Arg Ile Pro Gly Glu Asp Ala Tyr Arg Val Phe Thr Val Lys
        675                 680                 685

Pro Phe Ala Gln Glu Met Asp Val Leu Tyr Leu Val Glu Ala Trp Pro
    690                 695                 700

Ser Asp Ala Pro Phe Pro Gly Glu Ser Leu Glu Asn Pro Asp Asp
705                 710                 715                 720

Phe Leu Trp Ile Phe Asp Phe Lys Ala Thr Pro Gly Leu Arg Ser Arg
                725                 730                 735

Val Ala Ala Ile Ser Pro Gly Asp Asp Phe Glu Thr Ala Gln Ile Ser
            740                 745                 750

Val Val Pro Glu Pro Glu Tyr Trp Thr Phe Ile Lys Thr Gly Val
        755                 760                 765

Tyr Asn Pro Pro Val Arg Gln Ser Leu Leu Gln Thr Arg Pro Val Ala
    770                 775                 780

Ser Asn Leu Ala Val Ser Glu Val Gln Val Gln Gly Asn Thr Val
785                 790                 795                 800

Tyr Thr Glu Leu Arg Ala Val Phe Asp Ile Ser Gly Asp Ile Gly Tyr
                805                 810                 815

Thr Arg Val Tyr Ser Asp Leu Asp Gly Asn Gly Thr Leu Glu Glu Val
            820                 825                 830
```

-continued

```
Ala Asn Thr Arg Thr Arg Thr Ala Ser Trp Arg Ile Pro Gly Ala Gly
            835                 840                 845

Thr Tyr Ala Ile Val Val Arg Pro Phe Asn Pro Gln Gly Val Pro Gly
        850                 855                 860

Ile Ala Val Ser Thr Thr Tyr Val Thr Ile Asn Ala Asp Ala Ala Pro
865                 870                 875                 880

Ala Leu Val Asp Asn Leu Leu Ile Glu Glu Leu Thr Gly Gly Val Arg
                885                 890                 895

Arg Tyr Ser Trp Ser Phe Asp Asp Thr Thr Met Gln Ser Pro Asp Phe
            900                 905                 910

Ile Gly Val Gln Ile Arg Tyr Leu Gly Gly Ser Val Gly Asp Pro Asn
            915                 920                 925

Trp Val Asp Met Ile Pro Leu Gly Glu Gly Thr His Thr Ala Thr Phe
        930                 935                 940

Glu Ser Ile Leu Pro Pro Ala Gly Ala Trp Thr Phe Ala Val Arg Ser
945                 950                 955                 960

Val Asn Ser Ser Gly Ser Leu Ser Ser Met Arg Ile Val Asn Lys
                965                 970                 975

Thr Leu Thr Asp Ser Leu Gly Glu Arg Val Val Lys Ile Gln Asp
            980                 985                 990

Phe Ser Leu Asn Glu Gln Arg Leu Leu Glu Thr Ile Glu Glu Val Asp
            995                 1000                1005

Gln Tyr  Ser Glu Ser Val Ile  Gln Gln Ala Ile  Asn Ile Ser Glu
         1010                 1015                 1020

Ile Asn  Gly Arg Val Val Gln  Asn Arg Ser Phe Ile  Ser Leu Leu
         1025                 1030                 1035

Gln Asp  Thr Ala Val Thr Glu  Asp Ser Ala Lys Thr  Leu Ile Thr
         1040                 1045                 1050

Gln Gln  Val Gly Ala Gln Thr  Gly Asp Leu Arg Ala  Thr Val Glu
         1055                 1060                 1065

Gln Thr  Phe Gly Ala Val Thr  Asn Ile Asn Gly Glu  Leu Ser Ala
         1070                 1075                 1080

Tyr Ala  Asn Thr Lys Val Gln  Thr Thr Ile Asp Gly  Lys Lys Tyr
         1085                 1090                 1095

Leu Ala  Gly Ile Gly Leu Gly  Ile Asp Ala Ser Gly  Gly Val Ala
         1100                 1105                 1110

Gln Ser  Glu Ile Ala Ile Leu  Ala Asp Arg Phe Val  Phe Leu Asn
         1115                 1120                 1125

Ser Thr  Ala Gly Gly Asn Tyr  Tyr Tyr Pro Phe Glu  Ile Val Asn
         1130                 1135                 1140

Gly Val  Val Tyr Ala Asn Ala  Ala Met Ile Arg Asp  Gly Thr Ile
         1145                 1150                 1155

Thr Asn  Ala Lys Ile Gly Glu  Glu Ile Lys Ser Val  Asn Tyr Gln
         1160                 1165                 1170

Trp Asp  Gly Ala Asn Gly Ile  Tyr Ile Gly Trp Arg  Ile Gly Lys
         1175                 1180                 1185

Asp Gly  Thr Ala Gln Phe Gly  Gly Asp Val Glu Ile  Arg Gly Asn
         1190                 1195                 1200

Val Ser  Ala Asn Ser Ile Thr  Gly Thr Phe Glu Ser  Ala Val Ala
         1205                 1210                 1215

Val Asp  Tyr Ser Gly Asn Leu  Ala Thr Gly Val Thr  Ser Val Phe
         1220                 1225                 1230

Thr Leu  Pro Pro Pro Leu Lys  Val Thr Glu Ser His  Arg Pro Glu
```

```
                1235                1240                1245

Leu  Thr  Leu  Ala  Ile  Gln  Leu  Gln  Thr  Gly  Asp  Gly  Gln  Asp  Ala
          1250                1255                1260

Thr  Ser  Cys  Phe  Ile  Thr  Leu  Gln  Arg  Glu  Asn  Pro  Asn  Asn  Pro
          1265                1270                1275

Gly  Glu  Trp  Trp  Asn  Ile  Thr  Ser  Arg  Glu  Tyr  Ala  Ile  Phe  Lys
          1280                1285                1290

Phe  Met  Asn  Ile  Ser  Thr  Ala  Phe  Met  Phe  Leu  Asp  Ala  Trp  Thr
          1295                1300                1305

Asn  Val  Ala  Asn  Asn  Phe  Arg  Phe  Ser  Ile  Thr  Gln  Gly  Ser  Gly
          1310                1315                1320

Gln  Asp  Val  Arg  Ile  Thr  Arg  Ile  Asn  Gly  Arg  Ile  Arg  Gly  Ala
          1325                1330                1335

Arg

<210> SEQ ID NO 25
<211> LENGTH: 873
<212> TYPE: PRT
<213> ORGANISM: Phage P15

<400> SEQUENCE: 25

Met  Ala  Asp  Pro  Gly  Tyr  Leu  Ser  Asn  Ala  Glu  Leu  Ala  Asn  Gln  Val
1                   5                   10                  15

Val  Ala  Leu  Val  Gln  Lys  Tyr  Asn  Val  Phe  Thr  Asp  Gln  Met  Asp
              20                  25                  30

Phe  Phe  Thr  Ser  Ala  Asp  Asp  Thr  Val  Val  Ile  His  Asn  Pro  Asn  Gly
              35                  40                  45

Asp  Pro  Ile  Thr  Val  Pro  Ser  Leu  Lys  Ser  Ile  Leu  Glu  Ala  Ala  Gly
50                  55                  60

Pro  Val  Ala  Ser  Gly  Asp  Leu  Ser  Val  Tyr  Asp  Ser  Val  Glu  Glu  Gly
65                  70                  75                  80

Val  Ala  Ser  Val  Ile  Asp  Gly  Ala  Tyr  Phe  Phe  Val  Ser  Ile  Val  Asn
              85                  90                  95

Gly  Thr  Tyr  Leu  Gly  Leu  Phe  Lys  Arg  Ser  Ala  Asn  Leu  Gly  Ile  Glu
              100                 105                 110

Ile  Gly  Arg  Tyr  Pro  Ser  Ser  Arg  Val  Asp  Asn  Ser  Val  Asn  Asp  Leu
              115                 120                 125

Ala  Ser  Ala  Met  Glu  His  Ala  Asp  Ala  Ile  Met  Met  Thr  Pro  Phe  Asn
130                 135                 140

Glu  Phe  Asp  Leu  Asp  Thr  Val  Lys  Gln  Met  Ser  Asn  Ser  Gly  Asn  Gly
145                 150                 155                 160

Phe  Asn  Thr  Val  Met  Asp  Glu  Tyr  Val  Asn  Asn  Leu  Gln  Phe  Asp  Val
              165                 170                 175

Ala  Arg  Ala  Asn  Ile  Glu  His  Thr  Val  Ala  Asp  Asp  Leu  Gly  Ala  Met
              180                 185                 190

Pro  Ser  Ile  Lys  Thr  Val  Met  Val  Trp  Thr  Gln  Trp  Phe  Ser  Leu  Cys
              195                 200                 205

Asp  Ser  Thr  Glu  Gly  Leu  Asn  Pro  Gly  Val  Val  Gln  Pro  Ala  Ile  Asn
              210                 215                 220

Gly  Gly  Ile  Tyr  Gly  Lys  Leu  Leu  Asn  Thr  Asn  Gln  Trp  Met  Ser  Gly
225                 230                 235                 240

Asn  Val  Thr  Ala  Pro  Asn  Ala  Leu  Lys  Leu  Gln  Gly  Asp  Ala  Gly  Gly
              245                 250                 255

Ser  Gln  Asn  Asp  Met  Ser  Met  Ile  Arg  Gly  Met  Lys  Tyr  Met  Gln  Ala
              260                 265                 270
```

```
Arg Gly Tyr Asp Ile Gly Met Val Pro Ile Val Leu Gly Trp Val Asn
            275                 280                 285
Gln Ala Gly Leu Pro Asn Ser Gln Ser Leu Val Trp Arg Gly Phe Phe
            290                 295                 300
Arg Trp Asp Thr Thr Ala Lys Phe Gln Thr Trp Ile Asn Ser Tyr Lys
305                 310                 315                 320
Ala Phe Leu Val His Tyr Ile Asn Leu Phe Gln Ala Asn Gly Ile Ser
                325                 330                 335
Pro Thr Arg Trp Leu Val Gly Ser Glu Phe Asp Arg Ile Ile Thr Val
            340                 345                 350
Ser Thr Pro Glu Gln Trp Gly Ile Phe Val Glu Ala Cys Lys Glu Leu
            355                 360                 365
Ala Gly Gln Ile Lys Ala Ala Phe Pro Ala Cys Lys Val Thr Tyr Ala
            370                 375                 380
Ala Asn Tyr Ser Asp Tyr Gly Val Gly Gly Lys Phe Arg Leu Asp Ala
385                 390                 395                 400
Leu Trp Ser His Pro Asn Ile Asp Glu Val Gly Ile Glu Trp Tyr Phe
                405                 410                 415
Arg Leu Ser Asp Asn Pro Asn Val Gly Asn Glu Gly Leu Ile Gln Gly
            420                 425                 430
Gln Met Ala Gly Glu Asp Val Asp Tyr Thr Tyr Asn Leu Ser Asp Asp
            435                 440                 445
Asn Gln Arg Lys Leu Ile Gly Ser Asn Gly Arg Gly Lys Leu Asp Glu
450                 455                 460
Thr Arg Val Pro Met Gly Ala Asn Ala Gly Ile Lys Asn Val Gln Gly
465                 470                 475                 480
Phe Trp Asn Gly Cys His Tyr Ile Glu Lys Phe Ala Gly Ser Leu Ala
                485                 490                 495
Met Ala Thr Pro Thr Pro Gly Phe Ser Ala Asp Tyr Ala Pro Phe Asn
            500                 505                 510
Leu Lys Thr Met Gln Gly Thr Gly Gln Val Ile Ala Pro Ala Asp Ser
            515                 520                 525
Pro Leu Thr Ser Gly Gln His Pro Glu Pro Phe Leu Arg Ser Thr Tyr
            530                 535                 540
Phe Gln Thr Asn Gly Ser Thr Thr Trp Gly Glu Phe Lys Thr Pro Val
545                 550                 555                 560
Phe Thr Gly Gly Asn Gln Ser Ser Trp Arg Met Glu Val Asp Phe Gln
                565                 570                 575
Gly Thr Gln Ala Pro Ser Gly Asn Tyr Ala Arg Pro Phe Arg Leu Gly
            580                 585                 590
Gly Ala Ile Glu Phe Leu Val Asp Thr Gly Thr Leu Lys Phe Gly Ile
            595                 600                 605
Gly Pro Asp Gly Asn Gln Tyr Phe Ala Asp Ile Gly Pro Phe Asn Thr
            610                 615                 620
Ala Ala His Ser Leu Val Ala Thr Leu Asp Arg Asn Ser Gly Met Leu
625                 630                 635                 640
Thr Ile Val Tyr Asp Gly Ile Thr Ser Gln Tyr Ser Ile Pro Val Ala
                645                 650                 655
Gln Arg Ser Ala Ile Pro Ser Thr Thr Ala Tyr Leu Gly Gly Tyr
            660                 665                 670
Asn Thr Asn Ser Asn Met Ala Ala Met Arg Phe Tyr Lys Leu Gly Leu
            675                 680                 685
Thr Phe Val Arg Asp Gly Ile Thr Trp Gly Gly Thr Phe Trp Phe Asp
```

-continued

```
                690                 695                 700
Glu Ser Tyr Ala Gly Thr Arg Thr Ala Trp Val Pro Arg Met Lys Lys
705                 710                 715                 720

Leu Ser Ala Thr Glu Leu Gly Tyr Ala Ser Ile Ser Gly Thr Ser Val
                725                 730                 735

Glu Pro Ser Gln Phe Val Tyr Ala Asp Ile Gly Thr Thr Pro Pro Thr
            740                 745                 750

Leu Pro Ser Phe Ile Asp Asp Thr Thr Arg Ala Leu Phe Asn Ser Phe
                755                 760                 765

Phe Ala Arg Ser Trp Tyr Pro Ala Gln Ile Tyr Ala Ser Tyr Gly Ser
770                 775                 780

Ser Phe Asn Tyr Asp Pro Phe Glu Gln Ala Ala Ile Arg Glu Thr
785                 790                 795                 800

Cys Arg Phe Met Ala Ala Leu Arg Arg Gly Ala Phe Glu Ser Ile
                805                 810                 815

Cys Ile Tyr Asn Ile Asp Ala Arg Pro Ser Lys Ala Phe Thr Ala Ile
                820                 825                 830

Leu Gln Asn Lys Phe Tyr Tyr Ser Asp Ala Pro Thr Met Ile Phe Ser
            835                 840                 845

His Ala Val Asn Gly Lys Leu Ala Gly Gly Ser Thr Phe His Glu
        850                 855                 860

Leu Ile Thr Lys Gln Gly Lys Ile Ala
865                 870

<210> SEQ ID NO 26
<211> LENGTH: 155
<212> TYPE: PRT
<213> ORGANISM: Phage P15

<400> SEQUENCE: 26

Met Phe Ala Leu Ser Gln Lys Ser Gln His Ile Leu Asp Thr Val Gln
1               5                   10                  15

His Pro Leu Arg Asp Val Val Arg Leu Ala Ile Thr Arg Thr Thr Val
                20                  25                  30

Asp Phe Gly Val Ile Gln Gly Gly Arg Thr Leu Asp Glu Gln Met Arg
            35                  40                  45

Leu Tyr Gly Lys Gly Arg Asn Ala Ala Glu Cys Ala Lys Met Gly Val
50                  55                  60

Pro Ala Ala Tyr Ala Lys Pro Lys Glu Ser Lys Val Thr Trp Val Asn
65                  70                  75                  80

Pro Arg Asn Gly Asn His Val Val Asp Gly Ser Gly Phe Gly Arg Ala
                85                  90                  95

Val Asp Leu Ala Pro Tyr Ile Gln Gly Lys Leu Glu Trp Asp Asn Asp
            100                 105                 110

Gly Lys Leu Gly Leu Tyr Pro Lys Ile Ala Glu Ala Met Phe Ser Ala
        115                 120                 125

Ala Asn Glu Leu Gly Ile Gln Ile Val Trp Gly Gly Asn Trp Lys Ser
    130                 135                 140

Thr Pro Asp Arg Pro His Phe Glu Leu Ala Lys
145                 150                 155

<210> SEQ ID NO 27
<211> LENGTH: 179
<212> TYPE: PRT
<213> ORGANISM: Phage P15

<400> SEQUENCE: 27
```

```
Met Ser Trp Ala Ser Arg Ser Tyr Gly Val Glu Ile Gly Ser Leu Arg
1               5                   10                  15

Pro Ile Ala Arg Thr Ser Asn Trp Arg Asn Asp Lys Met Tyr Ala Lys
            20                  25                  30

Leu Leu Phe Ala Ala Gly Ala Ala Thr Thr Ala Ile Gln Val Ala
        35                  40                  45

Ala Glu Ala Pro Thr Ser Lys Glu Trp Ala Phe Ile Asp Val Thr Val
50                  55                  60

Ala Tyr Val Gly Val Pro Phe Asn Val Leu Ile Met Ala Ala Ile Gly
65                  70                  75                  80

Ser Ile Ile Ala Val Met Arg Asn Arg Val Ser Asp Pro Arg Thr Leu
                85                  90                  95

Ile Val Ser Phe Leu Tyr Ser Thr Leu Phe Ala Leu Gly Ala Ser Val
                100                 105                 110

Gly Ile Ala Glu Phe Thr Gly Tyr Gln Trp Ser Ser Thr Gly Ala Gln
            115                 120                 125

Ala Ile Phe Thr Ala Ile Leu Gly Phe Thr Ala Gln Asn Trp Gly Pro
        130                 135                 140

Val Leu Leu Asp Asn Ile Ala Pro Ala Val Asp Leu Trp Leu Lys Arg
145                 150                 155                 160

Gln Ile Lys Arg Ile Phe Asn Ile Ser Ile Glu Asp Lys Lys His Asp
                165                 170                 175

Asp Ser Gln

<210> SEQ ID NO 28
<211> LENGTH: 110
<212> TYPE: PRT
<213> ORGANISM: Phage P15

<400> SEQUENCE: 28

Met Met Thr Pro Asn Glu Ile Pro Val Trp Ser Leu Leu Thr Thr Pro
1               5                   10                  15

Ser Leu Ile Val Phe Phe Leu Thr Gly Leu Tyr Gly Val Asn Glu Trp
            20                  25                  30

Arg Leu Arg Pro Val Arg Gln Ile Val Gly Lys Arg Gly Leu Val Glu
        35                  40                  45

Leu Gly Leu Gly Leu Ser Leu Gly Thr Met Cys Val Leu Ser Phe Val
    50                  55                  60

Thr Leu Ile Ala Val Ile Met Met Ala Asn Leu Tyr Ser Trp Arg Gly
65                  70                  75                  80

Cys Leu Leu Leu Thr Ser Ile Ala Gly Val Leu Leu Thr Val Gly Arg
                85                  90                  95

His Ala Pro Trp Arg Phe Trp Ile His Arg Phe Pro Glu Asn
            100                 105                 110

<210> SEQ ID NO 29
<211> LENGTH: 109
<212> TYPE: PRT
<213> ORGANISM: Phage P15

<400> SEQUENCE: 29

Met Thr Pro Asn Glu Ile Pro Val Trp Ser Leu Leu Thr Pro Ser
1               5                   10                  15

Leu Ile Val Phe Phe Leu Thr Gly Leu Tyr Gly Val Asn Glu Trp Arg
            20                  25                  30

Leu Arg Pro Val Arg Gln Ile Val Gly Lys Arg Gly Leu Val Glu Leu
```

```
                35                  40                  45
Gly Leu Gly Leu Ser Leu Gly Thr Met Cys Val Leu Ser Phe Val Thr
 50                  55                  60

Leu Ile Ala Val Ile Met Met Ala Asn Leu Tyr Ser Trp Arg Gly Cys
 65                  70                  75                  80

Leu Leu Leu Thr Ser Ile Ala Gly Val Leu Thr Val Gly Arg His
                 85                  90                  95

Ala Pro Trp Arg Phe Trp Ile His Arg Phe Pro Glu Asn
            100                 105

<210> SEQ ID NO 30
<211> LENGTH: 148
<212> TYPE: PRT
<213> ORGANISM: Phage P15

<400> SEQUENCE: 30

Met Pro Ile Leu Ala Gln Ile Lys Ala Tyr Ser Glu Val Ile Lys Leu
 1               5                  10                  15

Val Val Leu Gly Ala Leu Val Ile Ile Leu Gly Ile Leu Cys Tyr Val
                20                  25                  30

Ala Trp Ser Ser Tyr Gln Asp Gly Gln Asp Ala Lys Val Leu Ser Gly
             35                  40                  45

Val Leu Ala Gln Lys Ala Glu Asp Thr Ala Gly Val Gln Asn Ala Leu
 50                  55                  60

Thr Gly Ala Gln Ala Gln Pro Ala Val Ile Glu His Arg Ile Leu Glu
 65                  70                  75                  80

Thr Arg Thr Gln Tyr Ile Thr Gln Tyr Glu Lys Leu Lys Asn Glu Asp
                 85                  90                  95

Ala Ile Val Ala Glu Phe Ala Asn Thr Ala Val Pro Asp Ser Leu Arg
            100                 105                 110

Lys Leu Ala Cys Glu Arg Arg Val Ala Arg Asp Gly Leu Thr Asp Thr
        115                 120                 125

Gln Gly Gly Cys Gln Arg Phe Gly Lys Gly Ala Thr Asp Phe Gly Ala
    130                 135                 140

Asn Pro Thr Pro
145

<210> SEQ ID NO 31
<211> LENGTH: 181
<212> TYPE: PRT
<213> ORGANISM: Phage P15

<400> SEQUENCE: 31

Met Pro Arg Lys Ser Asn His Ile Met Val Asp Leu Glu Thr Met Asp
 1               5                  10                  15

Thr Ala His Thr Ala Ala Ile Leu Ser Ile Gly Ala Cys Lys Val Asp
                20                  25                  30

Leu Asp Thr Gly Glu Ile Ser Asp Lys Phe Tyr Arg Val Val Asn Cys
             35                  40                  45

Asp Ser Ser Ser Ala Leu Gly Leu Thr Thr Ser Ser Ala Thr Lys Ser
 50                  55                  60

Trp Trp Asp Lys Gln Ser Pro Glu Ala Arg Lys Val Phe Thr Asp Pro
 65                  70                  75                  80

Asn Ile Pro Val Ile Gln Ala Leu Gly Glu Phe Ala Thr Tyr Leu Arg
                 85                  90                  95

Ile Phe Gly Val Asn Ser Val Lys Leu Trp Gly Asn Gly Ser Asp Phe
            100                 105                 110
```

```
Asp Asn Thr Ile Leu Thr Thr Ala Tyr Asn Leu Ala Gly Ser Pro Ile
            115                 120                 125

Pro Trp Arg Phe Tyr Asn Asn Arg Cys Phe Arg Thr Ile Arg Lys Ser
130                 135                 140

Leu Gly His Met Val Ala Glu Pro Ala Arg Glu Gly Thr Tyr His Asn
145                 150                 155                 160

Ala Leu Asp Asp Ala Ile Tyr Gln Ala Lys Ile Leu Ala Leu Phe Gly
            165                 170                 175

Lys Tyr Ile Gly Glu
            180

<210> SEQ ID NO 32
<211> LENGTH: 77
<212> TYPE: PRT
<213> ORGANISM: Phage P15

<400> SEQUENCE: 32

Met Glu Arg Ile Thr Asp Glu Ser Asp Leu Ala Ser Lys Leu Glu Glu
1               5                   10                  15

Leu Ala Lys Glu Asp Ala Ile Gln Lys Val Leu Arg Asp Gly Lys Val
                20                  25                  30

Pro Ser Asp Trp Val Ser Pro Asp Cys Tyr Asp Cys Asp Gln Glu Ile
            35                  40                  45

Pro Lys Asp Arg Leu Ala Thr Gly Ala Phe Arg Cys Ile His Cys Gln
50                  55                  60

Thr Lys Phe Glu Phe Asn Gln Arg Asn Tyr Lys Gly Arg
65                  70                  75

<210> SEQ ID NO 33
<211> LENGTH: 389
<212> TYPE: PRT
<213> ORGANISM: Phage P15
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid

<400> SEQUENCE: 33

Met Phe Ser His Ser Gln Ser Ala Ser Arg Pro Ser Lys Val Ile His
1               5                   10                  15

Gln Thr Ala Leu Ala Arg Ser Ile Cys Arg Ser Lys Ile Met Asp Glu
                20                  25                  30

Val Lys Leu Tyr Xaa Lys Asn Val Asn Ser Ile Gly Thr Trp Arg Ile
            35                  40                  45

Phe Pro Ile Tyr Glu Glu Gly Thr Ile Asn Ile Ala His Ala Thr Xaa
50                  55                  60

Gln Gly Gly Ser Glu Val Trp His Thr Glu Val Thr Arg Asn Gln
65                  70                  75                  80

Ser Gly Ser Ser Leu His Glu Gln Ile Asp Leu Arg Ile Lys Ser His
                85                  90                  95

Ile Ser Arg Met Arg Asp Lys Gly Tyr Lys Asp Thr Val Gln Glu Ala
                100                 105                 110

Ile Asp Asn Pro Gly Asn Gln Leu Gly Leu Asp Arg Pro Met Leu Ala
            115                 120                 125

Lys Gln Ile Gly Lys Val Lys Asn Val Asn Phe Ser Gln Gly Leu Leu
```

```
            130                 135                 140
Gln Lys Lys Leu Asp Gly His Arg Cys Leu Val Thr Leu Asp Gly Ala
145                 150                 155                 160

Glu Pro Leu Ala Tyr Ser Arg Leu Gly Lys Pro Ile Pro Ala Ile Arg
                165                 170                 175

His Ile Leu Arg Ala Leu Lys Asn Arg Leu Pro Pro Gly Thr Thr Leu
            180                 185                 190

Asp Gly Glu Leu Tyr Cys His Gly Ile Lys Leu Gln Thr Ile Gly Ser
                195                 200                 205

Trp Ile Lys Arg Glu Gln Ala Asp Thr Ala Arg Leu His Tyr Val Val
210                 215                 220

Tyr Asp Leu Ile Ser Glu Asp Ser Tyr Val Asp Arg His Lys Glu Leu
225                 230                 235                 240

Ser Glu Ile Ile Ala Gly Val Asp Thr Gly Thr Pro Gly Lys Val Leu
                245                 250                 255

Ala Leu Pro Tyr Arg Pro Tyr Glu Ser Ala Glu Thr Asn Arg Tyr
                260                 265                 270

Phe Arg Glu Val Arg Gly Gln Gly Tyr Glu Gly Leu Met Leu Arg Leu
                275                 280                 285

Asn Gly Ala Gly Tyr Gln Pro Gly Val Arg Ser Ser His Leu Leu Lys
290                 295                 300

Ile Lys Glu Phe Glu Asp Ala Glu Phe Arg Val Gly Phe Ser Gln
305                 310                 315                 320

Ser Lys Thr Gly Trp Ala Val Cys Arg Cys Val Thr Glu Thr Gly Arg
                325                 330                 335

Glu Phe Asp Cys Ser Ala Pro Gly Ser Val Ser Glu Lys Gln Asp Val
                340                 345                 350

Trp Asp Asn Gln Gly Lys Tyr Leu Gly Arg Ser Leu Thr Ile Glu Phe
                355                 360                 365

Ala His Trp Thr Asp Asp Gly Ile Pro Phe Gln Pro Thr Ala Ile Arg
                370                 375                 380

Trp Arg Glu Asp Val
385

<210> SEQ ID NO 34
<211> LENGTH: 268
<212> TYPE: PRT
<213> ORGANISM: Phage P15

<400> SEQUENCE: 34

Met Thr Tyr Thr Gln Thr Asn Ala Ile Asn Asp Ala Lys Arg Val His
1               5                   10                  15

Lys Ile Val Ala Thr Gly Val Ala Pro Gln Ala Val Ala Ala Arg
                20                  25                  30

Ala Val His Asn Leu Lys Gln Leu Val Glu His Ala Thr Gly Ile Thr
            35                  40                  45

Tyr Val Pro Glu Gln Glu Ser Leu Thr Trp Gln Asp Lys Tyr His Asn
        50                  55                  60

Val Asn Ala Leu Ala Asn Gln Lys Met Glu Lys Ile Ala Glu Leu Gln
65                  70                  75                  80

Asn Glu Val Ala Arg Leu Arg Glu Gly Leu Asn Ser Ala His Asp Leu
                85                  90                  95

Ile Lys His Leu Asp Glu Lys Ser Lys Pro Glu Thr Val Val Asn Ile
            100                 105                 110

Leu His Lys Ala Asn Asp Ile Ile Tyr Gly Asp Arg Glu Lys Ala Tyr
```

```
              115                 120                 125
Gly Ser Pro Arg Phe Asn Leu Asp Thr Ile Ala Gln Leu Trp Ser Val
130                 135                 140

Tyr Met His Arg Arg Phe His Ser Trp Gly Ile Asp Gly Leu Lys Ile
145                 150                 155                 160

Glu Ala Glu Asp Val Ser Gln Leu Met Ile Leu Lys Thr Ala Arg
                165                 170                 175

Leu Ile Ser Asn Pro Thr His Ala Asp Ser Leu Thr Asp Gln Ala Gly
                180                 185                 190

Tyr Ala Ala Leu Gln His Arg Ile Asn Thr Pro Glu Ser Glu Ser Lys
                195                 200                 205

Ile His Cys Gly Ser Asn Leu Ser Glu Lys Val Val Asp Glu Val Ala
        210                 215                 220

Lys Asp Ala Ser Lys Gly Val Thr Leu Asp Asp Ala Leu Arg Ala Phe
225                 230                 235                 240

Gly Asp Glu Met Val Lys Leu Asn Val His Phe Gly Glu Val Pro Phe
                245                 250                 255

Glu Glu Val His Gly Arg Lys Lys Asn Met Thr Lys
                260                 265

<210> SEQ ID NO 35
<211> LENGTH: 63
<212> TYPE: PRT
<213> ORGANISM: Phage P15

<400> SEQUENCE: 35

Met Lys Arg Phe Leu Leu Gln Asn Leu Gly Ala Leu Gly Glu Ala Gly
1               5                   10                  15

Lys Ser Leu Phe Ser Thr His Gly Thr Asp Tyr Ala Thr Gln Leu Ile
                20                  25                  30

Glu Glu Gly Trp Val Pro Cys Gly Met Cys Ile Asn Gln His Asn Glu
            35                  40                  45

Val Ile Gln Thr Phe Tyr Lys Pro Leu Thr Glu Glu Val Glu Ser
        50                  55                  60

<210> SEQ ID NO 36
<211> LENGTH: 160
<212> TYPE: PRT
<213> ORGANISM: Phage P15

<400> SEQUENCE: 36

Met Met Ala Met Ala Met Leu Ala Ala Ser Arg Gly Thr Cys Lys Arg
1               5                   10                  15

Arg Gln Val Gly Cys Ile Leu Val Asp Asp Leu Asn His Val Leu Ala
                20                  25                  30

Thr Gly Tyr Asn Gly Thr Pro Arg Asn Val Ala His Cys Gly Ser His
            35                  40                  45

Ile Cys Pro Gly Met Asn Ala Ser Ser Gly Thr Gln Leu Asp Gly Cys
        50                  55                  60

Met Ala Thr His Ala Glu Gln Asn Ala Leu Leu Gln Cys Met Asp Val
65                  70                  75                  80

Glu Lys Ile His Thr Val Tyr Cys Thr Thr Gln Pro Cys Leu Thr Cys
                85                  90                  95

Thr Lys Leu Leu Met Asn Thr Gly Ala Lys Trp Ile Val Tyr Leu Asp
            100                 105                 110

Ala Tyr Pro Asn Ser Gly Arg Asp Leu Trp Leu Ser Ser Gly Arg Asn
        115                 120                 125
```

Met Cys Thr Val Ser Leu Gln Glu Lys Val Gln Leu Gln Gln Leu Phe
            130                 135                 140

His Met Leu Ala Glu Arg Ser Asp Ser Ala Leu Ile Thr Ser Ala Lys
145                 150                 155                 160

<210> SEQ ID NO 37
<211> LENGTH: 273
<212> TYPE: PRT
<213> ORGANISM: Phage P15

<400> SEQUENCE: 37

Met Ser Tyr His Asn Ala Thr Leu Ser Ala Leu Arg Asp Leu Met Leu
1               5                   10                  15

Arg Thr Phe Thr Gln Gly Phe Val Ser Lys Pro Arg Gly Met Glu Ile
            20                  25                  30

Arg Glu Leu Leu Asn Ala Gln Val Thr Val Gln Thr Phe Val Pro Phe
        35                  40                  45

Gln Cys Trp Pro Asp Arg Lys Tyr Asp Ile Gly Tyr Phe Lys Lys Glu
    50                  55                  60

Met Arg Trp Lys Leu Gly Ala Ser Lys Phe Asp Asp Ser Ile Lys Gln
65                  70                  75                  80

His Ala Lys Met Trp Glu Ser Val Gln Asn Pro Asp Gly Thr Phe Asn
                85                  90                  95

Ser Asn Tyr Gly Gln Phe Trp Phe Gly Gln Gln Met Gly Val Met Lys
            100                 105                 110

Val Val Met Glu Leu Ile Arg Asp Gln Asp Ser Arg Arg Ala Ile Ile
        115                 120                 125

Pro Met Leu Thr Asp Asp His Leu Ser Pro Glu Thr Val Asp Thr Val
    130                 135                 140

Cys Thr Glu Ala Val Ser Phe His Ile Arg His Asn Thr Leu Tyr Thr
145                 150                 155                 160

Ser Val His Met Arg Ser Ser Asp Gln Ile Phe Gly Leu Gly Thr Asp
                165                 170                 175

Ile Pro Thr Phe Ser Val Leu Thr His Leu Val His Gly Leu Leu Gln
            180                 185                 190

Ala Asn Tyr Pro Ser Leu Gln Val Gly Ser Met Thr Ile Thr Ala Ala
        195                 200                 205

Ser Ser His Ile Tyr Glu Arg His Tyr Arg Met Val Asp Lys Ile Leu
    210                 215                 220

Asp Asn Leu Glu Asp Ile Pro Asp Ser Glu Ile Val Ile Leu Pro Gln
225                 230                 235                 240

Cys Ser Gly Pro Asp Glu Ala Met Ala Ile Ala His Arg Gly Ile
                245                 250                 255

Ala Gln Arg Leu Pro Ala Ser Trp His Leu Tyr Arg Phe Ile Tyr Gly
            260                 265                 270

Asp

<210> SEQ ID NO 38
<211> LENGTH: 160
<212> TYPE: PRT
<213> ORGANISM: Phage P15

<400> SEQUENCE: 38

Met Ala Ile Ile Leu Glu Gly Phe Asp Asn Ser Gly Lys Thr Ser Leu
1               5                   10                  15

Ser Ser Leu Phe Gly Leu Pro Ile Leu His Pro Gly Pro Arg Pro Arg

-continued

```
                20                  25                  30
Thr Leu Glu Ala Val Leu Asp Cys Ile His Leu Gln Gln Glu Gln Ala
            35                  40                  45
Thr Gln His Val Val Met Asp Arg Val Thr Ala Ile Ser His Asn Ala
        50                  55                  60
Tyr Cys Phe Asp Tyr Pro Asp Pro Lys Tyr Leu Phe Arg Arg Ser Met
65                  70                  75                  80
Asp Leu Val Gln Thr Glu Gly Val Val Leu Ile Tyr Cys Arg Pro Pro
                85                  90                  95
Thr Glu Val Met Leu Asp Phe Ser Arg His Asn Val Lys Asp His Asp
            100                 105                 110
Thr Glu Ala His Leu Ala Trp Leu Lys Lys Phe Gly Ser Glu Ile Ile
        115                 120                 125
Ile Arg Tyr Asp Ala Ile Met Ser Gln Leu Pro His Leu Thr Tyr Asp
130                 135                 140
Tyr Thr Asn Pro Asn Pro Asn Ile Val Ser Leu Ala Leu Gly Gly Lys
145                 150                 155                 160
```

<210> SEQ ID NO 39
<211> LENGTH: 139
<212> TYPE: PRT
<213> ORGANISM: Phage P15

<400> SEQUENCE: 39

```
Met Asn Thr Tyr Ser His Ala Glu Lys Pro Lys Asp Phe Thr His Ala
1               5                   10                  15
Ile Phe Gln Phe Asn Lys Gln Val Leu Asn Leu Asn Glu Pro Glu Leu
            20                  25                  30
Arg Leu Leu Asn Ala Gln Glu Leu Glu Trp Ser Lys Lys Ala Val Leu
        35                  40                  45
Glu Glu Leu Glu Glu Phe Ile Gln Ala His Arg Gln Gln Asp Phe Val
    50                  55                  60
Gly Ala Val Asp Ala Val Gly Asp Leu Val Tyr Phe Ala Ile Gly Phe
65                  70                  75                  80
Phe Phe Arg Met Gly Leu Thr Pro Asp Gln Val Asn Gln Val Met Met
                85                  90                  95
Ala Ile Asn Asp Ala Asn Met Glu Lys Lys Leu Gly Lys Val Ala Ala
            100                 105                 110
Arg Asn Ile Asp Gly Val Ala Asp Ala Thr Lys Pro Glu Gly Trp Val
        115                 120                 125
Gly Pro Glu Glu Arg Ile Ala Ala Ile Leu Gly
    130                 135
```

<210> SEQ ID NO 40
<211> LENGTH: 547
<212> TYPE: PRT
<213> ORGANISM: Phage P15

<400> SEQUENCE: 40

```
Met Thr Tyr Ala Leu Ala Ile Ser Leu Gly His Asn Ser Ser Ala Ile
1               5                   10                  15
Leu Ile Gln Asp Gly Val Val Leu Ala Gly Tyr Glu Glu Arg Phe
            20                  25                  30
Ser Gly Val Lys Ser Asp Ser Lys Phe Pro Tyr Gln Ser Ile Leu Glu
        35                  40                  45
Leu Lys Arg Arg Phe Asp Leu Pro Ser Asp Thr Asp Ser Phe Val Gly
    50                  55                  60
```

```
His Trp Phe Leu Asp Ala Gln Leu Pro Ala Pro Asn Lys Tyr Trp Asp
 65                  70                  75                  80

Pro Asp Phe Leu Arg Ser His Phe Pro Asn Gly Ser Ile Asp Ser Leu
                 85                  90                  95

Asn Ala Asp Phe Thr His His Asp Ser His Leu Ala Ser Ala Met Val
            100                 105                 110

Phe Ala Gly Glu Glu Trp Ser Asp Lys Ser Tyr Thr Ala Val Val Ala
            115                 120                 125

Asp Gly Phe Gly Ser Tyr Gly Glu Cys Leu Thr Ile Tyr Ala Val Thr
130                 135                 140

Gly Gln Ser Tyr Ser Val Lys His Arg Val Phe Gly Phe Glu Lys Ser
145                 150                 155                 160

Leu Gly Met Leu Tyr Gln Tyr Ala Thr Ala Phe Met Gly Met Lys Met
                165                 170                 175

His Asn His Glu Tyr Lys Met Leu Ala Tyr Glu Val His Ile Gly Glu
            180                 185                 190

Val Leu Asp Val Asp Gln Ile Asp Arg Leu Asp His Met Val Lys Thr
            195                 200                 205

Gln Ala Ser His Tyr Leu Lys Met Phe Gln Ser Asn Lys Ile Thr Asn
210                 215                 220

Glu Phe Asp Pro Val Thr Glu Ile Ser Ala Leu Pro Asn Val Gln Glu
225                 230                 235                 240

Lys Ile Asn Asp Leu Leu Ser Lys Val Leu Val Asp Leu Gly Met Ala
                245                 250                 255

Glu Ala Ala Asn Ser Asp Asp Arg Thr Lys Arg Ile Ile Ile Ser Tyr
            260                 265                 270

Phe Val Gln His Val Val Glu Ala Val Met Val Thr Met Val Gln Met
            275                 280                 285

Tyr Asn Asp Arg Ser Asn Leu Leu Val Val Gly Gly Leu Phe Tyr Asn
290                 295                 300

Val Lys Leu Asn His Leu Leu Ala Asn Ser Ile Lys Gly Gln Leu Cys
305                 310                 315                 320

Val Met Pro Leu Ala Gly Asp Gln Gly Ala Ala Leu Gly Val Tyr Gln
                325                 330                 335

Ala Tyr His Gly Asp Leu Thr Trp Pro Glu His Leu Phe Trp Gly Asp
            340                 345                 350

Arg Asn Leu Asp Pro Leu Glu Phe Ile Asn Val Pro Gly Met Val Val
            355                 360                 365

Val Thr Glu Ser Gln Ala Phe Ala Glu Ile Ala Ser Tyr Ile Ser Thr
370                 375                 380

His Gly Trp Val Asn Val Val Arg Gly Ala Met Glu Phe Gly Pro Arg
385                 390                 395                 400

Ser Leu Cys His Thr Ala Thr Leu Ser Leu Pro His Ala Gln Phe Ala
                405                 410                 415

Glu Glu Ile Asn Phe Ala Asn Asp Arg Thr Ala Glu Met Pro Met Ala
            420                 425                 430

Pro Val Met Thr Leu Asp Gln Ala Arg Asp Cys Phe Tyr Asp Ile Asp
            435                 440                 445

Lys Ile His Lys Ser Ala Glu Tyr Met Ile Val Ala Arg Gln Tyr Gln
450                 455                 460

Ala Gly Val Gly Ser Gln Leu Ser Gly Ala Ala His Trp Tyr Pro Lys
465                 470                 475                 480

Glu Lys Val Phe Thr Gly Arg Pro Gln Ile Thr Arg Asp Pro Leu Met
```

```
                            485                 490                 495
Val Ser Leu Leu Glu Glu Phe Gly Pro Leu Ile Asn Thr Ser Phe Asn
                500                 505                 510

Tyr His Gly Val Pro Ile Val Arg Ser Pro Glu Gln Ile Ile Asp Thr
            515                 520                 525

His Arg Lys Gln Tyr Glu Arg Asn Pro Lys Val Leu Thr Ile Ile Val
        530                 535                 540

Val Lys Asp
545

<210> SEQ ID NO 41
<211> LENGTH: 276
<212> TYPE: PRT
<213> ORGANISM: Phage P15

<400> SEQUENCE: 41

Met Ala Ser Gln Gln Ile Ser Ile Pro Glu His Leu Lys Lys Phe Leu
1               5                   10                  15

Thr Asn Ser Gly Thr Ser Ser Asp Ala Asp Ala Met Ala Ala Ala Ser
            20                  25                  30

Val Ser Ile Pro Arg Ile Ser Leu Arg Gly Arg Lys Phe Arg Leu Val
        35                  40                  45

Glu Gly Gly Glu Glu Ile Arg Lys Pro Ala Asp Glu Leu Leu Cys Val
    50                  55                  60

Ile Leu Ala Val Glu Pro Gly Ala Gly Leu Met Gln Lys Thr Phe Tyr
65                  70                  75                  80

Ala Lys Gly Tyr Val Ser Gly Glu Ser Ala Pro Pro Asp Cys Ala Ser
                85                  90                  95

Ser Asn Gly Val Thr Pro Asp Ala Trp Ile Ser Asp Pro Val Ser Ala
            100                 105                 110

Lys Cys Asn Gly Cys Pro Lys Asn Val Phe Gly Ser Ala Thr Ser Thr
        115                 120                 125

Asn Gly Lys Lys Thr Lys Ala Cys Lys Asp Ser Lys Arg Leu Trp Val
    130                 135                 140

Val Glu Pro Asp Asn Ile Asn Gly Thr Val Phe Ala Leu Gly Ile Pro
145                 150                 155                 160

Val Thr Ser Leu Lys Ala Met Ser Glu Tyr Gly Ala Met Leu Lys Ser
                165                 170                 175

Asn Gly Val Pro Ala Ala Ser Val Ile Thr Arg Leu Ser Met Lys Asp
            180                 185                 190

Ser Glu Phe Pro Glu Leu Glu Phe Ala Phe Ala Gly Val Leu Ser Glu
        195                 200                 205

Glu Pro Met Glu Gln Ala Met Leu Arg Asn Glu Gln Lys Asn Trp Asp
    210                 215                 220

Leu Lys Ser Ser Ala Pro Met Leu Glu His Asp Thr Gly Pro Lys Gln
225                 230                 235                 240

Pro Met Lys Ala Pro Gly Ala Asp Ala Leu Leu Glu His Lys Ala Ala
                245                 250                 255

Ala Ala Glu Pro Gly Val Thr Thr Ser Thr Val Ser Val Asp Glu Ala
            260                 265                 270

Thr Gly Asn Trp
        275

<210> SEQ ID NO 42
<211> LENGTH: 148
<212> TYPE: PRT
```

<213> ORGANISM: Phage P15

<400> SEQUENCE: 42

Met Ser Glu Asp Lys Val Ala Lys Val Thr Tyr Pro Asp Val Pro Glu
1               5                   10                  15

Asp Ile Asn Phe Asn Thr Ile Ser Gln Ala Val Glu Val Tyr Val Ala
                20                  25                  30

Thr Arg Asp Gln Leu Ala Ala Glu Arg Lys Ala Tyr Asn Ser Tyr Glu
            35                  40                  45

Leu Arg Ala Lys Ala Tyr Met Glu Arg Ile Ser Met Tyr Leu Arg Asp
50                  55                  60

Lys Ala Asp Glu Met Gly Val Asp Ser Phe Lys Thr Gln Ala Gly Thr
65                  70                  75                  80

Ala Tyr Arg Ser Val Lys Thr Gln Tyr Arg Val Gly Ser Phe Asp Gln
                85                  90                  95

Phe Val Glu Trp Met Lys Ala Thr Glu Asn Phe His Cys Leu Glu Lys
            100                 105                 110

Arg Ala Ala Lys Asn Ala Val Lys Glu Ile His Glu Thr Gly Glu
        115                 120                 125

Val Pro Pro Gly Leu Glu Phe Tyr Ser Glu Val Glu Phe Asp Val Arg
130                 135                 140

Arg Pro Ser Lys
145

<210> SEQ ID NO 43
<211> LENGTH: 587
<212> TYPE: PRT
<213> ORGANISM: Phage P15

<400> SEQUENCE: 43

Met Lys Trp Leu Lys His Leu Lys Ala Gly Leu Lys Thr Gly Ser Thr
1               5                   10                  15

Glu Pro Asp Lys Ser Gln Ala Asn Ser Thr Lys Leu Ser Lys Asp Pro
                20                  25                  30

Ser Gly Ser Ile Asn His Gln Val Glu Cys Ser Glu Ala Leu Glu Arg
            35                  40                  45

Arg Ile Ala Tyr Leu Cys Gly Asp Arg Ser Ser Leu Asp Trp Lys Ser
50                  55                  60

Arg Leu Lys Ala Ala Ser Gln Leu Leu Ser Ser Leu Lys Val Ser Val
65                  70                  75                  80

Gln Leu Gly Met Gln Ala Glu Leu Gln Pro Ser Leu Trp Gly Lys Thr
                85                  90                  95

Thr Tyr Gly Phe Phe Lys Ser Thr Pro Gln Leu Trp Gln Arg Ser Asp
            100                 105                 110

Met Thr Leu Arg Val Pro Phe Ser Glu Tyr Ala Trp Pro Met Ala Asn
        115                 120                 125

Lys Asn His Lys Pro Phe Asp His Gln Lys Arg Thr Ala Val Phe Leu
130                 135                 140

Leu Gln Asn Lys Arg Ala Tyr Asn Phe Ser Asp Leu Gly Thr Gly Lys
145                 150                 155                 160

Thr Leu Ser His Leu Trp Cys Ala Asp Phe Leu Met Val Asn Glu Lys
                165                 170                 175

Ile Lys Lys Val Leu Ile Ile Gly Pro Leu Ser Thr Leu Lys Ser Val
            180                 185                 190

Trp Gly Arg Glu Ile Phe Leu Asn Phe Pro His Arg Arg Tyr Ser Ile
        195                 200                 205

Ala His Gly Thr Gln Pro Glu Arg Leu Ala Leu Arg Ala Lys Val
    210                 215                 220

Glu Phe Val Ile Thr Asn His Asp Ala Val Thr Ile Pro Val Val Glu
225                 230                 235                 240

Gly Glu Ile Ile Lys Gln Ile Lys Ser Gly Ile Gly Leu Val Ile
                245                 250                 255

Ile Asp Glu Leu Thr Ala Tyr Lys Lys His Thr Thr Lys Arg Ser Lys
            260                 265                 270

Ala Met Gln Arg Ile Ala Asn Ala Cys Gly Asp Lys Val Gly Val His
        275                 280                 285

Gly Ile Thr Gly Ala Pro Thr Pro Asn Arg Ala Thr Glu Ala Phe Gly
    290                 295                 300

Gln Ala Lys Val Val Asn Pro Lys Asn Arg His Leu Pro Arg Tyr Tyr
305                 310                 315                 320

Lys Gln Phe Gln Met Met Val Glu Tyr Gln Val Gly Pro Tyr Leu Trp
                325                 330                 335

Leu Pro His Glu Gly Ala Asn Glu Ile Ala Asn Lys Ile Leu Gln Pro
            340                 345                 350

Ala Ile Arg Phe Lys Arg Asp Cys Ile Asp Ile Pro Asp Cys Gln
        355                 360                 365

Tyr Ile Thr Gln Val Val Glu Phe Thr Pro Glu Gln Lys Lys Met Tyr
    370                 375                 380

Glu Lys Met Lys Ser Asp Leu Leu Val Glu Tyr Glu Ala Gly Glu Ile
385                 390                 395                 400

Thr Ala Val Asn Ala Ala Val Lys Ala Met Lys Leu Leu Gln Ile Ala
                405                 410                 415

Ser Gly Ala Val Lys Asp Asp Glu Gly Arg Ile Val Lys Val Asp Ala
            420                 425                 430

Ser Thr Arg Glu Asp Ala Leu Trp Glu Ile Phe Glu Gly Thr Gly Glu
        435                 440                 445

Thr Lys Leu Val Ile Phe Ala Ala Phe Arg Ala Thr Ile Asp His Leu
    450                 455                 460

Val Gly Tyr Phe Gln Asp Arg Asn Val Lys Val Ala Thr Ile Asn Gly
465                 470                 475                 480

Asp Val Pro His Ala Leu Arg Ala Lys His Val Gln Asp Phe Gln Asp
                485                 490                 495

Ser Asp Leu Gln Val Leu Ile Ile Gln Pro Gln Ser Ser Ala His Gly
            500                 505                 510

Ile Thr Leu Thr Ala Ser Cys Thr Ile Val Trp Tyr Ser Leu Val Pro
        515                 520                 525

Ser Gly Glu Ile Tyr Val Gln Ala Asn Gly Arg Ile Thr Arg Ala Gly
    530                 535                 540

Gln Ser Arg Lys Gln Thr Ile Tyr His Leu Ile Gly Cys Arg Pro Glu
545                 550                 555                 560

Arg His Val Leu Asp Ile Leu Glu Gly Lys Val Ser Thr Ser Gln Asn
                565                 570                 575

Leu Leu Glu Met Phe Glu Leu Leu Lys Asp Ser
            580                 585

<210> SEQ ID NO 44
<211> LENGTH: 123
<212> TYPE: PRT
<213> ORGANISM: Phage P15

<400> SEQUENCE: 44

Met Asn Pro Ile Cys Pro Tyr Cys Asn Ala Val Ser Glu Leu Val Leu
1               5                   10                  15

Gly Arg Arg Ile Tyr Pro His Ile Pro Ser Ile His Ser Lys Lys Tyr
            20                  25                  30

Tyr Leu Cys Ala Pro Cys Lys Ala Trp Val Gly Cys His Pro Asp Ser
        35                  40                  45

Asp Thr Pro Leu Gly Thr Leu Ala Asp Ala Tyr Leu Arg Ala Ala Arg
    50                  55                  60

Ser Glu Ala His Lys Ala Phe Asp Thr Ile Trp Arg Gln Ser Val Met
65              70                  75                  80

Ser Arg Thr Lys Ala Tyr Ala Trp Leu Ser Lys Glu Met Asn Val Pro
                85                  90                  95

Pro Ala Lys Cys His Ile Gly Met Phe Asp Met Asp Gln Cys Arg Arg
            100                 105                 110

Val Val Ala Leu Cys Ser Ser Ala Phe Leu Asn
            115                 120

<210> SEQ ID NO 45
<211> LENGTH: 83
<212> TYPE: PRT
<213> ORGANISM: Phage P15

<400> SEQUENCE: 45

Met Arg Lys Phe Ser Glu Asp Arg Lys Ile Arg Asp Ile Val Tyr Asp
1               5                   10                  15

Asp Leu Leu Gln Lys His Tyr Glu Lys Thr Ser Leu Asp Pro Thr His
            20                  25                  30

Ile Lys Ile Ser Thr Asp Ala Tyr Ile Gln Ala Lys Ser Glu Asp Gln
        35                  40                  45

Gly Arg Ile Ser Ile Asp Arg Asn Pro Leu Phe Pro Ala Ser Cys Met
    50                  55                  60

Gly Ser Gly Ser Ser Gly Leu Met Gly Leu Val Tyr Trp Asn Tyr Ile
65              70                  75                  80

Gln Ser Ser

<210> SEQ ID NO 46
<211> LENGTH: 235
<212> TYPE: PRT
<213> ORGANISM: Phage P15

<400> SEQUENCE: 46

Met Ala Ile Ala Leu Ser Trp Ser Arg Leu Ser Asp Tyr Asn Gln Cys
1               5                   10                  15

Pro Leu Lys Phe Lys Met Lys Tyr Ile Asp Lys Ser Ser Ile Phe Lys
            20                  25                  30

Glu Asp Asp Ser Gln Ser Pro His Leu Val Arg Gly Ser Asn Val His
        35                  40                  45

Lys Lys Leu Glu Asp Tyr Val Val Gln Lys Leu Ser Asn Gly Gln Leu
    50                  55                  60

Glu Val Lys Ile Thr Ser Leu Pro Glu Val Glu Ser Thr Lys Pro Phe
65              70                  75                  80

Val Asp Arg Phe Leu Asn Asn Tyr Ala Thr Val Ile Pro Glu Thr Gln
                85                  90                  95

Ile Ala Val Asn Lys Asn Trp Glu Arg Val Glu Trp Phe Ser Arg Asp
            100                 105                 110

Ala Tyr Tyr Arg Ala Ile Phe Asp Leu Ile Ala Leu Arg Pro Ser Asp

```
                115                 120                 125
Val Ala Ile Ile Asp Tyr Lys Thr Gly Lys Ile Arg Asp Tyr Asp Gly
130                 135                 140

Gly Pro Ser Gly Lys Gly Gln Leu His Leu Ser Gly Ala Ile Ala Leu
145                 150                 155                 160

Asn Leu Trp Pro Asp Val Pro Thr Val Ser Thr Thr Tyr Ala Tyr Val
                165                 170                 175

Asp His Lys His Thr Leu Pro Lys Thr Phe Ser Gln Asp Arg Lys
            180                 185                 190

Ala Leu Thr Glu His Phe Asp Ala Glu His Ala Lys Val Asn Ser Asp
            195                 200                 205

Arg Glu Phe Lys Pro Thr Val Asn Glu Phe Cys Lys Tyr Cys Pro Val
    210                 215                 220

Thr Arg Lys Asp Cys Pro Tyr Ser Arg Lys Leu
225                 230                 235

<210> SEQ ID NO 47
<211> LENGTH: 640
<212> TYPE: PRT
<213> ORGANISM: Phage P15

<400> SEQUENCE: 47

Met Lys Ile Asn Ser Leu Asp Ile Glu Thr Glu Ala Val Asp Pro Ala
1               5                   10                  15

Glu Lys Leu Tyr Ala Ala Leu Gln Pro Trp Arg Leu Arg Gln Gly Arg
                20                  25                  30

Ser Arg Ile Thr Ser Ile Ala Val Cys Arg Pro Gly Phe Thr Val Asp
            35                  40                  45

Gln Ile Val Asn Arg Gly Asp Asn Thr Leu Trp Leu Arg Glu Met Ile
    50                  55                  60

Asp Leu Leu Asp Ser Val Gly Asn Asp Val Val Tyr Ala His Asn Ala
65                  70                  75                  80

Leu Phe Asp Ile Ala Phe Met Ile Ala Gln Leu Gln Pro Arg Arg Met
                85                  90                  95

Gly Ala Ile Pro Asp Val Leu Lys Arg Val Lys Trp Arg Asp Thr Gly
                100                 105                 110

Leu Leu Thr Lys Trp Leu Ile Asn Gly Gln Gln Pro Glu Thr Met Arg
            115                 120                 125

Phe Ser Tyr Ser Leu Ala Asn Leu Val Ala Thr Phe Leu Lys Asp Asp
    130                 135                 140

Glu Met Thr Pro Phe Phe Val Lys Met Lys Ser Gln Gly Val Ser Pro
145                 150                 155                 160

Gly Asp Asn Pro Glu Tyr Cys Glu Lys Arg Gly Glu Leu Asp Ala Ile
                165                 170                 175

Met Thr Leu Lys Leu Ala Leu Lys Leu Gln Ala His Met Ser Lys Glu
                180                 185                 190

Gln Arg Thr Gly Phe Leu Thr Glu Gln Asp Cys Leu Leu Pro Val Ala
            195                 200                 205

Asn Ser Trp Ile Met Gly Ile Arg Ile Asp Arg Glu Gln Val Arg Arg
    210                 215                 220

Asn Asp Lys Phe Ser Glu Ser Lys Thr Ala Ile Ala Lys Lys Leu
225                 230                 235                 240

Gly Leu Asp Glu Gly Ile Phe Thr Ser Thr Lys Arg Leu Pro Asp Leu
                245                 250                 255

Leu Phe Lys Glu Trp Leu Leu Pro Val Ile Ser Lys Thr Pro Ser Gly
```

```
                    260                 265                 270
Asn Pro Ser Cys Asn Ala Asp Thr Leu Lys Leu Leu Gln Tyr Gln Leu
            275                 280                 285
Asn Glu Ala Gly Asn Thr Glu Met Ala Asp Lys Leu Gly Leu Ile Leu
        290                 295                 300
Glu Ala Lys Gln Tyr Ser Thr Leu His Ser Lys Tyr Val Lys Ser Met
305                 310                 315                 320
Ile Glu Ala Leu Glu His Thr Gly Asp Gly Tyr Ile Tyr Ala Ser Pro
                325                 330                 335
Arg Ile Phe Gly Thr Tyr Thr Gly Arg Phe Thr Tyr Ser Ser Thr Thr
            340                 345                 350
Asn Gly Lys Asp Tyr Glu Asp Asn Ala Lys Thr Lys Lys Phe Lys
        355                 360                 365
Ser Ala Ile Ala Val His Gln Ile Pro Arg Arg Asp Lys Met Val Arg
370                 375                 380
Lys Ser Met Ile Ala Pro Glu Gly Tyr Glu Ile Tyr Glu Ala Asp Ala
385                 390                 395                 400
Ser Gly Gln Glu Ser Arg Leu Met Ala Leu Arg Ser Lys Asp Pro Val
                405                 410                 415
Met Ile Glu Ile Phe Ser Lys Asp Met Asn Phe His Ser Met Thr Gly
            420                 425                 430
Ala Ser Ile Ile Gly Glu Asp Tyr Ser Asp Phe Gln Val Lys Tyr Lys
        435                 440                 445
Ala Glu Gly Asp Glu Gly Gly Tyr Tyr Thr Glu Gln Arg Gln Leu Gly
450                 455                 460
Lys Leu Thr Asn Leu Ser Cys Asn Tyr Arg Ile Gly Gly Lys Ala Leu
465                 470                 475                 480
Ser Gln Lys Ala Phe Leu Asp Tyr Asp Thr Phe Leu Thr Val Gln Thr
                485                 490                 495
Gly Leu Phe Leu Val Gln Thr Phe Asn Arg Thr Tyr Lys Gly Val Pro
            500                 505                 510
Gln Tyr Trp Glu Asp Val Val Trp Glu Ser Arg Lys Gln Gly Tyr Thr
        515                 520                 525
Glu Thr Phe Gly Gly Arg Arg Tyr Lys Leu Thr Asp Trp His Ser His
530                 535                 540
Lys Trp Ile Thr Glu Ser Ser Ala Ile Asn Val Pro Ile Gln Gly Ala
545                 550                 555                 560
Gly Ala Asp Met Lys Glu Ile Ala Ile Lys Glu Thr Phe Glu Lys Val
                565                 570                 575
Pro Glu Ala Leu Phe Leu Leu Asp Leu His Asp Ala Asn Phe Phe Tyr
            580                 585                 590
Val Pro Ser Val Asn Ala Val Asp Leu His Glu Lys Leu Asp His Thr
        595                 600                 605
Leu Asn Thr Ile Asp Tyr Glu Lys Tyr Trp Gly Phe Lys Leu Glu Ile
        610                 615                 620
Glu Leu Pro Tyr Glu Ser Lys Arg Gly Lys Thr Phe Ala Glu Val Lys
625                 630                 635                 640

<210> SEQ ID NO 48
<211> LENGTH: 173
<212> TYPE: PRT
<213> ORGANISM: Phage P15

<400> SEQUENCE: 48

Met Asn Ile Phe Ile Leu Asp Tyr Asn Pro Val Val Ala Ala Gln Met
```

|   | 1   |     |     |     | 5   |     |     |     |     | 10  |     |     |     |     | 15  |     |
|---|-----|-----|-----|-----|-----|-----|-----|-----|-----|-----|-----|-----|-----|-----|-----|-----|

Leu Cys Asp Lys His Val Val Lys Met Ala Leu Glu Ser Ala Gln Met
                20                  25                  30

Leu Ser Ser Ala Leu Ser Leu Cys Gly Val Gln Gly Ile Gln Tyr Asp
            35                  40                  45

Ala Ser Asp Trp Arg Asp Asp Trp Asp Ser Pro Glu Arg Ala Glu Ser
        50                  55                  60

Ile Arg Ala Tyr Arg Pro Thr His Arg Asn His Pro Cys Thr Lys Trp
65                  70                  75                  80

Ala Met Arg Val Arg Asn Tyr Gln Trp Leu Arg Glu His Ala Glu Ala
                85                  90                  95

Ile Cys His Glu His Thr Tyr Arg Tyr Gly Thr Val Thr Gln Thr Ser
                100                 105                 110

Arg Val Ile Glu Gln Leu Pro Lys Phe Pro Gln Val Ser Gly Pro Leu
            115                 120                 125

Lys Phe Ala Leu Ala Met Asp Asp Val Tyr Lys Gln Ile Asp Pro Val
        130                 135                 140

Lys Ala Tyr Gln Ala Tyr Tyr Arg Gly Glu Lys Ser Arg Ile Ala Val
145                 150                 155                 160

Trp Thr Lys Arg Glu Thr Pro Glu Phe Met His Glu Asn
                165                 170

<210> SEQ ID NO 49
<211> LENGTH: 806
<212> TYPE: PRT
<213> ORGANISM: Phage P15

<400> SEQUENCE: 49

Met Glu Gln Gln Val Leu His Phe Ala Lys Arg Phe Ala Arg Asp Gly
1               5                   10                  15

Tyr Tyr Val Phe Pro Phe Tyr Gly Ser Ser Glu Gly Pro Gln Lys Pro
                20                  25                  30

Tyr Gly Trp Ala Arg Asn Thr Val Thr Lys Glu Gly Ile Asp Pro Arg
            35                  40                  45

Lys Ile Ile Pro Ala Thr Asp Asp Pro Glu Ile Val Glu Thr Trp Pro
        50                  55                  60

Glu Leu Ile Ala Ala Gly Tyr Lys Gly Ala Lys Leu Val Gly Tyr Gly
65                  70                  75                  80

Val Leu Gly Val Asn Cys Val Ile Phe Asp Leu Asp Val Lys Gly Gly
                85                  90                  95

Val Asn Gly Ile Ala Glu Phe Asn Lys Phe Ser Glu Lys Tyr Gly Ile
                100                 105                 110

Pro Lys Ser Glu Phe Val Val Lys Ser Lys Ser Gly Gly Phe His Leu
            115                 120                 125

Tyr Tyr Ala Lys Pro Glu Lys Leu Arg Ser Leu Ala Val Lys Thr Val
        130                 135                 140

Ala Gly Leu Thr Ile Gly Gly Thr Lys Tyr Pro Gly Leu Asp Val Arg
145                 150                 155                 160

Gly Glu Gly Gly Met Val Gly Pro Met Ala Glu Gly Gln Trp Val
                165                 170                 175

Glu Gly Thr Tyr Thr Ile Val Lys Gly Asn Thr Asp Thr Ala Leu Ser
                180                 185                 190

Glu Val Pro Thr Gln Ala Leu Met Ser Met Lys Ser Ser Ile Thr
            195                 200                 205

Met Asp Ala Pro Glu Val Leu Thr Pro Gln Ala Gly Ser Met Asp Glu

```
              210                 215                 220
Leu Glu Ile Leu Lys Arg Gly Glu Ile Pro Asp Lys Val Ser Asn Gly
225                 230                 235                 240

Asn Arg Asn Asn Gly Phe Tyr Leu Tyr Leu Asn Ala Leu Arg Asn Lys
                245                 250                 255

Gly Phe Ser Gln Glu Thr Ala Arg Arg Tyr Ile Lys Glu Leu Ile Lys
                260                 265                 270

Val Thr Glu Asn Pro Glu Thr Ile Glu Asp Ser Ile Asp Val Glu Asp
                275                 280                 285

Met Leu Ala Arg Ile Trp Lys Ile Asp Gln Asn Asn Pro Tyr Asp Val
            290                 295                 300

Cys Arg Asp Leu Ile Glu Gly Leu Tyr Arg Leu Thr Asn Phe Arg
305                 310                 315                 320

Ser Lys Leu Met Tyr Val Cys Leu Glu Asn Asn Gln Tyr Leu Asp Thr
                325                 330                 335

Lys Thr Pro His Asp Leu Thr Ser Met Lys Gln Leu Met Ser Arg Phe
                340                 345                 350

Ala Arg Lys Met Ala Asn Gln Asp Gly Lys Leu Lys Leu Val Asn Pro
            355                 360                 365

Ile Asp Val Leu Asp Gly Met Ile Thr Pro Arg Glu Val Ala Thr
370                 375                 380

Ile Gly Phe Lys Pro Gly Ala Ser Glu Val Phe Thr Ile Thr Glu Ala
385                 390                 395                 400

Glu Gly Gly Lys Lys Tyr Leu Asn Thr Trp Arg Asp Pro Arg Ile Gln
                405                 410                 415

Ile Gln Gly Ala His Gln Asn Gln Glu Ile Trp Asp Lys Phe Lys Phe
            420                 425                 430

Leu Val Ser Arg Ile Phe Gly Pro Glu Gly Ser Glu Glu Tyr Gln Leu
            435                 440                 445

Gly Ile Asp Phe Pro Ala Trp Leu Ile Gln Asn Pro Gly Ile Arg Pro
    450                 455                 460

Val Ile Ala Pro Tyr Val Met Ser Arg Val Arg Gly Ala Gly Lys Ser
465                 470                 475                 480

Val Tyr Leu Ser Met Leu Thr Gln Leu Phe Gly Phe Ser Lys Asp Gly
                485                 490                 495

Asp Met Gln Gly Gln Met Phe Glu Val Asp Gln Ile Gly Gly Arg Phe
                500                 505                 510

Phe Asn Pro Asn Gly Ala Ser Leu Leu Ile Phe Asp Glu Ile Gln Phe
            515                 520                 525

Pro Val His Arg Asn Met Arg Gln Glu Ser Ala Thr Phe Trp Arg His
    530                 535                 540

Leu Lys Ser Leu Ile Thr Leu Glu Thr Val Pro Val Glu Phe Lys Gly
545                 550                 555                 560

Gly Asp Thr Val Gln Met Pro Leu Tyr Ala Gly Val Val Leu Ala Gly
                565                 570                 575

Asn Thr Gly Ser Asn Phe Pro Leu Glu Glu Phe Asp Arg Arg Ile Trp
            580                 585                 590

Leu Ile Asp Asn Asp Pro Pro Ala Met Glu Glu Gly Leu Ile Asp Glu
            595                 600                 605

Phe Tyr Asp Ile Thr Lys Asn Arg Met Ser Arg Glu Gln Lys Arg Glu
    610                 615                 620

Ile Ile Gln Gly Leu Leu Val Ser Leu Asp Asn His Pro Ile Lys Leu
625                 630                 635                 640
```

```
Lys Leu Asp Arg Met Lys Ala Pro Met Asn Glu Ile Lys Arg Glu Met
            645                 650                 655

Tyr Leu Ser Thr Leu Ser Asp Ile Glu Glu Trp Trp Ile Thr Tyr Phe
            660                 665                 670

Glu Asp Arg Asp Asn Leu Leu Ala Arg Thr Pro Val Leu Thr Lys Ser
            675                 680                 685

Ala Val Ile Tyr Leu Ile Ser Ile Ala Glu Arg Leu Met Asn Ser Arg
            690                 695                 700

Trp Arg Glu Asp Pro Glu Gly Thr Phe Arg Glu Leu Lys Arg Arg Gly
705                 710                 715                 720

Leu Leu Gln Pro Ile Arg Thr Lys Gly Asn Asn Tyr Gln Thr Arg Asn
            725                 730                 735

Met Arg Asn Val Pro Ile Val Lys Gly Asp Gly Gly Ile Ser Gln Glu
            740                 745                 750

Gly Glu Gly Arg Asp Val Leu Tyr Thr Thr Arg Gln His Gly Asp Leu
            755                 760                 765

Asn Asp Glu Thr Asn Glu Ala Ile Leu Gln Met Tyr Leu Ala Asn Val
            770                 775                 780

Asn Gly Ile Asn Lys Trp Lys Arg Glu Ser Ile Leu Asn Arg Ser Ser
785                 790                 795                 800

Ser Ile Ala Ser Ser Leu
            805

<210> SEQ ID NO 50
<211> LENGTH: 288
<212> TYPE: PRT
<213> ORGANISM: Phage P15

<400> SEQUENCE: 50

Met Thr Val Glu Ser Lys Leu Pro Arg Thr Leu Ser Ile Lys Phe Trp
1               5                   10                  15

Arg Asn Ser Val Ile Ser Ala Asn Val Leu Gln Met Ser Val Gly Pro
            20                  25                  30

Val Lys Thr Ile Thr Ser Met Glu Leu Cys Tyr Pro Arg Phe Ile His
            35                  40                  45

Ala Glu Leu Met Thr His Arg Val Phe Ser Arg Asn Ala Ser Ser Ser
    50                  55                  60

Arg Ala Val Pro Ile Asp Arg Met Ile Arg Asp Ile Gln Glu Asn Pro
65                  70                  75                  80

Ala Met Pro Asn Ser Trp Met Gln Asn Lys Pro Gly Met Gln Gly Gly
            85                  90                  95

Asp Val Leu Gly Ala Arg Glu Ile Ser Glu Ala Lys Asp Ala Trp Ile
            100                 105                 110

Lys Ala Cys Asn Asp Ala Val Lys His Ala Arg Val Leu Lys Asp Leu
            115                 120                 125

Gly Cys His Lys Gln Ile Val Asn Arg Ile Leu Glu Pro Phe Ala His
            130                 135                 140

Ile Lys Val Ile Val Thr Ala Thr Glu Trp Asp Asn Phe Phe Met Leu
145                 150                 155                 160

Arg Leu Ser Asp Gln Ala Glu Pro Asn Ile Arg Glu Leu Ala Arg Lys
            165                 170                 175

Met Ile Arg Ala Met Tyr Arg Phe Glu Pro Gln His Val Gly Thr Gly
            180                 185                 190

Gly Leu His Ala Pro Tyr Val Asn Val Glu Glu Met Leu Ser Gln Gly
            195                 200                 205
```

```
Val Ser Val Glu Asp Ile Cys Met Ala Ser Ala Gly Arg Cys Ala Arg
    210                 215                 220

Val Ser Tyr Leu Asn His Asp Gly Thr Lys Ala Asp Val His Gln Asp
225                 230                 235                 240

Ile Leu Leu Ala Arg Arg Leu Leu Ala Asp Lys His Ala Ser Val Phe
                245                 250                 255

Glu His Gln Ala Phe Ala Leu Ser Asn Ser Val Ala Thr Asp Met Arg
            260                 265                 270

Ser Arg Asn Phe Tyr Gly Trp Thr Gln Phe Arg Glu Arg Val Asn Leu
        275                 280                 285

<210> SEQ ID NO 51
<211> LENGTH: 102
<212> TYPE: PRT
<213> ORGANISM: Phage P15

<400> SEQUENCE: 51

Met Lys Leu Ser Pro Ala Tyr Val Arg Phe Val Ser Glu Met Val Ser
1               5                   10                  15

Ile Leu Leu Ala Lys Tyr Tyr Met Leu Gly Met Asp His Leu Thr Thr
            20                  25                  30

Gln Glu Arg Ser Leu Leu Ile Ala Phe Ala Leu Val Cys Leu Asn Lys
        35                  40                  45

Asp Val Met Ser Gln Ile Met Glu Ala Leu Glu Asn His Gly Glu Leu
    50                  55                  60

Pro Cys Lys Met Trp Ile Glu Tyr Val Glu Phe Leu Arg Val His Asn
65                  70                  75                  80

Asp Ser Gly Val Gln Thr Ser Glu Asp Ser Val Asn Gln Ile Leu Glu
                85                  90                  95

Lys Phe Arg Asp Gln Arg
            100

<210> SEQ ID NO 52
<211> LENGTH: 117
<212> TYPE: PRT
<213> ORGANISM: Phage P15

<400> SEQUENCE: 52

Met Arg Pro Val Asp Ala Lys Ala His Glu Ala Arg Lys Ser Leu Leu
1               5                   10                  15

Lys Ser Leu Glu Pro Gly Asp Leu Ile Leu Val Asn Gly Ser Leu Arg
            20                  25                  30

Ile Val Arg Asp Ala Thr His Lys Ser Ser Gly Asn Phe Gly Trp Ile
        35                  40                  45

Thr Leu Ser Ile Met Arg Cys Ser Trp Thr Arg Lys Pro Tyr Thr Val
    50                  55                  60

Lys Thr Trp Ser Asp Leu Tyr Arg Val Asn Leu Gln Val Val Ala Lys
65                  70                  75                  80

Gly Phe Gly Leu Gly Gly Ser Lys Leu Asp Glu Leu Ile Gln Gln Asp
                85                  90                  95

Ile Met Asn Lys Gln Ser Gly Lys Thr Val Leu Glu Cys Cys Asp Val
            100                 105                 110

Ile Gly Asn Leu Ile
        115

<210> SEQ ID NO 53
<211> LENGTH: 90
<212> TYPE: PRT
```

<213> ORGANISM: Phage P15

<400> SEQUENCE: 53

Met Lys Ile Leu Leu Val Gly Ser Asp Met Arg Tyr Met Gln Glu Thr
1               5                   10                  15

Leu His Gln Met Val Lys Lys Asp Ile Val Phe Lys Ser Asn Pro Pro
            20                  25                  30

Arg Leu Leu His Ala Asp Gly Ser Thr Val Asp Val Leu Cys Ile Lys
        35                  40                  45

Gly Tyr Ser Asp Leu Glu Ser Val Arg Gly Met Arg Phe Asp Val Ile
    50                  55                  60

Phe Glu His Ala Ser Leu Asp His Arg Ile Arg Ser Leu Tyr Glu Ile
65                  70                  75                  80

Met Cys Glu Leu Lys Ala Arg Val Ile Arg
                85                  90

<210> SEQ ID NO 54
<211> LENGTH: 90
<212> TYPE: PRT
<213> ORGANISM: Phage P15

<400> SEQUENCE: 54

Met Arg Ser Glu Tyr Val Arg Ser Ser Tyr Ala Ile Cys Ser Cys Ala
1               5                   10                  15

Ser Lys Val Thr Thr Phe Arg Ala His Arg Arg Ala Gln Val Lys Arg
            20                  25                  30

Val Thr Ala Asn Val Phe Ser Ala Glu Val Lys Tyr Glu Phe Thr Lys
        35                  40                  45

Glu Glu Leu Glu Asp Met Ile Arg Lys His Ala Gly Leu Met Asp Gly
    50                  55                  60

Val Val Glu Trp Asp Ile Ser Asn Lys Asn Lys Ile Arg Gly Ala Thr
65                  70                  75                  80

Ile Lys Val Thr Arg Thr Glu Ile Lys Gly
                85                  90

<210> SEQ ID NO 55
<211> LENGTH: 111
<212> TYPE: PRT
<213> ORGANISM: Phage P15

<400> SEQUENCE: 55

Met Phe Pro Ile Lys Ala Lys Trp Ile Lys Gln Ser Ser Ser Ser Asn
1               5                   10                  15

Asn His Pro Ala Glu Gln Asp Val Met Val Leu Gly Phe Ser Leu His
            20                  25                  30

Cys Pro Asn Ser Asp Val Gly Ser Ala Val Arg Pro Val Ala Ile Val
        35                  40                  45

Met Asp Leu Ser Asp Asn Cys Leu Arg Tyr Ala Glu Leu Arg Phe Ile
    50                  55                  60

Lys Leu Glu Asn Val Pro Cys Ser Tyr Pro Ile Ala Thr Val Asp Thr
65                  70                  75                  80

Leu Gln Pro Thr Asp Ala Val Leu Asp Leu Gln Arg Ser Pro Glu Ala
                85                  90                  95

Val Leu Arg Lys Ser Pro Asp Gly Ser Val Lys Leu Ser Pro Gly
            100                 105                 110

<210> SEQ ID NO 56
<211> LENGTH: 134

```
<212> TYPE: PRT
<213> ORGANISM: Phage P15

<400> SEQUENCE: 56

Met Ser Thr Ile Ile Glu Lys Gly Pro Phe Cys Glu Cys Ile Lys Thr
1               5                   10                  15

Gly Phe Tyr Phe Thr Val Asp Thr Asp Arg Val Phe Asn Gly Asp
            20                  25                  30

Leu Phe Tyr Asp Phe Val Lys Ala Glu Phe Gln Val Arg Gly Ile Ala
            35                  40                  45

Gly Asp Glu His Gly Arg Pro Ile Pro Cys Ile Pro Lys Ser Glu Lys
50                  55                  60

Gly Pro Ile Ala Leu Glu Gly His Val Arg Gly Val Lys Lys Ile Gly
65                  70                  75                  80

His Arg Pro Ser Gly Lys Asn Thr Tyr Val Asp Leu Val Phe Thr Lys
                85                  90                  95

Ala Ile Ile Thr Asp Ala Met Met Ala His Ile Cys Met Trp Tyr Gly
            100                 105                 110

Asp Arg Ala Val Trp Ala Val Val Gln Lys Glu Trp Glu Ser Arg Asp
            115                 120                 125

Asn Leu Ala Trp Val Gly
        130

<210> SEQ ID NO 57
<211> LENGTH: 153
<212> TYPE: PRT
<213> ORGANISM: Phage P15

<400> SEQUENCE: 57

Met Ser Ile Phe Gln Asn Leu Leu Ala Asn Tyr Pro Lys Tyr Ser Ala
1               5                   10                  15

Arg Lys Val Arg Arg Leu Ala Glu His Leu Glu Phe Leu Ser Gly Ser
            20                  25                  30

Ala Asp Tyr Pro Val Ser Arg Gln Ile Ala Glu Asp Leu Gln Ala Tyr
            35                  40                  45

His Leu Leu Gln Ala Lys Met Glu Ser Gln Met Asn Asp Asp Val Gln
50                  55                  60

Val Gln Val Gln Val Thr Gly Pro His Glu His Thr Thr Glu His Ile
65                  70                  75                  80

Ser Val Thr Pro Val Gly Thr Ala Arg Lys Ala Leu Asp Val Ile His
                85                  90                  95

Asp Phe Ile Arg Ile Asn Ile Pro Ser Ile His Trp Asn Asn Asp Lys
            100                 105                 110

Tyr Glu Lys Val Arg Ala Ser Ala Asn Gly Tyr Ile Asn Gly Gln Ser
            115                 120                 125

Phe Tyr Thr Asp Arg Thr Ile Ile Gln Ala Arg Leu Ser Pro Gln Asn
            130                 135                 140

Asp Leu Pro Leu Asp Gly Ala Gly Lys
145                 150

<210> SEQ ID NO 58
<211> LENGTH: 115
<212> TYPE: PRT
<213> ORGANISM: Phage P15

<400> SEQUENCE: 58

Met Ser Ser Pro Asp Asn Glu Leu Asn Leu His Leu Ala Thr Glu Asp
1               5                   10                  15
```

```
Ala Ser Asp Ala Lys Asn Glu Arg Ala Asp Glu Leu Ile Gln Glu Trp
         20                  25                  30

Met Lys Asn Pro Ser Thr Val Ala Glu Trp Ile Ser Ala Val Leu Asp
         35                  40                  45

Glu Gln Ser Gln Ala Arg Asp Asp Phe Ala Ala Leu Leu Ala Glu Ala
     50                  55                  60

Ile Thr Val Asp Asp Tyr Asp Arg Cys Lys Glu Ala Leu Gly Glu Ala
 65                  70                  75                  80

Leu Asp Leu Ile Glu Thr His Val Met Tyr Glu Met Arg Gly Asp Ala
             85                  90                  95

Leu Ala Glu Leu Glu Ser Gln Ser Asn Pro Leu Pro Glu Ser Val
            100                 105                 110

Asp Leu Ile
        115
```

<210> SEQ ID NO 59
<211> LENGTH: 68
<212> TYPE: PRT
<213> ORGANISM: Phage P15

<400> SEQUENCE: 59

```
Met His Leu Pro Val Leu Tyr Thr His Ala Asn Glu Val Met Ser Met
 1               5                  10                  15

Thr Tyr Gln Glu Leu Cys Asp Gln Ser Lys Tyr Phe Lys Ala Ile Ile
         20                  25                  30

Ser Phe Glu Pro Arg Pro Met Met Asp Arg Lys Thr Ile Glu Ala Tyr
         35                  40                  45

Arg Thr Ala Arg Ala Asn Trp Lys Arg Glu Tyr Asn Glu Trp Leu Lys
     50                  55                  60

Lys Gln Gln His
 65
```

<210> SEQ ID NO 60
<211> LENGTH: 137
<212> TYPE: PRT
<213> ORGANISM: Phage P15

<400> SEQUENCE: 60

```
Met Thr Val Tyr Val Leu Gly Phe Ala Phe Trp Asn Asn Gln Val Cys
 1               5                  10                  15

Leu Ile Arg Lys Asn Arg Pro Lys Trp Gln Glu Asn His Phe Asn Gly
         20                  25                  30

Val Gly Gly His Val Glu Val Ser Asp Glu Ser Ser Arg Ala Ala Met
         35                  40                  45

Ala Arg Glu Phe Phe Glu Glu Thr Gly Val Lys Thr Leu Ala Ser Glu
     50                  55                  60

Trp Leu Tyr Thr Gly Lys Met Val Gly Asp Asp Trp Thr Val His Leu
 65                  70                  75                  80

Tyr Ala Gly Asn Ile Asn Ile Asp Asn Ala Thr Thr Met Thr Asp Glu
             85                  90                  95

Glu Val Leu Val Val Asp Leu Asn Gln Leu Met Asp Tyr Val Leu Ile
            100                 105                 110

Pro Asn Val His Thr Leu Ile Ser Trp Ser Leu Ala Arg Leu Asp Gly
            115                 120                 125

Ala Asp Gly Leu Met Lys Leu Tyr Tyr
            130                 135
```

-continued

<210> SEQ ID NO 61
<211> LENGTH: 33
<212> TYPE: PRT
<213> ORGANISM: Phage P15

<400> SEQUENCE: 61

Met Ala Ala Ser Gly Ile Ala Ser Thr Thr Ile Pro Ser Ser Ala Asn
1               5                   10                  15

Asp Val Glu Ser Asn Ser Thr Ser Glu Ala Thr Ser Asn Ile Gly Ala
            20                  25                  30

Leu

<210> SEQ ID NO 62
<211> LENGTH: 43
<212> TYPE: PRT
<213> ORGANISM: Phage P15

<400> SEQUENCE: 62

Met Ser Leu Ile Gln Lys Leu Arg Leu Trp Trp Ser Gly Glu Val Asn
1               5                   10                  15

Gly Cys Phe Trp His Arg Ile Asp His Asp Ser Leu Lys Cys Lys Arg
            20                  25                  30

Cys Gly Lys Gln Phe His Ile Arg Ser Asp Phe
        35                  40

<210> SEQ ID NO 63
<211> LENGTH: 54
<212> TYPE: PRT
<213> ORGANISM: Phage P15

<400> SEQUENCE: 63

Met Ile Lys Arg Leu Thr Ser Tyr Phe Thr Pro Met Thr Gln Val Lys
1               5                   10                  15

Ala Leu Phe Val Asp Arg Val Ser Gly Lys Thr Val Tyr Leu Trp Glu
            20                  25                  30

Asp Lys Tyr Gly Thr Gln Tyr Met Asn Thr His Ser Phe Gly Trp Gly
        35                  40                  45

Arg Val Lys Tyr Cys Gly
    50

<210> SEQ ID NO 64
<211> LENGTH: 124
<212> TYPE: PRT
<213> ORGANISM: Phage P15

<400> SEQUENCE: 64

Met Val Arg Leu Leu Cys Val Gln Asp Gly His Gly Cys Met Leu Leu
1               5                   10                  15

Val Pro Gly Val Leu Pro Glu Leu Ala Gly Arg Val Cys Ala Asp Glu
            20                  25                  30

Asp Leu Leu Gly Trp Asp His Phe Lys Arg Val Asn Lys Gly Lys Gln
        35                  40                  45

Ile Leu Val Leu Val Asp Pro Gln Thr Ile Glu Ile Ser Lys Asp Ile
    50                  55                  60

Arg Lys Ile Pro Val Asn Asp Leu Arg Val Asn Arg Thr Gly Val His
65                  70                  75                  80

Glu Val Leu Met Arg Ile Ala Val Ser Gly Trp Lys Leu Asn Pro Leu
                85                  90                  95

Leu Ser Glu Glu Leu Ala Tyr Leu Gln Glu Ala Ile Gln Asp Gly Pro

```
                100             105             110
Trp Ser Arg Gly Leu Val Ile Ile Gly Glu Val Ser
        115                 120
```

<210> SEQ ID NO 65
<211> LENGTH: 85
<212> TYPE: PRT
<213> ORGANISM: Phage P15

<400> SEQUENCE: 65

```
Met Ala Gln Val Cys Arg Val Pro Glu His Pro Gly Leu His Ser Gln
1               5                   10                  15

Ala Lys Asp Gln Thr Met Lys Ile Phe Met Ile Ala Trp Val Val Asn
            20                  25                  30

Met Ile Phe Met Cys Ile Pro Asn Ser Trp Met Ala Thr Thr Pro Gly
        35                  40                  45

Pro Ile Val Lys Gly Asp Val Val Lys Ala Leu Ile Gly Val Ile Tyr
    50                  55                  60

Leu Ala Val Asn Ser Leu Ala Ala Phe Gln Ala Leu Arg Leu Phe Leu
65                  70                  75                  80

Arg Trp Leu Val Leu
                85
```

<210> SEQ ID NO 66
<211> LENGTH: 88
<212> TYPE: PRT
<213> ORGANISM: Phage P15

<400> SEQUENCE: 66

```
Met Asp Ile Ile Leu Tyr Trp Tyr Leu Gly Thr Thr Val Ile Ala Phe
1               5                   10                  15

Val Leu Asn Phe Ala Phe Leu Tyr Asp Glu Tyr Asp Ser Cys Gly Ala
            20                  25                  30

Val Thr Tyr Gly Glu Ile Leu Ala Trp Val Leu Ile Tyr Ile Val Pro
        35                  40                  45

Val Ile Asn Ile Ile Leu Gly Leu Trp Val Ile Ile Asp Trp Ala Lys
    50                  55                  60

Asp Lys Ala Trp Pro Lys Phe Ala Glu Phe Leu Asn Thr Gln Ala Phe
65                  70                  75                  80

Thr Arg Lys Pro Arg Ile Lys Arg
                85
```

<210> SEQ ID NO 67
<211> LENGTH: 76
<212> TYPE: PRT
<213> ORGANISM: Phage P15

<400> SEQUENCE: 67

```
Met Val Ser His Gly Ser Ser Arg Cys Phe Leu Glu Ser Asn Arg Val
1               5                   10                  15

Ala Leu Val Arg Ser Asp Asp Ala Leu Asp Val His Thr Ala Ile
            20                  25                  30

Lys His Phe Glu Glu Met Arg Ile Arg Ala Pro Glu Leu Leu Glu
        35                  40                  45

Glu Arg Arg Asp Phe Ile Pro Leu Tyr Thr Lys Thr Arg Leu Gly Lys
    50                  55                  60

Gly Gln Arg Lys Lys Asn Lys Gly Gln Arg Trp Thr
65                  70                  75
```

<210> SEQ ID NO 68
<211> LENGTH: 64
<212> TYPE: PRT
<213> ORGANISM: Phage P15

<400> SEQUENCE: 68

Met Trp Ile Val Leu Thr Met Phe Trp Ala Ala Val Ala Thr Leu Val
1               5                   10                  15

Met Ile Gly Leu Gly His Gly Gln Glu Tyr Leu Leu Trp Glu Arg Ile
            20                  25                  30

Leu Ile Ser Ala Ser Ala Ala Thr Leu Trp Ser Gly Leu Phe Tyr Tyr
        35                  40                  45

Gly Thr Arg Gln Lys Ala Lys Trp Pro Arg Val Arg Lys Pro Arg Lys
    50                  55                  60

<210> SEQ ID NO 69
<211> LENGTH: 152
<212> TYPE: PRT
<213> ORGANISM: Phage P15

<400> SEQUENCE: 69

Met Arg Asn Cys Glu Glu Leu Arg Arg Phe Met Asp Arg Leu Val Arg
1               5                   10                  15

His Val His Pro Ala Leu Asp Ala Lys Val Gly Glu Glu Leu Lys Glu
            20                  25                  30

Leu Ala Lys Leu Ile Asp Asp Lys Leu Val Ile Val Thr Gly Pro
        35                  40                  45

Met Asp Gly Tyr Ala Val Phe Asp Ser Gly Gln Pro Glu Ala Val Ala
    50                  55                  60

Leu Leu Glu Ala Thr Ala Arg Arg Ile Ser Ala Ala Thr Ala Arg Ser
65                  70                  75                  80

Ala Thr Ile Ser Pro Ile Val Ser Lys Val Glu Leu Phe Asp Tyr Asn
                85                  90                  95

Gly Arg Val Tyr Gly Pro Val Gln Val Ile Lys Pro Thr Gln Glu Asp
            100                 105                 110

Ser Arg Ser Gln Met Leu Leu Asp Lys Glu Ala Ala Ile Glu Lys Arg
        115                 120                 125

Arg Lys Glu Val Met Ala Lys Ala Gln Ser Leu Gly Leu Thr Val Glu
    130                 135                 140

Glu Leu Glu Ile Leu Arg Arg Gln
145                 150

<210> SEQ ID NO 70
<211> LENGTH: 44
<212> TYPE: PRT
<213> ORGANISM: Phage P15

<400> SEQUENCE: 70

Met Thr Leu Gly Leu Gln Ile Arg Ile Ile Met Ala Ser Tyr Ile Ala
1               5                   10                  15

Gly His Lys Leu Val Trp Thr Val Val Gly Gly Gln Arg Cys Tyr Val
            20                  25                  30

Arg Lys Tyr Gly His Leu Thr Ser Tyr Thr Phe Arg
        35                  40

<210> SEQ ID NO 71
<211> LENGTH: 107
<212> TYPE: PRT
<213> ORGANISM: Phage P15

```
<400> SEQUENCE: 71

Met Arg Gly Lys Ala Ala Lys Cys Ala His Pro Gly Cys Pro His Phe
1               5                   10                  15

Ala Thr Lys Gly His Lys Trp Cys Ile Asn His Ala Pro Ile Arg Pro
            20                  25                  30

Lys Pro Ala Pro Val Pro Glu Pro Ala Pro Trp Asp Pro Ser Ile Gly
        35                  40                  45

Phe Tyr Val His Ser Pro Ser Ser Glu Glu Ile Ile Ala Tyr Arg Glu
    50                  55                  60

Glu Thr Gly Cys Gly Gln Met Glu Ala Lys Ala Ile Leu Arg Arg Lys
65                  70                  75                  80

Ala Leu Leu Glu Ala Ala Asp Arg Ala Val Val Trp Gly Asp Leu Lys
                85                  90                  95

Leu Ile Val Lys Met Leu Ile Asn Leu Asp Ser
                100                 105

<210> SEQ ID NO 72
<211> LENGTH: 75
<212> TYPE: PRT
<213> ORGANISM: Phage P15

<400> SEQUENCE: 72

Met Gln Leu Ile Lys Val Thr Tyr Phe Ser Gly Arg Val Met Tyr Phe
1               5                   10                  15

Asn Pro Asn Asn Val Val Thr Ile Thr Arg Lys Pro Asp Ser Thr Val
            20                  25                  30

Ile Thr Thr Val Thr Pro Ser Asp Tyr Val Asp Gly Val Pro Thr Tyr
        35                  40                  45

Glu His His Val Gln Glu Glu Ile Asp Lys Val Leu Ala Gln Ile Ser
    50                  55                  60

Pro Tyr Val Asp Val Met Ile Leu Gly Gly Ser
65                  70                  75

<210> SEQ ID NO 73
<211> LENGTH: 68
<212> TYPE: PRT
<213> ORGANISM: Phage P15

<400> SEQUENCE: 73

Met Ser Asp Val Pro Gln Pro Gly Thr Met Trp Arg His Tyr Asn Gly
1               5                   10                  15

Lys Gln Tyr Glu Val Leu Ala Ile Ala Asn Ile Ala Ser Glu Asn Pro
            20                  25                  30

Arg Tyr Pro Val Thr Val Ile Tyr Val Gly Asp Asn Gly Asn Ile Trp
        35                  40                  45

Thr Arg Asp Ala Ser Asp Trp His Arg Ser Met Thr Leu Ile Glu Asp
    50                  55                  60

Arg Lys Cys Asn
65

<210> SEQ ID NO 74
<211> LENGTH: 42
<212> TYPE: PRT
<213> ORGANISM: Phage P15

<400> SEQUENCE: 74

Met Trp Ile Tyr Ile Gly Leu Val Phe Leu Gly Ala Ser Ile Tyr Thr
1               5                   10                  15
```

-continued

Thr Ser Pro Gly Trp Phe Val Gly Leu Tyr Val Ala Ala Thr Val Cys
         20                  25                  30

Met Leu Ile Gly Cys Lys Gly Arg Thr Arg
         35                  40

<210> SEQ ID NO 75
<211> LENGTH: 62
<212> TYPE: PRT
<213> ORGANISM: Phage P15

<400> SEQUENCE: 75

Met Ser Asp Ile Leu Gln Tyr Phe Arg Leu Ser Asp Leu Leu Glu Ser
1               5                   10                  15

Ala Arg His Asp His Met Ala Ala Thr Phe Arg Gly Asp Lys Lys Gln
            20                  25                  30

Glu Lys Glu Phe Arg Thr Gln Cys Ala Asn Phe His Thr Glu Met Ile
        35                  40                  45

Ala Leu Arg Ala Lys Ile Thr Ala Ala Glu Phe Glu Lys Glu
    50                  55                  60

<210> SEQ ID NO 76
<211> LENGTH: 78
<212> TYPE: PRT
<213> ORGANISM: Phage P15

<400> SEQUENCE: 76

Met Lys Arg Leu Ser Leu Ile Lys Asn Met His Gly Asp Val Val Leu
1               5                   10                  15

Thr Gly Val Asp Glu Val Glu Val Ser Lys Leu Arg Tyr Gly Leu Thr
            20                  25                  30

His Tyr Gly Ile Asp Asn Ile Arg Pro Glu Gly Gln Ala Leu Ile Val
        35                  40                  45

Val Val Gln Ser Pro Ser Ala Glu Glu Ile Arg Ala Val Arg Asn Ile
    50                  55                  60

Val Ala Arg Leu Tyr Asp Thr Gln Met Val Asp Asp His Val
65                  70                  75

<210> SEQ ID NO 77
<211> LENGTH: 151
<212> TYPE: PRT
<213> ORGANISM: Phage P15

<400> SEQUENCE: 77

Met Val Val His Tyr Leu Ile Leu Glu Ile Arg Met Thr Ala Pro Arg
1               5                   10                  15

Val Asp Gly Val Thr Glu Leu Arg Phe Glu Val Glu Val Ser Glu Gly
            20                  25                  30

Leu Val Gln Gly Leu Arg Ala Leu Ala Arg Val His Tyr Asp Gly Val
        35                  40                  45

Cys Gln Arg Ala Ala Asp Gln Ile Ser Glu Arg Ala Val Val Ile Leu
    50                  55                  60

Arg Asn His Glu Glu Trp Met Leu Asp Leu Arg Pro Ala Glu Arg Lys
65                  70                  75                  80

Lys His Trp Pro Lys Ile Val Leu Lys Ser Ser Glu Val Asp Thr Leu
                85                  90                  95

Leu Lys Leu Leu Glu Cys Gln Ser Tyr Ile Arg Pro Asp His Val Ala
            100                 105                 110

Tyr Thr Tyr Leu Ser Asp Leu Arg Leu Ser Leu Ser Ala Ala Trp His

```
                115             120                 125
Tyr Met Lys Gly His Tyr Lys Val Tyr Pro Trp Ala Ser His Ser Gly
130                 135                 140

Val Thr Pro Asp Met Ala Pro
145                 150

<210> SEQ ID NO 78
<211> LENGTH: 61
<212> TYPE: PRT
<213> ORGANISM: Phage P15

<400> SEQUENCE: 78

Met Leu Ile Ile Ser Arg Ile Thr Ile Val Lys Lys Glu Gly Cys His
1               5                   10                  15

Phe Gly Asp Asn Tyr Lys Tyr Asn Leu Ile Met Asp Leu Met Ile Cys
                20                  25                  30

Ala Arg Thr Glu Arg Leu Pro Val Val Glu Tyr Thr Tyr Thr Phe Leu
            35                  40                  45

Arg Ile Leu Tyr Gly Pro Ala Ile Leu Arg Ser Ser Gly
        50                  55                  60

<210> SEQ ID NO 79
<211> LENGTH: 212
<212> TYPE: PRT
<213> ORGANISM: Phage P15

<400> SEQUENCE: 79

Met Gly Arg Leu Ser Phe Ala Val Leu Asp Lys Tyr Glu Tyr Leu Pro
1               5                   10                  15

Ser Lys Gln Glu Gly Thr Cys Tyr Phe Cys Gly Ala Gly Arg Leu
                20                  25                  30

Ser Asn Asp Leu Thr Pro Ala Asn Thr Ala Thr Val Ser Ala Gln Ala
            35                  40                  45

Met Phe Met Asp Lys Trp Val Tyr Val Lys Ala Cys Gln Lys Cys Trp
50                  55                  60

His Lys Ile Tyr Thr Ala Asn Thr Phe Asn Gln Gly Lys Asn Tyr Lys
65                  70                  75                  80

Val Leu Ser Gly Cys Met Thr Leu Asp Met Lys Phe His Leu Leu Gly
                85                  90                  95

Ile Gly Asn Leu Pro Asp Asn Lys Arg Ser Asn Gly Ile Gly Trp Val
            100                 105                 110

Lys Glu Gly Thr Arg Leu Ile Pro Leu Cys Leu Ala Pro Thr Asp Gln
        115                 120                 125

Asp Asp Tyr Phe Trp Asp Gln Tyr Arg Ile Thr Gly Glu Glu Ile Gln
130                 135                 140

Ala Leu Gln Gly Thr Leu Ala Thr Leu Tyr Met Gly Leu Pro Arg Leu
145                 150                 155                 160

Thr Val Asn Arg Thr Phe Asp Ala Ala Leu Ala Ser Gly Asp Leu Glu
                165                 170                 175

Leu Asp Arg Ile Asp Leu Tyr Arg Gly Met Met Gly Met Asn Asp Leu
            180                 185                 190

Glu Asp Arg Leu Glu Ala Lys Ser Pro Asn Tyr Glu Glu Asn Lys Asp
        195                 200                 205

Lys Leu Pro Trp
    210

<210> SEQ ID NO 80
```

```
<211> LENGTH: 116
<212> TYPE: PRT
<213> ORGANISM: Phage P15

<400> SEQUENCE: 80

Met Val Ser Leu Asn Leu Pro Ser Ser Gly Ala Leu Ile Gly Asp Thr
1               5                   10                  15

Ser Ser Met Val Asp Pro His Lys Leu Gly Lys Val Met Trp Ser Arg
            20                  25                  30

Ser Met Glu Gly Asp Met Ala Pro Leu Asp Leu His Asn Gln Leu Glu
        35                  40                  45

Arg Glu Asp Leu Met Ala Leu Asn His Val Tyr Glu Met Leu Arg Ala
50                  55                  60

Tyr Arg Lys Ile Arg Pro Ala Leu Gln Ile Val Val Arg Arg Lys Trp
65                  70                  75                  80

Ser Arg Met Asp Leu Ile Lys Pro Tyr Leu Ile Ala Thr Met Glu Gly
            85                  90                  95

Arg Ser Glu Ala Arg Glu Met Ile Ala Ser Asp Asp Trp His Gln Phe
        100                 105                 110

Trp Ala Asn Leu
        115

<210> SEQ ID NO 81
<211> LENGTH: 39
<212> TYPE: PRT
<213> ORGANISM: Phage P15

<400> SEQUENCE: 81

Met Ala Ser Ser Lys Lys Ser Thr Ile Val Thr Leu Phe Ser Ile Thr
1               5                   10                  15

Ile Leu Ala Pro Val Ile Phe Val Ile Ala Leu Val Val Gly Cys Leu
            20                  25                  30

Lys Ala Leu Leu His His Lys
        35

<210> SEQ ID NO 82
<211> LENGTH: 169
<212> TYPE: PRT
<213> ORGANISM: Phage P15

<400> SEQUENCE: 82

Met Ser Asp Gln Thr Asp Thr Thr Gln Thr Thr Pro Ala Glu Lys Ala
1               5                   10                  15

Pro Pro Lys Glu Ile Ile Arg Gly Arg Met Pro Ile Ala Val Val Ala
            20                  25                  30

Leu Ala Arg Phe Gly Ser Gln Ser Thr Thr Thr Lys Ala Ala Ala
        35                  40                  45

Asp Ala Leu Gly Thr Thr Val Gly Lys Ile Asp Ile Arg Lys Asn
50                  55                  60

Arg Asn Phe Ala Tyr Val Thr Ala Asp Phe Lys Pro Thr Glu Ala Gln
65                  70                  75                  80

Lys Ala Asp Gly Ile Glu Trp Leu Lys Arg His Pro Val Gly Ala Asp
            85                  90                  95

Ala Leu Ile Glu Glu Leu Gln Asn Leu Pro Val Ala Thr Ala Glu Glu
        100                 105                 110

Ser Ala Ala Phe Glu Gln Val Arg Ala Ser Arg Gly Gln Asn Ala
        115                 120                 125

Lys Thr Ala Glu Gly Glu Val Ala Gln Ala Gly Gly Gly Asn Arg Arg
```

```
                130             135             140
Lys Lys Lys Glu Lys Pro Ala Glu Ala Gly Glu Val Gln Asn Pro Pro
145                 150                 155                 160

Ala Ala Asp Gly Asp Ser Leu Leu Ser
                165
```

<210> SEQ ID NO 83
<211> LENGTH: 39
<212> TYPE: PRT
<213> ORGANISM: Phage P15

<400> SEQUENCE: 83

```
Met Pro Trp Ala Pro Pro Ser Ala Arg Ser Thr Thr Ser Ala Arg Thr
1               5                   10                  15

Ala Thr Ser Pro Thr Ser Pro Pro Thr Ser Ser Arg Pro Lys Pro Arg
            20                  25                  30

Arg Pro Thr Ala Ser Ser Gly
        35
```

<210> SEQ ID NO 84
<211> LENGTH: 40
<212> TYPE: PRT
<213> ORGANISM: Phage P15

<400> SEQUENCE: 84

```
Met Glu Pro Leu Phe Met Arg Glu Arg Lys Val Asp Thr Ile Ala Pro
1               5                   10                  15

His Cys Glu Val Asp Thr Ile Ala Pro His Cys Glu Val Asp Thr Leu
            20                  25                  30

His Met Tyr Ala Asn Gln Trp Arg
        35                  40
```

<210> SEQ ID NO 85
<211> LENGTH: 39
<212> TYPE: PRT
<213> ORGANISM: Phage P15

<400> SEQUENCE: 85

```
Met Pro Ile Asn Gly Val Asn Ser Glu Leu Thr Gly Ala Phe Leu Ser
1               5                   10                  15

Cys Ala Gln His Ile Pro Ala Phe Ser Tyr Ala Leu Pro Ser Lys Arg
            20                  25                  30

Asp Gln Ser Ala Pro Ala Ile
        35
```

<210> SEQ ID NO 86
<211> LENGTH: 75
<212> TYPE: DNA
<213> ORGANISM: Citrus sinensis

<400> SEQUENCE: 86

```
atgggtgtag gcacaaaagt tctggtgatc acgaccatgg caatatgcct aattagctca    60
gctgcatatg cccat                                                     75
```

<210> SEQ ID NO 87
<211> LENGTH: 25
<212> TYPE: PRT
<213> ORGANISM: Citrus sinensis

<400> SEQUENCE: 87

```
Met Gly Val Gly Thr Lys Val Leu Val Ile Thr Thr Met Ala Ile Cys
```

```
1               5                  10                 15
Leu Ile Ser Ser Ala Ala Tyr Ala His
            20                 25

<210> SEQ ID NO 88
<211> LENGTH: 87
<212> TYPE: DNA
<213> ORGANISM: Unknown
<220> FEATURE:
<223> OTHER INFORMATION: HSV::HIS C-terminal tag DNA sequence

<400> SEQUENCE: 88
gcttcactcg agatcaaacg ggctagccag ccagaactcg ccccggaaga ccccgaggat    60
gtcgagcacc accaccacca ccactga                                        87

<210> SEQ ID NO 89
<211> LENGTH: 28
<212> TYPE: PRT
<213> ORGANISM: Unknown
<220> FEATURE:
<223> OTHER INFORMATION: HSV::HIS C-terminal tag translation product

<400> SEQUENCE: 89

Ala Ser Leu Glu Ile Lys Arg Ala Ser Gln Pro Glu Leu Ala Pro Glu
1               5                  10                 15

Asp Pro Glu Asp Val Glu His His His His His His
            20                 25

<210> SEQ ID NO 90
<211> LENGTH: 699
<212> TYPE: DNA
<213> ORGANISM: Unknown
<220> FEATURE:
<223> OTHER INFORMATION: P12::holZ::HSV::HIS gene fusion

<400> SEQUENCE: 90
atgggtgtag gcacaaaagt tctggtgatc acgaccatgg caatatgcct aattagctca    60
gctgcatacg cccatatgag ctgggcatcc agatcgtatg gggtggaaat tggaagtcta   120
cgcccgatcg cccgcacttc gaactggcga atgataaaa tgtatgcaaa gctcttattc    180
gcagcaggcg cggctgccac aaccgcgatc caagtagccg ctgaggcacc gacgagtaaa   240
gagtgggctt ttattgatgt aactgtggct tatgttggag taccattcaa tgtcttgatc   300
atggcggcta tcggtagtat cattgctgta atgagaaatc gagtgtctga cccacgcact   360
ctgattgtat cattcctgta cagtactctc tttgcccttg gtgcgagtgt tggtattgcg   420
gagtttacag gttaccagtg gtcgagcaca ggggctcagg ccatattcac ggccatccta   480
ggttttacgg ctcagaactg ggcccagtc ctattggaca atatagcccc agctgtggat   540
ctgtggctta acgtcagat taaacggatt tcaatatca gcattgagga taagaaacat    600
gatgactccc aagcttcact cgagatcaaa cgggctagcc agccagaact cgccccggaa   660
gaccccgagg atgtcgagca ccaccaccac caccactga                          699

<210> SEQ ID NO 91
<211> LENGTH: 232
<212> TYPE: PRT
<213> ORGANISM: Unknown
<220> FEATURE:
<223> OTHER INFORMATION: P12::holZ::HSV::HIS gene fusion translation
      product

<400> SEQUENCE: 91
```

```
Met Gly Val Gly Thr Lys Val Leu Val Ile Thr Thr Met Ala Ile Cys
1               5                   10                  15

Leu Ile Ser Ser Ala Ala Tyr Ala His Met Ser Trp Ala Ser Arg Ser
            20                  25                  30

Tyr Gly Val Glu Ile Gly Ser Leu Arg Pro Ile Ala Arg Thr Ser Asn
                35                  40                  45

Trp Arg Asn Asp Lys Met Tyr Ala Lys Leu Leu Phe Ala Ala Gly Ala
    50                  55                  60

Ala Ala Thr Thr Ala Ile Gln Val Ala Ala Glu Ala Pro Thr Ser Lys
65                  70                  75                  80

Glu Trp Ala Phe Ile Asp Val Thr Val Ala Tyr Val Gly Val Pro Phe
                85                  90                  95

Asn Val Leu Ile Met Ala Ala Ile Gly Ser Ile Ile Ala Val Met Arg
            100                 105                 110

Asn Arg Val Ser Asp Pro Arg Thr Leu Ile Val Ser Phe Leu Tyr Ser
            115                 120                 125

Thr Leu Phe Ala Leu Gly Ala Ser Val Gly Ile Ala Glu Phe Thr Gly
    130                 135                 140

Tyr Gln Trp Ser Ser Thr Gly Ala Gln Ala Ile Phe Thr Ala Ile Leu
145                 150                 155                 160

Gly Phe Thr Ala Gln Asn Trp Gly Pro Val Leu Leu Asp Asn Ile Ala
                165                 170                 175

Pro Ala Val Asp Leu Trp Leu Lys Arg Gln Ile Lys Arg Ile Phe Asn
            180                 185                 190

Ile Ser Ile Glu Asp Lys Lys His Asp Asp Ser Gln Ala Ser Leu Glu
            195                 200                 205

Ile Lys Arg Ala Ser Gln Pro Glu Leu Ala Pro Glu Asp Pro Glu Asp
210                 215                 220

Val Glu His His His His His His
225                 230

<210> SEQ ID NO 92
<211> LENGTH: 564
<212> TYPE: DNA
<213> ORGANISM: Artificial Sequence
<220> FEATURE:
<223> OTHER INFORMATION: holSZ, a synthetically designed holin

<400> SEQUENCE: 92
cacgaaagct taagatcgta tggggtggaa attggaagtc tacgcccgat cgcccgcact      60
tcgaactggc gaaatgataa aatgtatgca aagctcttat tcgcagcagg cgcggctgcc     120
acaaccgcga tccaagtagc cgctgaggca ccgacgagta aagagtgggc ttttattgac     180
gtccatgaaa acgtaactgt ggcttatgtt ggagtaccat tcaatgtctt gatcatggcg     240
gctatcggtc acagggcccc tagtatcatt gctgtaatga aaatcgagt gtctgaccca      300 cgcactctga ttgtatcatt cctgtacagt actctctttg cccttggtgc gagtgttggt     360
attgcgagac acgagtttac aggttaccag tggtcgagca caggggctca ggccatattc     420
acggccatcc taggttttac ggctcagaac tggggcccag tcctattgga caatatagcc     480
ccagctgtgg atctgtggct taaacgtcag attaacgga ttttcaatat cagcattgag      540
gataagaaac atgatgactc ccaa                                            564

<210> SEQ ID NO 93
<211> LENGTH: 188
<212> TYPE: PRT
<213> ORGANISM: Artificial Sequence
```

<220> FEATURE:
<223> OTHER INFORMATION: holSZ translation product

<400> SEQUENCE: 93

His Glu Ser Leu Arg Ser Tyr Gly Val Glu Ile Gly Ser Leu Arg Pro
1               5                   10                  15

Ile Ala Arg Thr Ser Asn Trp Arg Asn Asp Lys Met Tyr Ala Lys Leu
            20                  25                  30

Leu Phe Ala Ala Gly Ala Ala Thr Thr Ala Ile Gln Val Ala Ala
        35                  40                  45

Glu Ala Pro Thr Ser Lys Glu Trp Ala Phe Ile Asp Val His Glu Asn
    50                  55                  60

Val Thr Val Ala Tyr Val Gly Val Pro Phe Asn Val Leu Ile Met Ala
65                  70                  75                  80

Ala Ile Gly His Arg Ala Pro Ser Ile Ile Ala Val Met Arg Asn Arg
                85                  90                  95

Val Ser Asp Pro Arg Thr Leu Ile Val Ser Phe Leu Tyr Ser Thr Leu
            100                 105                 110

Phe Ala Leu Gly Ala Ser Val Gly Ile Ala Arg His Glu Phe Thr Gly
        115                 120                 125

Tyr Gln Trp Ser Ser Thr Gly Ala Gln Ala Ile Phe Thr Ala Ile Leu
    130                 135                 140

Gly Phe Thr Ala Gln Asn Trp Gly Pro Val Leu Leu Asp Asn Ile Ala
145                 150                 155                 160

Pro Ala Val Asp Leu Trp Leu Lys Arg Gln Ile Lys Arg Ile Phe Asn
                165                 170                 175

Ile Ser Ile Glu Asp Lys Lys His Asp Asp Ser Gln
            180                 185

<210> SEQ ID NO 94
<211> LENGTH: 726
<212> TYPE: DNA
<213> ORGANISM: Unknown
<220> FEATURE:
<223> OTHER INFORMATION: P12::holSZ::HSV::HIS gene fusion

<400> SEQUENCE: 94
atgggtgtag gcacaaaagt tctggtgatc acgaccatgg caatatgcct aattagctca      60
gctgcatacg cccatcacga aagcttaaga tcgtatgggg tggaaattgg aagtctacgc     120
ccgatcgccc gcacttcgaa ctggcgaaat gataaaatgt atgcaaagct cttattcgca     180
gcaggcgcgg ctgccacaac cgcgatccaa gtagccgctg aggcaccgac gagtaaagag     240
tgggctttta ttgacgtcca tgaaaacgta actgtggctt atgttggagt accattcaat     300
gtcttgatca tggcggctat cggtcacagg gcccctagta tcattgctgt aatgagaaat     360
cgagtgtctg acccacgcac tctgattgta tcattcctgt acagtactct ctttgccctt     420
ggtgcgagtg ttggtattgc gagacacgag tttacaggtt accagtggtc gagcacaggg     480
gctcaggcca tattcaccgg catcctaggt tttacggctc agaactgggg cccagtccta     540
ttggacaata tagccccagc tgtggatctg tggcttaaac gtcagattaa acggattttc     600
aatatcagca ttgaggataa gaaacatgat gactcccaag cttcactcga gatcaaacgg     660
gctagccagc cagaactcgc cccggaagac cccgaggatg tcgagcacca ccaccaccac     720
cactga                                                                  726

<210> SEQ ID NO 95
<211> LENGTH: 241

```
<212> TYPE: PRT
<213> ORGANISM: Unknown
<220> FEATURE:
<223> OTHER INFORMATION: P12::holSZ::HSV::HIS gene fusion translation
      product

<400> SEQUENCE: 95

Met Gly Val Gly Thr Lys Val Leu Val Ile Thr Thr Met Ala Ile Cys
1               5                   10                  15

Leu Ile Ser Ser Ala Ala Tyr Ala His His Glu Ser Leu Arg Ser Tyr
            20                  25                  30

Gly Val Glu Ile Gly Ser Leu Arg Pro Ile Ala Arg Thr Ser Asn Trp
        35                  40                  45

Arg Asn Asp Lys Met Tyr Ala Lys Leu Leu Phe Ala Ala Gly Ala Ala
    50                  55                  60

Ala Thr Thr Ala Ile Gln Val Ala Ala Glu Ala Pro Thr Ser Lys Glu
65                  70                  75                  80

Trp Ala Phe Ile Asp Val His Glu Asn Val Thr Val Ala Tyr Val Gly
                85                  90                  95

Val Pro Phe Asn Val Leu Ile Met Ala Ala Ile Gly His Arg Ala Pro
            100                 105                 110

Ser Ile Ile Ala Val Met Arg Asn Arg Val Ser Asp Pro Arg Thr Leu
        115                 120                 125

Ile Val Ser Phe Leu Tyr Ser Thr Leu Phe Ala Leu Gly Ala Ser Val
130                 135                 140

Gly Ile Ala Arg His Glu Phe Thr Gly Tyr Gln Trp Ser Ser Thr Gly
145                 150                 155                 160

Ala Gln Ala Ile Phe Thr Ala Ile Leu Gly Phe Thr Ala Gln Asn Trp
                165                 170                 175

Gly Pro Val Leu Leu Asp Asn Ile Ala Pro Ala Val Asp Leu Trp Leu
            180                 185                 190

Lys Arg Gln Ile Lys Arg Ile Phe Asn Ile Ser Ile Glu Asp Lys Lys
        195                 200                 205

His Asp Asp Ser Gln Ala Ser Leu Glu Ile Lys Arg Ala Ser Gln Pro
210                 215                 220

Glu Leu Ala Pro Glu Asp Pro Glu Asp Val Glu His His His His
225                 230                 235                 240

His

<210> SEQ ID NO 96
<211> LENGTH: 489
<212> TYPE: DNA
<213> ORGANISM: Unknown
<220> FEATURE:
<223> OTHER INFORMATION: P12::holZA.1::HSV::HIS gene fusion

<400> SEQUENCE: 96
atgggtgtag gcacaaaagt tctggtgatc acgaccatgg caatatgcct aattagctca         60
gctgcatacg cccatatgac tcccaatgag attccggttt ggtctcttct gacaacccca        120
tctctgatag tcttcttcct gacgggccta tatggtgtga atgagtggag attgcgcccc        180
gtccggcaga tcgttggaaa acgtggcttg gttgagttgg gtttgggctt gtccctcgga        240
acgatgtgtg tactgagttt tgtgacgttg atcgctgtga tcatgatggc gaatctatat        300
tcgtggcgtg gctgtctgct actcaccagc atcgctggcg tgttgttgac ggtcggccgt        360
cacgcccctt ggcgttttttg gattcatcgt tttccggaga acgcttcact cgagatcaaa       420
cgggctagcc agccagaact cgccccggaa gaccccgagg atgtcgagca ccaccaccac        480
``` caccactga 489

<210> SEQ ID NO 97
<211> LENGTH: 162
<212> TYPE: PRT
<213> ORGANISM: Unknown
<220> FEATURE:
<223> OTHER INFORMATION: P12::holZA.1::HSV::HIS gene fusion
      translation product

<400> SEQUENCE: 97

```
Met Gly Val Gly Thr Lys Val Leu Val Ile Thr Thr Met Ala Ile Cys
1               5                   10                  15

Leu Ile Ser Ser Ala Ala Tyr Ala His Met Thr Pro Asn Glu Ile Pro
            20                  25                  30

Val Trp Ser Leu Leu Thr Thr Pro Ser Leu Ile Val Phe Phe Leu Thr
        35                  40                  45

Gly Leu Tyr Gly Val Asn Glu Trp Arg Leu Arg Pro Val Arg Gln Ile
    50                  55                  60

Val Gly Lys Arg Gly Leu Val Glu Leu Gly Leu Gly Leu Ser Leu Gly
65                  70                  75                  80

Thr Met Cys Val Leu Ser Phe Val Thr Leu Ile Ala Val Ile Met Met
                85                  90                  95

Ala Asn Leu Tyr Ser Trp Arg Gly Cys Leu Leu Leu Thr Ser Ile Ala
            100                 105                 110

Gly Val Leu Leu Thr Val Gly Arg His Ala Pro Trp Arg Phe Trp Ile
        115                 120                 125

His Arg Phe Pro Glu Asn Ala Ser Leu Glu Ile Lys Arg Ala Ser Gln
    130                 135                 140

Pro Glu Leu Ala Pro Glu Asp Pro Glu Asp Val Glu His His His His
145                 150                 155                 160

His His
```

<210> SEQ ID NO 98
<211> LENGTH: 1164
<212> TYPE: DNA
<213> ORGANISM: Unknown
<220> FEATURE:
<223> OTHER INFORMATION: P12::holZ::lysY::HSV::HIS gene fusion

<400> SEQUENCE: 98

| | | |
|---|---|---|
| atgggtgtag gcacaaaagt tctggtgatc acgaccatgg caatatgcct aattagctca | 60 |
| gctgcatacg cccatatgag ctgggcatcc agatcgtatg gggtggaaat tggaagtcta | 120 |
| cgcccgatcg cccgcacttc gaactggcga atgataaaa tgtatgcaaa gctcttattc | 180 |
| gcagcaggcg cggctgccac aaccgcgatc caagtagccg ctgaggcacc gacgagtaaa | 240 |
| gagtgggctt ttattgatgt aactgtggct tatgttggag taccattcaa tgtcttgatc | 300 |
| atggcggcta tcggtagtat cattgctgta atgagaaatc gagtgtctga cccacgcact | 360 |
| ctgattgtat cattcctgta cagtactctc tttgcccttg gtgcgagtgt tggtattgcg | 420 |
| gagtttacag gttaccagtg gtcgagcaca ggggctcagg ccatattcac ggccatccta | 480 |
| ggttttacgg ctcagaactg ggcccagtc tattggaca atatagcccc agctgtggat | 540 |
| ctgtggctta acgtcagat taacggatt ttcaatatca gcattgagga taagaaacat | 600 |
| gatgactccc aagcttttgg tggtggagga tctatgttcg cattgtccca gaagagtcag | 660 |
| cacatcctcg acaccgttca gcacccccctt cgcgatgtcg tccgtctcgc catcactcgt | 720 |

```
acaactgtgg acttcggtgt tatccaaggc ggtcgtacac ttgacgaaca aatgcgtttg   780
tacgggaagg ggcgcaacgc cgctgaatgt gccaagatgg gcgtccctgc cgcctatgct   840
aagcctaagg aatctaaggt tacttgggtc aatccacgaa acggcaacca tgtagtggac   900
gggtctggat ttggccgagc agtggatctc gccccgtaca tccagggtaa attggaatgg   960
gataacgacg gcaaactcgg actgtatccc aagattgccg aagcaatgtt cagcgcagca  1020
aatgagctgg gcatccagat cgtatggggt ggaaattgga agtctacgcc cgatcgcccg  1080
cacttcgaac tggcgaaagc tagccagcca gaactcgccc cggaagaccc cgaggatgtc  1140
gagcaccacc accaccacca ctga                                         1164
```

<210> SEQ ID NO 99
<211> LENGTH: 387
<212> TYPE: PRT
<213> ORGANISM: Unknown
<220> FEATURE:
<223> OTHER INFORMATION: P12::holZ::lysY::HSV::HIS gene fusion
      translation product

<400> SEQUENCE: 99

```
Met Gly Val Gly Thr Lys Val Leu Val Ile Thr Thr Met Ala Ile Cys
1               5                   10                  15

Leu Ile Ser Ser Ala Ala Tyr Ala His Met Ser Trp Ala Ser Arg Ser
            20                  25                  30

Tyr Gly Val Glu Ile Gly Ser Leu Arg Pro Ile Ala Arg Thr Ser Asn
        35                  40                  45

Trp Arg Asn Asp Lys Met Tyr Ala Lys Leu Leu Phe Ala Ala Gly Ala
    50                  55                  60

Ala Ala Thr Thr Ala Ile Gln Val Ala Ala Glu Ala Pro Thr Ser Lys
65                  70                  75                  80

Glu Trp Ala Phe Ile Asp Val Thr Val Ala Tyr Val Gly Val Pro Phe
                85                  90                  95

Asn Val Leu Ile Met Ala Ala Ile Gly Ser Ile Ile Ala Val Met Arg
            100                 105                 110

Asn Arg Val Ser Asp Pro Arg Thr Leu Ile Val Ser Phe Leu Tyr Ser
        115                 120                 125

Thr Leu Phe Ala Leu Gly Ala Ser Val Gly Ile Ala Glu Phe Thr Gly
    130                 135                 140

Tyr Gln Trp Ser Ser Thr Gly Ala Gln Ala Ile Phe Thr Ala Ile Leu
145                 150                 155                 160

Gly Phe Thr Ala Gln Asn Trp Gly Pro Val Leu Leu Asp Asn Ile Ala
                165                 170                 175

Pro Ala Val Asp Leu Trp Leu Lys Arg Gln Ile Lys Arg Ile Phe Asn
            180                 185                 190

Ile Ser Ile Glu Asp Lys Lys His Asp Asp Ser Gln Ala Phe Gly Gly
        195                 200                 205

Gly Gly Ser Met Phe Ala Leu Ser Gln Lys Ser Gln His Ile Leu Asp
    210                 215                 220

Thr Val Gln His Pro Leu Arg Asp Val Val Arg Leu Ala Ile Thr Arg
225                 230                 235                 240

Thr Thr Val Asp Phe Gly Val Ile Gln Gly Gly Arg Thr Leu Asp Glu
                245                 250                 255

Gln Met Arg Leu Tyr Gly Lys Gly Arg Asn Ala Ala Glu Cys Ala Lys
            260                 265                 270

Met Gly Val Pro Ala Ala Tyr Ala Lys Pro Lys Glu Ser Lys Val Thr
        275                 280                 285
```

```
Trp Val Asn Pro Arg Asn Gly Asn His Val Val Asp Gly Ser Gly Phe
    290                 295                 300

Gly Arg Ala Val Asp Leu Ala Pro Tyr Ile Gln Gly Lys Leu Glu Trp
305                 310                 315                 320

Asp Asn Asp Gly Lys Leu Gly Leu Tyr Pro Lys Ile Ala Glu Ala Met
                325                 330                 335

Phe Ser Ala Ala Asn Glu Leu Gly Ile Gln Ile Val Trp Gly Gly Asn
            340                 345                 350

Trp Lys Ser Thr Pro Asp Arg Pro His Phe Glu Leu Ala Lys Ala Ser
        355                 360                 365

Gln Pro Glu Leu Ala Pro Glu Asp Pro Glu Asp Val Glu His His His
    370                 375                 380

His His His
385

<210> SEQ ID NO 100
<211> LENGTH: 1191
<212> TYPE: DNA
<213> ORGANISM: Unknown
<220> FEATURE:
<223> OTHER INFORMATION: P12::holSZ::lysY::HSV::HIS gene fusion

<400> SEQUENCE: 100
atgggtgtag gcacaaaagt tctggtgatc acgaccatgg caatatgcct aattagctca        60
gctgcatacg cccatcacga aagcttaaga tcgtatgggg tggaaattgg aagtctacgc       120
ccgatcgccc gcacttcgaa ctggcgaaat gataaaatgt atgcaaagct cttattcgca       180
gcaggcgcgg ctgccacaac cgcgatccaa gtagccgctg aggcaccgac gagtaaagag       240
tgggctttta ttgacgtcca tgaaaacgta actgtggctt atgttggagt accattcaat       300
gtcttgatca tggcggctat cggtcacagg gcccctagta tcattgctgt aatgagaaat       360
cgagtgtctg acccacgcac tctgattgta tcattcctgt acagtactct ctttgccctt       420
ggtgcgagtg ttggtattgc gagacacgag tttacaggtt accagtggtc gagcacaggg       480
gctcaggcca tattcacggc catcctaggt tttacggctc agaactgggg cccagtccta       540
ttggacaata tagccccagc tgtggatctg tggcttaaac gtcagattaa acggatttc       600 aatatcagca ttgaggataa gaaacatgat gactcccaag cttttggtgg tggaggatct       660
atgttcgcat tgtcccagaa gagtcagcac atcctcgaca ccgttcagca cccccttcgc       720
gatgtcgtcc gtctcgccat cactcgtaca actgtggact cggtgtttat ccaaggcggt       780
cgtacacttg acgaacaaat gcgtttgtac gggaaggggc gcaacgccgc tgaatgtgcc       840
aagatgggcg tccctgccgc ctatgctaag cctaaggaat ctaaggttac ttgggtcaat       900
ccacgaaacg gcaaccatgt agtggacggg tctggatttg gccgagcagt ggatctcgcc       960
ccgtacatcc agggtaaatt ggaatgggat aacgacggca aactcggact gtatcccaag      1020
attgccgaag caatgttcag cgcagcaaat gagctgggca tccagatcgt atgggtgga      1080 aattggaagt ctacgcccga tcgccgcac ttcgaactgg cgaaagctag ccagccagaa      1140
ctcgccccgg aagaccccga ggatgtcgag caccaccacc accaccactg a              1191

<210> SEQ ID NO 101
<211> LENGTH: 396
<212> TYPE: PRT
<213> ORGANISM: Unknown
<220> FEATURE:
<223> OTHER INFORMATION: P12::holSZ::lysY::HSV::HIS gene fusion
      translation product
```

```
<400> SEQUENCE: 101

Met Gly Val Gly Thr Lys Val Leu Val Ile Thr Thr Met Ala Ile Cys
1               5                   10                  15

Leu Ile Ser Ser Ala Ala Tyr Ala His His Glu Ser Leu Arg Ser Tyr
            20                  25                  30

Gly Val Glu Ile Gly Ser Leu Arg Pro Ile Ala Arg Thr Ser Asn Trp
            35                  40                  45

Arg Asn Asp Lys Met Tyr Ala Lys Leu Leu Phe Ala Ala Gly Ala Ala
        50                  55                  60

Ala Thr Thr Ala Ile Gln Val Ala Glu Ala Pro Thr Ser Lys Glu
65                  70                  75                  80

Trp Ala Phe Ile Asp Val His Glu Asn Val Thr Val Ala Tyr Val Gly
                85                  90                  95

Val Pro Phe Asn Val Leu Ile Met Ala Ala Ile Gly His Arg Ala Pro
            100                 105                 110

Ser Ile Ile Ala Val Met Arg Asn Arg Val Ser Asp Pro Arg Thr Leu
            115                 120                 125

Ile Val Ser Phe Leu Tyr Ser Thr Leu Phe Ala Leu Gly Ala Ser Val
130                 135                 140

Gly Ile Ala Arg His Glu Phe Thr Gly Tyr Gln Trp Ser Ser Thr Gly
145                 150                 155                 160

Ala Gln Ala Ile Phe Thr Ala Ile Leu Gly Phe Thr Ala Gln Asn Trp
                165                 170                 175

Gly Pro Val Leu Leu Asp Asn Ile Ala Pro Ala Val Asp Leu Trp Leu
            180                 185                 190

Lys Arg Gln Ile Lys Arg Ile Phe Asn Ile Ser Ile Glu Asp Lys Lys
            195                 200                 205

His Asp Asp Ser Gln Ala Phe Gly Gly Gly Ser Met Phe Ala Leu
        210                 215                 220

Ser Gln Lys Ser Gln His Ile Leu Asp Thr Val Gln His Pro Leu Arg
225                 230                 235                 240

Asp Val Val Arg Leu Ala Ile Thr Arg Thr Thr Val Asp Phe Gly Val
                245                 250                 255

Ile Gln Gly Gly Arg Thr Leu Asp Glu Gln Met Arg Leu Tyr Gly Lys
            260                 265                 270

Gly Arg Asn Ala Ala Glu Cys Ala Lys Met Gly Val Pro Ala Ala Tyr
            275                 280                 285

Ala Lys Pro Lys Glu Ser Lys Val Thr Trp Val Asn Pro Arg Asn Gly
            290                 295                 300

Asn His Val Val Asp Gly Ser Gly Phe Gly Arg Ala Val Asp Leu Ala
305                 310                 315                 320

Pro Tyr Ile Gln Gly Lys Leu Glu Trp Asp Asn Asp Gly Lys Leu Gly
                325                 330                 335

Leu Tyr Pro Lys Ile Ala Glu Ala Met Phe Ser Ala Ala Asn Glu Leu
            340                 345                 350

Gly Ile Gln Ile Val Trp Gly Gly Asn Trp Lys Ser Thr Pro Asp Arg
            355                 360                 365

Pro His Phe Glu Leu Ala Lys Ala Ser Gln Pro Glu Leu Ala Pro Glu
        370                 375                 380

Asp Pro Glu Asp Val Glu His His His His His
385                 390                 395

<210> SEQ ID NO 102
```

```
<211> LENGTH: 993
<212> TYPE: DNA
<213> ORGANISM: Unknown
<220> FEATURE:
<223> OTHER INFORMATION: P12::holZA.1::lysY::HSV::HIS gene fusion

<400> SEQUENCE: 102
atgggtgtag gcacaaaagt tctggtgatc acgaccatgg caatatgcct aattagctca      60
gctgcatacg cccatatgac tcccaatgag attccggttt ggtctcttct gacaacccca     120
tctctgatag tcttcttcct gacgggccta tatggtgtga atgagtggag attgcgcccc     180
gtccggcaga tcgttggaaa acgtggcttg gttgagttgg gtttgggctt gtccctcgga     240
acgatgtgtg tactgagttt tgtgacgttg atcgctgtga tcatgatggc gaatctatat     300
tcgtggcgtg gctgtctgct actcaccagc atcgctggcg tgttgttgac ggtcggccgt     360
cacgccccct tggcgttttt gattcatcgt tttccggaga acaatatcag cattgaggat     420
aagaaacatg atgactccca gcttttggt ggtggaggat ctatgttcgc attgtcccag     480
aagagtcagc acatcctcga caccgttcag caccccttc gcgatgtcgt ccgtctcgcc     540
atcactcgta caactgtgga cttcggtgtt atccaaggcg tcgtacact tgacgaacaa     600
atgcgtttgt acgggaaggg gcgcaacgcc gctgaatgtg ccaagatggg cgtccctgcc     660
gcctatgcta agcctaagga atctaaggtt acttgggtca atccacgaaa cggcaaccat     720
gtagtggacg ggtctggatt tggccgagca gtggatctcg ccccgtacat ccagggtaaa     780
ttggaatggg ataacgacgg caaactcgga ctgtatccca agattgccga agcaatgttc     840
agcgcagcaa atgagctggg catccagatc gtatggggtg gaaattggaa gtctacgccc     900
gatcgcccgc acttcgaact ggcgaaagct agccagccag aactcgcccc ggaagacccc     960
gaggatgtcg agcaccacca ccaccaccac tga                                  993

<210> SEQ ID NO 103
<211> LENGTH: 317
<212> TYPE: PRT
<213> ORGANISM: Unknown
<220> FEATURE:
<223> OTHER INFORMATION: P12::holZA.1::lysY::HSV::HIS gene fusion
      translation product

<400> SEQUENCE: 103

Met Gly Val Gly Thr Lys Val Leu Val Ile Thr Thr Met Ala Ile Cys
1               5                   10                  15

Leu Ile Ser Ser Ala Ala Tyr Ala His Met Thr Pro Asn Glu Ile Pro
            20                  25                  30

Val Trp Ser Leu Leu Thr Thr Pro Ser Leu Ile Val Phe Phe Leu Thr
        35                  40                  45

Gly Leu Tyr Gly Val Asn Glu Trp Arg Leu Arg Pro Val Arg Gln Ile
    50                  55                  60

Val Gly Lys Arg Gly Leu Val Glu Leu Gly Leu Gly Leu Ser Leu Gly
65                  70                  75                  80

Thr Met Cys Val Leu Ser Phe Val Thr Leu Ile Ala Val Ile Met Met
                85                  90                  95

Ala Asn Leu Tyr Ser Trp Arg Gly Cys Leu Leu Leu Thr Ser Ile Ala
            100                 105                 110

Gly Val Leu Leu Thr Val Gly Arg His Ala Pro Trp Arg Phe Trp Ile
        115                 120                 125

His Arg Phe Pro Glu Asn Ala Phe Gly Gly Gly Ser Met Phe Ala
    130                 135                 140
```

```
Leu Ser Gln Lys Ser Gln His Ile Leu Asp Thr Val Gln His Pro Leu
145                 150                 155                 160

Arg Asp Val Val Arg Leu Ala Ile Thr Arg Thr Val Asp Phe Gly
            165                 170                 175

Val Ile Gln Gly Gly Arg Thr Leu Asp Glu Gln Met Arg Leu Tyr Gly
            180                 185                 190

Lys Gly Arg Asn Ala Ala Glu Cys Ala Lys Met Gly Val Pro Ala Ala
            195                 200                 205

Tyr Ala Lys Pro Lys Glu Ser Lys Val Thr Trp Val Asn Pro Arg Asn
210                 215                 220

Gly Asn His Val Val Asp Gly Ser Gly Phe Gly Arg Ala Val Asp Leu
225                 230                 235                 240

Ala Pro Tyr Ile Gln Gly Lys Leu Glu Trp Asp Asn Asp Gly Lys Leu
            245                 250                 255

Gly Leu Tyr Pro Lys Ile Ala Glu Ala Met Phe Ser Ala Ala Asn Glu
            260                 265                 270

Leu Gly Ile Gln Ile Val Trp Gly Asn Trp Lys Ser Thr Pro Asp
            275                 280                 285

Arg Pro His Phe Glu Leu Ala Lys Ala Ser Gln Pro Glu Leu Ala Pro
290                 295                 300

Glu Asp Pro Glu Asp Val Glu His His His His His
305                 310                 315

<210> SEQ ID NO 104
<211> LENGTH: 17
<212> TYPE: DNA
<213> ORGANISM: Unknown
<220> FEATURE:
<223> OTHER INFORMATION: IPG 436 primer

<400> SEQUENCE: 104
tggacgtcat cgctggg                                                  17

<210> SEQ ID NO 105
<211> LENGTH: 26
<212> TYPE: DNA
<213> ORGANISM: Unknown
<220> FEATURE:
<223> OTHER INFORMATION: IPG 437 primer

<400> SEQUENCE: 105
aattcccagc gatgacgtcc aacatg                                        26

<210> SEQ ID NO 106
<211> LENGTH: 1371
<212> TYPE: DNA
<213> ORGANISM: Citrus

<400> SEQUENCE: 106
aagcttgcat gcctgcagaa gcttcaggtg gtcagttggc tagtccaatt aaaccaaata   60
caattatttg aaaatcactc gattaaaccc ttaagaggac ctctacataa atatatacta  120
aacaatacgc tgtctattat ataaagactc ttacagcgtg tttattgttt aattgcataa  180
gagtgacaaa atttaaccca tttgcaataa aagggagctt aacttttcaa tataaaccaa  240
ttacacctaa accatttcat ccgaacacct cacttaatgg gagtccgcgc tagtctcgat  300
agaattttgg gctgtgttat aaatttatat atgtagattc ttaatagatt gatatcaaat  360
tatagtatat ttctaaattg tagcaattta taaaaaaaaa cacacacccc cttacttcat  420
gtggtaaaat ttaaaccaaa agcaaattaa gtaaatgatc attgcttata attgaaaaat  480
```

-continued

```
tgtggatgtt gtaactcgta atatgccaaa cagataaaaa ttgagtgatg ctgccattgg    540
agacattaat tcttttttcta aatttaacaa tgaaatgggt atccatgccc ataaaatggc    600
catttcttac actactcgac atatatgaga ttttttttcct tatcatacaa taaatgctta    660
tcctctctat aaatgaaatt caatgaattt acttctacta gaatatcgaa ataatacaca    720
ataatttgta acgtgcataa tggtatagag tgtccattgg tgtgaaaaga gggaccttga    780
tttttaaata taaatcaatt ataactaagc catttcatcg aaacacctca ctcatttgat    840
gttgcaattt ccaaacccag cagtcaaaaa acgagtgaag taaatgacca tgcaattgct    900
taaatggata cttaaaagta ttcattttgg aaccaatttt ggggcttggt gaatatgagg    960
tatagatata aattggattg ggggggggtgg tgacgttgtg ctttcgtgcc ccctcaccaa   1020
ccccaaaaaa gtccatgcca ccaatcacct tgcttccatg tggcgagatc ttaaccatct   1080
aaaaccatga aaatccaacg gccgcgtgtt tctttcaact aacccgtcgg ccaaccccac   1140
caaacactca atgttgcaac cccccaact ctatttaaag ccccgttttt aggtctccaa   1200
actcaggaat tttcacttgg cttgaaaatt tcccttttcat catcgtcaca gattcacgtt   1260
tacatgcaat aaatatataa ttgccccccac aaaagatttt cccacccatt ttctctccca   1320
cccatcagta catttacttc ttttaactca aaaacaacaa ggaaaggatc c             1371

<210> SEQ ID NO 107
<211> LENGTH: 588
<212> TYPE: DNA
<213> ORGANISM: Artificial Sequence
<220> FEATURE:
<223> OTHER INFORMATION: Modified intron from citrus

<400> SEQUENCE: 107
gtaaatttct atttctcttc tgtttgcttc cgtttgatga cgattttctt taatgacact     60
gatttggaat ttcatgagg aattagtttg ttttattgtt agtattttca aaatgtttgt    120
tttggcttgc tctttgtttt tttttttttttc cttttttcat gtattttgtt ttcttaaata    180
tattaattga ggaatctttg gacgttgaag aaacttgttg atcaaggcat tgaagttggt    240
tgaaaatctt cttgatttaa atgatgactg gcttataatt atccaattct ttagaatatc    300
tctatctact taatttgtag aggaaatttg tttgatcatt gacacatgaa ctagtctcat    360
ttatttaatg tgatttcaaa tttggctgtc aagtctatat ggcttgctgc actatataaa    420
ttgtgatctc agtgaagaat gagaatagta gtgaagagga accagactcg tgaagaagaa    480
aaggaagaaa aaaactgttt accggttgtt tgctccttgt ctaggttcta gtttccttca    540
gaactacaca ggttaggaga tttcaatttg tgtgtatttt gctgacag                 588

<210> SEQ ID NO 108
<211> LENGTH: 12368
<212> TYPE: DNA
<213> ORGANISM: Artificial Sequence
<220> FEATURE:
<223> OTHER INFORMATION: pIPG534 plant transformation vector

<400> SEQUENCE: 108
catgccaacc acagggttcc cctcgggatc aaagtacttt gatccaaccc ctccgctgct     60
atagtgcagt cggcttctga cgttcagtgc agccgtcttc tgaaaacgac atgtcgcaca    120
agtcctaagt tacgcgacag gctgccgccc tgcccttttc ctggcgtttt cttgtcgcgt    180
gttttagtcg cataaagtag aatacttgcg actagaaccg gagacattac gccatgaaca    240
agagcgccgc cgctggcctg ctgggctatg cccgcgtcag caccgacgac caggacttga    300
```

```
ccaaccaacg ggccgaactg cacgcggccg gctgcaccaa gctgttttcc gagaagatca    360
ccggcaccag gcgcgaccgc ccggagctgg ccaggatgct tgaccaccta cgccctggcg    420
acgttgtgac agtgaccagg ctagaccgcc tggcccgcag cacccgcgac ctactggaca    480
ttgccgagcg catccaggag gccggcgcgg gcctgcgtag cctggcagag ccgtgggccg    540
acaccaccac gccggccggc cgcatggtgt tgaccgtgtt cgccggcatt gccgagttcg    600
agcgttccct aatcatcgac cgcacccgga gcgggcgcga ggccgccaag gcccgaggcg    660
tgaagtttgg cccccgccct accctcaccc cggcacagat cgcgcacgcc cgcgagctga    720
tcgaccagga aggccgcacc gtgaaagagg cggctgcact gcttggcgtg catcgctcga    780
ccctgtaccg cgcacttgag cgcagcgagg aagtgacgcc caccgaggcc aggcggcgcg    840
gtgccttccg tgaggacgca ttgaccgagg ccgacgccct ggcggccgcc gagaatgaac    900
gccaagagga acaagcatga aaccgcacca ggacggccag gacgaaccgt ttttcattac    960
cgaagagatc gaggcggaga tgatcgcggc cgggtacgtg ttcgagccgc ccgcgcacgt   1020
ctcaaccgtg cggctgcatg aaatcctggc cggtttgtct gatgccaagc tggcggcctg   1080 gccgccagc ttggccgctg aagaaaccga gcgccgccgt ctaaaaaggt gatgtgtatt    1140
tgagtaaaac agcttgcgtc atgcggtcgc tgcgtatatg atgcgatgag taaataaaca   1200
aatacgcaag gggaacgcat gaaggttatc gctgtactta accagaaagg cgggtcaggc   1260
aagacgacca tcgcaaccca tctagcccgc gccctgcaac tcgccggggc cgatgttctg   1320
ttagtcgatt ccgatcccca gggcagtgcc cgcgattggg cggccgtgcg gaagatcaa    1380 ccgctaaccg ttgtcggcat cgaccgcccg acgattgacc gcgacgtgaa ggccatcggc   1440
cggcgcgact tcgtagtgat cgacggagcg ccccaggcgg cggacttggc tgtgtccgcg   1500
atcaaggcag ccgacttcgt gctgattccg gtgcagccaa gcccttacga catatgggcc   1560
accgccgacc tggtggagct ggttaagcag cgcattgagg tcacggatgg aaggctacaa   1620
gcggcctttg tcgtgtcgcg ggcgatcaaa ggcacgcgca tcggcggtga ggttgccgag   1680
gcgctggccg ggtacgagct gcccattctt gagtcccgta tcacgcagcg cgtgagctac   1740
ccaggcactg ccgccgccgg cacaaccgtt cttgaatcag aacccgaggg cgacgctgcc   1800
cgcgaggtcc aggcgctggc cgctgaaatt aaatcaaaac tcatttgagt taatgaggta   1860
aagagaaaat gagcaaaagc acaaacacgc taagtgccgg ccgtccgagc gcacgcagca   1920
gcaaggctgc aacgttggcc agcctggcag acacgccagc catgaagcgg gtcaactttc   1980
agttgccggc ggaggatcac accaagctga agatgtacgc ggtacgccaa ggcaagacca   2040
ttaccgagct gctatctgaa tacatcgcgc agctaccaga gtaaatgagc aaatgaataa   2100
atgagtagat gaattttagc ggctaaagga ggcggcatgg aaaatcaaga acaaccaggc   2160
accgacgccg tggaatgccc catgtgtgga ggaacgggcg gttggccagg cgtaagcggc   2220
tgggttgtct gccggccctg caatggcact ggaaccccca gcccgaggga tcggcgtga   2280 cggtcgcaaa ccatccggcc cggtacaaat cggcgcggcg ctgggtgatg acctggtgga   2340
gaagttgaag gccgcgcagg ccgcccagcg gcaacgcatc gaggcagaag cacgccccgg   2400
tgaatcgtgg caagcggccg ctgatcgaat ccgcaaagaa tcccggcaac cgccggcagc   2460
cggtgcgccg tcgattagga agccgcccaa gggcgacgag caaccagatt ttttcgttcc   2520
gatgctctat gacgtgggca cccgcgatag tcgcagcatc atggacgtgg ccgttttccg   2580
tctgtcgaag cgtgaccgac gagctggcga ggtgatccgc tacgagcttc agacgggca    2640 cgtagaggtt tccgcagggc cggccggcat ggccagtgtg tgggattacg acctggtact   2700
```

```
gatggcggtt tcccatctaa ccgaatccat gaaccgatac cgggaaggga agggagacaa    2760
gcccggccgc gtgttccgtc cacacgttgc ggacgtactc aagttctgcc ggcgagccga    2820
tggcggaaag cagaaagacg acctggtaga aacctgcatt cggttaaaca ccacgcacgt    2880
tgccatgcag cgtacgaaga aggccaagaa cggccgcctg gtgacggtat ccgagggtga    2940
agccttgatt agccgctaca agatcgtaaa gagcgaaacc gggcggccgg agtacatcga    3000
gatcgagcta gctgattgga tgtaccgcga gatcacagaa ggcaagaacc cggacgtgct    3060
gacggttcac cccgattact ttttgatcga tcccggcatc ggccgttttc tctaccgcct    3120
ggcacgccgc gccgcaggca aggcagaagc cagatggttg ttcaagacga tctacgaacg    3180
cagtggcagc gccggagagt tcaagaagtt ctgtttcacc gtgcgcaagc tgatcgggtc    3240
aaatgacctg ccggagtacg atttgaagga ggaggcgggg caggctggcc cgatcctagt    3300
catgcgctac cgcaacctga tcgagggcga agcatccgcc ggttcctaat gtacggagca    3360
gatgctaggg caaattgccc tagcagggga aaaaggtcga aaaggtctct ttcctgtgga    3420
tagcacgtac attgggaacc caaagccgta cattgggaac cggaacccgt acattgggaa    3480
cccaaagccg tacattggga accggtcaca catgtaagtg actgatataa aagagaaaaa    3540
aggcgatttt tccgcctaaa actctttaaa acttattaaa actcttaaaa cccgcctggc    3600
ctgtgcataa ctgtctggcc agcgcacagc cgaagagctg caaaaagcgc ctacccttcg    3660
gtcgctgcgc tccctacgcc ccgccgcttc gcgtcggcct atcgcggccg ctggccgctc    3720
aaaaatggct ggcctacggc caggcaatct accaggcgc ggacaagccg cgccgtcgcc    3780
actcgaccgc cggcgcccac atcaaggcac cctgcctcgc gcgtttcggt gatgacggtg    3840
aaaacctctg acacatgcag ctcccggaga cggtcacagc ttgtctgtaa gcggatgccg    3900
ggagcagaca agcccgtcag ggcgcgtcag cgggtgttgg cgggtgtcgg ggcgcagcca    3960
tgacccagtc acgtagcgat agcggagtgt atactggctt aactatgcgg catcagagca    4020
gattgtactg agagtgcacc atatgcggtg tgaaataccg cacagatgcg taaggagaaa    4080
ataccgcatc aggcgctctt ccgcttcctc gctcactgac tcgctgcgct cggtcgttcg    4140
gctgcggcga gcggtatcag ctcactcaaa ggcggtaata cggttatcca cagaatcagg    4200
ggataacgca ggaaagaaca tgtgagcaaa aggccagcaa aaggccagga accgtaaaaa    4260
ggccgcgttg ctggcgtttt tccataggct ccgcccccct gacgagcatc acaaaaatcg    4320
acgctcaagt cagaggtggc gaaacccgac aggactataa agataccagg cgtttccccc    4380
tggaagctcc ctcgtgcgct ctcctgttcc gaccctgccg cttaccggat acctgtccgc    4440
ctttctccct tcgggaagcg tggcgctttc tcatagctca cgctgtaggt atctcagttc    4500
ggtgtaggtc gttcgctcca agctgggctg tgtgcacgaa ccccccgttc agcccgaccg    4560
ctgcgcctta tccggtaact atcgtcttga gtccaacccg gtaagacacg acttatcgcc    4620
actggcagca gccactggta acaggattag cagagcgagg tatgtaggcg gtgctacaga    4680
gttcttgaag tggtggccta actacggcta cactagaagg acagtatttg gtatctgcgc    4740
tctgctgaag ccagttacct tcggaaaaag agttggtagc tcttgatccg gcaaacaaac    4800
caccgctggt agcggtggtt tttttgtttg caagcagcag attacgcgca gaaaaaaagg    4860
atctcaagaa gatcctttga tcttttctac ggggtctgac gctcagtgga acgaaaactc    4920
acgttaaggg attttggtca tgcattctag gtactaaaac aattcatcca gtaaatata     4980
atatttatt ttctcccaat caggcttgat ccccagtaag tcaaaaaata gctcgacata    5040
ctgttcttcc ccgatatcct ccctgatcga ccggacgcag aaggcaatgt cataccactt    5100
```

```
gtccgccctg ccgcttctcc caagatcaat aaagccactt actttgccat ctttcacaaa    5160
gatgttgctg tctcccaggt cgccgtggga aaagacaagt tcctcttcgg gcttttccgt    5220
ctttaaaaaa tcatacagct cgcgcggatc tttaaatgga gtgtcttctt cccagttttc    5280
gcaatccaca tcggccagat cgttattcag taagtaatcc aattcggcta agcggctgtc    5340
taagctattc gtatagggac aatccgatat gtcgatggag tgaaagagcc tgatgcactc    5400
cgcatacagc tcgataatct tttcagggct ttgttcatct tcatactctt ccgagcaaag    5460
gacgccatcg gcctcactca tgagcagatt gctccagcca tcatgccgtt caaagtgcag    5520
gacctttgga acaggcagct ttccttccag ccatagcatc atgtccttt cccgttccac    5580 atcataggtg gtccctttat accggctgtc cgtcattttt aaatataggt tttcattttc    5640
tcccaccagc ttatatacct tagcaggaga cattccttcc gtatctttta cgcagcggta    5700
tttttcgatc agtttttca attcggtga tattctcatt ttagccattt attatttcct    5760
tcctcttttc tacagtattt aaagataccc caagaagcta attataacaa gacgaactcc    5820
aattcactgt tccttgcatt ctaaaacctt aaataccaga aaacagcttt ttcaaagttg    5880
ttttcaaagt tggcgtataa catagtatcg acggagccga ttttgaaacc gcggtgatca    5940
caggcagcaa cgctctgtca tcgttacaat caacatgcta ccctccgcga gatcatccgt    6000
gtttcaaacc cggcagctta gttgccgttc ttccgaatag catcggtaac atgagcaaag    6060
tctgccgcct tacaacggct ctcccgctga cgccgtcccg gactgatggg ctgcctgtat    6120
cgagtggtga ttttgtgccg agctgccggt cggggagctt ttggctggct ggtggcagga    6180
tatattgtgg tgtaaacaaa ttgacgctta gacaacttaa taacacattg cggacgtttt    6240
taatgtactg aattaacgcc gaattaattc ggggatctg gatttagta ctggattttg    6300 gttttaggaa ttagaaattt tattgataga agtatttac aaatacaaat acatactaag    6360
ggtttcttat atgctcaaca catgagcgaa accctatagg aaccctaatt cccttatctg    6420
ggaactactc acacattatt atggagaaac tcgagcttgt cgatcgacag atccggtcgg    6480
catctactct atttctttgc cctcggacga gtgctgggc gtcggtttcc actatcggcg    6540
agtacttcta cacagccatc ggtccagacg gccgcgcttc tgcgggcgat ttgtgtacgc    6600
ccgacagtcc cggctccgga tcggacgatt gcgtcgcatc gacccctgcgc ccaagctgca    6660 tcatcgaaat tgccgtcaac caagctctga tagagttggt caagaccaat gcggagcata    6720
tacgcccgga gtcgtggcga tcctgcaagc tccggatgcc tccgctcgaa gtagcgcgtc    6780
tgctgctcca tacaagccaa ccacggcctc cagaagaaga tgttggcgac ctcgtattgg    6840
gaatccccga acatcgcctc gctccagtca atgaccgctg ttatgcggcc attgtccgtc    6900
aggacattgt tggagccgaa atccgcgtgc acgaggtgcc ggacttcggg gcagtcctcg    6960
gcccaaagca tcagctcatc gagagcctgc gcgacggacg cactgacggt gtcgtccatc    7020
acagtttgcc agtgatacac atggggatca gcaatcgcgc atatgaaatc acgccatgta    7080
gtgtattgac cgattccttg cggtccgaat gggccgaacc cgctcgtctg gctaagatcg    7140
gccgcagcga tcgcatccat agcctccgcg accggttgta aacagcggg cagttcggtt    7200 tcaggcaggt cttgcaacgt gacaccctgt gcacggcggg agatgcaata ggtcaggctc    7260
tcgctaaact ccccaatgtc aagcacttcc ggaatcggga gcgcggccga tgcaaagtgc    7320
cgataaacat aacgatcttt gtagaaacca tcggcgcagc tatttacccg caggacatat    7380
ccacgccctc ctcatcgaa gctgaaagca cgagattctt cgcctccga gagctgcatc    7440 aggtcggaga cgctgtcgaa cttttcgatc agaaacttct cgacagacgt cgcggtgagt    7500
```

```
tcaggctttt tcatatctca ttgccccccc ggatctgcga aagctcgaga gagatagatt    7560
tgtagagaga gactggtgat ttcagcgtgt cctctccaaa tgaaatgaac ttccttatat    7620
agaggaaggt cttgcgaagg atagtgggat tgtgcgtcat cccttacgtc agtggagata    7680
tcacatcaat ccacttgctt tgaagacgtg gttggaacgt cttcttttc cacgatgctc     7740 ctcgtgggtg ggggtccatc tttgggacca ctgtcggcag aggcatcttg aacgatagcc    7800
tttcctttat cgcaatgatg gcatttgtag gtgccacctt ccttttctac tgtccttttg    7860
atgaagtgac agatagctgg gcaatggaat ccgaggaggt ttcccgatat tacccttgt     7920 tgaaaagtct caatagccct ttggtcttct gagactgtat ctttgatatt cttggagtag    7980
acgagagtgt cgtgctccac catgttatca catcaatcca cttgctttga agacgtggtt    8040
ggaacgtctt cttttccac gatgctcctc gtgggtgggg gtccatcttt gggaccactg     8100
tcggcagagg catcttgaac gatagccttt cctttatcgc aatgatggca tttgtaggtg    8160
ccaccttcct tttctactgt cctttgatg aagtgacaga tagctgggca atggaatccg     8220 aggagtttc ccgatattac cctttgttga aaagtctcaa tagcccttg gtcttctgag      8280 actgtatctt tgatattctt ggagtagacg agagtgtcgt gctccaccat gttggcaagc    8340
tgctctagcc aatacgcaaa ccgcctctcc ccgcgcgttg gccgattcat taatgcagct    8400
ggcacgacag gtttcccgac tggaaagcgg gcagtgagcg caacgcaatt aatgtgagtt    8460
agctcactca ttaggcaccc caggctttac actttatgct tccggctcgt atgttgtgtg    8520
gaattgtgag cggataacaa tttcacacag gaaacagcta tgaccatgat tacgaattcc    8580
cgatctagta acatagatga caccgcgcgc gataatttat cctagtttgc gcgctatatt    8640
ttgttttcta tcgcgtatta aatgtataat tgcgggactc taatcataaa aacccatctc    8700
ataaataacg tcatgcatta catgttaatt attacatgct taacgtaatt caacagaaat    8760
tatatgataa tcatcgcaag accggcaaca ggattcaatc ttaagaaact ttattgccaa    8820
atgtttgaac gatcggggaa attcgagctc actagtctaa tgatgatgat gatgatggac    8880
gtcgtcttct gggtcctcag gtgctagttc tgggctagct tttgcaagtt cgaaatgtgg    8940
cctatcagga gtagacttcc aatttccacc ccacacaatc tgaatgccca actcgttagc    9000
tgcagaaaac atagcctcag caatcttagg atacagtcca agtttgccgt cattatccca    9060
ttccaattta ccctgaatat atggtgcgag atcaactgct ctgccaaatc cggacccgtc    9120
caccacatga ttgccgttcc taggattgac ccatgtaacc ttagattcct taggcttagc    9180
ataggcggca ggcactccca tcttggcaca ttcagcagcg tttcttccct tcccgtacaa    9240
cctcatctgt tcgtccaatg ttctaccgcc ttgaataaca ccgaagtcaa cagttgtcct    9300
agtgatggcg agtctgacga cgtccctaag aggatgctga acagtgtcga ggatatgctg    9360
actcttctgg gacaatgcga acatagatcc tccaccacca aaagcttggg agtcatcatg    9420
tttcttatcc tcaatgctaa tattgaatat cctttttaatt tgtcttttaa gccacagatc    9480
cacagctggg gctatattgt ccaataggac tgggccccag ttctgagctg taaaacctag    9540
gatggctgtg aatatggcct gagccctgt gcttgaccac tggtaacctg taaactcatg     9600
tcttgcaata ccaacacttg caccaagggc aaagagagta ctgtacagga atgatacaat    9660
cagagttctt gggtcagaca ctctatttct cattacagca atgatactag ggccctatg     9720 accgatagct gccatgatca agacattgaa tggtactcct acgtaagcca cagttacgtt    9780
ttcatggacg tcaataaaag cccactcttt acttgtaggt gcctcagcgg ctacttggat    9840
tgcagttgtg gcagctgcgc ctgctgcgaa taagagtttt gcatacattt tatcatttct    9900
```

```
ccagttacta gttctggcga taggtcttag acttccaatt tccaccccat atgatcttaa    9960
gctttcatga tgggcgtatg cagctgagct aattagacat atggccatag ttgtgatcac   10020
cagaacctgt cagcaaaata cacacaaatt gaaatctcct aacctgtgta gttctgaagg   10080
aaactagaac ctagacaagg agcaaacaac cggtaaacag ttttttttctt cctttctttc   10140
ttcacgagtc tggttcctct tcactactat tctcattctt cactgagatc acaatttata   10200
tagtgcagca agccatatag acttgacagc caaatttgaa atcacattaa ataaatgaga   10260
ctagttcatg tgtcaatgat caaacaaatt tcctctacaa attaagtaga tagagatatt   10320
ctaaagaatt ggataattat aagccagtca tcatttaaat caagaagatt ttcaaccaac   10380
ttcaatgcct tgatcaacaa gtttcttcaa cgtccaaaga ttcctcaatt aatatattta   10440
agaaaacaaa atacatgaaa aaggaaaaa aaaaaaaaca aagagcaagc caaaacaaac    10500
attttgaaaa tactaacaat aaaacaaact aattcctcat agaaattcca aatcagtgtc   10560
attaaagaaa atcgtcatca aacggaagca aacagaagag aaatagaaat ttacctttgt   10620
gcccacaccc attttttcgg atcctttcct tgttgttttt gagttaaaag aagtaaatgt   10680
actgatgggt gggagagaaa atgggtggga aaatcttttg tgggggcaat tatatattta   10740
ttgcatgtaa acgtgaatct gtgacgatga tgaagggaa attttcaagc caagtgaaaa   10800
ttcctgagtt tggagaccta aaacgggggc tttaaataga gttggggggg ttgcaacatt   10860
gagtgtttgg tggggttggc cgacgggtta gttgaaagaa acacgcggcc gttggatttt   10920
catggtttta gatggttaag atctcgccac atggaagcaa ggtgattggt ggcatggact   10980
tttttggggt tggtgagggg gcacgaaagc acaacgtcac cacccccccc aatccaattt   11040
atatctatac ctcatattca ccaagcccca aaattggttc caaatgaat acttttaagt   11100
atccatttaa gcaattgcat ggtcatttac ttcactcgtt ttttgactgc tgggtttgga   11160
aattgcaaca tcaaatgagt gaggtgtttc gatgaaatgg cttagttata attgattat   11220
attttaaaaat caaggtccct ctttttcacac caatggacac tctataccat tatgcacgtt   11280
acaaattatt gtgtattatt tcgatattct agtagaagta aattcattga atttcattta   11340
tagagaggat aagcatttat tgtatgataa ggaaaaaaat ctcatatatg tcgagtagtg   11400
taagaaatgg ccattttatg ggcatggata cccatttcat tgttaaattt agaaaagaa   11460
ttaatgtctc caatggcagc atcactcaat ttttatctgt ttggcatatt acgagttaca   11520
acatccacaa tttttcaatt ataagcaatg atcatttact taatttgctt ttggtttaaa   11580
ttttaccaca tgaagtaagg gggtgtgtgt tttttttat aaattgctac aatttagaaa    11640
tatactataa tttgatatca atctattaag aatctacata tataaattta taacacagcc   11700
caaaattcta tcgagactag cgcggactcc cattaagtga ggtgttcgga tgaaatggtt   11760
taggtgtaat tggtttatat tgaaaagtta agctccctt tattgcaaat gggttaaatt     11820
ttgtcactct tatgcaatta acaataaac acgctgtaag agtctttata taatagacag   11880
cgtattgttt agtatatatt tatgtagagg tcctcttaag ggtttaatcg agtgattttc   11940
aaataaattgt atttggttta attggactag ccaactgacc acctgaagct tctgcaggca   12000
tggggggatcc tctagagtcg acctgcaggc atgcaagctt ggcactggcc gtcgttttac   12060
aacgtcgtga ctgggaaaac cctggcgtta cccaacttaa tcgccttgca gcacatcccc   12120
ctttcgccag ctggcgtaat agcgaagagg cccgcaccga tcgcccttcc caacagttgc   12180
gcagcctgaa tggcgaatgc tagagcagct tgagcttgga tcagattgtc gtttcccgcc   12240
ttcagtttaa actatcagtg tttgacagga tatattggcg ggtaaaccta agagaaaaga   12300
```

-continued

```
gcgtttatta gaataacgga tatttaaaag ggcgtgaaaa ggtttatccg ttcgtccatt   12360
tgtatgtg                                                            12368

<210> SEQ ID NO 109
<211> LENGTH: 8
<212> TYPE: PRT
<213> ORGANISM: Unknown
<220> FEATURE:
<223> OTHER INFORMATION: C-terminal hydrophobic sequence

<400> SEQUENCE: 109

Ala Ser Leu Glu Pro Gly Ile Ser
1               5

<210> SEQ ID NO 110
<211> LENGTH: 26
<212> TYPE: PRT
<213> ORGANISM: Phage P15

<400> SEQUENCE: 110

Met Pro Arg Phe Ala Thr Val Thr Cys Val Arg Leu Phe His Gly Tyr
1               5                   10                  15

Ala Met Arg Asp Ile Val Ile Ser Ile Thr
            20                  25
```

IDENTIFICATION AND USE OF GENES ENCODING HOLINS AND HOLIN-LIKE PROTEINS IN PLANTS FOR THE CONTROL OF MICROBES AND PESTS

CROSS REFERENCE TO RELATED APPLICATION

This application claims priority from and is the National Stage Entry of International Patent Application No. PCT/US2004/015099 filed on May 14, 2004, which in turn claims priority from and is a continuation-in-part of U.S. Provisional Patent Application No. 60/470,799 filed on May 14, 2003. Both the International Patent Application No. PCT/US2004/015099 and the U.S. Provisional Patent Application No. 60/470,799 are incorporated herein by reference in their entirety for all purposes.

STATEMENT OF RIGHTS TO INVENTIONS MADE UNDER FEDERALLY SPONSORED RESEARCH

This invention was partially made with government support under United States National Science Foundation Grant No. 0111331. The U.S. government has certain rights in this invention.

FIELD OF THE INVENTION

This invention relates generally to the field of genetic engineering. More specifically, this invention relates to compositions and methods of designing gene fusions based upon bacteriophage holin gene sequences expressed in plants for the purposes of inter alia: 1) controlling plant pathogens and pests, including bacterial, fungal, insect and nematode diseases of plants; 2) increasing the useful storage life of plants, including cut plants and flowers; 3) the use of such plants as trap plants for killing bacteria, fungi, insects and nematodes in the environment; and 4) the use of extracts of such plants for controlling medically important pathogens and pests and contamination of food and feed. The invention also relates to gene fusions comprising combinations of plant secretion signal peptides and bacteriophage holins and optionally, bacteriophage endolysins or combinations of these, including those synthetically designed. Also the invention relates to methods for the isolation and identification of holins and holin-like proteins useful for the control of bacteria, fungi, insects and nematodes and methods for increasing the efficacy of holins and stability of holins in plants.

The invention further relates to *Xanthomonas* bacteriophage biosynthetic genes that produce a family of holins and holin-like proteins, the isolation and expression of a *Xanthomonas* bacteriophage gene producing an endolysin, and the generation of translational gene fusions incorporating functional fragments of plant leader sequences, holins and hydrophilic enzymes such as endolysins, including synthetic genes modeled on the gene fusions, resulting in novel protein antibiotics that can be expressed in microbes and in plants to kill bacteria, fungi, insects and nematodes, including those pathogenic to plants. The invention also relates to the creation of synthetic holin-like proteins designed to fit into the bacterial cell membrane, but not into plant cell membranes, and the secretion and targeting of the holins and holin/endolysin fusions to the plant apoplast and xylem.

BACKGROUND OF THE INVENTION

All publications and patent applications herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

A wide variety of antibacterial and antifungal proteins have been isolated from both animals and plants. Because of the major differences in the structures of fungal, gram positive bacterial and gram negative bacterial cell walls, many of these proteins attack only fungi, gram positive or gram negative bacteria. Due to the very different natures of the outer cell walls of these microbes (see FIG. 1A-1C), those antimicrobial proteins that kill fungi and gram positive bacteria tend to be enzymes that can depolymerize the exposed cell walls of these microbes; those that attack gram negative bacteria tend to destabilize and permeabilize the exposed cell membrane.

During the last two decades, literally hundreds of antimicrobial proteins and peptides (proteins with less than 50 amino acids) have been discovered in plants and in the cells and body fluids of multicellular animals from mollusks to humans. Some antimicrobial peptides are always present in the host, while others are induced in response to infection or inflammation (Jaynes et al 1987; Mitra and Zhang 1994; Broekaert et al 1997; Nakajima et al 1997; Vunnam et al 1997). Among the most well described antimicrobial proteins are peptides with broad spectrum activity against bacteria, fungi, enveloped viruses, parasites, and tumor cells (Hancock and Lehrer 1998). More than 500 such peptides have been found in diverse organisms.

Antimicrobial peptides vary greatly in length and primary structure, but a common feature is that they are amphiphathic and cationic (Andreu and Rivas 1998; Gacia-Olmedo et al 1998; Nissen-Meyer and Nes 1997). Antimicrobial peptides have a cationic charge at physiological pH because of an excess of lysine and arginine residues and they have approximately 50% hydrophobic amino acids. This charge facilitates electrostatic attraction to negatively charged surfaces of a wide range of microbes. Their ability to assume amphipathic structures allows direct interaction with ubiquitous phosphoglycerol-lipids and incorporate into microbial membranes, resulting in membrane depolarization, electrolyte leakage, and lysis. Antimicrobial peptides can be categorized as either linear peptides (e.g. cecropins, attacins and magainins) or disulfide-linked peptides (e.g. defensins, prophenins and thaumatins).

Antimicrobial Linear Peptides.

Cecropins and melittins belong to the most abundant class of linear antimicrobial peptides. Both form α-helices in solution. Cecropins were first isolated from the hemolymph of *Hyalophora cecropia*, the giant silk-moth, and very similar molecules have since been isolated from other insects. Cecropins are cylindrical, amphipathic molecules with long hydrophobic regions on one end. Cecropins cause leaky cell membranes and can lyse bacterial and fungal cells; in effect, acting like detergents. Linear peptides are not found naturally in plants. Although highly effective in killing bacteria in petri dishes, linear peptides are usually rapidly degraded by plant proteases, and are therefore much less effective in plata. Transgenic tobacco plants expressing cecropins have slightly increased resistance to *Pseudomanas syringae* pv. *tabaci*, the cause of tobacco wildfire (Huang et al 1997). Cecropin residues crucial for lethality have been well-defined, and shortened synthetic analogs also exhibit antifungal activity. Synthetic cecropin analogs Shiva-1 and SB-37, expressed from transgenes in potato plants, reduced bacterial infection caused by *Erwinia* carotovora (Arce et al 1999). Transgenic apple expressing the SB-37 peptide analog showed increased resistance to *E. amylovora* in field tests (Norelli et al 1998). However, several researchers have reported that the antimicrobial protein cecropin B is rapidly degraded when incubated with intercellular fluid, with a half-life in intercellular fluids ranging from about three minutes in potato to about 25 hours in rice (Owens & Heutte, 1997).

Synthetic cecropins also appear to suffer from proteolytic degradation by plants. Melittin is the principal toxic component in the venom of the European honeybee (*Apis mellifera*) and by contrast with cecropins, is highly hemolytic and also phytotoxic. Using molecular modeling and genetic engineering, the melittin residues involved in toxicity were identified and replaced by those from the structurally related cecropin peptide. The resulting chimeric gene MsrA1 showed reduced hemolytic activity and phytotoxicity but retained its broad-spectrum antimicrobial properties (Osusky et al 2000). When MsrA1 is expressed in transgenic potatoes, the potato tubers show resistance to the fungal pathogens *Phytophthora cactorum* and *Fusarium solani* and the bacterium *E. carotovora*.

Attacins form another group of linear antibacterial proteins that are considerably larger than cecropins (>180 amino acids). The mechanism of antibacterial activity of these proteins is to inhibit the synthesis of outer membrane proteins in gram negative bacteria. Transgenic potatoes expressing the attacin gene showed resistance to bacterial infection by *Erwinia carotovora* (Arce et al 1999). Transgenic pear and apple expressing attacin genes have also shown enhanced resistance to *E. amylovora* (Norelli et al 1994; Reynoird et al 1999; Ko et al 2000). Ko and coworkers engineered transgenic apple plants using the attacin E gene, both with and without a signal peptide to transport the attacin into the intercellular space. They found that transgenic plants with attacin fused to a signal peptide had better disease resistance than plants carrying attacin without the signal peptide, even though the plants with the signal peptide had a much lower attacin content than lines without a signal peptide. Attacin E was also found to be rapidly degraded by plants.

Magainins are a third group of linear antimicrobial peptides, 22-24 amino acids in length, originally isolated from frog skin (Li et al 2001). The mode of action of these peptides involves the disruption of microbial cell membranes. They show strong inhibitory activity against a variety of bacteria and fungi in vitro, including many plant pathogens, but as with all linear peptides, are also highly susceptible to plant proteases. Li et al (2001) tested a synthetic magainin analog, Myp30, that had been modified to be less sensitive to extracellular plant proteases. Transgenic tobacco plants expressing Myp30 were somewhat resistant to the fungal pathogen *Peronospora tabacina* and the bacterial pathogen *E. carotovora*.

Searches for shorter, more potent antimicrobial peptides have led to the development of entirely synthetic peptides and also synthetic derivatives of natural peptides with broader and higher antimicrobial activity than their natural counterparts. Cary et al (2000) reported that the expression of the 17 amino acid synthetic peptide D4E1 in transgenic tobacco gave resistance to several fungal and bacterial pathogens. Ali and Reddy (2000) tested four synthetic peptides for their ability to inhibit growth of important plant pathogens in vitro and in detached potato leaf and tuber assays. Fungal growth was inhibited by all four peptides, while growth of two *Erwinia* species was inhibited by two of the peptides.

Antimicrobial, Disulfide-Linked Peptides.

Lysozymes are enzymes that hydrolyze the peptidoglycan layer of the bacterial cell wall. Hen egg-white lysozyme, bacteriophage T4 lysozyme, and human lysozyme genes have been cloned and transferred to several plant species in attempts to enhance bacterial or fungal disease resistance. Hen egg-white lysozyme genes have been used to confer bacterial disease resistance to transgenic tobacco plants (Trudel et al 1995; Kato et al 1998). Bacteriophage T4 lysozyme has also been reported to enhance resistance in transgenic potato against the bacterial soft rot pathogen *E. carotovora* (During et al 1993; Ahrenholz et al., 2000) and in transgenic apple plants against the bacterial fire blight pathogen *E. amylovora* fireblight infection (Ko 1999). Human lysozyme transgenes have conferred disease resistance in tobacco through inhibition of fungal and bacterial growth, suggesting the possible use of the human lysozyme gene for controlling plant disease (Nakajima et al 1997). However, lysozymes can be skin irritants, and have the potential to become allergenic.

Thanatin is a 21-residue inducible peptide found in the hemipteran insect *Podisus maculiventris*. Thanatin exhibits the broadest range of antimicrobial activity so far characterized (Taguchi et al 2000). Unfortunately, thanatin exhibits powerful cytotoxic effects on many eukaryotic cell types, making them unsuitable for any therapeutic use as antibiotics and also likely unsuitable for use in plants to control pathogens.

Plant, mammalian and insect defensins belong to the class of antimicrobial peptides characterized by β-sheet structures. These complex folded molecules contain four, six, or eight invariant cysteine residues that form several intramolecular disulfide bonds. The active peptides have antibacterial, antifungal, and antiviral activities. Defensins display antimicrobial activity through binding and disruption of microbial plasma membranes. A 5.6 kDa antifungal peptide alfAFP was isolated from alfalfa seeds (*Medicago sativa*) (Guo et al 2000). Expression of the peptide in transgenic potato plants gave robust resistance to the fungal pathogen *Verticiliuin dahliae*. The construct was not tested against bacteria.

Prophenins belong to a new class of antimicrobial peptides first discovered in mammalian white blood cells (Wang et al 1999). Prophenins display exceptionally strong endotoxin (LPS) binding activity as well as antimicrobial activity, even after proteolytic degradation. They are stabilized by two disulfide bonds. These peptides show promise as a potent new class of antibiotics for gram-negative bacterial infections in animals.

Thaumatin and thaumatin-like proteins are made by plants and constitute one of five major classes of PR proteins that are characterized by a sweet taste (to humans), small size (22 kDa) and most importantly, a highly stabilized, compact structure with eight disulfide bonds that renders them very resistant to protease degradation (Selitrennikoff, 2001).

Antimicrobial Bacteriophage Proteins.

All bacteriophages must escape from bacterial host cells, either by extrusion from the host cell, as with filamentous phages, or by host cell lysis. Host cell lysis requires two events: ability to penetrate the inner membrane of both gram negative and gram positive bacteria (see FIGS. 1A and 1B), and ability to depolymerize the murein layer, which is relatively thick in gram positive cell walls.

Penetration of the inner membrane is accomplished in many, but evidently not all, phage by use of small membrane-localized proteins called "holins" that appear to accumulate in the bacterial inner membrane until reaching a specific concentration, at which time they are thought to self-assemble to permeabilize the inner membrane (Grundling et al., 2001; Wang et al. 2000; Young et al., 2000). The terms "holin" and "holin-like" are not biochemically or even functionally accurate terms, but instead as used herein refer to any phage protein capable of permeabilizing the inner membrane, thereby allowing molecules other than holins that are normally sequestered in the cyctoplasm by the inner membrane, including proteins such as endolysins, to breach or penetrate the bacterial cell membrane barrier to reach the cell wall. Holins are sometimes found with "accessory proteins" of unknown function. The biochemical function(s) of holins is speculative; most, if not all of the current knowledge on holins is based on the λ phage S protein (Haro et al. 2003).

Holins are encoded by genes in at least 35 different families, having at least three topological classes (classes I, II, and III, with three, two and one transmembrane domains [TMD], respectively), all with no detected orthologous relationships (Grundling et al., 2001). At least two holins are known to be hemolytic and this hemolytic function has been hypothesized to play a role in the pathogenesis of certain bacteria towards insects and nematodes (Brillard et al., 2003). Only a few have been partially characterized in terms of in vivo function, leading to at least two very different theories of how they may function. Indeed, no holin genes have been found or suggested in many phage, despite the ready availability of genomic sequence data. The most widely accepted theory is that holins function to form oligomeric membrane pores (Graschopf & Blasi, 1999; Young et al., 2000); most of the supporting data is based upon studies of the holin of phage B. A second theory is that holins form an oligomeric "raft" in the membrane that constitutes a lesion (Wang et al., 2003). Both theories may be correct for different holins, and other holins may perform their functions in very different manners.

Depolymerization of the murein layer is accomplished by lytic enzymes called endolysins. There are at least three functionally distinct classes of endolysins: 1) glucosaminidases (lysozymes) that attack the glycosidic linkages between the amino sugars of the peptidoglycan; 2) amidases that attack the N-acetylmuramoyl-L-alanine amide linkage between the glycan strand and the cross-linking peptide, and 3) endopeptidases that attack the interpeptide bridge linkages (Sheehan et al., 1997). Endolysins are synthesized without an export signal sequence that would permit them access to the peptidoglycan (murein) layer, and they therefore usually accumulate in the cytoplasm of phage infected bacteria until they are released by the activity of holins (Young and Blasi, 1995).

Lysozymes have been suggested as useful antibiotics that can be used as external agents against both Gram-positive and Gram-negative bacteria because at least some of them are multifunctional (During et al., 1999). This dual functionality is based on the finding that both phage T4 and hen egg white lysozyme have both glucosaminidase activity as well as amphipathic helical stretches that allow them to penetrate and disrupt bacterial, fungal and plant membranes (During et al., 1999). The microbicidal activity of lysozymes can be affected by C-terminal additions; additions of hydrophobic amino acids decreased activity against gram positive, but increased activity against E. coli (Arima et al., 1997; Ito et al., 1997). Additions of histidine, a hydrophilic amino acid, to T4 lysozyme doubled its antimicrobial activity against Gram-positive and Gram-negative bacteria (During et al., 1999). The nonenzymatic, microbicidal function of lysozymes appeared to be due to amphipathic C-terminal domains that could be mimicked by small synthetic peptides modeled after the C-terminal lysozyme domains (During et al., 1999). As described above, transgenic plants have been created that express lysozymes and give some resistance to certain plant pathogens. Since most endolysins accumulate to high titers within the bacterial cell without causing lysis, endolysins other than certain lysozymes such as T4 would not be expected to attack Gram-negative bacteria if externally applied, since Gram-negative bacteria are surrounded with an outer membrane comprised of a lipid bilayer that would protect its murein layer from enzymatic attack just as effectively as its inner membrane does. Also as mentioned earlier, lysozymes are also skin irritants, probably as a result of their ability to invade membranes.

Attempts have been made to treat bacterial diseases of both animals and plants by use of intact bacteriophage. All of these attempts have severe limitations in their utility. For examples, U.S. Pat. No. 5,688,501 discloses a method for treating an infectious disease of animals using intact bacteriophage specific for the bacterial causal agent of that disease. U.S. Pat. No. 4,957,686 discloses a method for preventing dental caries by using intact bacteriophage specific for the bacterial causal agent of dental caries. Flaherty et al. (2000) describe a method for treating an infectious disease of plants using intact bacteriophage specific for the bacterial causal agent of that disease. In all these cases and in similar cases using intact bacteriophage, the bacteriophage must attach to the bacterial host, and that attachment is highly host specific, limiting the utility of the phage to specific bacterial host species, and sometimes specific bacterial host strains. In addition, for attachment to occur, the bacteria must be in the right growth phase, and the phage must be able to gain access to the bacteria, which are often buried deep within tissues of either animals or plants, or shielded by bacterial biofilms.

Attempts have been made to treat gram-positive bacterial diseases of animals, but not plants, by use of lytic enzyme preparations extracted from bacteriophage infected bacteria or from bacteria expressing bacteriophage genes. These, too, have serious limitations. For example, U.S. Pat. No. 5,985,271 discloses a method of treating an animal disease caused by a specific gram positive bacterium, Streptococcus, by use of a crude specific endolysin preparation. Similarly, U.S. Pat. No. 6,017,528 discloses a method of preventing and treating Streptococcus infection of animals by use of a crude specific endolysin preparation. Similarly, WO 01/90331 and US 2002/0058027 disclose methods of preventing and treating Streptococcus infection of animals by use of a purified preparation consisting of a specific endolysin. In all of these cases, the enzyme preparations must be purified, buffered, prepared for delivery to the target areas and preserved at the target site. In addition, the enzyme must be able to gain access to the infecting bacteria, and be present in sufficient quantity to kill the growing bacteria. None of these methods would be useful in the treatment of gram negative bacteria, because the endolysins could not penetrate the outer membrane of such bacteria. Attempts have been made to treat both gram-positive and gram-negative bacterial diseases of animals, but not plants, by use of lytic enzyme preparations extracted from bacteriophage infected bacteria or from bacteria expressing bacteriophage genes. WO 01/51073, WO 01/82945, WO 01/019385, US 2002/0187136 and US 2002/0127215 disclose methods of preventing and treating a variety of gram positive and gram negative bacterial infections of animals by use of lytic enzymes that may optionally include specific "holin lytic enzymes" or "holin enzymes".

Since holins are not known to exhibit enzymatic function, and since examples of such holin lytic enzymes are not demonstrated or taught in WO 01/51073, WO 01/82945, WO 01/19385, US 2002/0187136 and US 2002/0127215, such enzymes appear to represent a theoretical and undemonstrated enzyme defined by reference to a desirable characteristic or property. As correctly stated elsewhere by the same inventors: "Holin has no enzymatic activity" (refer WO 01/90331, page 9 line 12). Lytic enzymes, which form the basis for the methods disclosed in all of these PCT publications, are internally defined: "The present invention is based upon the discovery that phage lytic enzymes specific for bacteria infected with a specific phage can effectively and efficiently break down the cell wall of the bacterium in question. At the same time, the substrate for the enzyme is not present in mammalian tissues . . . " (WO 01/51073 paragraph 3, page 4). "The lytic enzymes produced by bacterial phages are specific and effective for killing select bacteria." (paragraph 2, page 7).

The term "holin enzyme" as used in Claim #3 of WO 01/51073 refers to the enzymes defined in Claim #1 as "the group consisting of lytic enzymes, modified lytic enzymes and combinations thereof . . . " Similar references in the claims of WO 01/82945, WO 01/019385 and US 2002/0187136 and US 2002/0127215 may be found. None of these patent applications disclose or claim the use of holin or holins alone, without enzymatic activity, in any manner, including the formulation of a compound or method of treatment of animal or plant diseases. Indeed, absent the teachings of the present invention, one skilled in the art would not have expected holins without lytic activity to kill gram positive bacteria, since holins without lytic activity would not be able to penetrate the thick gram positive bacterial cell wall.

WO 02/102405 discloses a method of preventing food poisoning in animals by inclusion of a purified preparation consisting of specific lytic enzymes and optionally, specific lytic "holin enzymes". Again, since holins are not known to exhibit enzymatic function, it is unclear as to what is taught or specified in the claims, other than a theoretical and undemonstrated enzyme defined by reference to a desirable characteristic or property.

In all previously published cases wherein holins are incorporated, used or described, enzyme preparations are involved. These enzyme preparations must be purified, buffered, prepared for delivery to the target areas and preserved at the target site.

Thus, the prior art reviewed herein fails to teach the use of holins, holin genes or of chimeric holins, without enzyme activity, for the control of bacterial or fungal diseases and pests. This prior art also fails to teach the use of holins combined with endolysin genes in the formulation of a compound or method of treatment of plant diseases. Furthermore, this prior art fails to teach the use of holin genes or modified holin genes or of chimeric holin and endolysin genes in the creation of transgenic animals or plants capable of fighting diseases.

It has been suggested that a specific endolysin from a bacteriophage that attacks a gram negative bacterial plant pathogen might be effective in providing resistance to that pathogen if the endolysin gene were cloned and expressed in plants (Ozawa et al., 2001). This suggestion is most unlikely, since endolysins other than T4 lysozyme are not known to penetrate bacterial membranes, and Gram-negative bacteria have a distinctive outer membrane that provides a strong environmental barrier that is impermeable to most molecules.

As described elsewhere herein, the present invention provides membrane destabilization and permeabilization based upon the action of unique bacteriophage proteins called holins. The present invention is based, in part, on our discovery that holins not only destabilize and permeabilize bacterial inner membranes from inside bacterial cells, but in addition, work externally as well, presumably destabilizing and permeabilizing outer membranes as well as inner membranes. Activity of holins in destabilization and permeabilization of the outer membrane presumably allows natural defense molecules secreted by plants and/or by other microbes to breach the outer membrane of the target cells, thereby compromising the "barrier function" of the outer membrane. Kingsley et al., (1993) provide strong evidence that the outer membrane of a plant pathogenic bacterium can function as a barrier in preventing plant defense molecules from the killing the bacteria. Target cells can be bacterial, fungal, insect or nematode. The invention also provides the incorporation of enzymatic cell wall depolymerization based upon unique bacteriophage proteins called endolysins and provides the incorporation of both holin and endolysin function in a series of gene fusions and completely synthetic genes modeled on the gene fusions.

This invention provides: 1) methods for the identification of broad-spectrum holins with a high level of nonenzymatic activity to breach microbial outer membranes and thereby increasing the efficacy of both natural plant defense compounds and artificially applied compounds; 2) conditions required for maintaining and increasing the anti-microbial and anti-pest efficacy of holins in gene fusions; 3) methods for effective targeting of holins expressed in plants through use of a xylem enhanced promoter and a leader peptide to direct the holin protein to the plant apoplast and xylem; 4) methods for the control of bacterial and fungal diseases of plants and control of insect and nematode pests that attack plants by expression of gene fusions involving holins, C-terminal additions and leader peptides, and optionally, endolysins; 5) methods for increasing the shelf-life of cut flowers; and 6) transgenic plants useful for the production of novel antimicrobial proteins based upon holins.

SUMMARY OF THE INVENTION

One object of the present invention is to provide methods of identifying bacteriophage that capable of producing broad-spectrum holin and holin-like proteins. The present invention also provides the isolated holin and holin-like genes that produce such proteins and the isolated proteins themselves. For example, the instant invention provides the holin and holin-like genes which code for the amino acid sequences of holin Z (SEQ ID No: 27), holin ZA (SEQ ID No. 28), holin ZA.1 (SEQ ID No. 29) and holin ZB (SEQ ID No. 30), as well as the protein products of such genes.

One object of the present invention is to provide holin and holin-like nucleic acids and the holin and holin-like proteins produced thereby. The invention includes isolated nucleic acid molecules selected from the group consisting of isolated nucleic acid molecules that encode an amino acid sequence of HOLIN Z (SEQ ID No. 27), HOLIN ZA (SEQ ID No. 28), HOLIN ZA.1 (SEQ ID No. 29) and HOLIN ZB (SEQ ID No. 30) and orthologs thereof. The present invention provides an isolated nucleic acid molecule that encodes a fragment of at least 20 amino acids of any one of SEQ ID Nos. 26-30, and an isolated nucleic acid molecules which hybridize to a nucleic acid molecule comprising SEQ ID Nos: 27, 28, 29 or 30. A nucleic acid molecule can include functional equivalents of natural nucleic acid molecules encoding a peptide, polypeptide or protein of the present invention. Functional equivalents of natural nucleic acid molecules can include, but are not limited to, natural allelic variants and modified nucleic acid molecules in which nucleotides have been inserted, deleted, substituted, and/or inverted in such a manner that such modifications do not substantially interfere with the nucleic acid molecule's ability to encode a molecule of the present invention. Said amino acid substitutions may be conservative or non-conservative.

Preferred functional equivalents include sequences capable of hybridizing under stringent or nonstringent conditions (i.e., sequences having at least about 70% identity), to at least a portion of a holin or holin-like peptide, polypeptide or protein encoding nucleic acid molecule. Nucleic acid molecules of the invention may encode a protein having at least 50 or 60% amino acid sequence identity with the sequence set forth in any one of SEQ ID Nos. 27-30, preferably at least about 70 or 75%, more preferably at least about 80%, still more preferably at least about 85%, yet more preferably at least about 90%, even more preferably at least about 95% and most preferably at least about 98% sequence identity with the protein sequence set forth in SEQ ID Nos. 27-30.

The present invention further includes the nucleic acid molecules operably linked to one or more expression control elements, including vectors comprising the isolated nucleic acid molecules. The invention further includes host cells transformed to contain the nucleic acid molecules of the invention and methods for producing a peptide, polypeptide or protein comprising the step of culturing a host cell transformed with a nucleic acid molecule of the invention under conditions in which the protein is expressed.

The invention further provides an isolated polypeptide selected from the group consisting of an isolated polypeptide comprising the amino acid sequence of in any one of SEQ ID Nos. 27-30, an isolated polypeptide comprising a fragment of at least 20 amino acids of in any one of SEQ ID Nos. 27-30, an isolated polypeptide comprising conservative amino acid substitutions of in any one of SEQ ID Nos. 27-30 and an isolated polypeptide comprising naturally occurring amino acid sequence variants of in any one of SEQ ID Nos. 27-30. Polypeptides of the invention also include polypeptides with an amino acid sequence having at least about 50 or 60% amino acid sequence identity with the sequence set forth in any one of SEQ ID Nos. 27-30, preferably at least about 70 or 75%, more preferably at least about 80%, still more preferably at least about 85%, yet more preferably at least about 90%, even more preferably at least about 95% and most preferably at least about 98% sequence identity with the protein sequence set forth in SEQ ID NO: in any one of SEQ ID Nos. 27-30.

This invention provides vectors comprising the nucleic acid constructs of the present invention as well as host cells, recombinant cells and transgenic tissues and organisms comprising the vectors of the present invention. More particularly, this invention provides such cells and transgenic tissues and organisms that are hemizygotic, heterozygotic or homozygotic for the nucleic acid constructs, wherein if the organism is a plant it can be monoploid, diploid or polyploid. It is an object of the present invention to provide such cells and transgenic tissues and organisms wherein they express a single copy or multiple copies of one or more of the holin or holin-like proteins, or holin or holin-like ortholog protein products of the present invention. Cells or transgenic tissues and organisms which express multiple copies of one of the holin or holin-like proteins, mutant holin or holin-like proteins, or holin or holin-like ortholog proteins, or which express more than one of the holin or holin-like proteins, mutant holin or holin-like proteins, or holin or holin-like ortholog proteins, may be desirable, for example, to produce broad-spectrum resistance or tolerance to a variety of different pathogens.

The invention further provides nucleic acid probes for the detection of expression of the holin or holin-like proteins of the present invention, or mutants, or homologs, or orthologs thereof, in for example, plants which either have been genetically altered to express at least one of said proteins or which may naturally express holin or holin-like proteins, or mutants, or homologs, or orthologs thereof.

The invention further provides the use of antibodies to holin or holin-like proteins of the present invention, or mutants, or homologs, or orthologs thereof to probe a biological sample or a tissue section for expression of holin or holin-like proteins, or mutants, or homologs, or orthologs. Said biological sample or tissue section may be from, for example, a plant which has been genetically altered to express said peptide, polypeptide or protein or which may naturally express the holin or holin-like proteins of the present invention, or mutants, or homologs, or orthologs.

This invention provides methods of identifying a phage sample that produces a holin or holin-like protein, said method comprising: a) infecting a strain of gram negative bacteria with a bacteriophage; b) selecting one or more individual phage samples from the infected strain of gram negative bacteria; c) separately contacting the selected phage samples with one or more biological test cells, said biological test cells selected from the group consisting of gram negative bacteria cells, gram positive bacteria cells, fungal cells, and blood cells, wherein the phage samples are not capable of infecting the one or more biological test cells; and d) identifying a phage sample that produces a holin or holin-like protein as one that kills the one or more biological test cells. This invention also provides such methods wherein the contacting comprises using one or more agar plate overlay assays. This invention further provides such methods wherein the biological test cells comprise one or more strains of gram negative bacterium. This invention also provides such methods further comprising sequencing the DNA of the identified phage sample.

In another embodiment, these methods further comprise identifying one or more genes encoding holin or holin-like proteins by a method comprising: a) selecting DNA fragments of the sequenced DNA, wherein the DNA fragments comprise one or more trans-membrane domains typical of holin and holin-like genes; b) attempting to express the selected DNA fragments in *E. coli* with and without a promoter operably-linked to the one or more trans-membrane domains; and c) selecting those DNA fragments which could not be expressed without the promoter; thereby identifying one or more genes encoding holin or holin-like proteins.

In still another embodiment, these methods further comprising identifying a broad-spectrum holin or holin-like protein, said method comprising: a) producing holin or holin-like proteins by expressing the one or more identified genes; b) evaluating the ability of the produced holin or holin-like proteins to kill one or more biological test cells, said biological test cells selected from the group consisting of gram negative bacteria cells, gram positive bacteria cells, fungal cells and blood cells; and c) selecting the holin or holin-like proteins that can kill one or more of the biological test cells.

This invention provides methods of repressing, preventing or otherwise reducing bacterial or fungal infections of a plant comprising expressing a holin or holin-like protein in the plant. This invention further provides such methods wherein the holin or holin-like protein expressed in the plant is the holin or holin-like protein identified by the methods of this invention.

This invention also provides the methods as described herein, where such methods utilize holin or holin-like protein selected from the group consisting of HOLIN Z (SEQ ID No. 27), HOLIN ZA (SEQ ID No. 28), HOLIN ZA.1 (SEQ ID No. 29), HOLIN ZB (SEQ ID No. 30), a protein having at least 70% amino acid sequence similarity with HOLIN Z (SEQ ID No. 27), a protein having at least 70% amino acid sequence similarity with HOLIN ZA (SEQ ID No. 28), a protein having at least 70% amino acid sequence similarity with HOLIN ZA.1 (SEQ ID No. 29), a protein having at least 70% amino acid sequence similarity with HOLIN ZB (SEQ ID No. 30), a peptide fragment consisting of at least 20 contiguous amino acids of HOLIN Z (SEQ ID No. 27), a peptide fragment consisting of at least 20 contiguous amino acids of HOLIN ZA (SEQ ID No. 28), a peptide fragment consisting of at least 20 contiguous amino acids of HOLIN ZA.1 (SEQ ID No. 29), and a peptide fragment consisting of at least 20 contiguous amino acids of HOLIN ZB (SEQ ID No. 30).

This invention provides isolated holin or holin-like proteins incapable of infecting a microbe, wherein the holin or holin-like proteins are able to lyse the cells of the microbe when contacted with the microbe, as well as the nucleic acids coding for such proteins.

This invention provides isolated nucleic acid molecules coding for holin or holin-like proteins operably-linked to a nucleic acid molecule coding for a hydrophilic C terminus.

This invention provides isolated nucleic acid molecules coding for holin or holin-like proteins operably-linked to nucleic acid molecules coding for a plant leader sequence, wherein the plant leader sequence targets the holin or holin-like proteins to the xylem and/or apoplast.

This invention provides isolated nucleic acid molecules coding for holin or holin-like proteins operably-linked to nucleic acid molecules coding for a hydrophilic C terminus and a nucleic acid molecule coding for a plant leader sequence, wherein the plant leader sequence targets the holin or holin-like proteins to the xylem and/or apoplast.

This invention provides isolated nucleic acid molecules coding for holin or holin-like proteins operably-linked to a nucleic acid molecule coding for an endolysin derived from a phage.

This invention provides isolated nucleic acid molecules coding for holin or holin-like proteins operably-linked to nucleic acid molecules coding for a hydrophilic C terminus, a nucleic acid molecule coding for a plant leader sequence, and nucleic acid molecules coding for an endolysin derived from a phage, wherein the plant leader sequence targets the holin or holin-like proteins to the xylem and/or apoplast.

This invention further provides such methods wherein the plant leader sequence is a P12 plant leader sequence (SEQ ID No. 87); a polypeptide exhibiting at least about 70% amino acid sequence identity with SEQ ID No. 87; a polypeptide exhibiting at least about 75% amino acid sequence identity with SEQ ID No. 87; a polypeptide exhibiting at least about 80% amino acid sequence identity with SEQ ID No. 87; a polypeptide exhibiting at least about 85% amino acid sequence identity with SEQ ID No. 87; a polypeptide exhibiting at least about 90%, a polypeptide exhibiting at least about 95% amino acid sequence identity with SEQ ID No. 87; or a polypeptide exhibiting at least about 99% amino acid sequence identity with SEQ ID No. 87.

This invention further provides such methods wherein the nucleic acid molecules are operably linked to a nucleic acid molecule coding for one or more expression control elements.

This invention further provides such methods wherein the nucleic acid molecules are operably linked to a nucleic acid molecule coding for a lytic enzyme. For example, this invention provides such methods wherein the lytic enzyme is lysY (SEQ ID No. 26); a polypeptide exhibiting at least about 70% amino acid sequence identity with SEQ ID No. 26; a polypeptide exhibiting at least about 75% amino acid sequence identity with SEQ ID No. 26; a polypeptide exhibiting at least about 80% amino acid sequence identity with SEQ ID No. 26; a polypeptide exhibiting at least about 85% amino acid sequence identity with SEQ ID No. 26; a polypeptide exhibiting at least about 90%, a polypeptide exhibiting at least about 95% amino acid sequence identity with SEQ ID No. 26; or a polypeptide exhibiting at least about 99% amino acid sequence identity with SEQ ID No. 26.

This invention also provides such methods wherein the nucleic acid molecules are operably linked to a nucleic acid molecule coding for more than one hydrophilic C terminal region.

This invention further provides vectors and host cells comprising the isolated nucleic acid molecules of the invention, wherein such host cells can be eukaryotic or prokaryotic host cells. In some embodiments, the eukaryotic host cell is a plant cell or a yeast cell. In some embodiments, the plant cell is a dicotyledon plant cell or a monocotyledon plant cell. In some embodiments, the nucleic acid molecules have been codon optimized for expression in plant cells. In some embodiments, the prokaryotic host cell is a microbe.

This invention provides methods for producing polypeptides comprising culturing a host cell transformed with the nucleic acid molecules of the present invention under conditions in which the protein encoded by said nucleic acid molecule is expressed. This invention also provides the isolated polypeptides produced by the methods of this invention.

This invention provides methods of preventing, treating or reducing microbial infection and/or insect and/or nematode infestations of a plant cell, plant tissue, or whole plant, said method comprising contacting the plant cell, plant tissue, or whole plant with the isolated polypeptides of this invention.

This invention provides methods of preventing, treating or reducing microbial and/or insect contamination of food or food stuff, said method comprising contacting the food or food stuff with the isolated polypeptides of this invention.

This invention provides methods of preventing, treating or reducing microbial infection of an animal cell, animal tissue, or whole animal by contacting the animal cell, animal tissue, or whole animal with the isolated polypeptides of the invention. In one embodiment, the treated animal is a human.

This invention provides methods of preventing, treating or reducing microbial contamination of water by adding the isolated polypeptides of the present invention to the water. In one embodiment, this invention provides such methods which comprise placing cut plant parts into the water, including cut plant parts such as flowers, stems and/or leaves. This invention provides such methods for providing cut plant parts with a longer shelf life than similar cut plant parts that are not placed in water comprising the polypeptides of the present invention.

This invention provides isolated nucleic acid molecules coding for a holin or holin-like protein operably-linked to an intron, wherein the intron lacks prokaryotic promoter elements.

This invention provides methods wherein the holin or holin-like polypeptide is active against a microbe selected from the group consisting of *Agrobacterium* (including *A. tumefaciens*), *Xanthomoas* (including *X. campestris* pv. *campestris, X. campestris* pv. *pelargonii, X. campestris* pv. *vesicatoria, X. phaseoli, X. citri, X. otyzae, Ralstonia* (including *R. solanacearum*), *Erwinia* (including *E. chrysanthemi, E. carotovora,* and *E. amylovora*), *Xylella*, including *X. fastidiosa, E. coli; Corynebacterium* (syn.=*Clavibacter*; including *C. michiganense* and *C. nebraskense*), *Lactococcus, Streptococcus* (including *S. mutans, S. fasciae* and *S. pneumoniae*), *Listeria, Pseudomonas, Salmonella, Campylobacter, Helicobacter* (including *H. pylori*), *Mycobacterium*: (including *M. tuberculosis*); *Saccharomyces, Phytophthora* (including *P. infestans* and *P. nicotianae, Pythium* (including *P. aphanidermatum*), *Tinea* (including *T. pedis, T. cruris* and *T. captius*), *Cryptococcus* (including *C. neoformans*) and *Candida* (including *C. albicans*).

This invention also provides plant cells that are resistant or immune to one or more microbial pathogens, including but not limited to, *Agrobacterium* (including *A. tumefaciens*), *Xanthomonas* (including *X. campestris* pv. *campestris*, *X. campestris* pv. *pelargonii*, *X. campestris* pv. *vesicatoria*, *X. phaseoli*, *X. citri*, *X. oryzae*, *Ralstonia* (including *R. solanacearum*), *Erwinia* (including *E. chrysanthemi*, *E. carotovora*, and *E. amylovora*), *Xylella*, including *X. fastidiosa*, *E. coli*; *Corynebacterium* (syn.=*Clavibacter*; including *C. michiganense* and *C. nebraskense*), *Pseudomonas*, *Phytophthora* (including *P. infestans* and *P. nicotianae*, *Pythium* (including *P. aphanidermatum*).

This invention also provides plant breeding methods which utilize the transformed plants of this invention, as well as the progeny of such transformed plants, including the seed and asexual sports.

This invention provides isolated nucleic acid molecules, or their complements, including an isolated nucleic acid molecule that encodes the amino acid sequence of HOLIN Z (SEQ ID No. 27), an isolated nucleic acid molecule that encodes the amino acid sequence of HOLIN ZA (SEQ ID No. 28), an isolated nucleic acid molecule that encodes the amino acid sequence of HOLIN ZA.1 (SEQ ID No. 29), an isolated nucleic acid molecule that encodes the amino acid sequence of HOLIN ZB (SEQ ID No. 30), an isolated nucleic acid molecule that encodes a fragment of at least 20 amino acids of HOLIN Z (SEQ ID No. 27), an isolated nucleic acid molecule that encodes a fragment of at least 20 amino acids of HOLIN ZA (SEQ ID No. 28), an isolated nucleic acid molecule that encodes a fragment of at least 20 amino acids of HOLIN ZA.1 (SEQ ID No. 29), an isolated nucleic acid molecule that encodes a fragment of at least 20 amino acids of HOLIN ZB (SEQ ID No. 30), an isolated nucleic acid molecule which hybridizes to the complement of a nucleic acid molecule that encodes the amino acid sequence of HOLIN Z (SEQ ID No. 27), an isolated nucleic acid molecule which hybridizes to the complement of a nucleic acid molecule that encodes the amino acid sequence of HOLIN ZA (SEQ ID No. 28), an isolated nucleic acid molecule which hybridizes to the complement of a nucleic acid molecule that encodes the amino acid sequence of HOLIN ZA.1 (SEQ ID No. 29), an isolated nucleic acid molecule which hybridizes to the complement of a nucleic acid molecule that encodes the amino acid sequence of HOLIN ZB (SEQ ID No. 30), an isolated nucleic acid molecule which hybridizes under stringent conditions to the complement of a nucleic acid molecule that encodes the amino acid sequence of HOLIN Z (SEQ ID No. 27), an isolated nucleic acid molecule which hybridizes under stringent conditions to the complement of a nucleic acid molecule that encodes the amino acid sequence of HOLIN ZA (SEQ ID No. 28), an isolated nucleic acid molecule which hybridizes under stringent conditions to the complement of a nucleic acid molecule that encodes the amino acid sequence of HOLIN ZA.1 (SEQ ID No. 29), an isolated nucleic acid molecule which hybridizes under stringent conditions to the complement of a nucleic acid molecule that encodes the amino acid sequence of HOLIN ZB (SEQ ID No. 30), an isolated nucleic acid molecule that encodes a protein that exhibits at least about 70%, or at least about 75%, or at least about 80%, or at least about 85%, or at least about 90%, or at least about 95%, or at least about 99% amino acid sequence identity to HOLIN Z (SEQ ID No. 27); an isolated nucleic acid molecule that encodes a protein that exhibits at least about 70%, or at least about 75%, or at least about 80%, or at least about 85%, or at least about 90%, or at least about 95%, or at least about 99% amino acid sequence identity to HOLIN ZA (SEQ ID No. 28); an isolated nucleic acid molecule that encodes a protein that exhibits at least about 70%, or at least about 75%, or at least about 80%, or at least about 85%, or at least about 90%, or at least about 95%, or at least about 99% amino acid sequence identity to HOLIN ZA.1 (SEQ ID No. 29); and an isolated nucleic acid molecule that encodes a protein that exhibits at least about 70%, or at least about 75%, or at least about 80%, or at least about 85%, or at least about 90%, or at least about 95%, or at least about 99% amino acid sequence identity to HOLIN ZB (SEQ ID No. 30).

This invention also provides isolated polypeptides or proteins including an isolated polypeptide comprising the amino acid sequence of HOLIN Z (SEQ ID No. 27), an isolated polypeptide comprising the amino acid sequence of HOLIN ZA (SEQ ID No. 28), an isolated polypeptide comprising the amino acid sequence of HOLIN ZA.1 (SEQ ID No. 29), an isolated polypeptide comprising the amino acid sequence of HOLIN ZB (SEQ ID No. 30), an isolated polypeptide comprising a fragment of at least 20 amino acids of HOLIN Z (SEQ ID No. 27), an isolated polypeptide comprising a fragment of at least 20 amino acids of HOLIN ZA (SEQ ID No. 28), an isolated polypeptide comprising a fragment of at least 20 amino acids of HOLIN ZA.1 (SEQ ID No. 29), an isolated polypeptide comprising a fragment of at least 20 amino acids of HOLIN ZB (SEQ ID No. 30), an isolated polypeptide comprising conservative amino acid substitutions of HOLIN Z (SEQ ID No. 27), an isolated polypeptide comprising conservative amino acid substitutions of HOLIN ZA (SEQ ID No. 28), an isolated polypeptide comprising conservative amino acid substitutions of HOLIN ZA.1 (SEQ ID No. 29), an isolated polypeptide comprising conservative amino acid substitutions of HOLIN ZB (SEQ ID No. 30), an isolated polypeptide exhibiting at least about 70%, or at least about 75%, or at least about 80%, or at least about 85%, or at least about 90%, or at least about 95%, or at least about 99% amino acid sequence identity with HOLIN Z (SEQ ID No. 27); an isolated polypeptide exhibiting at least about 70%, or at least about 75%, or at least about 80%, or at least about 85%, or at least about 90%, or at least about 95%, or at least about 99% amino acid sequence identity with HOLIN ZA (SEQ ID No. 28); an isolated polypeptide exhibiting at least about 70%, or at least about 75%, or at least about 80%, or at least about 85%, or at least about 90%, or at least about 95%, or at least about 99% amino acid sequence identity with HOLIN ZA.1 (SEQ ID No. 29); and an isolated polypeptide exhibiting at least about 70%, or at least about 75%, or at least about 80%, or at least about 85%, or at least about 90%, or at least about 95%, or at least about 99% amino acid sequence identity with HOLIN ZB (SEQ ID No. 30).

This invention also provides transformed plant cells and the progeny of such transformed plant cells, wherein the plant cells kill insects and nematodes or cause insects and nematodes to fail to thrive or to avoid feeding on said plant cells.

FIGS. 4A-4F show lysis of Gram-negative bacteria (A-C), Gram-positive bacteria (D, E) and a fungus (F) by holin gene fusions and modified holin gene fusions with hydrophobic or hydrophilic N termini, expressed in *E. coli*. The microbes to be tested were grown overnight in liquid PYGM medium and overlayed on PYGM medium on agar plates, and droplets of *E. coli* carrying and expressing the indicated gene constructs were placed on the overlays and incubated for several days: pKD46, empty vector; 349, holZ with hydrophobic C terminus expressed from pKD46; 350, holZA with hydrophobic C terminus expressed from pKD46; 351, holZ with hydrophobic C terminus expressed from pKD46; 363, holZ with hydrophilic C terminus expressed from pKD46; 373, P12::holZ with hydrophilic C terminus expressed from pKD46; pIPG377, P12::holZ::lysY expressed from pKD46; pIPG392, P12::holSZ with hydrophilic C terminus expressed from pKD46.

FIGS. 5A-5B show a transient expression, nonhost assay for holin activity. Shown are two different sweet pepper (Capsicum) variety Pimiento leaves inoculated with *X. phaseoli*, 24 hrs. after inoculation with *A. tumefaciens* GV2260 carrying the indicated clones. Photos taken 3 days after inoculation with *X. phaseoli*, and 4 days after inoculation with GV2260 containing plant expression clone pIPG377 and empty vector pIPG167. pIPG377 carries P12::holZ::lysY::HSV::HIS, operably cloned and expressed by a CaMV promoter in pIPG167.

Figure 6:
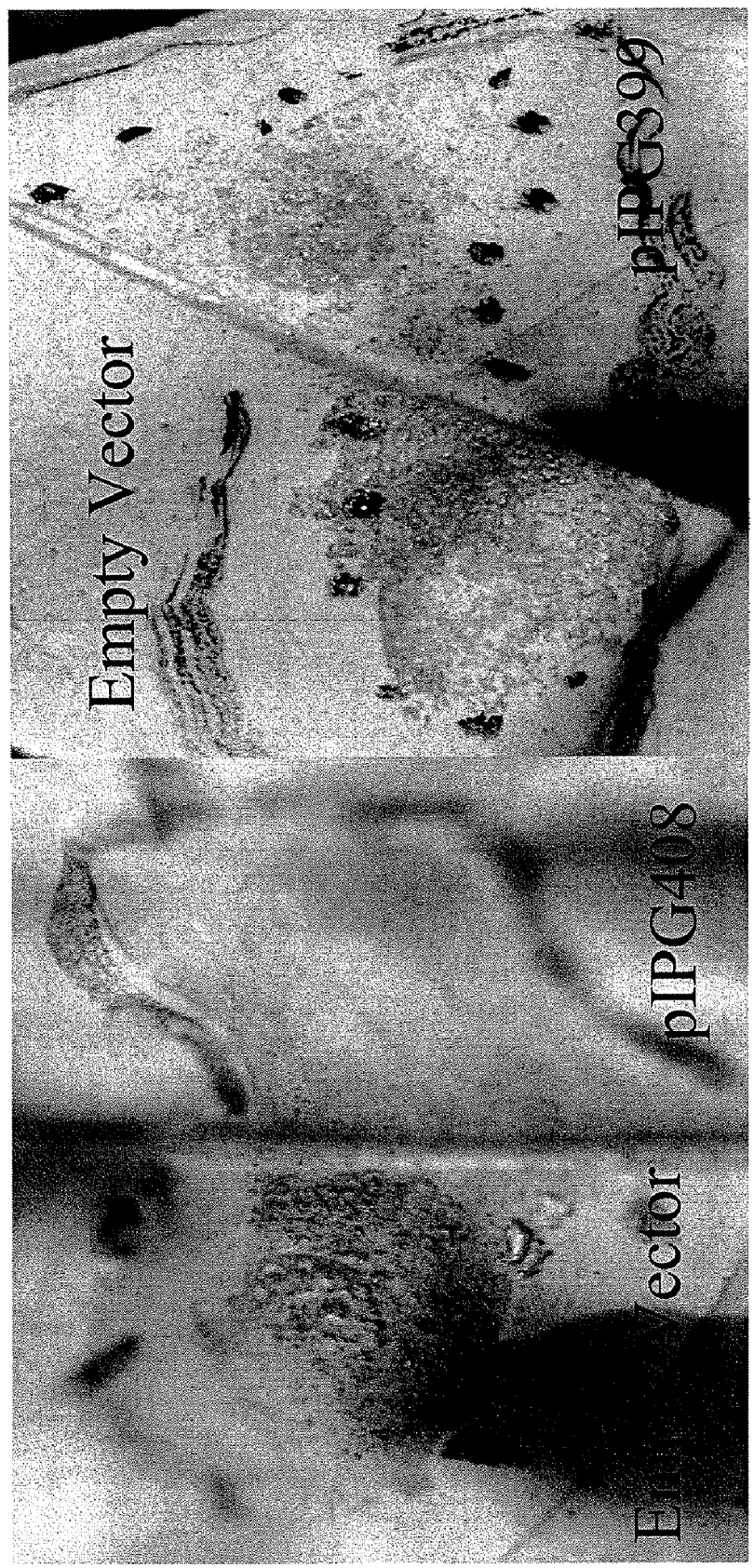

FIG. 6 shows a transient expression, host assay for holin activity. Shown are Duncan grapefruit (*Citrus paradise*) citrus leaves inoculated with *X. citri*, 24 hrs. after inoculation with *A. tumefaciens* GV2260 carrying the indicated clones. Photos taken 8 days after inoculation with *X. citri*, and 9 days after inoculation with GV2260 containing plant expression clones pIPG377, pIPG408 and empty vector pIPG167. pIPG377 carries P12::holZ::lysY::HSV::HIS operably cloned and expressed by a CaMV promoter in pIPG167. pPIG408 carries P12::synSZ::HSV::HIS, operably cloned and expressed by a CaMV promoter in pIPG167.

FIGS. 7A-7C show the process of citrus transformation used. 7A shows internodal stem sections of grapefruit (*C. paradise*) cultivar "Flame" under kanamycin selection, 7B shows a kanamycin resistant shoot (26% survive but only half are transformed); 7C shows a transgenic shoot after grafting onto a nontransgenic rootstock (80% of grafted shoots survive).

Figure 8:
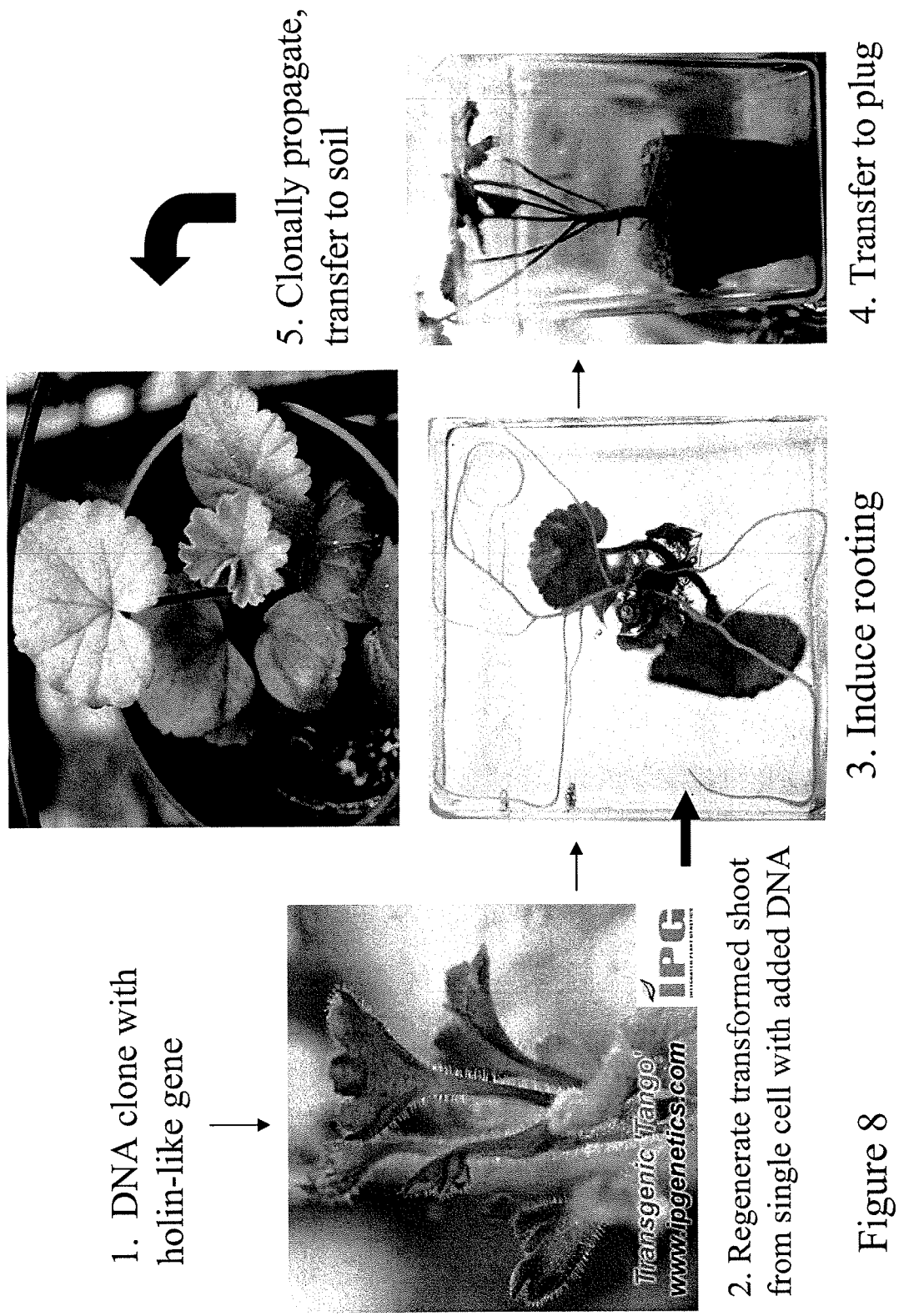

FIG. 8 shows the process of geranium (*P. hortorum*) transformation used. Leaf hypocotyl sections, in this example cultivar "Tango", were excised and hygromycin resistant shoots formed (left), which were then transferred to media inducing root formation. Following root formation, the entire rooted transformant was transferred to a synthetic support medium (plug), which was allowed to grow and harden before transfer to soil.

FIGS. 9A-9C show the process of rice transformation and confirmation of gene expression using a GUS carboxy terminal fusion. 9A shows rice seeds forming callus under hygromycin selection. The hygromycin resistant callus formed shoots and then roots on appropriate media. 9B shows putative transgenic rice seedlings after transfer to soil. 9C shows expression of a GUS gene fusion using a small clipped rice leaf segment in GUS stain. About 70% of the putative transgenic rice seedlings were GUS positive.

Figure 10:
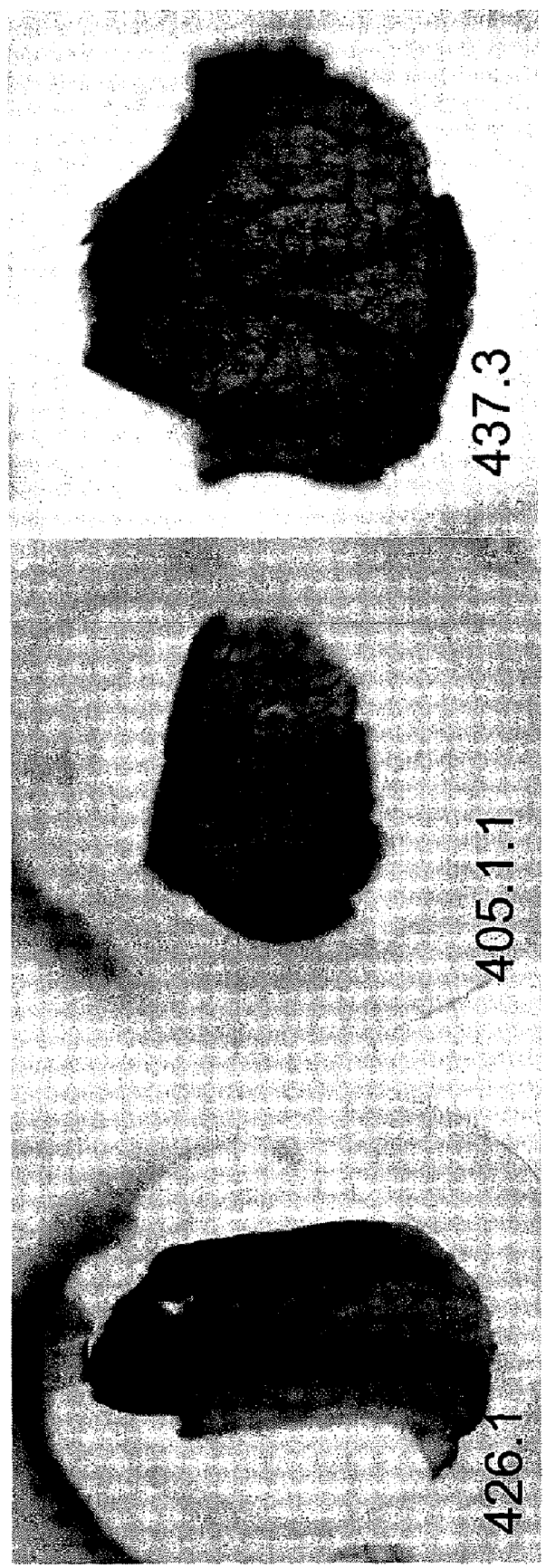

FIG. 10 shows three different transgenic geranium transformants (*P. hortorum* cv. "Avenida") expressing pIPG492. This clone carries the following gene fusion: PAL promoter:: P12 leader::holZ::lysY::GUS. Note the uniform and concentrated GUS staining around the xylem tissues of the three transgenic geranium lines (426.1, 405.1.1 and 437.3).

Figure 11:
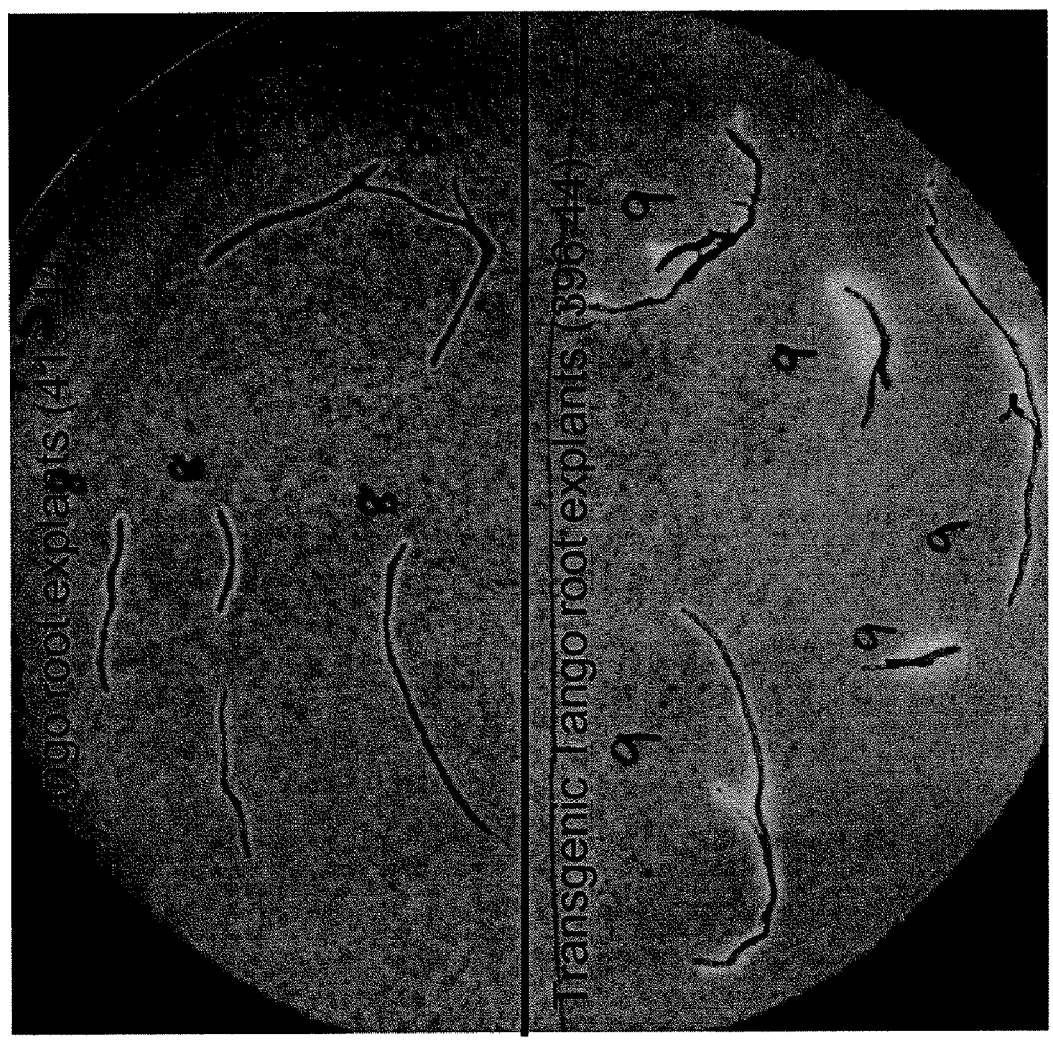

FIG. 11 shows killing of *Rastonia solanacearum* by roots from a transgenic geranium (*P. hortorum* cv. 'Tango') plant expressing pIPG492. Six root segments from a control geranium (identical age and condition) were placed on the upper half of plate and five root segments from the transgenic geranium plant were placed on the bottom half of a plate. The plate was previously covered with a “lawn” of ca. $10^8$ *R. solanacearum* bacteria. Photo taken 48 hrs. after inoculation.

FIG. 12 shows a mature, transgenic tomato plant (904B, right) exhibiting resistance to *Xanthomonas campestris* pv. *vesicatoria*. Transgenic plant 904B carries pIPG409, expressing the holSZ holin with the P12 leader. A nontransgenic, tissue culture “escape” plant of identical age and condition is shown to the left. Both plants were inoculated with ca. $10^5$ cfu/ml of *X. vesicatoria* using a leaf-dip inoculation method. Photo taken two weeks after inoculation.

DETAILED DESCRIPTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The present invention is based on our discovery that at least some holins, both natural and synthetic, can be stably produced by plant cells without toxic effects to plants, and that holins alone provide a novel means of protecting plants against gram negative bacteria. The present invention is also based, in part, on our discovery that at least some plant leader peptides, particularly those found on proteins secreted through the plant cell wall and accumulating in plant xylem tissue, greatly potentiate the effect of the antimicrobial effect of externally applied holins, not only on gram negative bacteria, but surprisingly, also extending to gram positive bacteria and fungi, and without enzymatic action. Since at least two holins are known to be hemolytic, and this hemolytic activity has been suggested to play a role in the pathogenesis of certain bacteria towards insects and nematodes (Brillard et al., 2003), holins or holing-like proteins should have potential applications for the control of insect and nematodes. The present invention is also based on our discovery that these same plant leader peptides provide a means for targeting the antimicrobial effect of holins to the plant apoplast and xylem, where they accumulate, providing a novel means of protecting plants against a wide variety of pathogens and pests, including gram positive and gram negative bacteria, fingi, insects and nematodes. Furthermore, we have discovered that a combination of plant leader peptide, holins and endolysins together provide a particularly stable conformation to provide an antimicrobial effect in plants. Even furthermore, we have discovered that plants may be used to produce crude or purified extracts of antimicrobial compounds based on holins and holin/endolysin fusions.

It is an object of the invention to identify genes encoding functional and broad-spectrum holin and holin-like proteins in bacteriophage by a series of bacterial suspension overlay tests, phage infectivity tests, DNA sequencing, genomic and functional analyses. Transgenic plants are then created containing the holin genes or synthetic variants of the holin genes fused with specific plant secretion leader sequences derived from a group of proteins found in plant xylem, and optionally fused with bacteriophage endolysins or other lytic enzymes. These DNA constructs are operably linked with plant promoters and expressed in plant cells, where the holin or holin/lytic enzyme combinations are available in sufficient quantity to kill gram negative bacteria, insects and nematodes.

To identify broad-spectrum holin and/or holin-like genes, it is first necessary to isolate and purify a DNA bacteriophage that has very strong antimicrobial activity against a variety of target organisms. This is accomplished by first obtaining bacteriophage that attack target gram negative bacteria. Bacteriophage that attack a specific bacterium may be isolated with ease from raw sewage, pond water, or drainage from greenhouse complexes using well publicized methods known to those skilled in the art. Secondly, a variety of bacteriophage plaques are evaluated by size of the plaques formed after plating the bacteriophage with a gram negative host bacterium using methods known to those skilled in the art. Thirdly and unique to this invention, bacteriophage are selected by their ability to lyse additional gram negative bacteria that they are incapable of infecting. This is accomplished by a series of infection assays and overlay assays. Finally, phage nucleic acid is isolated and treated with DNAse and separately with RNAse using methods known to those skilled in the art. Only DNA based phage are selected.

Following phage purification, the bacteriophage DNA is fragmented and fully sequenced, as exemplified by SEQ ID No. 1. There are a variety of strategies available for this purpose known to those skilled in the art; sequencing may be accomplished by shot-gun library sequencing or by subcloning, restriction mapping and sequencing using primer walking techniques. Phage genomic regions expressing holins from gram negative bacteria are not clonable in *E. coli* and are readily recognized by the fact that they are not clonable with their native promoters. These regions may be sequenced directly from phage DNA.

Following DNA sequencing of the bacteriophage genome, transcriptional direction is determined by identification of promoters and transcriptional terminators using programs well known to those skilled in the art. Phage genomes are typically transcribed as polycistronic messages in large blocks. All open reading frames (ORFs) are then identified using programs well known to those skilled in the art, and likely functional genes (LFGs) are also identified, based on length of the ORF, codon usage, third position codon bias, presence or absence of Shine-Delgarno sequences and transcriptional context, including likely promoters, transcriptional terminators and direction of transcription. The biochemical functions of some of the LFGs are then determined by comparisons with other, often characterized genes catalogued in large databases such as GenBank®. Since holins are encoded by genes in at least 35 different families, and with no detected orthologous relationships (Grundling et al., 2001), the holin genes are unlikely to be discovered by comparisons with any known genes in public or private databases.

The genes encoding holins and/or holin-like genes are identified by examining every LFG of the phage, starting with those found in any DNA fragment that is not sub-clonable, through any computer assisted program that identifies predicted transmembrane domains. Holins and/or holin-like proteins can have anywhere from one to three such domains. Any LFG with from one to three transmembrane domains is then selected for further testing using a functional gene expression assay. The predicted peptide coding regions of the putative holin genes are amplified by polymerase chain reaction (PCR) from the phage DNA and cloned without promoters in a suitable vector. These coding regions are then operably fused with strongly regulated, repressible promoters in suitable bacterial expression vectors. Repression of the promoter operably fused with the putative holin genes is then released, which should result in a noticeable reduction or termination of growth of the *E. coli* strains carrying the clones. Any such clones are then further tested for their effect on other, externally applied bacteria by agar plate overlay tests, consisting of mid-log phase liquid cultures of gram negative bacteria plated to form a uniform lawn. Ten microliter drops of overnight *E. coli* cultures expressing putative holin genes are placed on these bacterial lawns and gene expression is induced. Any clones exhibiting zones of inhibition and/or lysis around the *E. coli* droplets within 48 hrs may be considered as presumptive for presence of expressed holins.

Some plant stress-associated and/or disease-associated proteins have been found to accumulate preferentially and most abundantly in the xylem of plants. Only a very few proteins are found in the xylem; it is unclear how they are secreted through the plant cell wall to reach the xylem. Such proteins have secretion signal peptides that we have discovered are useful for targeting antimicrobial compounds to the plant apoplast and xylem; we call these "xylem secretion signal peptides". For example, we found that a 24 amino acid plant signal peptide derived from one such protein, P12 (GenBank Accession #AF015782; Ceccardi et al., 1998) is useful for the purpose. More significantly, we have determined that holin genes reconstructed with P12 as a leader have greatly enhanced inhibition and/or lethal activity, covering a wide variety of microbes, including gram positive bacteria and fingi. The xylem secretion signal peptide sequence is amplified from an appropriate plant source by PCR and cloned upstream of the holin sequence. Lysis of additional microbes and cells, including gram positive, fungi and blood cells can be performed using the holin alone or with P12 or similar leaders using overlay assays in a manner similar to that described above for gram negative bacteria. Blood agar may be used to detect hemolytic (potentially insecticidal and nematicidal) activity (Brillard, 2003), and may be used in overlay assays in a manner similar to that described above. Fungal mycelium ground from agar plates in a food blender may be used for preparations of overlays of filamentous fungi.

It is also an object of the invention to prevent diseases of both monocot and dicot plants prophylatically by killing any bacterium, fungus, nematode or insect that infects or feeds on the plant. In one embodiment of the invention, the prophylactic and therapeutic treatment of a variety of diseases caused by various species and pathovars of *Xanthomonas, Pseudomonas, Erwinia, Agrobacterium, Corynebacterium, Pythium, Phytopthora, Erysiphe, Magnaportha*, and *Puccinia*. Transgenic plants are created using plants that are hosts of the indicated pathogen or pest genus, said host plants carrying one or more holin or holin-like peptide fused with a xylem secretion signal peptide, operably linked with a plant promoter such that the holin(s) and/or holin-like peptides are made by the plants.

In another embodiment of the invention, transgenic plants are created that are hosts of the indicated genus, said host plants carrying one or more holin or holin-like peptides fused with a xylem secretions signal peptide together with a lytic enzyme, all operably linked with plant promoters such that the holin and/or holin-like peptides and lytic enzymes are made by the plant hosts.

It is a further object of the invention to prevent or to dampen epidemics or plagues by planting these transgenic plants as "trap" plants in an environment such that populations of infectious bacteria, fungi, nematodes or insects are reduced by feeding upon the transgenic plants. Such an environment may include commercial crops, including nontransgenic crops of the same or different plant species as the transgenic trap plants, gardens and inside buildings.

It is also an object of the invention to prophylatically prevent and to cure diseases of animals and humans prophylatically by killing any bacterium or fungus that infects animals or people. In a another embodiment of the invention, a crude, semi-pure or pure extract of holin and/or holin-like peptides are extracted from a transgenic plant carrying one or more genes encoding holin(s) and/or holin-like peptides and incorporated into a compound for treatment of bacterial or fungal infections of animals, including those caused by *Candida, Heinophilus, Escherichia* and *Salmonella*.

It is also an object of the invention to prophylactically prevent contamination of livestock feed and human foods by killing any bacterium or fungus that might contaminate the feed or foods. In another embodiment of the invention, livestock feeds may incorporate or consist of transgenic whole plants, transgenic plant parts or a crude, semi-pure or pure extract of transgenic plants expressing holin and/or holin-like peptides. In another embodiment of the invention, human foods such as eggs or sprouts may be treated with a spray preparation of holins and or holin-like peptides made from transgenic plants.

DEFINITIONS

As used herein, the term "allele" refers to any of several alternative forms of a gene.

As used herein, the term "amino acid" refers to the aminocarboxylic acids that are components of proteins and peptides. The amino acid abbreviations are as follows:

| | | | | | |
|---|---|---|---|---|---|
| A (Ala) | C (Cys) | D (Asp) | E (Glu) | F (Phe) | G (Gly) |
| H (His) | I (Iso) | K (Lys) | L (Leu) | M (Met) | N (Asn) |
| P (Pro) | Q (Gln) | R (Arg) | S (Ser) | T (Thr) | V (Val) |
| W (Trp) | Y (Tyr) | | | | |

As used herein, the term "crop plant" refers to any plant grown for any commercial purpose, including, but not limited to the following purposes: seed production, hay production, ornamental use, fruit production, berry production, vegetable production, oil production, protein production, forage production, animal grazing, golf courses, lawns, flower production, landscaping, erosion control, green manure, improving soil tilth/health, producing pharmaceutical products/drugs, producing food or food additives, smoking products, pulp production and wood production.

As used herein, the terms "cross pollination" or "crossbreeding" refer to the process by which the pollen of one flower on one plant is applied (artificially or naturally) to the ovule (stigma) of a flower on another plant.

As used herein, the term "cultivar" refers to a variety, strain or race of plant that has been produced by horticultural or agronomic techniques and is not normally found in wild populations.

As used herein, the terms "dicotyledon" and "dicot" refer to a flowering plant having an embryo containing two seed halves or cotyledons. Examples include tobacco; tomato; the legumes, including peas, alfalfa, clover and soybeans; oaks; maples; roses; mints; squashes; daisies; walnuts; cacti; violets and buttercups.

As used herein, the term "female plant" refers to a plant that produces ovules. Female plants generally produce seeds after fertilization. A plant designated as a "female plant" may contain both male and female sexual organs. Alternatively, the "female plant" may only contain female sexual organs either naturally (e.g., in dioecious species) or due to emasculation (e.g., by detasselling).

As used herein, the term "filial generation" refers to any of the generations of cells, tissues or organisms following a particular parental generation. The generation resulting from a mating of the parents is the first filial generation (designated as "F1" or "$F_1$"), while that resulting from crossing of F1 individuals is the second filial generation (designated as "F2" or "$F_2$").

As used herein, the term "gamete" refers to a reproductive cell whose nucleus (and often cytoplasm) fuses with that of another gamete of similar origin but of opposite sex to form a zygote, which has the potential to develop into a new individual. Gametes are haploid and are differentiated into male and female.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, organism (e.g., a plant), or group of organisms.

As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

As used herein, the terms "heterologous polynucleotide" or a "heterologous nucleic acid" or an "exogenous DNA segment" refer to a polynucleotide, nucleic acid or DNA segment that originates from a source foreign to the particular host cell, or, if from the same source, is modified from its original form. Thus, a heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

As used herein, the term "heterologous trait" refers to a phenotype imparted to a transformed host cell or transgenic organism by an exogenous DNA segment, heterologous polynucleotide or heterologous nucleic acid.

As used herein, the term "heterozygote" refers to a diploid or polyploid individual cell or plant having different alleles (forms of a given gene) present at least at one locus.

As used herein, the term "heterozygous" refers to the presence of different alleles (forms of a given gene) at a particular gene locus.

As used herein, the terms "homolog" or "homologue" refer to a nucleic acid or peptide sequence which has a common origin and functions similarly to a nucleic acid or peptide sequence from another species.

As used herein, the term "homozygote" refers to an individual cell or plant having the same alleles at one or more loci.

As used herein, the term "homozygous" refers to the presence of identical alleles at one or more loci in homologous chromosomal segments.

As used herein, the term "hybrid" refers to any individual cell, tissue or plant resulting from a cross between parents that differ in one or more genes.

As used herein, the term "inbred" or "inbred line" refers to a relatively true-breeding strain.

As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses effected such that a gene or a combination of genes, in heterozygous (hemizygous) or homozygous condition, imparts a desired trait to the plant.

As used herein, the term "locus" (plural: "loci") refers to any site that has been defined genetically. A locus may be a gene, or part of a gene, or a DNA sequence that has some regulatory role, and may be occupied by different sequences.

As used herein, the term "male plant" refers to a plant that produces pollen grains. The "male plant" generally refers to the sex that produces gametes for fertilizing ova. A plant designated as a "male plant" may contain both male and female sexual organs. Alternatively, the "male plant" may only contain male sexual organs either naturally (e.g., in dioecious species) or due to emasculation (e.g., by removing the ovary).

As used herein, the term "mass selection" refers to a form of selection in which individual plants are selected and the next generation propagated from the aggregate of their seeds.

As used herein, the term "monocotyledon" or "monocot" refer to any of a subclass (Monocotyledoneae) of flowering plants having an embryo containing only one seed leaf and usually having parallel-veined leaves, flower parts in multiples of three, and no secondary growth in stems and roots. Examples include lilies; orchids; rice; corn, grasses, such as tall fescue, goat grass, and Kentucky bluegrass; grains, such as wheat, oats and barley; irises; onions and palms.

As used herein, the terms "mutant" or "mutation" refer to a gene, cell, or organism with an abnormal genetic constitution that may result in a variant phenotype.

As used herein, the terms "nucleic acid" or "polynucleotide" refer to deoxyribonucleotides or ribonucleotides and polymers thereof in either single- or double-stranded form. Unless specifically limited, the terms encompass nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260:2605-2608; Cassol et al. (1992); Rossolini et al. (1994) Mol. Cell. Probes 8:91-98). The term nucleic acid is used interchangeably with gene, cDNA, and mRNA encoded by a gene. The term "nucleic acid" also encompasses polynucleotides synthesized in a laboratory using procedures well known to those skilled in the art.

As used herein, a DNA segment is referred to as "operably linked" when it is placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof.

As used herein, the term "open pollination" refers to a plant population that is freely exposed to some gene flow, as opposed to a closed one in which there is an effective barrier to gene flow.

As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

As used herein, the terms "ortholog" and "orthologue" refer to a nucleic acid or peptide sequence which functions similarly to a nucleic acid or peptide sequence from another species. For example, where one gene from one plant species has a high nucleic acid sequence similarity and codes for a protein with a similar function to another gene from another plant species, such genes would be orthologs.

As used herein when discussing plants, the term "ovule" refers to the female gametophyte, whereas the term "pollen" means the male gametophyte.

As used herein, the term "phenotype" refers to the observable characters of an individual cell, cell culture, organism (e.g., a plant), or group of organisms which results from the interaction between that individual's genetic makeup (i.e., genotype) and the environment.

As used herein, the term "plant line" is used broadly to include, but is not limited to, a group of plants vegetatively propagated from a single parent plant, via tissue culture techniques or a group of inbred plants which are genetically very similar due to descent from a conunon parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses effected such that a gene or a combination of genes, in heterozygous (hemizygous) or homozygous condition, imparts a desired trait to the plant.

As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

As used herein, the term "promoter" refers to a region of DNA involved in binding RNA polymerase to initiate transcription.

As used herein, the terms "protein," "peptide" or "polypeptide" refer to amino acid residues and polymers thereof. Unless specifically limited, the terms encompass amino acids containing known analogues of natural amino acid residues that have similar binding properties as the reference amino acid and are metabolized in a manner similar to naturally occurring amino acid residues. Unless otherwise indicated, a particular amino acid sequence also implicitly encompasses conservatively modified variants thereof (e.g. conservative substitutions) as well as the sequence explicitly indicated. The term "polypeptide" also encompasses polypeptides synthesized in a laboratory using procedures well known to those skilled in the art.

As used herein, the term "recombinant" refers to a cell, tissue or organism that has undergone transformation with recombinant DNA. The original recombinant is designated as "R0" or "$R_0$." Selfing the R0 produces a first transformed generation designated as "R1" or "$R_1$."

As used herein, the term "self pollinated" or "self-pollination" means the pollen of one flower on one plant is applied (artificially or naturally) to the ovule (stigma) of the same or a different flower on the same plant.

As used herein, the term "signal sequence" refers to an amino acid sequence (the signal peptide) attached to the polypeptide which binds the polypeptide to the endoplasmic reticulum and is essential for protein secretion.

As used herein, the term "transcript" refers to a product of a transcription process.

As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

As used herein, the term "transformant" refers to a cell, tissue or organism that has undergone transformation. The original transformant is designated as "T0" or "$T_0$." Selfing the T0 produces a first transformed generation designated as "T1" or "$T_1$."

As used herein, the term "transgene" refers to a nucleic acid that is inserted into an organism, host cell or vector in a manner that ensures its function.

As used herein, the term "transgenic" refers to cells, cell cultures, organisms (e.g., plants), and progeny which have received a foreign or modified gene by one of the various methods of transformation, wherein the foreign or modified gene is from the same or different species than the species of the organism receiving the foreign or modified gene.

As used herein, the term "transposition event" refers to the movement of a transposon from a donor site to a target site.

As used herein, the term "variety" refers to a subdivision of a species, consisting of a group of individuals within the species that are distinct in form or function from other similar arrays of individuals.

As used herein, the terms "untranslated region" or "UTR" refer to any part of a mRNA molecule not coding for a protein (e.g., in eukaryotes the poly(A) tail).

As used herein, the term "vector" refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057-3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

Plant Transformation

As discussed herein, several embodiments of the present invention employ expression units (or expression vectors or systems) to express an exogenously supplied nucleic acid sequence in a plant. Methods for generating expression units/systems/vectors for use in plants are well known in the art and can readily be adapted for use in the instant invention. A skilled artisan can readily use any appropriate plant/vector/expression system in the present methods following the outline provided herein.

The expression control elements used to regulate the expression of the protein can either be the expression control element that is normally found associated with the coding sequence (homologous expression element) or can be a heterologous expression control element. A variety of homologous and heterologous expression control elements are known in the art and can readily be used to make expression units for use in the present invention. Transcription initiation regions, for example, can include any of the various opine initiation regions, such as octopine, mannopine, nopaline and the like that are found in the Ti plasmids of *Agrobacterium tumafacians*. Alternatively, plant viral promoters can also be used, such as the cauliflower mosaic virus 19S and 35S promoters (CaMV 19S and CaMV 35S promoters, respectively) to control gene expression in a plant (U.S. Pat. Nos. 5,352,605; 5,530,196 and 5,858,742 for example). Enhancer sequences derived from the CaMV can also be utilized (U.S. Pat. Nos. 5,164,316; 5,196,525; 5,322,938; 5,530,196; 5,352,605; 5,359,142; and 5,858,742 for example). Lastly, plant promoters such as prolifera promoter, fruit-specific promoters, Ap3 promoter, heat shock promoters, seed-specific promoters, etc. can also be used.

Either a gamete-specific promoter, a constitutive promoter (such as the CaMV or Nos promoter), an organ-specific promoter (such as the E8 promoter from tomato) or an inducible promoter is typically ligated to the protein or antisense encoding region using standard techniques known in the art. The expression unit may be further optimized by employing supplemental elements such as transcription terminators and/or enhancer elements.

Thus, for expression in plants, the expression units will typically contain, in addition to the protein sequence, a plant promoter region, a transcription initiation site and a transcription termination sequence. Unique restriction enzyme sites at the 5' and 3' ends of the expression unit are typically included to allow for easy insertion into a preexisting vector.

In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include, but are not limited to the *Agrobacterium* octopine synthase signal (Gielen et al., EMBO *J*3:835-846 (1984)) or the nopaline synthase signal (Depicker et al., Mol. and Appl. Genet. 1:561-573 (1982)).

The resulting expression unit is ligated into or otherwise constructed to be included in a vector that is appropriate for higher plant transformation. The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow on a medium containing the particular antibiotic. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as ampicillin, kanamycin or tetracycline.

Other DNA sequences encoding additional functions may also be present in the vector, as is known in the art. For instance, in the case of *Agrobacterium* transformations, T-DNA sequences will also be included for subsequent transfer to plant chromosomes.

The sequences of the present invention can also be fused to various other nucleic acid molecules such as Expressed Sequence Tags (ESTs), epitopes or fluorescent protein markers.

ESTs are gene fragments, typically 300 to 400 nucleotides in length, sequenced from the 3' or 5' end of complementary-DNA (cDNA) clones. Nearly 30,000 *Arabidopsis thaliana* ESTs have been produced by a French and an American consortium (Delseny et al., FEBS Lett. 405(2):129-132 (1997); *Arabidopsis thaliana* Database, http://genome.www-.stanford.edu/Arabidopsis). For a discussion of the analysis of gene-expression patterns derived from large EST databases, see, e.g. M. R. Fannon, TIBTECH 14:294-298 (1996).

Biologically compatible fluorescent protein probes, particularly the self-assembling green fluorescent protein (GFP) from the jellyfish *Aequorea victoria*, have revolutionized research in cell, molecular and developmental biology because they allow visualization of biochemical events in living cells (Murphy et al., Curr. Biol. 7(11):870-876 (1997); Grebenok et al., Plant J. 11(3):573-586 (1997); Pang et al., Plant Physiol 112(3) (1996); Chiu et al., Curr. Biol. 6(3):325-330 (1996); Plautz et al., Gene 173(1):83-87 (1996); Sheen et al., Plant J. 8(5):777-784 (1995)).

Site-directed mutagenesis has been used to develop a more soluble version of the codon-modified GFP called soluble-modified GFP (smGFP). When introduced into *Arabidopsis*, greater fluorescence was observed when compared to the codon-modified GFP, implying that smGFP is 'brighter' because more of it is present in a soluble and functional form (Davis et al., Plant Mol. Biol. 36(4):521-528 (1998)). By fusing genes encoding GFP and beta-glucuronidase (GUS), researchers were able to create a set of bifunctional reporter constructs which are optimized for use in transient and stable expression systems in plants, including *Arabidopsis* (Quaedvlieg et al., Plant Mol. Biol. 37(4):715-727 (1998)).

Berger et al. (Dev. Biol. 194(2):226-234 (1998)) report the isolation of a GFP marker line for *Arabidopsis* hypocotyl epidermal cells. GFP-fusion proteins have been used to localize and characterize a number of *Arabidopsis* genes, including geranylgeranyl pyrophosphate (GGPP) (Zhu et al., Plant Mol. Biol. 35(3):331-341 (1997).

To introduce a desired gene or set of genes by conventional methods requires a sexual cross between two lines, and then repeated back-crossing between hybrid offspring and one of the parents until a plant with the desired characteristics is obtained. This process, however, is restricted to plants that can sexually hybridize, and genes in addition to the desired gene will be transferred.

Recombinant DNA techniques allow plant researchers to circumvent these limitations by enabling plant geneticists to identify and clone specific genes for desirable traits, such as resistance to an insect pest, and to introduce these genes into already useful varieties of plants. Once the foreign genes have been introduced into a plant, that plant can then be used in conventional plant breeding schemes (e.g., pedigree breeding, single-seed-descent breeding schemes, reciprocal recurrent selection) to produce progeny which also contain the gene of interest.

Genes can be introduced in a site directed fashion using homologous recombination. Homologous recombination permits site-specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451, 513; 5,501,967 and 5,527,695.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation. See, for example, U.S. Pat. Nos. 5,405,765; 5,472,869; 5,538,877; 5,538,880; 5,550,318; 5,641,664; 5,736,369 and 5,736,369; Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and, Raineri et al, Bio/Tech. 8:33-38 (1990)), each of which is expressly incorporated herein by reference in their entirety.

*Agrobacterium tumefaciens* is a naturally occurring bacterium that is capable of inserting its DNA (genetic information) into plants, resulting in a type of injury to the plant known as crown gall. Most species of plants can now be transformed using this method, including alfalfa. See, for example, Wang et al., Australian Journal of Plant Physiology 23(3): 265-270 (1996); Hoffman et al., Molecular Plant-Microbe Interactions 10(3): 307-315 (1997); and, Trieu et al., Plant Cell Reports 16:6-11 (1996).

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E. I. du Pont de Nemours and Company. Most species of plants have been transformed using this method, including alfalfa (U.S. Pat. No. 5,324,646) and clover (Voisey et al., Biocontrol Science and Technology 4(4): 475-481 (1994); Quesbenberry et al., Crop Science 36(4): 1045-1048 (1996); Khan et al., Plant Physiology 105 (1): 81-88 (1994); and, Voisey et al., Plant Cell Reports 13(6): 309-314 (1994)).

Developed by ICI Seeds Inc. (Garst Seed Company) in 1993, WHISKERS™ is an alternative to other methods of inserting DNA into plant cells (e.g., the Biolistic® Gene Gun, *Agrobacterium tumefaciens*, the "Shotgun" Method, etc.); and it consists of needle-like crystals ("whiskers") of silicon carbide. The fibers are placed into a container along with the plant cells, then mixed at high speed, which causes the crystals to pierce the plant cell walls with microscopic "holes" (passages). Then the new DNA (gene) is added, which causes the DNA to flow into the plant cells. The plant cells then incorporate the new gene(s); and thus they have been genetically engineered.

The essence of the WFHSKERS™ technology is the small needle-like silicon carbide "whisker" (0.6 microns in diameter and 5-80 microns in length) which is used in the following manner. A container holding a "transformation cocktail" composed of DNA (e.g., agronomic gene plus a selectable marker gene), embryogenic corn tissue, and silicon carbide "whiskers" is mixed or shaken in a robust fashion on either a dental amalgam mixer or a paint shaker. The subsequent collisions between embryogenic corn cells and the sharp silicon carbide "whiskers" result in the creation of small holes in the plant cell wall through which DNA (the agronomic gene) is presumed to enter the cell. Those cells receiving and incorporating a new gene are then induced to grow and ultimately develop into fertile transgenic plants.

Silicon carbide "whisker" transformation has now produced stable transformed calli and/or plants in a variety of plants species such as *Zea mays*. See, for example, U.S. Pat. Nos. 5,302,523 and 5,464,765, each of which is incorporated herein by reference in their entirety; Frame et al., The Plant Journal 6: 941-948 (1994); Kaeppler et al., Plant Cell Reports 9:415-418 (1990); Kaeppler et al, Theoretical and Applied Genetics 84:560-566 (1992); Petolino et al, Plant Cell Reports 19(8):781-786 (2000); Thompson et al., Euphytica 85:75-80 (1995); Wang et al., In Vitro Cellular and Developmental Biology 31:101-104 (1995); Song et al., Plant Cell Reporter 20:948-954 (2002); Petolino et al., Molecular Methods of Plant Analysis, In Genetic Transformation of Plants, Vol. 23, pp. 147-158, Springer-Verlag, Berlin (2003). Other examples include *Lolium multifloruin, Lolium perenne, Festuca arundinacea, Agrostis stolonifera* (Dalton et al., Plant Science 132:3143 (1997)), *Oryza sativa* (Nagatani et al., Biotechnology Techniques 11:471-473 (1997)), and *Triticum aestivum* and *Nicotiana tobacum* (Kaeppler et al., Theoretical and Applied Genetics 84:560-566 (1992)). Even *Chlamydomonas* (see, for example, Dunahay, T. G., Biotechniques 15:452-460 (1993)) can be transformed with a "whiskers" approach. As it is currently practiced on higher plants, the "whisker" system is one of the least complex ways to transform some plant cells.

Genes successfully introduced into plants using recombinant DNA methodologies include, but are not limited to, those coding for the following traits: seed storage proteins, including modified 7S legume seed storage proteins (see, for example, U.S. Pat. Nos. 5,508,468, 5,559,223 and 5,576,203); herbicide tolerance or resistance (see, for example, De Greef et al., Bio/Technology 7:61 (1989); U.S. Pat. No. 4,940,835; U.S. Pat. No. 4,769,061; U.S. Pat. No. 4,975,374; Marshall et al. (1992) Theor. Appl. Genet. 83, 435; U.S. Pat. No. 5,489,520; U.S. Pat. No. 5,498,544; U.S. Pat. No. 5,554,798; Powell et al, Science 232:738-743 (1986); Kaniewski et al., Bio/Tech. 8:750-754 (1990)); Day et al., Proc. Natl. Acad. Sci. USA 88:6721-6725 (1991)); phytase (see, for example, U.S. Pat. No. 5,593,963); resistance to bacterial, fungal, nematode and insect pests, including resistance to the *lepidoptera* insects conferred by the Bt gene (see, for example, U.S. Pat. Nos. 5,597,945 and 5,597,946; Johnson et al., Proc. Natl. Acad. Sci. USA, 86:9871-9875 (1989); Perlak et al., Bio/Tech. 8:939-943 (1990)); lectins (U.S. Pat. No. 5,276,269); flower color (Meyer et al., Nature 330:677-678 (1987); Napoli et al., Plant Cell 2:279-289 (1990); van der Krol et al., Plant Cell 2:291-299 (1990)); Bt genes (Voisey et al., supra); neomycin phosphotransferase II (Quesbenberry et al., supra); the pea lectin gene (Diaz et al., Plant Physiology 109(4): 1167-1177 (1995); Eijsden et al., Plant Molecular Biology 29(3):431-439 (1995)); the auxin-responsive promoter GH3 (Larkin et al., Transgenic Research 5(5):325-335 (1996)); seed albumin gene from sunflowers (Khan et al., Transgenic Research 5(3):179-185 (1996)); and genes encoding the enzymes phosphinothricin acetyl transferase, beta-glucuronidase (GUS) coding for resistance to the Basta® herbicide, neomycin phosphotransferase, and an alpha-amylase inhibitor (Khan et al., supra), each of which is expressly incorporated herein by reference in their entirety.

For certain purposes, different antibiotic or herbicide selection markers may be preferred. Selection markers used routinely in transformation include the nptII gene which confers resistance to kanamycin and related antibiotics (see, for example, Messing & Vierra, Gene 19: 259-268 (1982); Bevan et al., Nature 304:184-187 (1983)), the bar gene which confers resistance to the herbicide phosphinothricin (White et al., Nucl Acids Res 18: 1062 (1990), Spencer et al., Theor Appl Genet. 79: 625-631 (1990)), and the dhfr gene, which confers resistance to methotrexate (Bourouis et al., EMBO J. 2(7): 1099-1104 (1983)).

Transgenic alfalfa plants have been produced using a number of different genes isolated from both alfalfa and non-alfalfa species including, but not limited to, the following: the promoter of an early nodulin gene fused to the reporter gene gusA (Bauer et al., The Plant Journal 10(1):91-105 (1996)); the early nodulin gene (Charon et al., Proc. Natl. Acad. of Sci. USA 94(16):8901-8906 (1997); Bauer et al., Molecular Plant-Microbe Interactions 10(1):39-49 (1997)); NADH-dependent glutamate synthase (Gantt, The Plant Journal 8(3): 345-358 (1995)); promoter-gusA fusions for each of three lectin genes (Bauchrowitz et al., The Plant Journal 9(1):31-43 (1996)); the luciferase enzyme of the marine soft coral *Renilla* reniforms fused to the CaMV promoter (Mayerhofer et al., The Plant Journal 7(6):1031-1038 (1995)); Mn-superoxide dismutase cDNA (McKersie et al., Plant Physiology 111(4): 1177-1181 (1996)); synthetic cryIC genes encoding a *Bacillus thuringiensis* delta-endotoxin (Strizhov et al., Proc. Natl. Acad. Sci. USA 93(26):15012-15017 (1996)); glucanse (Dixon et al., Gene 179(1):61-71 (1996); and leaf senescence gene (U.S. Pat. No. 5,689,042).

Genetic transformation has also been reported in numerous forage and turfgrass species (Conger B. V., Genetic Transformation of Forage Grasses in Molecular and Cellular Technologies for Forage Improvement, CSSA Special Publication No. 26, Crop Science Society of America, Inc. E. C. Brummer et al. Eds. 1998, pages 49-58). These include, but are not limited to, orchardgrass (*Dactylis glomerata* L.), tall fescue (*Festuca arundinacea* Schreb.) red fescue (*Festuca rubra* L.), meadow fescue (*Festuca pratenisis* Huds.) perennial ryegrass (*Lolium perenne* L.) creeping bentgrass (*Agrostis palustris* Huds.) and redtop (*Agrostis alba* L.).

A transgenic plant formed using *Agrobacterium* transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

Assuming normal hemizygosity, selfing will result in maximum genotypic segregation in the first selfed recombinant generation, also known as the R1 or $R_1$ generation. The R1 generation is produced by selfing the original recombinant line, also known as the R0 or $R_0$ generation. Because each insert acts as a dominant allele, in the absence of linkage and assuming only one hemizygous insert is required for tolerance expression, one insert would segregate 3:1, two inserts, 15:1, three inserts, 63:1, etc. Therefore, relatively few R1 plants need to be grown to find at least one resistance phenotype (U.S. Pat. Nos. 5,436,175 and 5,776,760).

As mentioned above, self-pollination of a hemizygous transgenic regenerated plant should produce progeny equivalent to an F2 in which approximately 25% should be homozygous transgenic plants. Self-pollination and testcrossing of the F2 progeny to non-transformed control plants can be used to identify homozygous transgenic plants and to maintain the line. If the progeny initially obtained for a regenerated plant were from cross-pollination, then identification of homozygous transgenic plants will require an additional generation of self-pollination (U.S. Pat. No. 5,545,545).

Breeding Methods

Open-Pollinated Populations. The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

Mass Selection. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (Vicia) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic vary widely. In practice, numbers of parental lines range from 10 to several hundred, with 100-200 being the average. Broad based synthetics formed from 100 or more clones would be expected to be more stable during seed multiplication than narrow based synthetics.

Hybrids. A hybrid is an individual plant resulting from a cross between parents of differing genotypes. Commercial hybrids are now used extensively in many crops, including corn (maize), sorghum, sugarbeet, sunflower and broccoli.

Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, Commercial Hybrid Seed Production 8:161-176, In Hybridization of Crop Plants.

It should be understood that the examples and embodiments described herein are for illustrative purposes only and that various modifications or changes in light thereof will be suggested to persons skilled in the art and are to be included within the spirit and purview of this application.

EXAMPLES

Example 1

Isolation of Bacteriophage Infecting *Xanthomonas pelargonii*

An overnight culture of *X. campestris* pv. *pelargonii* (syn. *X. pelargonii*) strain CHSC was grown at 30° C. in PYGM medium (peptone, yeast extract, glycerol and morpholinepropanesulfonic acid; DeFeyter et al. 1990) with moderate shaking. Five ml of this overnight culture plus 50 ml of unsterilized water taken from the edge of a large pond in an agricultural setting was added to 50 ml of PYGM plus 2.5 g $CaCO_3$ and allowed to incubate at 30° C. for 48 hours without shaking. Following incubation, 1 ml of this enrichment culture was centrifuged for 1 minute at 5000 g to remove most bacteria and debris, and 500 µl of the supernatant was removed and sterilized with a drop of chloroform. Droplets of this supernatant were placed atop an overlay plate containing strain CHSC in top agar. Overlay plates were PYGM agar plates overlayed with 200 µl of overnight CHSC broth culture added to 3 ml 0.7% water agar held at 50° C. and allowed to cool and solidify. Plaques were observed after 24 hrs. incubation; these were collected by scraping the plaques from the plates, titered and stored according to standard procedures (Sambrook et al., 1989). These mixtures of phage were then purified from single plaques, and individual phage tested for bacterial host range against *X. citri* strain B21.2, *X. campestris* strain 528, and *Ralstonia solanacearum* strain G2. All phage were specifically able to attack only *X. pelargonii* strain CHSC and did not infect the other strains.

Example 2

Characterization of Phage Host Range and Efficacy Using Agar Plate Overlay Assays: Identification of Broad-Spectrum Holin and/or Holin-Like Proteins PYGM plates were overlaid with *X. pelargonii* CHSC and droplets of various purified phage samples obtained from Example 1 were added to the plates and incubated at 30° C. for 48 hours. All phage were able to infect CHSC and cause clear zones of lysis. Cell suspensions of overnight broth cultures of *X. citri* B21.2, *X. campestris* 528 and *R. solanacearum* G2 were added to 0.7% water agar as described in Example 1 and individually overlayed on the phage infected CHSC plates.

Plates were incubated an additional 48 hrs at 30° C. and phage were evaluated for ability to kill gram negative bacteria that they could not infect, and also gram positive bacteria, and fungi. Some phage exhibited presence of a strong, diffusible killing factor for all bacteria, and fungi tested. Phage isolate 15 (P15) was selected as the most efficient at killing all microbes tested.

Example 3

Phage P15 Genomic Sequencing

The P15 genome was completely sequenced in order to identify the gene(s) expressing the diffusible killing factor. P15DNA was made according to standard protocols using *X. pelargonii* CHSC as the host bacterium. The P15DNA was digested with EcoRV, yielding eleven fragments, ranging in size from 12.4 kb to 357 bp. The DNA fragments are listed according to size in Table 1 below and were mapped (see FIG. 2). Most of the fragments were cloned; some were not cloned, despite repeated attempts, and the probable reason is given in Table 1. The cloned DNA fragments were used directly for sequencing, using vector-based primers initially, and primer walking thereafter until each fragment was completed. Fragments that were not cloned were sequenced using P15 genomic DNA. Fragment assembly was accomplished using P15 genomic DNA and primers extending outside each fragment in both directions. P15 has a double stranded DNA genome which is 55,770 bp in length (SEQ ID No. 1).

TABLE 1

EcoRV fragments of Bacteriophage P15.

| Fragment | Size | Cloned? | Reason if not cloned |
|---|---|---|---|
| 1 | 12,441 bp | ✓ | |
| 2 | 9,303 bp | No | O-carbamoyl transferase (SEQ ID No. 40) |
| 3 | 7,945 bp | No | Holins & endolysin (SEQ ID Nos. 26-30) |
| 4 | 7,255 bp | No | Endoglucanases (SEQ ID Nos. 71, 83) |
| 5 | 4,516 bp | ✓ | |
| 6 | 4,196 bp | ✓ | |
| 7 | 3,313 bp | ✓ | |
| 8 | 3,304 bp | ✓ | |
| 9 | 1,869 bp | ✓ | |
| 10 | 1,271 bp | ✓ | |
| 11 | 357 bp | ✓ | |

Example 4

Phage P15 Genome Annotation and Identification of Holin Genes and Holin-Like Genes ORF analysis of the sequenced phage was done using a combination of several programs including PromScan, Terminator (GCG), GeSTer (Unniraman et al. 2001, 2002), Glimmer, Genie, Codon preference (GCG), ORF finder (NCBI) and Blast (NCBI) analyses. Potential Shine-Delgarno sequences were identified manually by examining the sequence. Using default Glimmer settings, only 32 ORFs were identified; none of these ORFs corresponded to functional genes later identified as holins or holin-like proteins by functional analyses (see below; SEQ ID Nos. 27-30). As with the holins of several other phage, these were clustered just downstream of a putative endolysin (SEQ ID No. 26). After identifying the promoters and terminators in the genome, careful analysis of all ORFs using Codon preference (GCG) allowed the identification of an additional 52 ORFs, including the holins and holin-like proteins. The genome encodes 84 putative ORFS (SEQ ID Nos. 2-85 and 110).

A single putative endolysin gene (SEQ ID No. 26) was identified based on sequence comparison of known endolysin proteins, specifically to L-alanyl-D-glutamate peptidases. The endolysin protein lacked a transmembrane domain typical of the holins. The four putative holin or holin-like genes were identified by analysing the trans-membrane domains associated with the proteins using a transmembrane prediction program. The first gene of the holin cluster (holin Z; SEQ ID No. 27) contained a Shine Delgarno sequence and initiated translation within the endolysin gene in an alternate reading frame. Three transmembrane domains typical of class I holins were identified in this holin. The second holin gene, holin ZA (SEQ ID No. 28), has a Shine Delgarno sequence and double methionine start codon as observed in several other holins; holin ZA.1 (SEQ ID No. 29) is the term given to the protein translated from the second methionine; both have three transmembrane domains typical of class I holins. The third holin gene, holin ZB (SEQ ID No. 30), has one transmembrane domain typical of class III holins.

Example 5

Cloning and Expression of Native Endolysin and Holin Genes

The predicted peptide coding regions of the endolysin, holin Z, holin ZA, holin ZA.1 and holin ZB (SEQ ID Nos. 26-30) were amplified by polymerase chain reaction (PCR) from the phage DNA and cloned in pGemT without promoters. These coding regions were operably fused with repressible promoters; the endolysin gene was recloned in a modified pET 27b expression vector (Novagen) without a pelB leader, while the holins were recloned in bacterial expression vector pKD46 (Datsenko & Wanner, 2000).

To determine if the endolysin gene from phage 15 had muranolytic activity, the cloned gene in the modified pET vector was expressed in *E. coli* by inducing with IPTG (Isopropyl β-D-thiogalactoside) and the culture was treated with chloroform (2% final concentration) as described by Garcia et al. (2002). Since the pelB leader was not present in the clone, the expressed endolysin protein was not exported to the periplasm. The chloroform treatment helps in permeabilizing the membrane (similar to holin action in a natural phage infection) so that the endolysin can cross the membrane barrier and attack the murein layer. Lysis of the bacteria was observed only after treatment with chloroform. All attempts to clone the endolysin gene into pET27b with a pelB leader sequence failed.

Figure 1A:
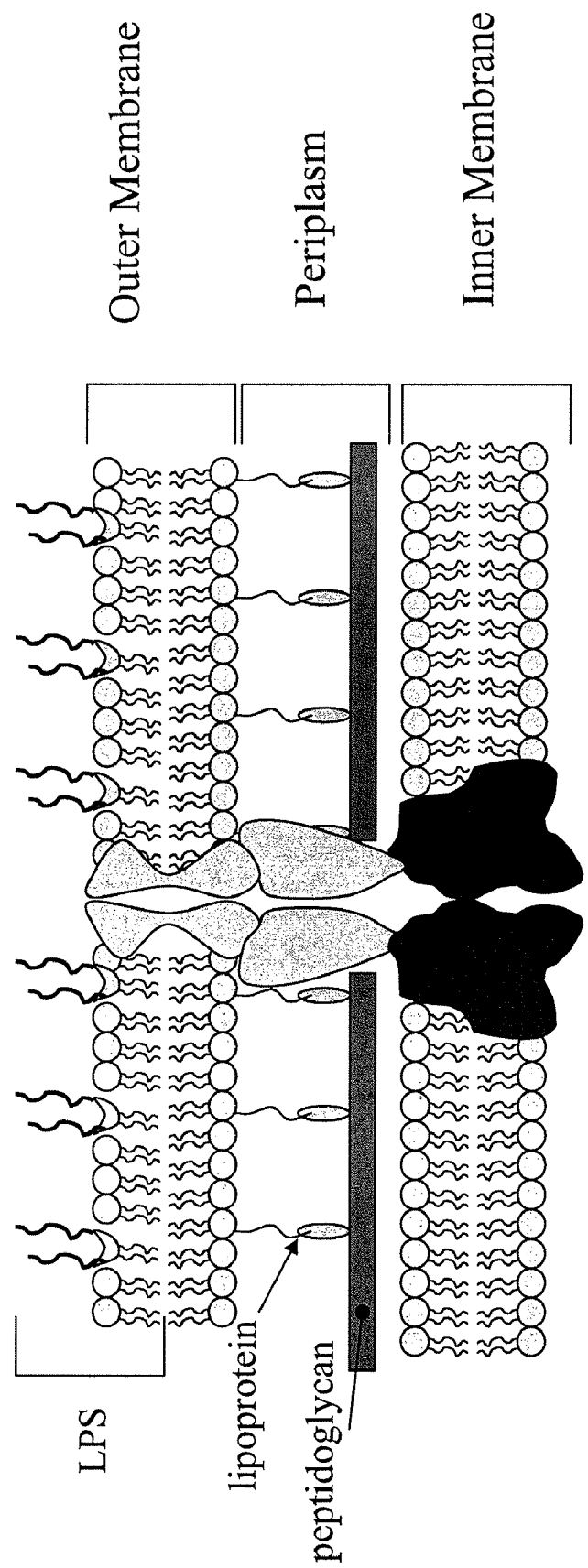
FIGS. 1A-1C is comprised of three cartoons illustrating: A) gram positive bacterial cell wall; B) gram negative bacterial cell wall; C) fungal cell wall.
Figure 1B:
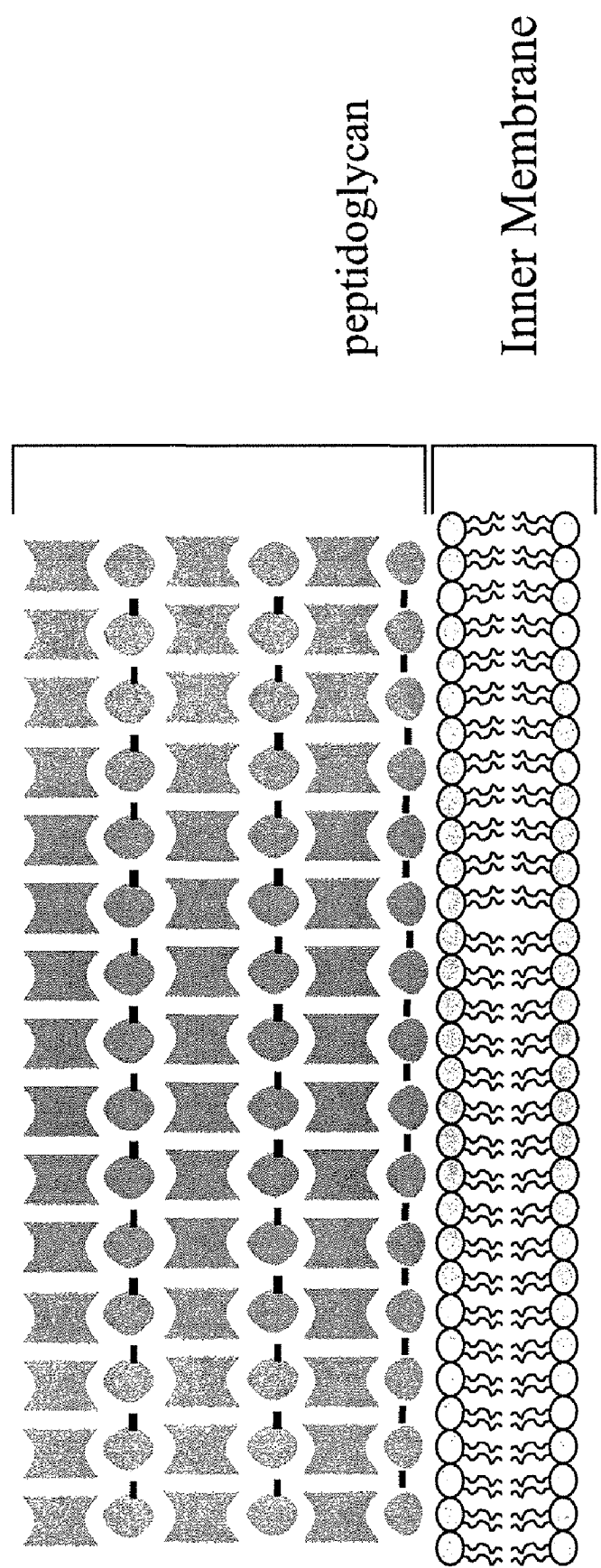
Figure 1C:
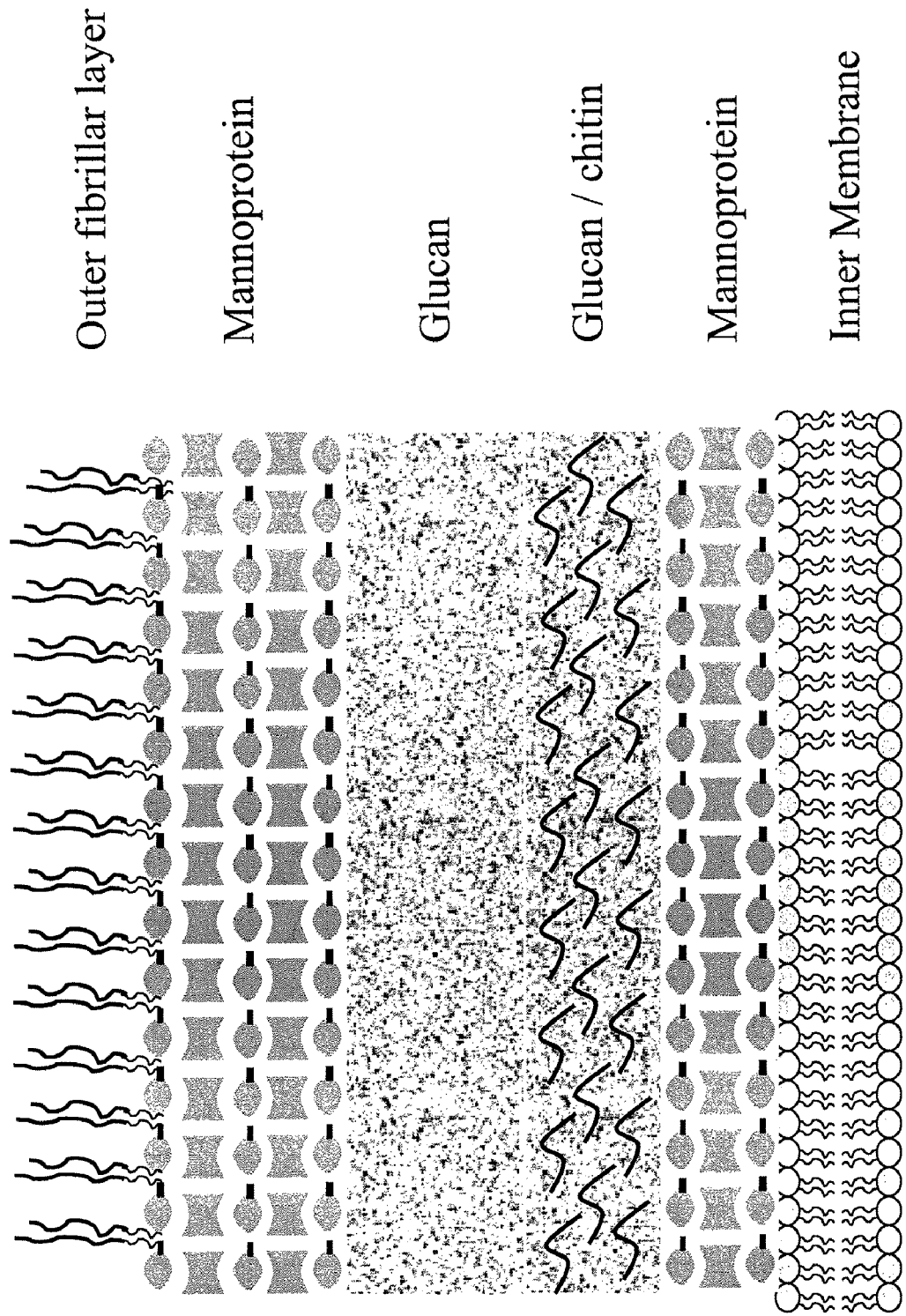
Figure 2:
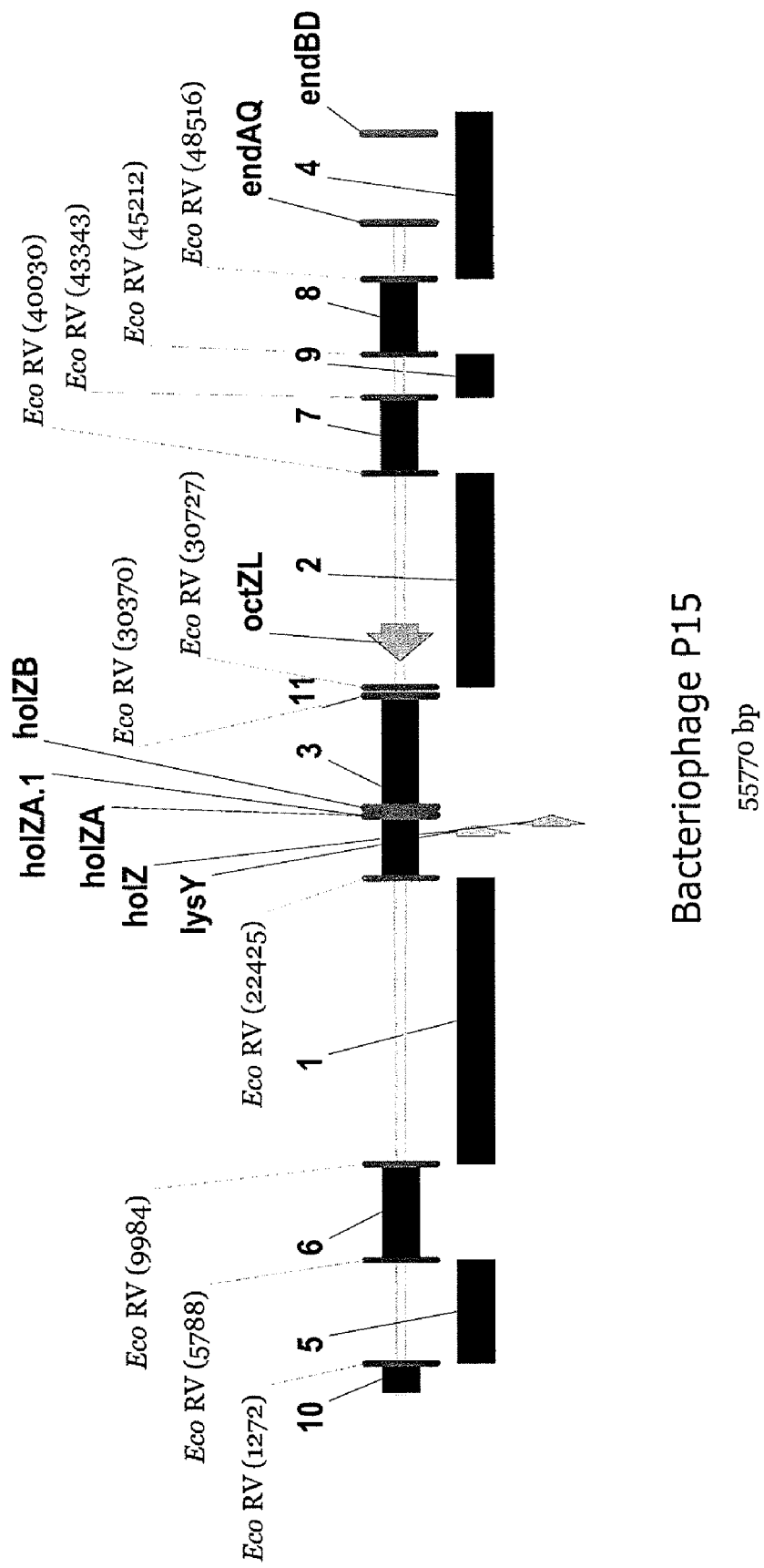
FIG. 2 shows a map of *Xanthoinonas* Bacteriophage P15, including the restriction enzyme EcoRV, predicted ORFs that are likely functional genes (LFGs), and transcriptional start and stop sites.
Figure 3:
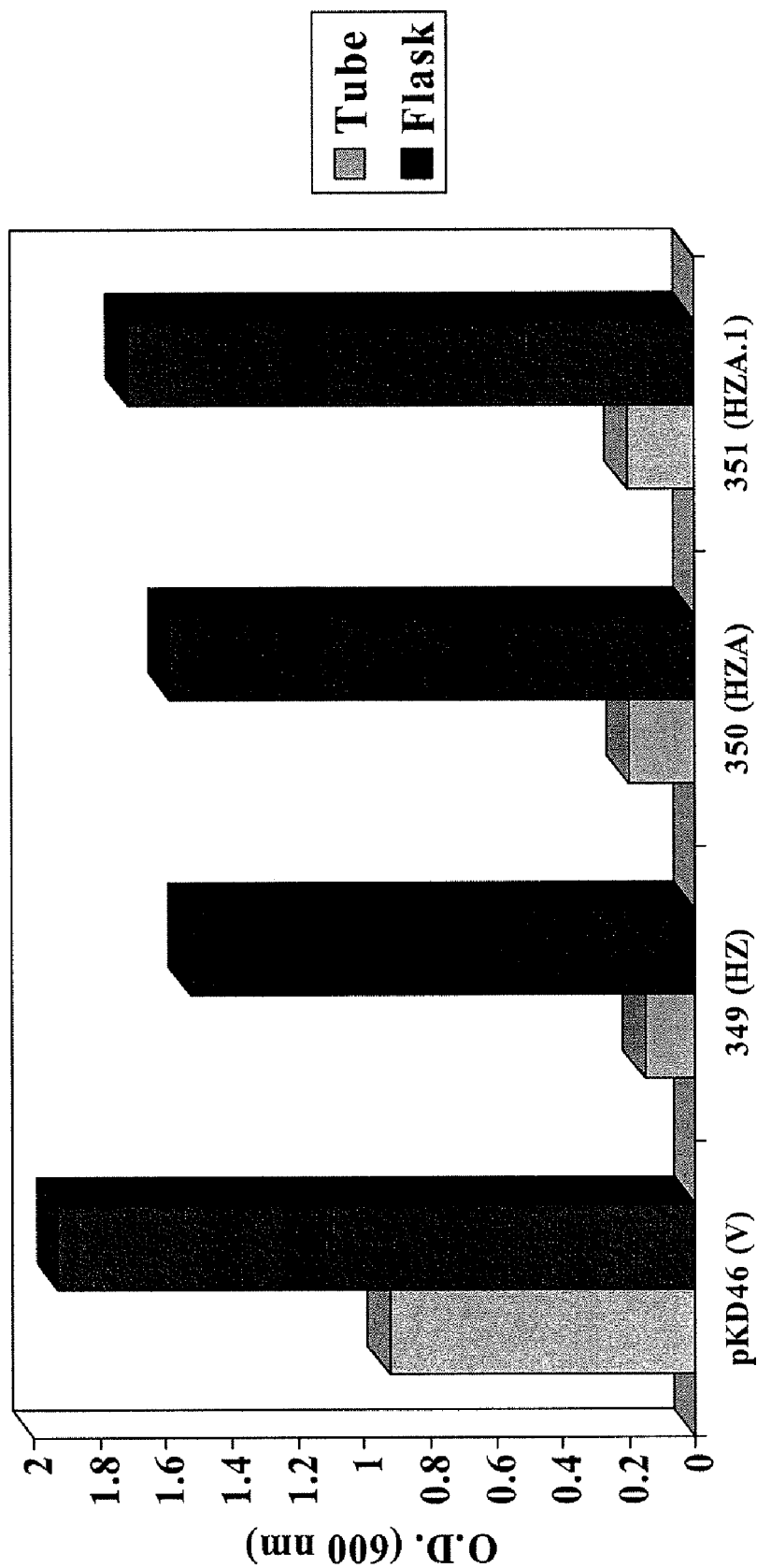
FIG. 3 shows growth of *E. coli* DH5α cells carrying the pKD46 expression vector with and without the various indicated Bacteriophage P15 holins. Cells were grown on LB plates with carbenicillin (50 µg/ml) at 30° C. overnight. Approximately equal amounts of inoculum were added to 15 ml of liquid LB with carbenicillin, vortexed to ensure homogeneity and duplicate 6 ml cultures were grown either in 250 ml conical flasks or in 15 ml glass culture tubes. All the cultures were grown with shaking (130 rpm) at 30° C. overnight. The cultures were vortexed and optical density (O.D.) of the cultures measured at 600 nm. pKD46 (V), empty vector; 349 (HZ), pKD46 expressing holZ (SEQ ID No. 27); 350 (HZA), pKD46 expressing holZA (SEQ ID No. 28); 351 (HZA.1), pKD46 expressing holZA.1 (SEQ ID No. 29).

All attempts to clone the holin genes into pET27b, with or without the pelB leader, also failed. Even when cloned into the more tightly regulated vector pKD46, there was evidently low level expression in both the uninduced and glucose repressed cells. All liquid cultures of holin genes cloned in pKD46 and grown in repressed conditions partially lysed the host *E. coli* cells, particularly when grown with poor aeration (FIG. 3). This evident low level expression also caused slower growth of all colonies carrying holin genes cloned in pKD46 on agar plates as compared to cells carrying the vector alone. On uninduced PYGM plates, *E. coli* carrying holin Z grew very slowly, *E. coli* with holin ZA grew slowly but exhibited profuse sectoring of the colonies, and *E. coli* carrying holin ZA.1 (one methionine) also grew slowly but showed less sectoring than holin ZA.

Example 6

Lytic Activity Resides Primarily in the Holin Genes

The three holin genes holZ, holZA, and holZA.1 (SEQ ID No. 27-29) in pKD46 were tested for their ability to lyse the following microbes: gram negative, *Agrobacterium tumefaciens, X. campestris* pv. *campestris, X. campestris* pv. *pelargoii, X. campestris* pv. *vesicatoria, X. phaseoli, X. citri, Ralstoizia solanacearium, Erwinia chrysanthemi, Xylella fastidiosa, E. coli*; gram positive, *Corynebacteriui michiganensis* (syn.=*Clavibacter michiganensis*), *Lactococcus lactis*; fungi, *Saccharomyces cerevisiae, Phytophthora nicotianae* and *Pythium aphanidermatum* from the outside.

PYGM plates were overlaid with mid-log phase liquid cultures of each of these bacteria to form a uniform lawn. Ten microliter drops of overnight *E. coli* cultures of each of the holin clones were then dropped onto the bacterial lawns and incubated at 30° C. A culture of *E. coli* carrying vector pKD46 alone was used as a negative control. After 48 hours, lytic zones were observed on top of clones of holZ, holZA and holZA.1 but not on top of vector control pKD46 for all of the microbes tested. All three holins had a clearly inhibitory or lethal effect exerted from the outside of the microbial cells.

Example 7

Enhancement and Extension of the Lytic Effect of the Holin Clones in Plate Overlay Assays to Include Gram Positive Bacteria, Fungi and Red Blood Cells A variety of gene fusions were then constructed to determine if fusions at the N or C termini affected the lytic ability of holins. First, the DNA coding region for two amino acids (LE) was added to the C terminal end of the holins identified in Example 6, making the ends slightly more hydrophobic. Second, the DNA coding regions for eight amino acids (ASLEPGIS, SEQ ID No. 109) was added to the C terminal end of the holins identified in Example 6, making the ends moderately hydrophobic. These additions diminished the activity of each holin slightly. Third, the DNA coding region for a 28 amino acid, strongly hydrophilic C terminal tail (SEQ ID Nos. 88, 89), including a HIS tag (6H residues; Novagen) and including an HSV tag (QPELAPEDPED, residues 10-20 of SEQ ID No. 87; Novagen) was added onto the C terminal end of the holZ and holZA.1 holin genes identified in Example 6. This addition strongly enhanced the activity of each holin, making hydrophilic additions to the C terminus of holins a preferred embodiment of this invention. This idea was reinforced by a fourth substitution, wherein the hydrophilic lysY endolysin from the P15 phage (SEQ ID No. 26) was used to replace the 28 amino acid C terminal tail (SEQ ID No. 88, 89) of each holin. The enhanced activity remained. Fifth, a 24 amino acid xylem secretion signal peptide derived from the P12 xylem protein found in citrus (Ceccardi et al., 1998; SEQ ID No. 87) was added onto the N terminal end of the holin gene fusions carrying the HIS and HSV tags (SEQ ID Nos. 90-91, 96-97). The DNA sequence encoding the P12 peptide (SEQ ID No. 86) was cloned by PCR from *Citrus sinensis*.

Finally, an entirely synthetic version of holZ was constructed, holSZ, in which the length of each of the three transmembrane domains was shortened from 23 to 18-19 amino acids (SEQ ID 92-93). This synthetic gene was fused with P12 at the N terminus and a hydrophilic domain at the C terminus (SEQ ID 94-95). These holin gene fusions were constructed in a stepwise manner in pKD46 and used in plate overlay assays. The DNA and predicted amino acid sequences of the encoded proteins carrying endolysin fusions are provided in SEQ ID 98-103.

Figure 4:
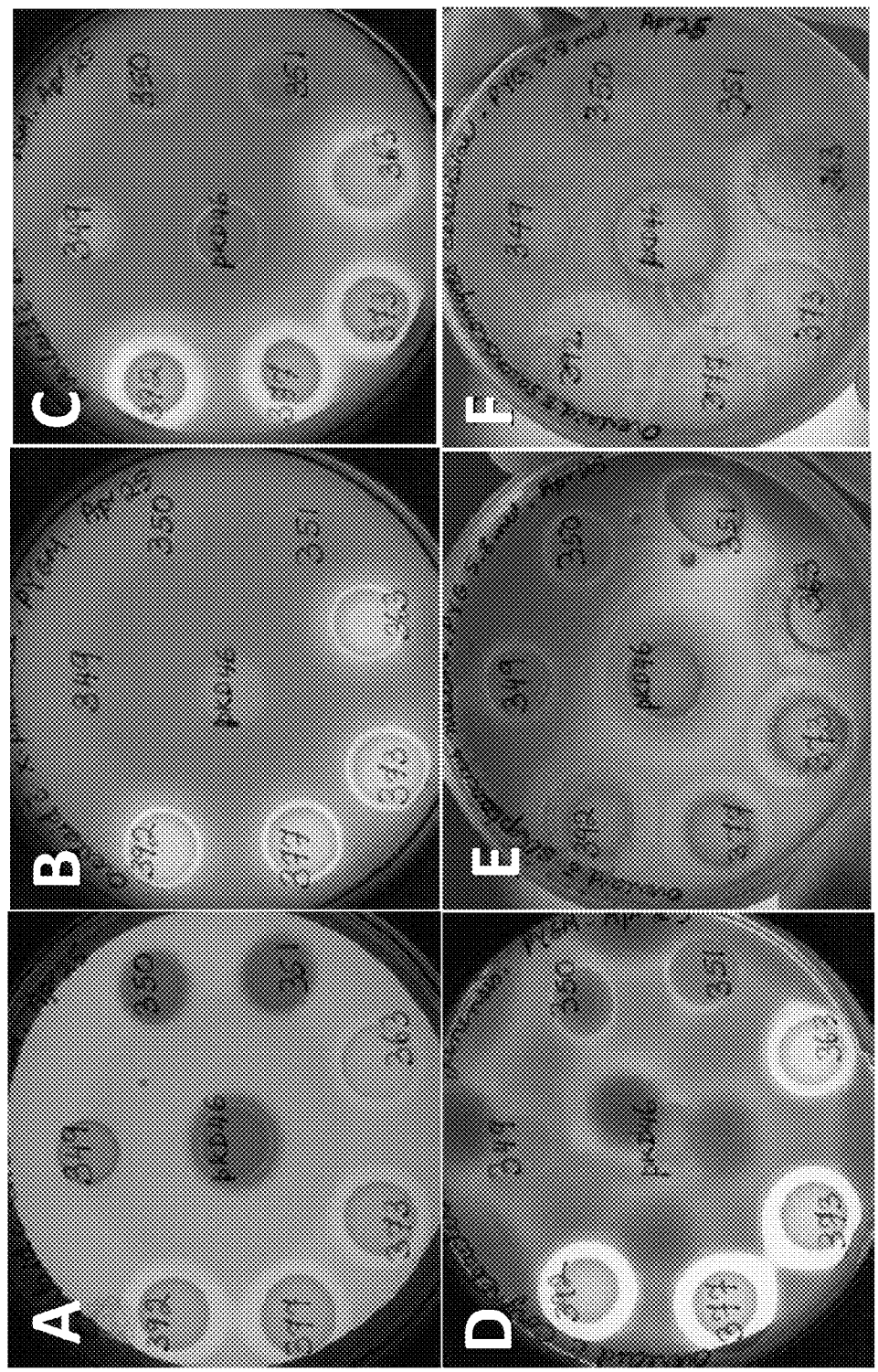

As can be readily seen in FIG. 4, addition of a hydrophobic C terminus dramatically increases holin activity. The hydrophilic C terminus could be an enzyme such as an endolysin or a synthetic sequence, such as an antibody tag. The enhancement effect exhibited with the endolysin was not due to the enzymatic action of the endolysin, since enzymatic activity is not present in the 28 amino acid C terminal tail. Also shown in FIG. 4 is the finding that the P12 leader sequence fused to the N terminus of the holins had no effect on holin activity in plate assays. Plate overlay assays were performed using these gene constructs, and clear zones of lysis were observed with the following microbes: gram negative, *Agrobacterium tumefaciens*, *X. campestris* pv. *campestris* 528, *X. campestris* pv. *pelargonii* CHSC, *X. campestris* pv. *vesicatoria*, *X. phaseoli*, *X. citri* B21.2, *X. oryzae* pv. *oryzae*, *Ralstonia solanacearum*, *Erwinia chrysanthemi*, *Xylella fastidiosa*, *E. coli* DH5α; gram positive, *Corynebacterium michiganensis* (syn.=*Clavibacter michiganensis*), *Lactococcus lactis*, *Streptococcus mutans* NG8; fungi, *Saccharomyces cerevisiae* MAVI 04K, *Phytophthora nicotianae* and *Pythium aphanidermatum*. Similar plate overlay assays may be performed using commercial blood agar for the overlay assays, resulting in a screen for holins and holin-like proteins with ability to lyse red blood cells. Ability to lyse red blood cells is one factor among other bacterial pathogenicity factors hypothesized to enhance pathogenicity of certain bacteria towards insects and nematodes (Brillard, 2003).

Example 8

Transient Expression Assays in a Variety of Plants Against Various *Xanthomonas* pathogens In order to determine if the peptides would be efficiently processed and available in the plant apoplast for controlling bacterial plant pathogens, the gene constructs that were tested as efficacious in killing pathogens in agar plate overlay assays in Examples 6 and 7 were recloned into plant transformation/expression vectors such that they were operably expressed in plants. The resulting gene constructs could not be expressed in bacteria that were used for cloning (eg., *E. coli*) or delivery into plants (eg., *Agrobacterium*). Plant transformation and expression vector pIPG421 carries a neomycin phosphotransferase gene for plant selection, and was used for transient expression purposes in citrus and tomato. pIPG421 was created from the pCAMBIA-2200 binary plant transformation vector (GenBank Accession #AF234313) by removing the lacZ promoter region (that could drive expression of cloned holin genes in bacteria) using BstXI (cuts at nucleotide 8267) and EcoRI (cuts at nucleotide 8511) digestion. Two short complimentary primers, IPG 436 and IPG 437 (SEQ ID Nos. 104, 105) were then synthesized, annealed and cloned into the BstXI-EcoRI sites to create pIPG421. This plant transformation and expression vector has no bacterial promoter that could drive expression of a genes of interest (but allowed expression of such genes from a plant promoter) and added an AatII site.

Similarly, plant transformation and expression vector pIPG420 was derived from pCAMBIA-1302 (GenBank Accession #AF234298) by deleting both the lacZ bacterial promoter region and the jellyfish green fluorescent protein (GFP) reporter region. pCAMBIA 1302 was digested with NheI and EcoRI. The 5568 bp fragment that resulted was recovered and ligated to the 3391 bp AriaI/EcoRI fragment recovered from pCAMBIA 2200. The lacZ promoter was removed exactly as described above for pIPG421. pIPG420 has a hygromycin phosphotransferase gene for plant selection, and was used for both transient expression and transformation purposes in rice and geranium.

For transient expression assays, the plant transformation and expression vectors were moved into *A. tumefaciens* strain GV2260 by either electroporation or bacterial conjugation as described (Kapila et al., 1997). GV2260 carrying various holin DNA constructs operably linked to a cauliflower mosaic virus (CaMV) promoter on the plant transformation and expression vectors was used for transient expression in citrus, common bean, tomato, pepper, geranium and rice plants as described (Kapila et al. 1997; Duan et al., 1999). Cultures of *Agrobacterium* harboring the constructs of interest were grown in minimal medium in the presence of acetosyringone to induce the *Agrobacterium* vir genes. The optical density of the cultures was maintained at 0.008 for bean, pepper and tomato and at 0.25 for citrus, geranium and rice.

Strain GV2260 was first flooded into the apoplastic space through open stomata by injection using a tuberculin syringe without a needle, flooding an area of 1-2 $cm^2$; the area inoculated was then circled with a permanent marker. This was followed 24 hrs later by challenge inoculation with ca. $2\times10^6$ colony forming units (cfu) from an overnight *Xanthomonas* bacterial culture within the zone previously inoculated with GV2260 carrying the holin clones expressed from the transformation and expression vector. This gave an inoculum density of *Xanthomonas* pathogen of about $2\times10^4$ $cfu/cm^2$. All *Xanthomonas* strains used were published reference strains of confirmed pathogens and all strains used are known to be very host specific: *X. citri* attacks only citrus and causes citrus canker disease, *X. phaseoli* attacks only bean and causes common bean blight, *X. campestris* pv. *vesicatoria* attacks only pepper and tomato and causes pepper and tomato speck disease, *X. campestris* pv. *pelargonii* attacks only geranium and causes geranium blight disease, *X. oryzae* attacks only rice and causes rice blight disease. The plants that P are attacked are considered to be "hosts" of the indicated pathogens. All other plants are considered to be "nonhosts" of the indicated pathogens. When these same pathogens are inoculated at the indicated densities onto nonhost plants, a rapid hypersensitive response (HR), is observed. The HR appears as a confluent, necrotic, collapsed zone at the inoculation site within 24-48 hrs. Pepper plants appeared to be the best plants for HR indication, while citrus appeared to be the best plants for a pathogenic response.

Figure 5:
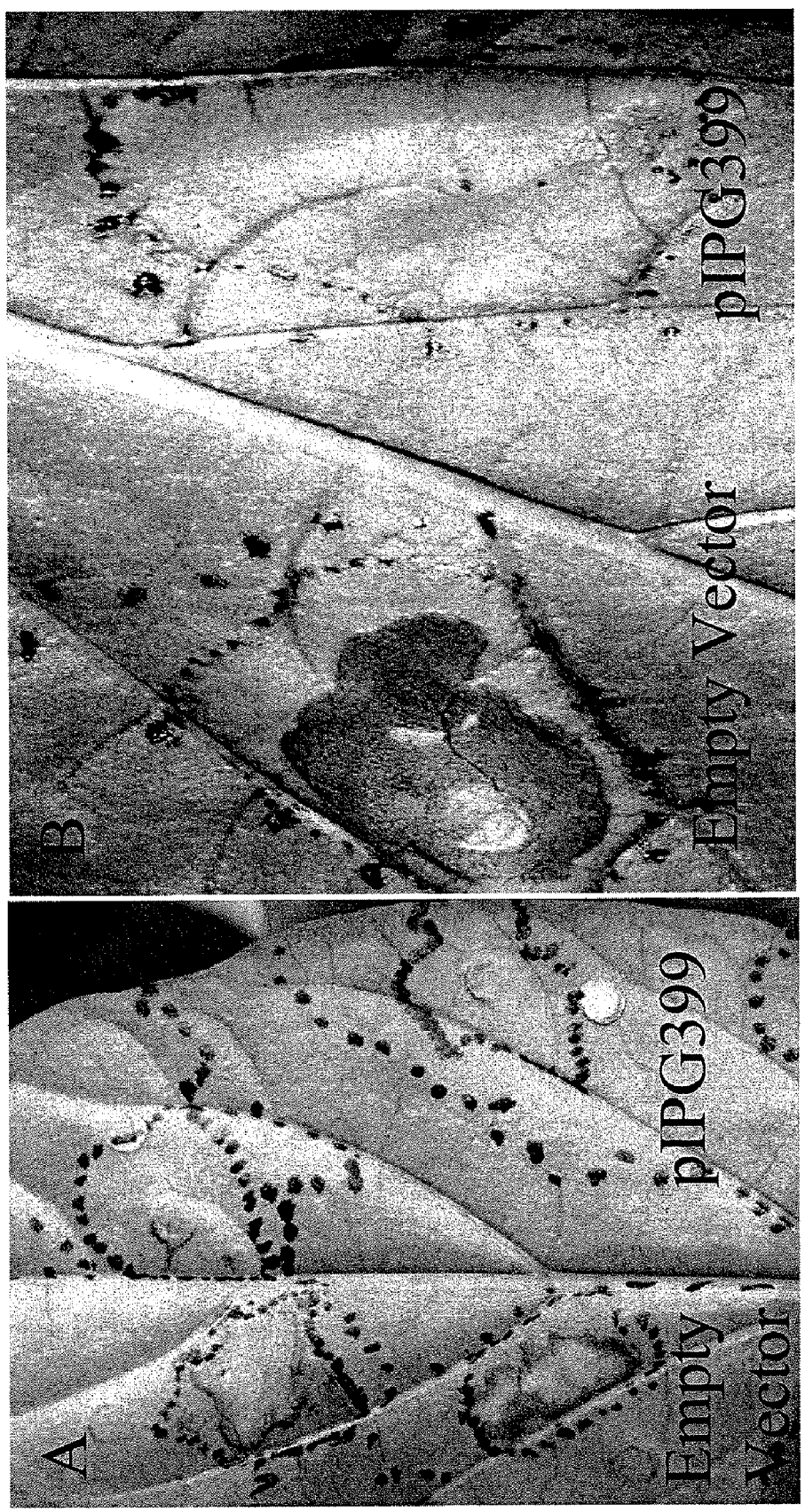

Results were assessed visually according to disease symptoms observed after 48 hrs for *Xanthomonas* inoculations on non-host pepper plants, within 4 days for *Xanthomonas* inoculations on host bean and pepper and within 2 weeks for *Xanthomonas* inoculations on hosts citrus, geranium and rice. In all cases except those involving blight pathogens on hosts (geranium blight, rice blight and bean blight), a "split leaf" assay was used in which an empty vector control was inoculated on the same leaf as the experimental clone to be tested. The empty vector control consisted of the plant transformation and expression vector without any gene to be expressed, placed in GV2260 and inoculated as described on one side of the leaf. The experimental clone was operationally expressed from the same vector in GV2260 and inoculated as described on the other side of the leaf. In FIG. 5 is shown sweet pepper (Capsicum) leaves inoculated with *X. phaseoli*; symptoms were abolished in the presence of a transiently expressed clone carrying a gene fusion that included P12, holZ and lysY. In FIG. 6 is shown citrus leaves inoculated with *X. citri*; symptoms were greatly reduced in the presence of a transiently expressed clone carrying a gene fusion that included P12 and a synthetic holin. Holin fusions carrying a P12 leader, whether synthetic or natural, and whether attached to an endolysin or not, killed *Xanthomonas* cells and greatly suppressed or abolished disease symptoms.

Example 9

Figure 7:
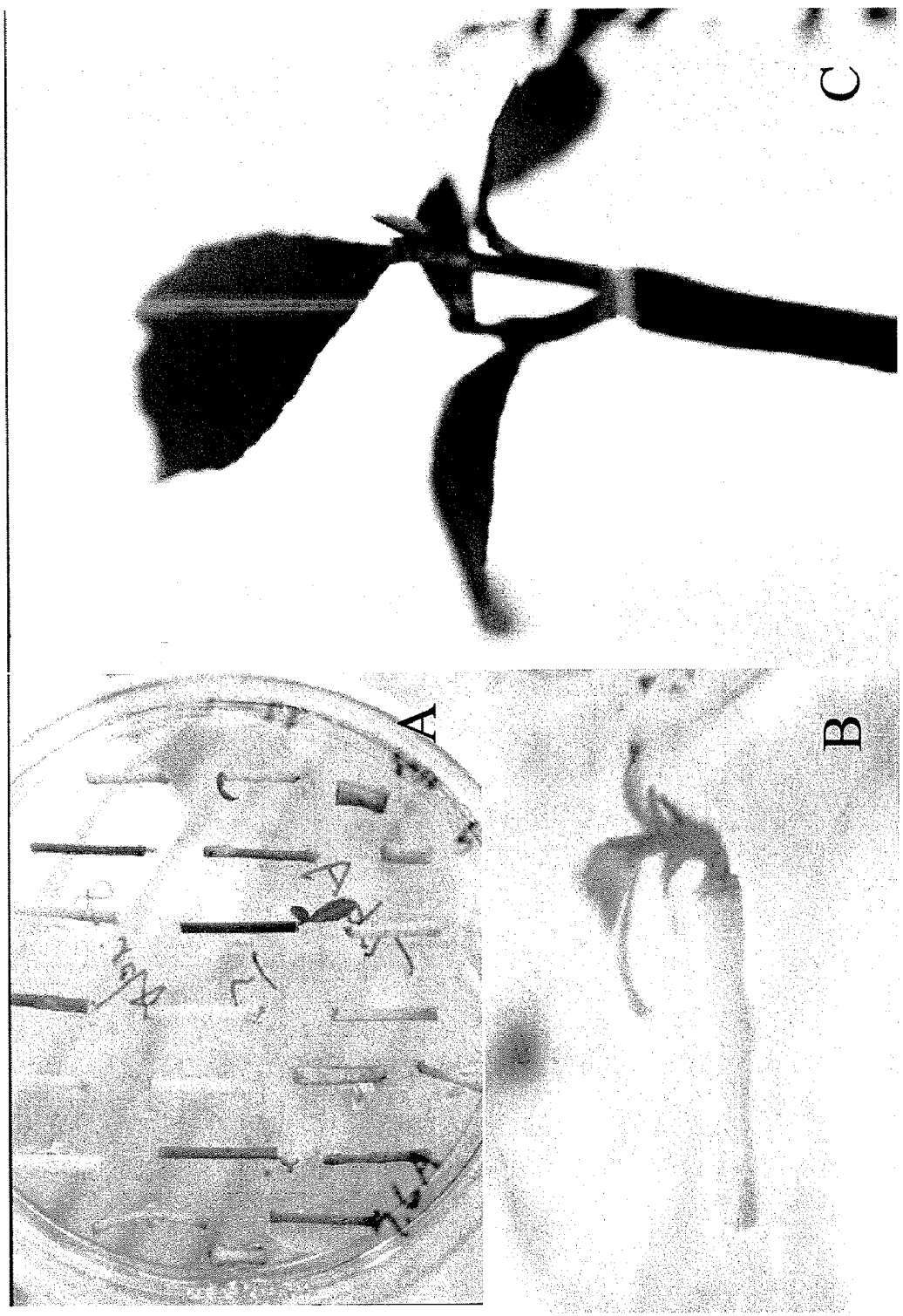
Figure 9:
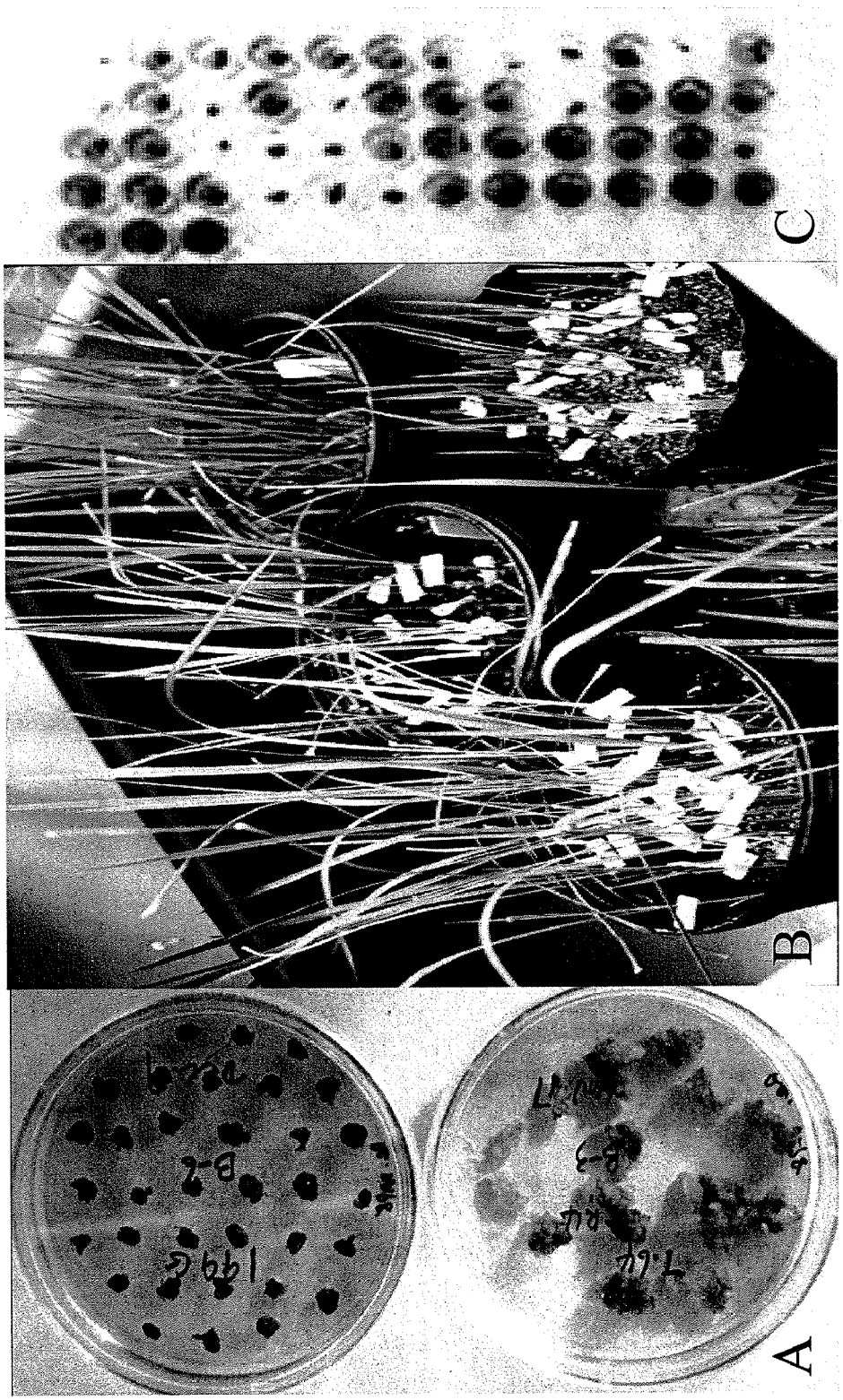

Transgenic (Permanently Transformed) Plant Expression Assays in a Variety of Plants Against Various Microbes and Microbial Pathogens Transgenic dicot plants (tomato, citrus and geranium; FIGS. 7, 8) and monocot plants (rice; FIG. 9) were created using *Agrobacterium tumefaciens* that carried the same plant transformation and expression clones as disclosed in Example 8. Transformations were by published protocols (Riggs et al., 2001 (tomato), Moore et al., 1992 (citrus); Robichon et al., 1995 (geranium) and Hiei et al., 1997 (rice)). Two vector versions were used: pIPG420 (hygromycin resistance for selection in rice and geranium) and pIPG421 (neomycin resistance for selection in tomato and citrus). In order to enhance expression of the holin constructs in the xylem region, a citrus PAL promoter was used (Harakava, 2000). This PAL promoter (SEQ ID 106) was cloned from citrus (sweet orange) by PCR and used to drive all holin constructs in both plasmid transformation vectors.

After demonstrating that the plants were transgenic by PCR and/or Southern blots, GUS assays (FIG. 9) and/or Western blots were performed to ensure gene expression. For the GUS assays in FIG. 9, the beta-glucuronidase gene from pBI221 (purchased from Clontech in 1996) was fused to the 3' end of the coding region for P12::holZ::lysY (SEQ ID No. 99), replacing the HSV::HIS tags. Leaf pieces and root sections from plants that expressed holin gene fusions were removed from sterile culture or from greenhouse grown plants and placed on petri dishes containing lawns of *Xanthomonas* and *Ralstonia*. Lysis zones appeared to surround transgenic leaf pieces or root sections, while control leaf pieces caused no lysis.

Figure 12:
Figure 12:

Pathogen challenge inoculations of tomato were made with *Xanthomonas campestris* pv. *vesicatoria* and *Ralstonia solanacearum*, pathogen challenge inoculations on geranium (*P. hortorum*) were made with *Xanthomonas campestris* pv. *pelargonii* and *Ralstonia solanacearum*, using overnight cultures of ca. $2 \times 10^6$ colony forming units (cfu) of each pathogen. Holin clones, whether synthetic or natural, and carrying a P12 leader, whether attached to an endolysin or not, rapidly killed cells of all pathogens inoculated on their hosts and controlled disease symptoms (compare FIGS. 11, 12). In FIG. 11 is shown killing of *Ralstonia solanacearum* by transgenic geranium carrying pIPG492 (P12 leader::holZ::lysY). In FIG. 12 is shown killing of *X. campestris* pv. *vesicatoria* by transgenic tomato plant 904B carrying pIPG409 (P12 leader, holSZ).

Example 10

Use of Codon Optimized Holin Constructs and an Intron to Increase Holing Gene Expression in Plants Enhanced expression of several constructs carrying holins was obtained by codon optimization of the genes for plant expression and by the use of an intron. Codon optimization was achieved by creating synthetic genes using a very rapid (1 day) PCR method (Di Donato et al., 1993). The resulting gene constructs could not be expressed in bacteria that were used for cloning (eg., *E. coli*) or delivery into plants (eg., *Agrobacterium*) until prokaryotic promoter elements inadvertently included in the optimization were eliminated.

Expression of codon-optimized holins and gene fusions that incorporate holins was further enhanced by use of an intron. One or more introns are known to be required for abundant expression of many genes in plants, including dicots and ornamental plants, possibly by enhancing transcript stability or facilitating mRNA maturation (Callis et al., 1987; Mun, J. H. et al. 2002; Rose & Beliakoff, 2000; Rose, 2002, Simpson & Filipowicz, 1996). In this example, the second intron found in a citrus sucrose synthase gene (Genbank accession no. AB025778) was identified. Prokaryotic promoter sequences in the intron sequence were also identified. PCR primers were designed to both amplify the intron and eliminate the prokaryotic promoters. The intron was inserted at the 5' end of the holin genes between a lysine at the sixth position in the holZ ORF and a valine (splice site: AAG/GUUCUG), thus mimicking precisely the known slice site for the intron in the sucrose synthase gene.

Plant transformation and expression vector pIPG534 (SEQ ID 108) is provided as one example of the plant transformation vectors used. This vector carries a hygromycin resistance gene for plant selection (geranium and rice) and a kanamycin resistance gene for bacterial cloning and selection. In another version, pIPG537, the hygromycin resistance gene is replaced by a neomycin phosphotransferase gene (nptII) for plant selection (tomato and citrus), and a chloramphenicol acetyl transferase (cat) gene for bacterial cloning and selection. Both constructs carry a codon optimized P12 leader interrupted by an intron, fused to holSZ, fused to lysY, fused to HSV/HIS tags, and operably driven by a citrus PAL promoter. Both constructs provide resistance in plants and kill both bacteria and fungi in inoculations and/or plate overlay assays.

Example 11

Asexual Reproduction of Transgenic Plants Expressing Holin Proteins

Transgenic geranium and citrus plants were obtained as set forth in Example 9, wherein the transgenic plants expressed the introduced nucleic acid molecule coding for a holin protein. The transgenic geranium and citrus plants were asexually propagated to produce progeny clones using techniques well known to one skilled in the art of geranium or citrus propagation. For geranium and other vegetative species that are normally propagated by taking cuttings, an internode with two nodes are cut from a mother plant and rooted, normally using a support medium, with or without root inducing hormones, producing a single new plant for each such clone or "cutting". The cuttings were in all cases genetically identical to the mother plant; the genetic modifications performed in the mother plant were stable through at least two generations. For citrus and similarly propagated woody species and vines, such as grape, a "scion" cutting is taken from a transgenic stem section with leaves and grafted or spliced onto a nontransgenic rootstock, such that the roots and lower main stem are comprised of the nontransgenic rootstock, while the upper main stem and shoots are comprised of the transgenic scion. The scion cuttings were in all cases genetically identical to the mother plant; the genetic modifications performed in the mother plant were stable.

Pathogen challenge inoculations of the geranium clones was conducted as set forth in Example 9. The transgenic progeny clones obtained from the transgenic parental plants rapidly killed cells of the tested pathogens and controlled disease symptoms. Untransformed check plants became infected and displayed disease symptoms typical for the applied pathogen. These tests show that that the introduced nucleic acid molecules coding for the holin proteins have been stably integrated into geranium using the methods of the present invention.

Example 12

Sexual Reproduction of Transgenic Plants Expressing Holin Proteins

Transgenic diploid tomato and rice plants were obtained as set forth in Example 9, wherein the transgenic plants expressed the introduced nucleic acid molecule coding for a holin protein. The transgenic tomato plants were self-pollinated and the seed will be harvested from the self-pollinated plants, processed, planted, and progeny plants grown from the self-pollinated-seed. Similarly, the transgenic rice plants will be self-pollinated and the seed will be harvested from the self-pollinated plants, processed, planted, and progeny plants grown from the self-pollinated-seed Pathogen challenge inoculations of the progeny plants will be conducted as set forth in Example 9. The progeny plants will have a classical genetic 1:2:1 ratio, wherein ¾ths of the plants (¼ homozygous transgenic and ½ heterozygous transgenic) will rapidly kill the cells of the tested pathogens and control disease symptoms, and ¼th of the plants will become infected and displayed disease symptoms typical for the applied pathogen on untransformed check plants. These tests will show that that the introduced nucleic acid molecules coding for the holin proteins have been stably integrated into tomato and rice using the methods of the present invention and that such nucleic acid molecules are heritable.

Example 13

Method of Using the Holin and Holin-Like Proteins Expressed in Transgenic Plants to Extend the Shelf-Life of Cut Flowers The holin and holin-like proteins, when produced in transgenic plants that are typically marketed as cut flowers, such as roses, carnations, chrysanthemums, gladiolas, etc., will enhance longevity of the cut transgenic flowers by suppression of bacterial growth in the vase water by opportunistic or soft-rotting bacteria such as *Erwinia carotovora* and *Erwinia chrysanthemi*. Transgenic plants that will later be marketed as cut flowers will be produced by methods described in the above examples.

Example 14

Method of Using the Holin and Holin-Like Proteins as an Additive to Extend the Shelf Life of Cut Flowers and Animal Feed The holin and holin-like proteins, when added to the vase or shipping container water of nontransgenic plants that are typically marketed as cut flowers, such as roses, carnations, chrysanthemums, gladiolas, etc., will enhance longevity of the cut transgenic flowers by suppression of fungal and bacterial growth in the vase water. Typical microbial species that shorten the shelf life of cut flowers are *Erwinia carotovora* and *Erwinia chrysanthemi*. For example, adding the dried protein to water used to sustain cut flowers will result in a longer shelf-life for the cut flowers when compared to cut flowers sustained in water from the same source without the addition of the dried protein The holins will be produced in microbes, such as *E. coli* as illustrated in Example 5, or preferably in yeast, such as *Pichia pastoris*, possibly using a secretion signal peptide and unique fermentation conditions (for example, refer Murasugi et al., 2001). Crude extracts of protein samples are harvested, and either dried using a granular additive or suspended in an appropriate liquid packaged.

In another example, when the dried protein is added to animal feed, it will control microbial and fungal contamination, including those microbes that may cause food poisoning. A dry or liquid preparation of holins or holing-like proteins could be added to animal feed during factory preparation or afterwards by the animal owner by mixing. Either way, the result will be a longer shelf life of the feed and reduced opportunity for growth of microbes that can result in food poisoning.

Example 15

Method of Using the Holin and Holin Like Proteins in a Foliar Spray or Soil Drench Application to Control Microbial Plant Diseases When the dried protein of Example 14 is formulated for spray application to the foliage of nontransgenic plants, it will control microbial, fungal and insect diseases of said plants. For example, when the dried protein is sprayed onto greenhouse grown plants or field crop plants, it will control microbial diseases that infect the foliage of these plants, by the combined action of the holins or holin-like proteins with natural plant defense compounds. When the dried protein of Example 14 is formulated for soil drench application to nontransgenic plants, it will control soil-borne microbial and fungal diseases of said plants. For example, when the dried protein is dissolved in water and used to treat the soil of greenhouse grown plants or field crops, it will control microbial diseases that infect the roots or crown areas of these plants by the combined action of the holins or holin-like proteins and natural plant defense compounds.

Method of Using the Holin and Holin Like Proteins in a Foliar Spray or Soil Drench Application to Control Insects and Nematodes When the dried protein of Example 14 is formulated for spray application to the foliage of nontransgenic plants as in Example 15, it will control insects that feed on the foliage of said plants. When the dried protein of Example 14 is formulated for soil drench application to nontransgenic plants as in Example 15, it will control nematode diseases of said plants. In both cases, control of the pests is achieved through the combined action of the holins or holin-like proteins and natural plant defense compounds.

Example 17

Method of Using the Holin and Holin Like Proteins in Transgenic (permanently Plants to Control Microbial, Insect and Nematode Diseases. When transgenic plants produced according to Examples 9-12 are planted in greenhouses or in field situations, they exhibit resistance to bacterial, fungal, insect and nematode diseases of said plants. Resistance in all cases is achieved through the combined action of natural defense compounds produced by the transgenic plants and the holin or holin-like proteins produced by the transgenic plants.

It must be noted that as used in this specification and the appended claims, the singular forms "a," "and," and "the" include plural referents unless the contexts clearly dictates otherwise. Thus, for example, reference to "a holin" includes any one, two, or more of the holins encoded by genes in at least 35 different families; reference to "a transgenic plant" includes large numbers of transgenic plants and mixtures thereof, and reference to "the method" includes one or more methods or steps of the type described herein.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications cited herein are incorporated herein by reference for the purpose of disclosing and describing specific aspects of the invention for which the publication is cited.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

LITERATURE CITED

Ali GS and Reddy ASN. 2000. Inhibition of fungal and bacterial plant pathogens by synthetic peptides: in vitro growth inhibition, interaction between peptides and inhibition of disease progression. Molecular Plant Microbe Interactions 13:847-859.

Arce P et al. 1999. Enhanced resistance to bacterial infection by *Erwinia* carotovora subsp. *Atroseptica* in transgenic potato plants by expressing the attacin or the cecropin SB-37 genes. American Journal of Potato Research 76:169-177.

Arima, H., H. R Ibrahim, T. Kinoshita, and A. Kato. 1997. Bactericidal action of lysozymes attached with various sizes of hydrophobic peptides to the C-terminal using genetic modification. FEBS Letters 415:114-118.

Brillard, J., M. H. Boyer-Giglio, N. Boemare, and A. Givaudan. 2003. Holin locus characterisation from lysogenic *Xenorhabdus nematophila* and its involvement in *Escherichia coli* SheA haemolytic phenotype. Fems Microbiology Letters 218:107-113.

Broekaert, W. F. et al. 1997. Antimicrobial peptides from plants. Critical Reviews in Plant Sciences 16:297-323

Cary J W et al. 2000. Transgenic expression of a gene encoding a synthetic antimicrobial peptide results in inhibition of fungal growth in vitro and in plants. Plant Science 154:171-181

Callis, J., M. Fromm, and V. Walbot. 1987. Introns increase gene-expression in cultured maize cells. Genes & Development 1:1183-1200.

Ceccardi, T. L., G. A. Barthe, and K. S. Derrick. 1998. A novel protein associated with citrus blight has sequence similarities to expansin. Plant Molecular Biology 38:775-783.

Datsenko, K. A. and B. L. Wanner. 2000. One-step inactivation of chromosomal genes in *Escherichia coli* K-12 using PCR products. Proc. Natl. Acad. Sci. USA 97:6640-6645.

DeFeyter, R., C. I. Kado, and D. W. Gabriel. 1990. Small stable shuttle vectors for use in *Xanthomonas*. Gene 88:65-72.

De Feyter, R., Y. Yang, and D. W. Gabriel. 1993. Gene-for-genes interactions between cotton R genes and *Xanthomonas campestris* pv. *malvacearum* avr genes. Molec. Plant-Microbe Interact. 6:225-237.

Derrick, K. S., R. F. Lee, R. H. Brlansky, L. W. TIMMER, B. G. HEWITT, and G. A. Barthe. 1990. Proteins associated with citrus blight. Plant Disease 74:168-170.

Di Donato, A., de Nigis, M., Russo, N., Di Biase, S., D'Alessio, G. 1993. A method for synthesizing genes and cDNAs by the Polymerase Chain Reaction. Anal. Biochem. 212:291-293.

Duan Y P et al. 1999. Expression of a single, host-specific gene in citrus cells elicits division, enlargement and cell death. Molecular Plant-Microbe Interactions 12:556-560

During K et al. 1993. Transgenic potato plants resistant to the phytopathogenic bacterium *Erwinia carotovora*. Plant J 3:587-598

During, K., P. Porsch, A. Mahn, O. Brinklmann, and W. Gieffers. 1999. The non-enzymatic microbicidal activity of lysozymes. FEBS Letters 449:93-100.

Flaherty, J. E., Harbaugh, B. K., Jones, J. B., Somodi, G. C. and Jackson, L. E., 2001. H-mutant bacteriophages as a potential biocontrol of bacterial blight of geranium. HortScience 36: 98-100.

Gao A-G et al. 2000. Fungal pathogen protection in potato by expression of a plant defensin peptide. Nature 18:1307-1310

Garcia M., Pimentel, M. and Moniz-Pereira, J., 2002. Expression of mycobacteriophage Ms6 lysis genes is driven by two $\sigma^{70}$-like promoters and is dependent on a transcription termination signal present in the leader RNA. J Bacteriol. 184: 3034-3043.

Hiei Y, Komari T, Kubo T., 1997. Transformation of rice mediated by *Agrobacterium tumefaciens*. Plant Mol. Biol. 35:205-18.

Ito, Y., O. H. Kwon, M. Ueda, A. Tanaka, and Y. Imanishi. 2000. Gene-engineered hydrophobilization to alter the bactericidal activity of lysozyme. Journal of Bioactive and Compatible Polymers 15:376-395.

Ito, Y., O. H. Kwon, M. Ueda, A. Tanaka, and Y. Imanishi. 1997. Bactericidal activity of human lysozymes carrying various lengths of polyproline chain at the C-terminus. FEBS Letters 415:285-288.

Jaynes J M et al. 1987. Increasing bacterial disease resistance in plants utilizing antibacterial genes from insects. Bioassays 6:263-270

Kapila, J., R. De Rycke, M. Van Montagu, and G. Angenon. 1997. An *Agrobacterium*-mediated transient gene expression system for intact leaves. Plant Science 122:101-108.

Kato, A., S, Nakamura, H. Ibrahim, T. Matsumi, C. Tsumiyama, and M. Kato. 1998. Production of genetically modified lysozymes having extreme heat stability and antimicrobial activity against Gram negative bacteria in yeast and in plant. Nahrung-Food 42:128-130.

Kingsley, M. T., D. W. Gabriel, G. C. Marlow, and P. D. Roberts. 1993. The opsX locus of *Xanthomonas campestris* affects host range and biosynthesis of lipopolysaccharide and extracellular polysaccharide. J. Bacteriol. 175: 5839-5850.

Ko K. 1999. Attacin and T4 lysozyme transgenic ☐Galaxy☐ apple: Regulation of transgene expression and plant resistance to fire blight (*Erwinia amylovora*). PhD dissertation, Cornell University, Ithaca N.Y. 194 pp Ko K et al. 2000. Effect of untranslated leader sequence of AMV RNA 4 and signal peptide of pathogenesis-related protein 1b on attacin gene expression, and resistance to fire blight in transgenic apple. Biotechnology Letters 22:373-381

Kragol G et al. 2001. The antibacterial peptide pyrrhocoricin inhibits the ATPase actions of DnaK and prevents chaparone-assisted protein folding. Biochemistry 40:3016-3026

Li Q et al. 2001. Enhanced disease resistance conferred by expression of an antimicrobial magainin analog in transgenic tobacco. Planta 212:635-639

Mitra A and Zhang Z. 1994. Expression of a human lactoferrin cDNA in tobacco cells produces antibacterial protein(s). Plant Physiol 106:977-981.

Moore G. A., Jacono, C. C., Neidigh J. L., Lawrence S. D. and Cline K., 1992. *Agrobacterium*-mediated transformation of citrus stem segments and regeneration of transgenic plants. Plant Cell Rep 11:238-242.

Mun, J. H., Lee, S. Y., Yu, H. J., Jeong, Y. M., Shin, M. Y., Kim, H., Lee, I., and Kim, S. G. Petunia actin-depolymerizing factor is mainly accumulated in vascular tissue and its expression is enhanced by the first intron. Gene 292, 233-243. 2004.

Murasugi, A., Asami, Y., and Mera-Kikuchi, Y. Production of recombinant human bile salt-stimulated lipase in *Pichia pastoris*. Protein Expression and Purification 23, 282-288. 2001.

Nakajima H et al. 1997. Fungal and bacterial disease resistance in transgenic plants expressing human lysozyme. Plant Cell Rep 16:674-679 Norelli J L et al 1994. Transgenic ☐Malling 26☐ apple expressing the attacin E gene has increased resistance to *Erwinia amylovora*. Euphytica 77:123-128

Norelli J L et al. 1998. Effect of cercropin-type transgenes on fire blight resistance of apple. Acta Hort 489:273-278

Norelli J L et al. 1999. Genetic transformation for fire blight resistance in apple. Acta Hort 489:295-296

Osusky et al. 2000. Transgenic plants expressing cationic peptide chimeras exhibit broad-spectrum resistance to phytopathogens. Nature Biotechnology 18:1162-1166

Owens, L. D. and Heutte, T. M. (1997) A single amino acid substitution in the antimicrobial defense protein cecropin B is associated with diminished degradation by leaf intercellular fluid. Molecular Plant-Microbe Interactions. 10, 525-528.

Reynoird J P et al. 1999. First evidence for differences in fire blight resistance among transgenic pear clones expressing attacin gene. Plant Science 149:23-31 Riggs, C. D., K. Zeman, R. DeGuzman, A. Rzepczyk and A. A. Taylor. 2001. Antisense inhibition of a tomato meiotic proteinase suggests functional redundancy of proteinases during microsporogenesis Genome 44: 644-650.

Robichon, M. P., J. P. Renou and R. Jalouzot, 1995. Genetic transformation of Pelargonium X hortorum Plant Cell Reports 15:63-67.

Rose, A. B. and Beliakoff, J. A. Intron-mediated enhancement of gene expression independent of unique intron sequences and splicing. Plant Physiol. 122, 535-542. 2004.

Rose, A. B. 2002. Requirements for intron-mediated enhancement of gene expression in *Arabidopsis*. Rna-A Publication of the Rna Society 8:1444-1453.

Sambrook, J., Fritsch, E. F. and Maniatis, T., 1989. Molecular Cloning A Laboratory Manual, Cold Spring Harbor Laboratory Press, NY Selitrennikoff, C. P. 2001. Antifungal proteins. Appl. Environ. Microbiol. 67:2883-2894.

Shepherd M G. 1987. Cell envelope of *Candida albicans*. CRC Clin. Rev. Microbiol. 15: 7-25.

Simpson, G. G. and Filipowicz, W. Splicing of precursors to mRNA in higher plants: mechanism, regulation an subnuclear organization of the spliceosomal machinery. Plant Mol. Biol. 32, 1-41. 1996.

Swarup, S., Y. Yang, M. T. Kingsley, and D. W. Gabriel. 1992. A *Xanthomonas citri* pathogenicity gene, pthA, pleiotropically encodes gratuitous avirulence on nonhosts. Molec. Plant-Microbe Interact. 5:204-213.

Trudel J et al. 1995. Secreted hen lysozyme in transgenic tobacco: Recovery of bound enzyme and in vitro growth inhibition of plant pathogens. Plant Science 106:55-62

Taguchi S et al. 2000. Functional mapping against *Escherichia coli* for the broad-spectrum antimicrobial peptide, thanatin, based on an in vivo monitoring assay system. J Biochem 128:745-754

Unniraman, S., R. Prakash, and V. Nagaraja. 2002. Conserved economics of transcription termination in eubacteria. Nucleic Acids Research 30:675-684.

Unniraman, S., R. Prakash, and V. Nagaraja. 2001. Alternate paradigm for intrinsic transcription termination in eubacteria. Journal of Biological Chemistry 276:41850-41855.

Vunnam S et al. 1997. Synthesis and antibacterial action of cecropin and proline-arginine-rich peptides from pig intestine. J Peptide Res 49:59-66

Wang Y et al. 1999. Porcine pulmonary surfactant preparations contain the antibacterial peptide prophenin and a C-terminal 18-residue fragment thereof. FEBS Lett 460: 257-262

Yang, Y., R. De Feyter, and D. W. Gabriel. 1994. Host-specific symptoms and increased release of *Xanthomonas citri* and *X. campestris* pv. *malvacearum* from leaves are determined by the 102 bp tandem repeats of pthA and avrb6, respectively. Molec. Plant-Microbe Interact. 7:345-355.

We claim:

1. An isolated nucleic acid molecule comprising a nucleic acid sequence coding for a bacteriophage outer membrane breaching protein, wherein the bacteriophage outer membrane breaching protein has the amino acid sequence of SEQ ID No. 82.

2. The isolated nucleic acid molecule of claim 1 further comprising a nucleic acid sequence coding for a plant leader sequence operably-linked to the nucleic acid sequence coding for the bacteriophage outer membrane breaching protein.

3. The isolated nucleic acid molecule of claim 2, wherein the plant leader sequence is a P12 plant leader sequence.

4. The isolated nucleic acid molecule of claim 3, wherein the P12 plant leader sequence has the amino acid sequence of SEQ ID No. 87.

5. The isolated nucleic acid molecule of claim 2, wherein the plant leader sequence targets the bacteriophage outer membrane breaching protein to xylem and/or apoplast.

6. The isolated nucleic acid molecule of claim 1 further comprising a nucleic acid sequence coding for one or more expression control elements operably-linked to the nucleic acid sequence coding for the bacteriophage outer membrane breaching protein.

7. The isolated nucleic acid molecule of claim 1 further comprising a nucleic acid sequence coding for a lytic enzyme operably-linked to the nucleic acid sequence coding for the bacteriophage outer membrane breaching protein.

8. The isolated nucleic acid molecule of claim 7, wherein the lytic enzyme has an amino acid sequence with at least about 99% amino acid sequence identity to SEQ ID No. 26.

9. The isolated nucleic acid molecule of claim 7, wherein the lytic enzyme has the amino acid sequence of SEQ ID No. 26.

10. A vector comprising the isolated nucleic acid molecule of claim 1, claim 2, claim 6 or claim 7.

11. An isolated host cell transformed to contain the nucleic acid molecule of claim 1, claim 2, claim 6 or claim 7.

12. The host cell of claim 11, wherein the host cell is a eukaryotic or prokaryotic host cell.

13. The isolated nucleic acid molecule of claim 7, wherein the nucleic acid molecule coding for the lytic enzyme is linked translationally in frame to the nucleic acid molecule coding for the bacteriophage outer membrane breaching protein.

14. An isolated host cell comprising the isolated nucleic acid of claim 1 and further comprising a nucleic acid molecule coding for a lytic enzyme on a separate gene from the nucleic acid molecule coding for the bacteriophage outer membrane breaching protein.

* * * * *